(12) United States Patent
Ginn et al.

(10) Patent No.: US 8,952,004 B2
(45) Date of Patent: Feb. 10, 2015

(54) CXCR3 RECEPTOR ANTAGONISTS

(75) Inventors: John David Ginn, New Milford, CT (US); Ronald John Sorcek, Bethel, CT (US); Michael Robert Turner, Danbury, CT (US); Di Wu, Danbury, CT (US); Frank Wu, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 130 days.

(21) Appl. No.: 13/520,234

(22) PCT Filed: Jan. 5, 2011

(86) PCT No.: PCT/US2011/020191
§ 371 (c)(1),
(2), (4) Date: Oct. 17, 2012

(87) PCT Pub. No.: WO2011/084985
PCT Pub. Date: Jul. 14, 2011

(65) Prior Publication Data
US 2013/0029971 A1 Jan. 31, 2013

Related U.S. Application Data

(60) Provisional application No. 61/292,870, filed on Jan. 7, 2010.

(51) Int. Cl.
| | | |
|---|---|---|
| A61K 31/4545 | (2006.01) |
| A61K 31/496 | (2006.01) |
| A61K 31/5377 | (2006.01) |
| A61K 31/541 | (2006.01) |
| A61K 31/55 | (2006.01) |
| A61K 31/551 | (2006.01) |
| C07D 401/04 | (2006.01) |
| C07D 401/14 | (2006.01) |
| C07D 405/14 | (2006.01) |
| C07D 409/14 | (2006.01) |
| C07D 413/14 | (2006.01) |
| C07D 417/14 | (2006.01) |
| C07D 471/04 | (2006.01) |
| C07D 487/04 | (2006.01) |
| C07D 498/08 | (2006.01) |
| C07D 407/14 | (2006.01) |
| C07D 211/26 | (2006.01) |
| C07D 211/32 | (2006.01) |
| C07D 213/74 | (2006.01) |
| C07D 401/06 | (2006.01) |
| C07D 401/12 | (2006.01) |
| C07D 417/06 | (2006.01) |

(Continued)

(52) U.S. Cl.
CPC .......... *C07D 407/14* (2013.01); *C07D 211/26* (2013.01); *C07D 211/32* (2013.01); *C07D 213/74* (2013.01); *C07D 401/04* (2013.01); *C07D 401/06* (2013.01); *C07D 401/12* (2013.01); *C07D 401/14* (2013.01); *C07D 409/14* (2013.01); *C07D 413/06* (2013.01); *C07D 413/14* (2013.01); *C07D 417/06* (2013.01); *C07D 417/12* (2013.01); *C07D 471/04* (2013.01); *C07D 487/06* (2013.01); *C07D 497/04* (2013.01)
USPC ................... 514/217.04; 514/218; 514/227.8; 514/235.5; 514/253.01; 514/300; 514/303; 514/305; 514/316; 514/211.15; 540/544; 540/575; 540/597; 544/58.2; 544/130; 544/349; 544/364; 546/113; 546/118; 546/121; 546/187; 546/194

(58) Field of Classification Search
None
See application file for complete search history.

(56) References Cited

U.S. PATENT DOCUMENTS

| | | |
|---|---|---|
| 2004/0192728 A1 | 9/2004 | Codd et al. |
| 2009/0099201 A1 | 4/2009 | Bolin et al. |

(Continued)

FOREIGN PATENT DOCUMENTS

| | | |
|---|---|---|
| EP | 1505068 A1 | 2/2005 |
| EP | 2009005 A1 | 12/2008 |

(Continued)

OTHER PUBLICATIONS

CA Registry No. 1115906-35-8, entered into the Registry File on Mar. 5, 2009, supplied by Aurora Fine Chemicals.*

(Continued)

*Primary Examiner* — Emily Bernhardt
(74) *Attorney, Agent, or Firm* — Michael P. Morris; Edward S. Lazer

(57) ABSTRACT

The present invention relates to compounds of formula (I):

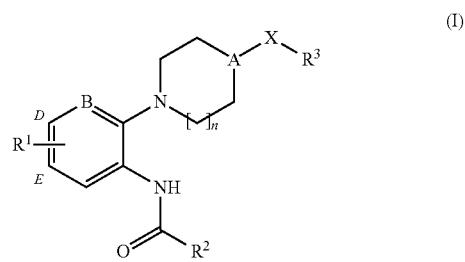

and pharmaceutically acceptable salts thereof, wherein $R^1$ to $R^3$, A, B, X, and n are as defined herein. The invention also relates to pharmaceutical compositions comprising these compounds, methods of using these compounds in the treatment of various diseases and disorders, processes for preparing these compounds and intermediates useful in these processes.

8 Claims, No Drawings

(51) Int. Cl.
*C07D 417/12* (2006.01)
*C07D 487/06* (2006.01)
*C07D 497/04* (2006.01)
*A61K 31/553* (2006.01)
*C07D 413/06* (2006.01)

(56) References Cited

U.S. PATENT DOCUMENTS

| | | |
|---|---|---|
| 2009/0286766 A1 | 11/2009 | Sugasawa et al. |
| 2010/0273781 A1 | 10/2010 | Ginn et al. |
| 2010/0280028 A1 | 11/2010 | Kowalski et al. |
| 2013/0029971 A1 | 1/2013 | Ginn et al. |

FOREIGN PATENT DOCUMENTS

| | | |
|---|---|---|
| WO | 03048164 A2 | 6/2003 |
| WO | 2007002742 A1 | 1/2007 |
| WO | 2007100610 A2 | 9/2007 |
| WO | 2007123269 A1 | 11/2007 |
| WO | 2007127635 A2 | 11/2007 |
| WO | 2008054702 A1 | 5/2008 |
| WO | 2008148849 A2 | 12/2008 |
| WO | 2009074300 A2 | 6/2009 |
| WO | 2009105435 A1 | 8/2009 |
| WO | 2010126811 A1 | 11/2010 |
| WO | 2010126851 A1 | 11/2010 |
| WO | 2011084985 A1 | 7/2011 |

OTHER PUBLICATIONS

CA Registry No. 1243019-26-2, entered into the Registry File on Sep. 27, 2010, supplied by AKos Consulting and Solutions GmbH.*
CA Registry No. 1216894-27-7, entered into the Registry File on Apr. 5, 2010, supplied by Aurora Fine Chemicals.*
CA Registry No. 124947-42-7, entered into the Registry File on Sep. 27, 2010, supplied by Akos Consulting and Solurions GmbH.*
Chemical Abstract by IUPAC Chemical Data Series, http://www.iupac.org/goldbook/A00228.pdf (1997) p. 1 titled "alkyl groups".
Chemical Abstract by IUPAC Chemical Data Series, http://www.iupac.org/goldbook/A00464.pdf (1997) p. 1 titled "aryl groups".
Chemical Abstract Registry No. 1025924-29-1, entered into the Registry File on Jun. 6, 2008, supplied by ChemZoo, Inc., p. 1.
Chemical Abstract Registry No. 1115906-32-5, entered into the Registry File on Mar. 5, 2009, supplied by Chemical Abstract Service, Columbus, Ohio, US p. 1.
Chemical Abstract Registry No. 1115906-35-8, entered into the Registry File on Mar. 5, 2009, supplied by Chemical Abstract Service, Columbus, Ohio, US p. 1.
Chemical Abstract Registry No. 1242874-28-7, entered into the Registry File on Sep. 27, 2010 supplied by Chemical Abstract Service, Columbus, Ohio, US p. 1.
Chemical Abstract Registry No. 1252349-95-3, entered into the Registry File on Nov. 10, 2010, supplied by Chemical Abstract Service, Columbus, Ohio, US p. 1.
Chemical Abstract Registry No. 903856-50-8, entered into the Registry File on Aug. 23, 2006, supplied by Chemical Abstract Service, Columbus, Ohio, US p. 1.
Chemical Abstract Registry No. 903858-09-3, entered into the Registry File on Aug. 23, 2006, supplied by Chemical Abstract Service, Columbus, Ohio, US p. 1.
Cheng, Cliff C., et al; Puridine Carboxamides: Potent Palm Site Inhibitors of HCV NS5B Polymerase; ACS Medicinal Chemistry Letters (2010) vol. 1, No. 9 pp. 466-471.
Havlioglu, Necat, et al; Slit Proteins, Potential Endogenous Modulators of Inflammation; Journal of NeuroVirology (2002) vol. 8 pp. 486-495.
International Search Report and Written Opinion for PCT/US2011/020191 mailed Apr. 12, 2011.
International Search Report for PCT/US2010/032347 mailed Jul. 23, 2010.
International Search Report for PCT/US2010/032477 mailed Jul. 16, 2010.
Pease, James E., et al; Chemokine Receptor Antagonists: Part 2; Expert Opinion on Therapeutic Patents (2009) vol. 19, No. 2 pp. 199-221.
Shin, Youseung, et al; Synthesis and SAR or Piperazine Amides as Novel c-jun N-Terminal Kinase (JNK) Inhibitors; Bioorganic & Medicinal Chemistry Letters (2009) vol. 19 pp. 3344-3347.

* cited by examiner

CXCR3 RECEPTOR ANTAGONISTS

FIELD OF THE INVENTION

This invention relates to heterocyclic compounds that are useful as antagonists of CXCR3 and are thus useful for treating a variety of diseases and disorders that are mediated or sustained through the interaction of CXCR3 and its ligands including multiple sclerosis, psoriasis, rheumatoid arthritis, inflammatory bowel disease and atherosclerosis. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Chemokine receptors, a subclass of the G-protein coupled receptors (GPCRs) are expressed on the surface of T-cells and other leukocytes. The interaction of chemokine receptors with their ligands plays an important role in the migration of leukocytes to sites of inflammation (A. D. Luster, New Engl. J. Med., 1998, 338, 436). The chemokine receptor CXCR3 is preferentially expressed on T helper (Th1) cells but is also found on natural killer cells and subsets of dendritic cells. Three major chemokine ligands for CXCR3 have been identified: Mig (Monokine Induced by γ-IFN/CXCL9), IP-10 (γ-interferon inducible protein) and I-TAC (IFN-Inducible T Cell α Chemoattractant/CXCR11) (K. E. Cole et al., J. Exp. Med., 1998, 187, 2009; Y. Weng et al., J. Biol. Chem., 1998, 273, 18288).

Histological evaluations of numerous inflammatory lesions, including those from patients with multiple sclerosis (T. L. Sorenson et al., J. Clin. Invest., 1999, 103, 807), rheumatoid arthritis (S. Qin et al., J. Clin. Invest., 1998, 101, 746), psoriasis (J. Flier et al., J. Pathol., 2001, 194, 398) and inflammatory bowel disease (Y. H. Yuan et al., Inflamm. Bowel Dis., 2001, 7, 281) have shown elevated expression of CXCR3 ligands accompanied by an increased frequency of T cells bearing CXCR3. This is in marked contrast to what is found in most normal tissues, where expression of CXCR3 and its ligands is extremely low. This correlative evidence suggests a role of CXCR3 in Th1-mediated chronic inflammation.

Studies with CXCR3 and IP-10 deficient mice also suggest a role for CXCR3 and IP-10 in Th1 mediated disease. For example, in one study CXCR3 −/− mice showed significant resistance to allograft rejection (W. W. Hancock et al., J. Exp. Med., 2000, 192, 1515). In another study, IP-10 deficient mice showed protection against the development of colitis (U. P. Singh et al., J. Immunol., 2003, 171, 1401). Further evidence of a role for CXCR3 and IP-10 as mediators of disease is provided by studies utilizing blocking antibodies. For example in a rat model of adjuvant induced arthritis (I. Salomon et al., J. Immunol., 2002, 169, 2685) a DNA vaccine approach to overexpress self IP-10 was used to induce the production of self-IP-10 antibodies. These Abs are specific for IP-10 and do not cross react with other proinflammatory cytokines or chemokines including Mig and I-TAC. Pretreatment with this vaccine protected rats from the development of severe arthritis and reduced the time to remission of symptoms. In addition, affinity purified anti-IP-10 from vaccinated rats could therapeutically transfer protection to newly diseased rats. In another study, this vaccine approach was successful in suppressing disease in a mouse model of multiple sclerosis (G. Wildbaum et al., J. Immunol., 2002, 168, 5885).

In a study of pulmonary inflammation, (N. Li et al., Acta Pharmacol. Sinica, 2008, 29, 14) CXCR3 knockout mice showed alleviated inflammation compared to wild type mice in cigarette smoke induced pulmonary injury as well as lower influx of inflammatory T cells. Similarly, in a model of nephrotoxic nephritis, CXCR3 knockout mice showed reduced influx of T cells, less severe nephritis and improved renal function compared to wild type mice (U. Panzer et al., J. Am. Soc. Nephrol., 2007, 18, 2071). Thus CXCR3 may play a role in inflammatory pulmonary diseases such as COPD and inflammatory kidney disease.

Studies such as those cited above suggest that inhibitors of CXCR3 may be useful in treating inflammatory and autoimmune diseases in which CXCR3-mediated cellular recruitment plays a role, including multiple sclerosis, psoriasis, rheumatoid arthritis, inflammatory bowel disease, COPD and kidney disease.

Recent work has also implicated CXCR3 in the pathogenesis of atherosclerosis. In one study (F. Mach et al., J. Clin. Invest., 1999, 104, 1041) CXCR3 was found expressed in all T lymphocytes within human atherosclerotic lesions. The ligands IP10, Mig and I-TAC were all found within lesion-associated cells including endothelial and smooth muscle cells (Mig and I-TAC) and macrophages (IP10), suggesting these ligands play a role in recruitment of activated T lymphocytes within vascular wall lesions in atherogenesis. Left untreated and allowed to progress, atherosclerosis can result in narrowing of the lumen of the artery and plaque rupture which can lead to coronary heart disease, myocardial infarction and stroke (J. Sanz and Z. A. Fayad, Nature, 2008, 451, 953).

Further evidence has come from genetic deletion studies in mice. CXCR3 deletion on an ApoE$^{-/-}$ background resulted in a significant reduction in atherosclerotic lesion formation following ten weeks on a high cholesterol diet (N. R. Veillard et al., Circulation, 2005, 112, 870). Moreover, deletion of the CXCR3 ligand, IP-10 on an ApoE$^{-/-}$ background similarly reduced atherosclerotic lesion load (E. Heller et al., Circulation, 2006, 113, 2301). More recently, NBI-74330 a CXCR3 antagonist was dosed prophylactically in a LDL receptor knockout model. Similar to the CXCR3 deletion studies in the ApoE−/− results, NBI-74330 significantly attenuated atherosclerotic lesion formation (E. J. A. van Wanrooij et al., Arterioscler. Thromb. Vasc. Biol., 2008, 28, 251).

As a result of studies such as those cited above implicating the interaction of CXCR3 and its ligands in the etiology of various inflammatory and autoimmune diseases as well as atherosclerosis, considerable effort has been directed towards discovering antagonists of this interaction. A number of inhibitors have been reported in the scientific literature, including small molecule antagonists, antibodies and modified ligands (see for example J. C. Medina et al., Ann. Rep. Med. Chem., 2005, 40, 215). However, to date, no CXCR3 antagonist has been approved as a marketed drug.

BRIEF SUMMARY OF THE INVENTION

The present invention provides novel compounds which block the interaction of CXCR3 and its ligands and are thus useful for treating diseases and disorders that are mediated or sustained through the activity of CXCR3 including multiple sclerosis, psoriasis, rheumatoid arthritis, inflammatory bowel disease, COPD, kidney disease and atherosclerosis, myocardial infarction and stroke. This invention also relates to pharmaceutical compositions comprising these compounds, methods of using these compounds in the treatment of various

DETAILED DESCRIPTION OF THE INVENTION

In its broadest embodiment, the present invention relates compounds of formula (I):

(I)

wherein:
A is C or N;
B is C or N;
X is —$CH_2$—, —$CH(CH_3)$—, —$CH_2C(O)$—, —C(O)—, —$CH_2CH_2$— or —$CH_2CH_2CH_2$—;
$R^1$ is in the D- or E-position and is selected from H, —CN, halogen, —$CF_3$, —$OCF_3$, $C_{1-3}$alkyl, $C_{1-3}$alkoxy, —$CH_2OH$, —$S(O)_2CH_3$, —$S(O)_2NH_2$, amino, mono- or dimethylamino, —NHC(O)$C_{1-3}$alkyl, —$NO_2$, —$C(O)NH_2$, —C(O)$C_{1-3}$alkyl, phenyl and pyridyl; and if B=N, $R^1$ may also be selected from —C(O)NH$C_{1-3}$alkyl, —C(O)NH$C_{3-6}$cycloalkyl and —C(O)N($C_{1-3}$alkyl)$_2$;
$R^2$ is aryl or heteroaryl each optionally substituted with one to three $R^6$;
$R^3$ is heteroaryl, heterocyclyl, or —N($R^4$)($R^5$), wherein each heteroaryl, heterocyclyl or $R^5$ group is optionally and independently substituted with one to two $R^7$;
$R^4$ is H or $C_{1-3}$alkyl;
$R^5$ is selected from
 (A) $C_{2-6}$alkyl,
 (B) —$(CH_2)_{0-1}C_{3-7}$cycloalkyl,
 (C) —$CH(CH_3)C_{3-7}$cycloalkyl,
 (D) —$C(R^8)(R^9)$phenyl,
 (E) —$[C(R^8)(R^9)]_{0-1}$heteroaryl,
 (F) —$[C(R^8)(R^9)]_{0-1}$heterocyclyl,
 (G) —$C(O)NHR^{10}$, wherein $R^{10}$ is selected from ethyl, benzyl and phenyl,
 (H) —$S(O)_2CH_2$phenyl,
 (I) cyclopropyl, optionally substituted with a CN,
 (J) —$CH_2CF_3$,
 (K) —$CH_2CF_2H$,
 (L) —NHC(O)CH($CH_3$)phenyl
 (M) —C(O)(1-methylpiperidin-3-yl),
 (N) —$CH_2C(O)NHC_{1-3}$alkyl, and
 (O) indan-1-yl,
 (P) —$CH_2C(O)N(C_{1-3}$alkyl)$_2$,
wherein each $C_{2-5}$alkyl, heteroaryl, heterocyclyl or phenyl is optionally and independently substituted with one to four $R^7$;
$R^6$ is independently selected from halogen, —$CF_3$, —$OCF_3$CN, —$NO_2$, —$SO_2CH_3$, $C_{1-3}$alkoxy, phenoxy, benzoyl and phenyl;
$R^7$ is independently selected from $C_{1-4}$alkyl, $C_{3-6}$cycloalkyl, $C_{1-3}$alkoxy, —$CH_2OC_{1-3}$alkyl, —OH, oxo, —CHO, —C(O)$C_{1-3}$alkyl, halogen, —$CF_3$, —CN, and —$S(O)_2C_{1-3}$alkyl;
$R^8$ and $R^9$ are independently selected from H and $C_{1-2}$alkyl; or $R^8$ and $R^9$, together with the carbon they are bonded to, may form a cyclopropyl ring;
n is 1 or 2;
or the pharmaceutically acceptable salts thereof.

In another embodiment there is provided a compound of formula (I) as described in the broadest embodiment above and wherein:
A is C;
or the pharmaceutically acceptable salts thereof.

In another embodiment there is provided a compound of formula (I) as described in the broadest embodiment above and wherein:
A is C;
B is N; and
X is —$CH_2$—, —$CH_2C(O)$—, —C(O)— or —$CH_2CH_2$—;
or the pharmaceutically acceptable salts thereof.

In another embodiment there is provided a compound of formula (I) as described in the broadest embodiment above and wherein:
A is C;
B is C; and
X is —$CH_2C(O)$— or —$CH_2CH_2$—;
or the pharmaceutically acceptable salts thereof.

In another embodiment there is provided a compound of formula (I) as described in the broadest embodiment above and wherein:
A is C;
$R^1$ is in the E-position and is selected from H, —CN, halogen, —$CF_3$, —$OCF_3$, $C_{1-3}$alkyl, $C_{1-3}$alkoxy, —$CH_2OH$, —$S(O)_2CH_3$, —$S(O)_2NH_2$, amino, mono- or dimethylamino, —NHC(O)$C_{1-3}$alkyl, —$NO_2$, —$C(O)NH_2$, —C(O)$C_{1-3}$alkyl, phenyl and pyridyl; and if B=N, $R^1$ may also be selected from —C(O)NH$C_{1-3}$alkyl, —C(O)NH$C_{3-6}$cycloalkyl and —C(O)N($C_{1-3}$alkyl)$_2$;
$R^2$ is phenyl, naphthyl, 2-pyridyl, 4-pyridyl or benzothiazolyl each optionally substituted with one to two $R^6$, wherein $R^6$ is not ortho to the —C(O)NH— group;
$R^3$ is heterocyclyl selected from azabicyclo[2.2.1]hept-2-yl, azepan-1-yl, 1,4-diazepan-1-yl, hexahydropyrrolo[1,2-a]pyrazin-2-yl, morpholin-4-yl, 2-oxa-5-azabicyclo[2.2.1]hept-5-yl, oxazepan-4-yl, piperazin-1-yl, piperidin-1-yl, pyrrolidin-1-yl and thiomorpholin-4-yl, or —N($R^4$)($R^5$), or
$R^3$ is heteroaryl selected from benzimidazol-1-yl, imidazol-1-yl, pyrazol-1-yl imidazo[4,5-b]pyridine-3-yl and 1H-pyrrolo[2,3-b]pyridine-1-yl, with the proviso that X is —$CH_2CH_2$—,
wherein each heteroaryl, heterocyclyl group is optionally and independently substituted with one to two $R^7$; and
$R^5$ is selected from
 (A) $C_{2-6}$alkyl,
 (B) —$(CH_2)_{0-1}C_{3-7}$cycloalkyl,
 (C) —$CH(CH_3)C_{3-7}$cycloalkyl,
 (D) —$C(R^8)(R^9)$phenyl
 (E) —$[C(R^8)(R^9)]_{0-1}$heteroaryl, wherein the heteroaryl is selected from furan-2-yl, 1,2,4-oxadiazol-3-yl, 1,3-oxazol-4-yl, pyrazol-3-yl, 2-, 3- or 4-pyridinyl, thiophen-2-yl, thiazol-2-yl and 1,2,4-triazol-2-yl, thiophen-2-yl, thiazol-2-yl and 1,2,4-triazol-2-yl,
 (F) —$[C(R^8)(R^9)]_{0-1}$heterocyclyl, wherein the heterocyclyl is selected from azabicyclo[2.2.2]oct-3-yl, azepan-3-yl, 2,3-dihydro-1H-indol-3-yl, piperidin-3-yl, piperidin-4-yl, pyrrolidin-3-yl, tetrahydrofuran2-yl, tetrahydrofuran-3-yl and 4,5,6,7-tetrahydro[1,3]thiazolo[5,4-c]pyridine-2-yl, (G) —C(O)NHR$^{10}$, wherein R$^{10}$ is selected from ethyl, benzyl and phenyl,
(H) —S(O)$_2$CH$_2$phenyl,
(I) cyclopropyl, optionally substituted with a CN,
(J) —CH$_2$CF$_3$,
(K) —CH$_2$CF$_2$H,
(L) —NHC(O)CH(CH$_3$)phenyl
(M) —NHC(O)(1-methylpiperidin-3-yl),
(N) —CH$_2$C(O)NHC$_{1-3}$alkyl, and
(O) indan-1-yl,
wherein each C$_{2-5}$alkyl, heteroaryl, heterocyclyl or phenyl is optionally and independently substituted with one to four R$^7$;
or the pharmaceutically acceptable salts thereof.

In another embodiment there is provided a compound of formula (I) as described above and wherein:
X is —CH$_2$—, —CH$_2$C(O)— or —CH$_2$CH$_2$—;
R$^1$ is in the E-position and is selected from H, —CN, —F, —Cl, —CH$_3$, —S(O)$_2$CH$_3$, —S(O)$_2$NH$_2$, phenyl and pyridyl; and if B=N, R$^1$ may also be selected from —C(O)NHC$_{1-3}$alkyl, —C(O)NHcyclopropyl and —C(O)N(C$_{1-3}$alkyl)$_2$;
R$^2$ is phenyl, 2-pyridyl or 4-pyridyl each optionally substituted with one to two R$^6$ wherein R$^6$ is not ortho to the —C(O)NH— group;
R$^4$ is H;
R$^5$ is selected from
(A) C$_{2-6}$alkyl,
(B) —(CH$_2$)$_{0-1}$C$_{3-7}$cycloalkyl,
(C) —CH(CH$_3$)C$_{3-7}$cycloalkyl,
(D) —C(R$^8$)(R$^8$)phenyl,
(E) —[C(R$^8$)(R$^9$)]$_{0-1}$heteroaryl, wherein the heteroaryl is selected from furan-2-yl, 1,2,4-oxadiazol-3-yl, 1,3-oxazol-4-yl, pyrazol-3-yl, 2-, 3- or 4-pyridinyl, thiophen-2-yl, thiazol-2-yl and 1,2,4-triazol-2-yl,
(F) —[C(R$^8$)(R$^9$)]$_{0-1}$heterocyclyl, wherein the heterocyclyl is selected from azabicyclo[2.2.2]oct-3-yl, azepan-3-yl, 2,3-dihydro-1H-indol-3-yl, piperidin-3-yl, piperidin-4-yl, pyrrolidin-3-yl, tetrahydrofuran2-yl, tetrahydrofuran-3-yl and 4,5,6,7-tetrahydro[1,3]thiazolo[5,4-c]pyridine-2-yl,
(G) —C(O)NHR$^{10}$, wherein R$^{10}$ is selected from ethyl, benzyl and phenyl,
(H) —S(O)$_2$CH$_2$phenyl,
(I) cyclopropyl, optionally substituted with a CN,
(J) —CH$_2$CF$_3$,
(K) —CH$_2$CF$_2$H,
(L) —NHC(O)CH(CH$_3$)phenyl
(M) —NHC(O)(1-methylpiperidin-3-yl),
(N) —CH$_2$C(O)NHC$_{1-3}$alkyl, and
(O) indan-1-yl,
wherein each C$_{2-5}$alkyl, heteroaryl, heterocyclyl or phenyl is optionally and independently substituted with one to four R$^7$; and
n is 1;
or the pharmaceutically acceptable salts thereof.

In another embodiment there is provided a compound of formula (I) as described above and wherein:
R$^1$ is in the E-position and is selected from H, —CN, —Cl, —S(O)$_2$CH$_3$ and —S(O)$_2$NH$_2$; and if B=N, R$^1$ may also be —C(O)NHcyclopropyl or —C(O)N(Et)$_2$;
R$^2$ is phenyl optionally substituted with one to two R$^6$ wherein R$^6$ is not ortho to the —C(O)NH— group;
R$^3$ is heterocyclyl selected from azabicyclo[2.2.1]hept-2-yl, azepan-1-yl, 1,4-diazepan-1-yl, hexahydropyrrolo[1,2-a]pyrazin-2-yl, morpholin-4-yl, 2-oxa-5-azabicyclo[2.2.1]hept-5-yl, oxazepan-4-yl, piperazin-1-yl, piperidin-1-yl, pyrrolidin-1-yl and thiomorpholin-4-yl, or —N(R$^4$)(R$^5$)

wherein each heterocyclyl is optionally substituted with one to two R$^7$; and
R$^6$ is independently selected from —Cl, —CF$_3$, —OCF$_3$CN, —SO$_2$CH$_3$ and —OCH$_3$;
or the pharmaceutically acceptable salts thereof.

In another embodiment there is provided a compound of formula (I) as described above and wherein:
R$^2$ is phenyl substituted with R$^6$ wherein R$^6$ is not ortho to the —C(O)NH— group;
R$^5$ is selected from
(A) C$_{2-6}$alkyl,
(B) —(CH$_2$)$_{0-1}$C$_{3-7}$cycloalkyl,
(C) —CH(CH$_3$)C$_{3-7}$cycloalkyl,
(D) —C(R$^8$)(R$^9$)phenyl
(E) —[C(R$^8$)(R$^9$)]$_{0-1}$heteroaryl, wherein the heteroaryl is selected from furan-2-yl, 1,2,4-oxadiazol-3-yl, 1,3-oxazol-4-yl, pyrazol-3-yl, 2-, 3- or 4-pyridinyl, thiophen-2-yl, thiazol-2-yl and 1,2,4-triazol-2-yl,
(F) —[C(R$^8$)(R$^9$)]$_{0-1}$heterocyclyl, wherein the heterocyclyl is selected from azabicyclo[2.2.2]oct-3-yl, azepan-3-yl, 2,3-dihydro-1H-indol-3-yl, piperidin-3-yl, piperidin-4-yl, pyrrolidin-3-yl, tetrahydrofuran2-yl and tetrahydrofuran-3-yl, and
(G) —C(O)NHR$^{10}$, wherein R$^{10}$ is selected from ethyl, benzyl and phenyl,
wherein each C$_{2-5}$alkyl, heteroaryl, heterocyclyl or phenyl is optionally and independently substituted with one to two R$^7$;
R$^6$ is selected from 3-Cl, 3-CF$_3$, 4-OCH$_3$ and 4-SO$_2$CH$_3$; and
R$^7$ is independently selected from —CH$_3$, —CH$_2$CH$_3$, cyclopropyl, OCH$_3$, —OH, —C(O)CH$_3$, Br, Cl, F, —CF$_3$, —CN, and —S(O)$_2$CH$_3$;
or the pharmaceutically acceptable salts thereof.

In another embodiment there is provided a compound of formula (I) as described above and wherein:
X is —CH$_2$C(O)—;
or the pharmaceutically acceptable salts thereof.

In another embodiment there is provided a compound of formula (I) as described in the embodiment two above this embodiment and wherein:
X is —CH$_2$— or —CH$_2$CH$_2$—; and
R$^3$ is heterocyclyl selected from azabicyclo[2.2.1]hept-2-yl, azepan-1-yl, 1,4-diazepan-1-yl, hexahydropyrrolo[1,2-a]pyrazin-2-yl, morpholin-4-yl, 2-oxa-5-azabicyclo[2.2.1]hept-5-yl, oxazepan-4-yl, piperazin-1-yl, piperidin-1-yl, pyrrolidin-1-yl and thiomorpholin-4-yl;
wherein each heterocyclyl is optionally substituted with one to two R$^7$;
or the pharmaceutically acceptable salts thereof.

In another embodiment there is provided a compound of formula (I) as described in the embodiment three above this embodiment and wherein:
B=N;
or the pharmaceutically acceptable salts thereof.

The following are representative compounds of the invention which can be made by the methods described in the general synthetic schemes, the synthetic examples, and known in the art.

TABLE 1
| Cpd # | Structure | Name |
| --- | --- | --- |
| 1 | 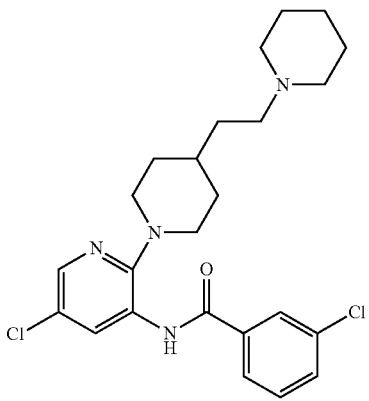 [SMILES: O=C(Nc1cc(Cl)cnc1N1CCC(CCN2CCCCC2)CC1)c1cccc(Cl)c1] | 3-Chloro-N-[5'-chloro-4-(2-piperidin-1-yl-ethyl)-3,4,5,6-tetrahydro-2H-[1,2']bipyridinyl-3'-yl]-benzamide |
| 2 | 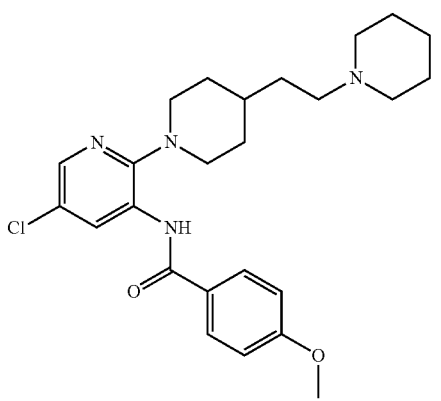 [SMILES: COc1ccc(C(=O)Nc2cc(Cl)cnc2N2CCC(CCN3CCCCC3)CC2)cc1] | N-[5'-Chloro-4-(2-piperidin-1-yl-ethyl)-3,4,5,6-tetrahydro-2H-[1,2']bipyridinyl-3'-yl]-4-methoxy-benzamide |
| 3 | 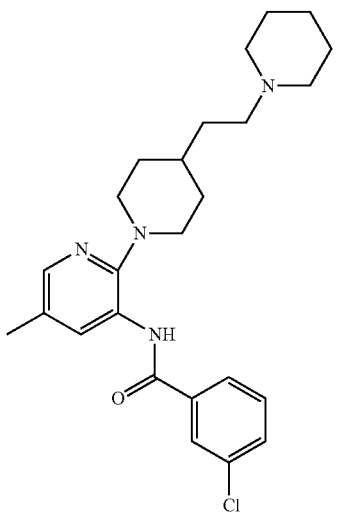 [SMILES: Cc1cnc(N2CCC(CCN3CCCCC3)CC2)c(NC(=O)c2cccc(Cl)c2)c1] | 3-Chloro-N-[5'-methyl-4-(2-piperidin-1-yl-ethyl)-3,4,5,6-tetrahydro-2H-[1,2']bipyridinyl-3'-yl]-benzamide |

TABLE 1-continued

| Cpd # | Structure | Name |
|---|---|---|
| 4 | 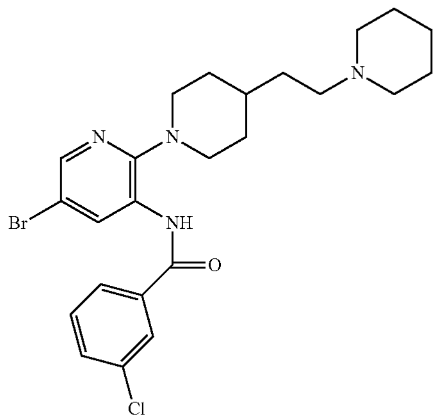 [SMILES: O=C(Nc1cc(Br)cnc1N1CCC(CCN2CCCCC2)CC1)c1cccc(Cl)c1] | N-[5'-Bromo-4-(2-piperidin-1-yl-ethyl)-3,4,5,6-tetrahydro-2H-[1,2']bipyridinyl-3'-yl]-3-chloro-benzamide |
| 5 | 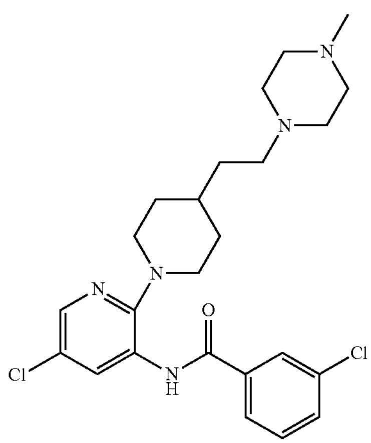 [SMILES: CN1CCN(CCC2CCN(c3ncc(Cl)cc3NC(=O)c3cccc(Cl)c3)CC2)CC1] | 3-Chloro-N-{5'-chloro-4-[2-(4-methyl-piperazin-1-yl)-ethyl]-3,4,5,6-tetrahydro-2H-[1,2']bipyridinyl-3'-yl}-benzamide |
| 6 | 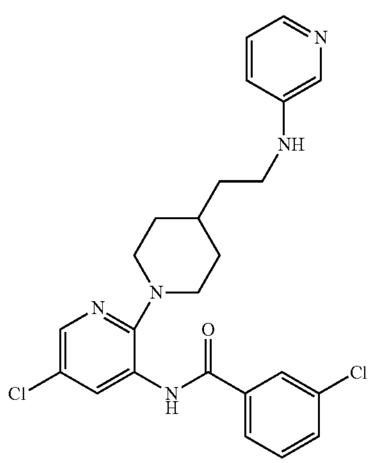 [SMILES: O=C(Nc1cc(Cl)cnc1N1CCC(CCNc2cccnc2)CC1)c1cccc(Cl)c1] | 3-Chloro-N-{5'-chloro-4-[2-(pyridin-3-ylamino)-ethyl]-3,4,5,6-tetrahydro-2H-[1,2']bipyridinyl-3'-yl}-benzamide |

TABLE 1-continued

| Cpd # | Structure | Name |
|---|---|---|
| 7 | 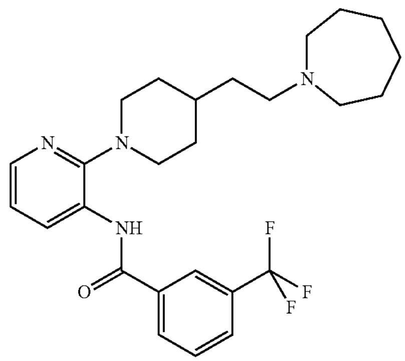 [SMILES: O=C(Nc1cccnc1N1CCC(CCN2CCCCCC2)CC1)c1cccc(C(F)(F)F)c1] | N-[4-(2-Azepan-1-yl-ethyl)-3,4,5,6-tetrahydro-2H-[1,2']bipyridinyl-3'-yl]-3-trifluoromethyl-benzamide |
| 8 | 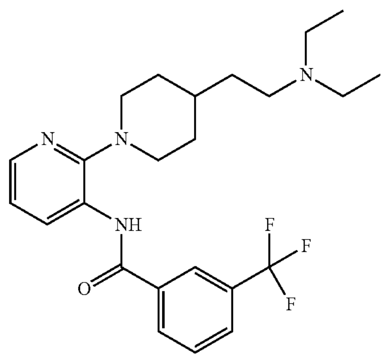 [SMILES: CCN(CC)CCC1CCN(c2ncccc2NC(=O)c2cccc(C(F)(F)F)c2)CC1] | N-[4-(2-Diethylamino-ethyl)-3,4,5,6-tetrahydro-2H-[1,2']bipyridinyl-3'-yl]-3-trifluoromethyl-benzamide |
| 9 | 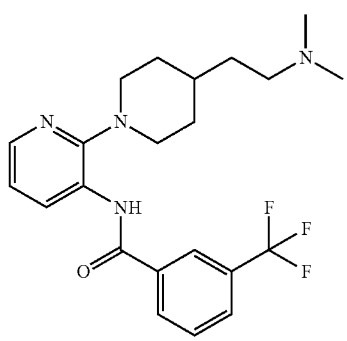 [SMILES: CN(C)CCC1CCN(c2ncccc2NC(=O)c2cccc(C(F)(F)F)c2)CC1] | N-[4-(2-Dimethylamino-ethyl)-3,4,5,6-tetrahydro-2H-[1,2']bipyridinyl-3'-yl]-3-trifluoromethyl-benzamide |
| 10 | 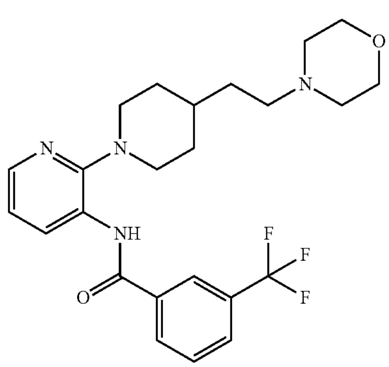 [SMILES: O=C(Nc1cccnc1N1CCC(CCN2CCOCC2)CC1)c1cccc(C(F)(F)F)c1] | N-[4-(2-Morpholin-4-yl-ethyl)-3,4,5,6-tetrahydro-2H-[1,2']bipyridinyl-3'-yl]-3-trifluoromethyl-benzamide |

TABLE 1-continued

| Cpd # | Structure | Name |
|---|---|---|
| 11 | 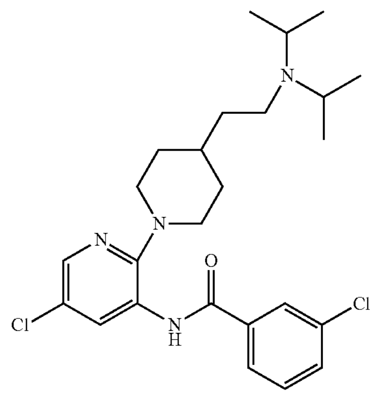 [SMILES: CC(C)N(CCC1CCN(c2ncc(Cl)cc2NC(=O)c2cccc(Cl)c2)CC1)C(C)C] | 3-Chloro-N-[5'-chloro-4-(2-diisopropylamino-ethyl)-3,4,5,6-tetrahydro-2H-[1,2']bipyridinyl-3'-yl]-benzamide |
| 12 | 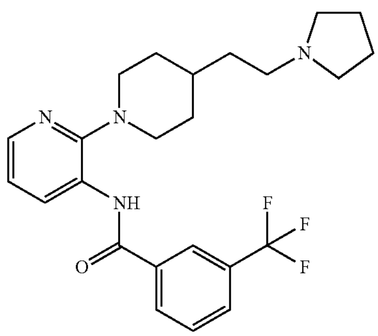 [SMILES: O=C(Nc1cccnc1N1CCC(CCN2CCCC2)CC1)c1cccc(C(F)(F)F)c1] | N-[4-(2-Pyrrolidin-1-yl-ethyl)-3,4,5,6-tetrahydro-2H-[1,2']bipyridinyl-3'-yl]-3-trifluoromethyl-benzamide |
| 13 | 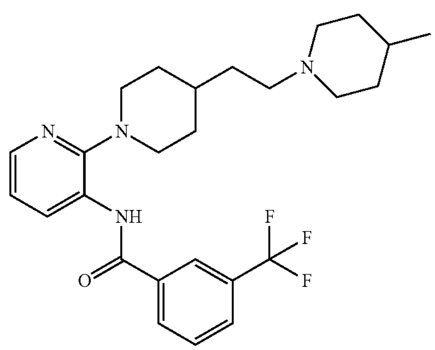 [SMILES: CC1CCN(CCC2CCN(c3ncccc3NC(=O)c3cccc(C(F)(F)F)c3)CC2)CC1] | N-{4-[2-(4-Methyl-piperidin-1-yl)-ethyl]-3,4,5,6-tetrahydro-2H-[1,2']bipyridinyl-3'-yl}-3-trifluoromethyl-benzamide |
| 14 | 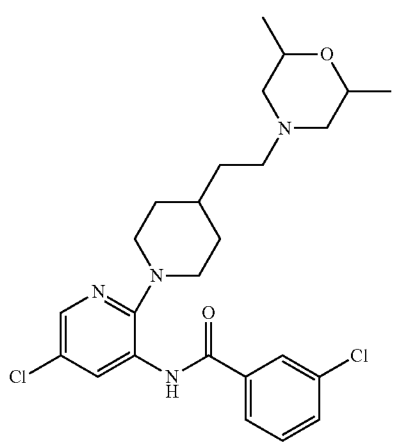 [SMILES: CC1CN(CCC2CCN(c3ncc(Cl)cc3NC(=O)c3cccc(Cl)c3)CC2)CC(C)O1] | 3-Chloro-N-{5'-chloro-4-[2-(2,6-dimethyl-morpholin-4-yl)-ethyl]-3,4,5,6-tetrahydro-2H-[1,2']bipyridinyl-3'-yl}-benzamide |

TABLE 1-continued
| Cpd # | Structure | Name |
|---|---|---|
| 15 | 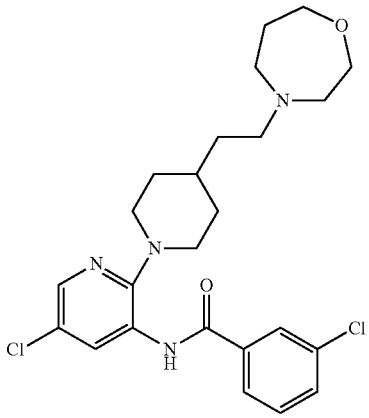 [SMILES: O=C(Nc1cc(Cl)cnc1N1CCC(CCN2CCCOCC2)CC1)c1cccc(Cl)c1] | 3-Chloro-N-[5'-chloro-4-(2-[1,4]oxazepan-4-yl-ethyl)-3,4,5,6-tetrahydro-2H-[1,2']bipyridinyl-3'-yl]-benzamide |
| 16 | 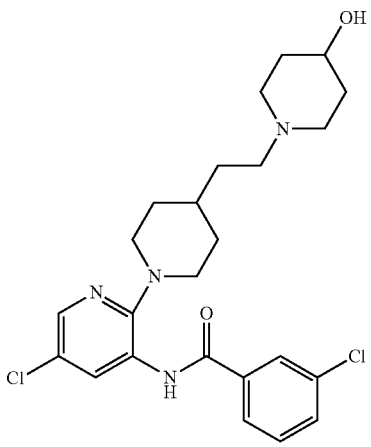 [SMILES: O=C(Nc1cc(Cl)cnc1N1CCC(CCN2CCC(O)CC2)CC1)c1cccc(Cl)c1] | 3-Chloro-N-{5'-chloro-4-[2-(4-hydroxy-piperidin-1-yl)-ethyl]-3,4,5,6-tetrahydro-2H-[1,2']bipyridinyl-3'-yl}-benzamide |
| 17 | 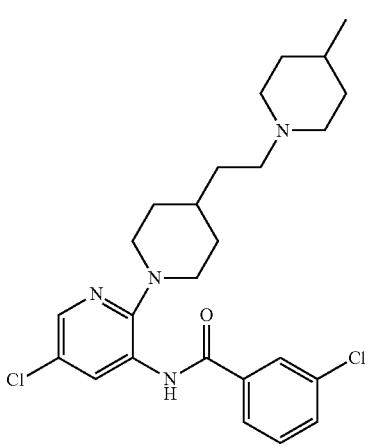 [SMILES: CC1CCN(CCC2CCN(c3ncc(Cl)cc3NC(=O)c3cccc(Cl)c3)CC2)CC1] | 3-Chloro-N-{5'-chloro-4-[2-(4-methyl-piperidin-1-yl)-ethyl]-3,4,5,6-tetrahydro-2H-[1,2']bipyridinyl-3'-yl}-benzamide |

TABLE 1-continued

| Cpd # | Structure | Name |
|---|---|---|
| 18 | 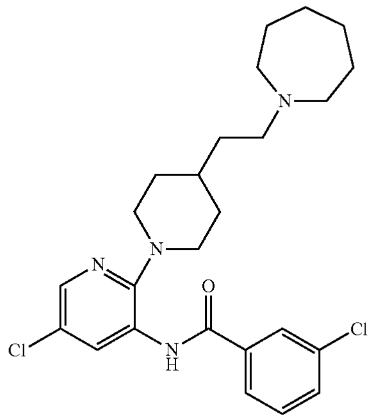 [SMILES: O=C(Nc1cc(Cl)cnc1N1CCC(CCN2CCCCCC2)CC1)c1cccc(Cl)c1] | N-[4-(2-Azepan-1-yl-ethyl)-5'-chloro-3,4,5,6-tetrahydro-2H-[1,2']bipyridinyl-3'-yl]-3-chloro-benzamide |
| 19 | 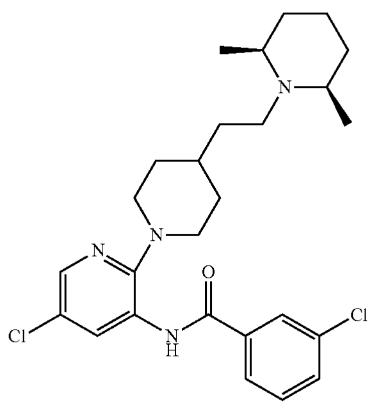 [SMILES: C[C@@H]1CCC[C@H](C)N1CCC1CCN(c2ncc(Cl)cc2NC(=O)c2cccc(Cl)c2)CC1] | 3-Chloro-N-{5'-chloro-4-[2-((2S,6R)-2,6-dimethyl-piperidin-1-yl)-ethyl]-3,4,5,6-tetrahydro-2H-[1,2']bipyridinyl-3'-yl}-benzamide |
| 20 | 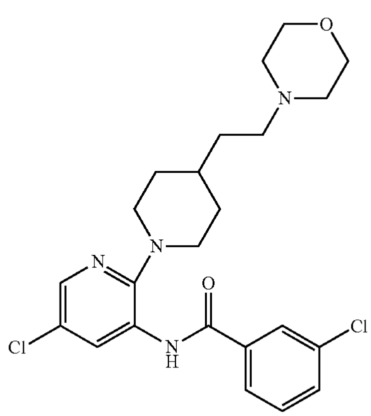 [SMILES: O=C(Nc1cc(Cl)cnc1N1CCC(CCN2CCOCC2)CC1)c1cccc(Cl)c1] | 3-Chloro-N-[5'-chloro-4-(2-morpholin-4-yl-ethyl)-3,4,5,6-tetrahydro-2H-[1,2']bipyridinyl-3'-yl]-benzamide |

TABLE 1-continued
| Cpd # | Structure | Name |
|---|---|---|
| 21 | 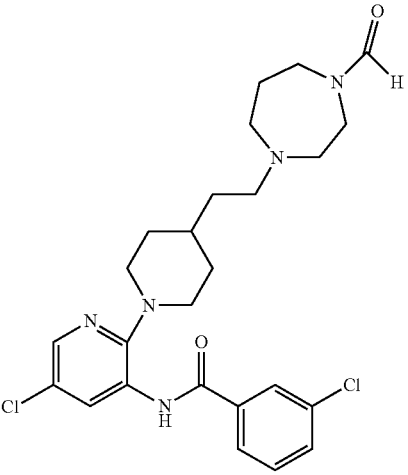 [SMILES: O=CN1CCCN(CCC2CCN(c3ncc(Cl)cc3NC(=O)c3cccc(Cl)c3)CC2)CC1] | 3-Chloro-N-{5'-chloro-4-[2-(4-formyl-[1,4]diazepan-1-yl)-ethyl]-3,4,5,6-tetrahydro-2H-[1,2']bipyridinyl-3'-yl}-benzamide |
| 22 | 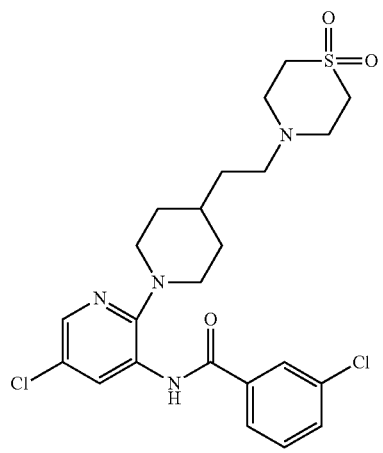 [SMILES: O=C(Nc1cc(Cl)cnc1N1CCC(CCN2CCS(=O)(=O)CC2)CC1)c1cccc(Cl)c1] | 3-Chloro-N-{5'-chloro-4-[2-(1,1-dioxo-1lambda*6*-thiomorpholin-4-yl)-ethyl]-3,4,5,6-tetrahydro-2H-[1,2']bipyridinyl-3'-yl}-benzamide |
| 23 | 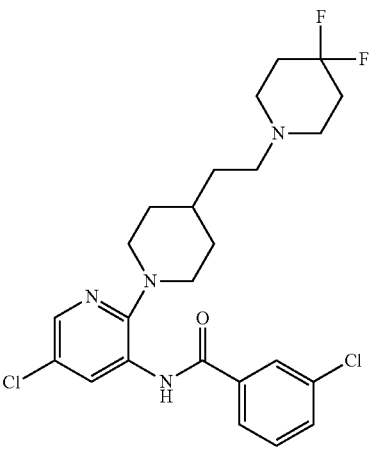 [SMILES: O=C(Nc1cc(Cl)cnc1N1CCC(CCN2CCC(F)(F)CC2)CC1)c1cccc(Cl)c1] | 3-Chloro-N-{5'-chloro-4-[2-(4,4-difluoro-piperidin-1-yl)-ethyl]-3,4,5,6-tetrahydro-2H-[1,2']bipyridinyl-3'-yl}-benzamide |

TABLE 1-continued

| Cpd # | Structure | Name |
|---|---|---|
| 24 | 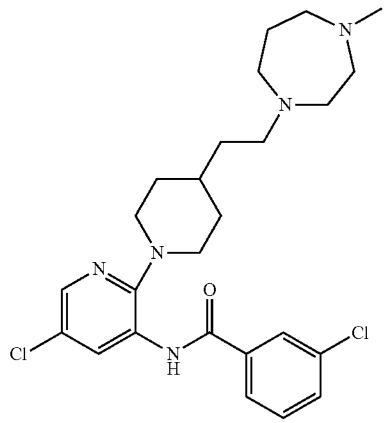 [SMILES: CN1CCCN(CCC2CCN(c3ncc(Cl)cc3NC(=O)c3cccc(Cl)c3)CC2)CC1] | 3-Chloro-N-{5'-chloro-4-[2-(4-methyl-[1,4]diazepan-1-yl)-ethyl]-3,4,5,6-tetrahydro-2H-[1,2']bipyridinyl-3'-yl}-benzamide |
| 25 | 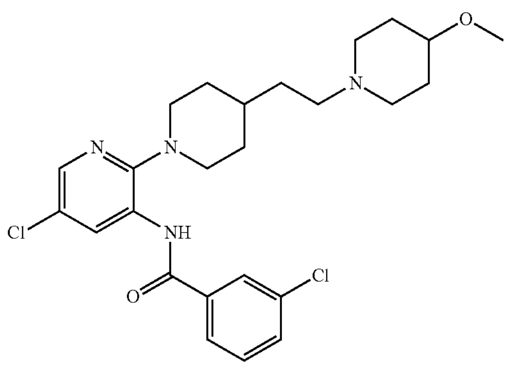 [SMILES: COC1CCN(CCC2CCN(c3ncc(Cl)cc3NC(=O)c3cccc(Cl)c3)CC2)CC1] | 3-Chloro-N-{5'-chloro-4-[2-(4-methoxy-piperidin-1-yl)-ethyl]-3,4,5,6-tetrahydro-2H-[1,2']bipyridinyl-3'-yl}-benzamide |
| 26 | 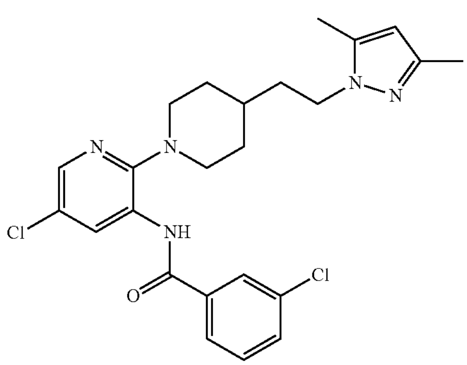 [SMILES: Cc1cc(C)n(CCC2CCN(c3ncc(Cl)cc3NC(=O)c3cccc(Cl)c3)CC2)n1] | 3-Chloro-N-{5'-chloro-4-[2-(3,5-dimethyl-pyrazol-1-yl)-ethyl]-3,4,5,6-tetrahydro-2H-[1,2']bipyridinyl-3'-yl}-benzamide |
| 27 | 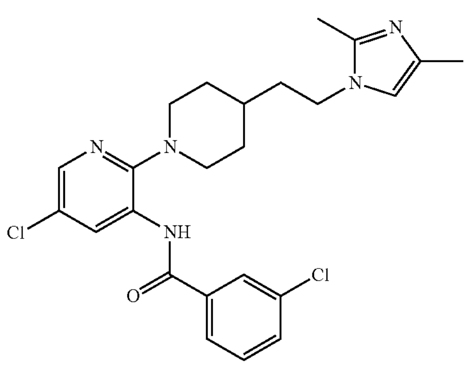 [SMILES: Cc1cn(CCC2CCN(c3ncc(Cl)cc3NC(=O)c3cccc(Cl)c3)CC2)c(C)n1] | 3-Chloro-N-{5'-chloro-4-[2-(2,4-dimethyl-imidazol-1-yl)-ethyl]-3,4,5,6-tetrahydro-2H-[1,2']bipyridinyl-3'-yl}-benzamide |

TABLE 1-continued

| Cpd # | Structure | Name |
|---|---|---|
| 28 | 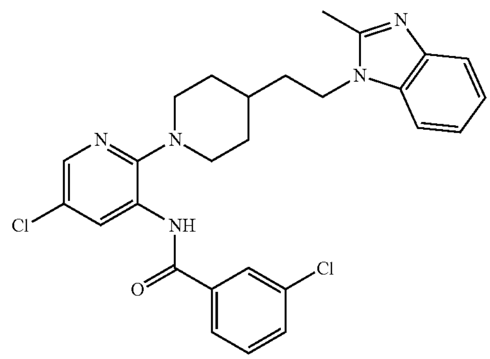 [SMILES: Cc1nc2ccccc2n1CCC1CCN(c2ncc(Cl)cc2NC(=O)c2cccc(Cl)c2)CC1] | 3-Chloro-N-{5'-chloro-4-[2-(2-methyl-benzoimidazol-1-yl)-ethyl]-3,4,5,6-tetrahydro-2H-[1,2']bipyridinyl-3'-yl}-benzamide |
| 29 | 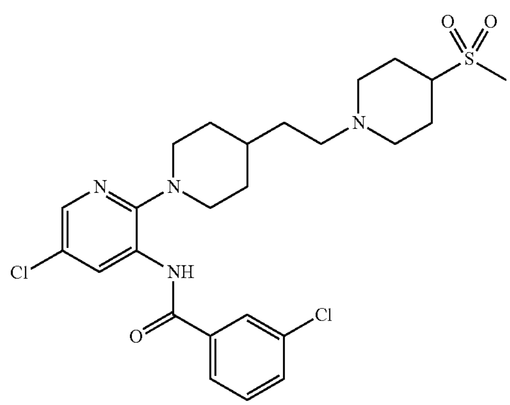 [SMILES: CS(=O)(=O)C1CCN(CCC2CCN(c3ncc(Cl)cc3NC(=O)c3cccc(Cl)c3)CC2)CC1] | 3-Chloro-N-{5'-chloro-4-[2-(4-methanesulfonyl-piperidin-1-yl)-ethyl]-3,4,5,6-tetrahydro-2H-[1,2']bipyridinyl-3'-yl}-benzamide |
| 30 | 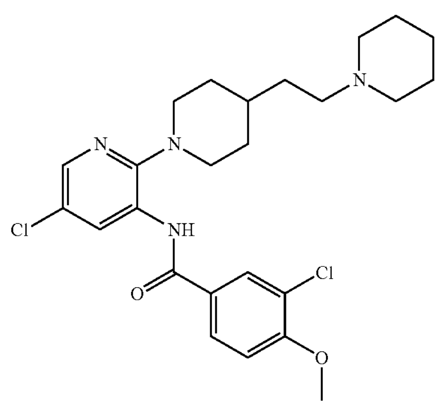 [SMILES: COc1ccc(C(=O)Nc2cc(Cl)cnc2N2CCC(CCN3CCCCC3)CC2)cc1Cl] | 3-Chloro-N-[5'-chloro-4-(2-piperidin-1-yl-ethyl)-3,4,5,6-tetrahydro-2H-[1,2']bipyridinyl-3'-yl]-4-methoxy-benzamide |
| 31 | 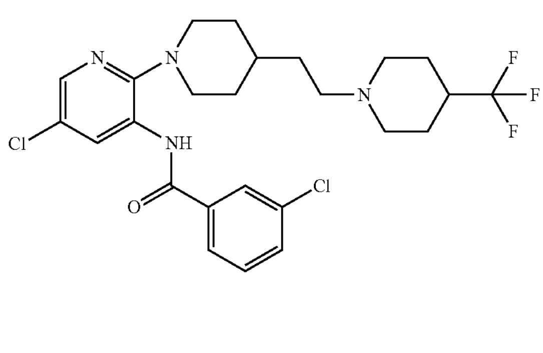 [SMILES: O=C(Nc1cc(Cl)cnc1N1CCC(CCN2CCC(C(F)(F)F)CC2)CC1)c1cccc(Cl)c1] | 3-Chloro-N-{5'-chloro-4-[2-(4-trifluoromethyl-piperidin-1-yl)-ethyl]-3,4,5,6-tetrahydro-2H-[1,2']bipyridinyl-3'-yl}-benzamide |

TABLE 1-continued

| Cpd # | Structure | Name |
|---|---|---|
| 32 | 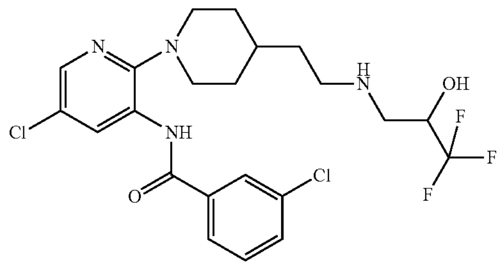 [SMILES: O=C(Nc1cc(Cl)cnc1N1CCC(CCNCC(O)C(F)(F)F)CC1)c1cccc(Cl)c1] | 3-Chloro-N-{5'-chloro-4-[2-(3,3,3-trifluoro-2-hydroxy-propylamino)-ethyl]-3,4,5,6-tetrahydro-2H-[1,2']bipyridinyl-3'-yl}-benzamide |
| 33 | 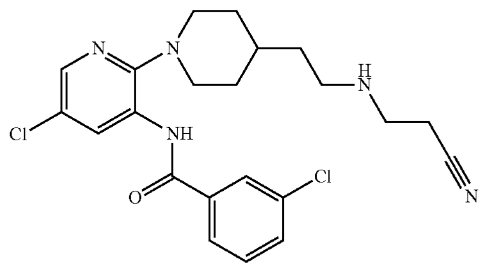 [SMILES: N#CCCNCCC1CCN(c2ncc(Cl)cc2NC(=O)c2cccc(Cl)c2)CC1] | 3-Chloro-N-{5'-chloro-4-[2-(2-cyano-ethylamino)-ethyl]-3,4,5,6-tetrahydro-2H-[1,2']bipyridinyl-3'-yl}-benzamide |
| 34 | 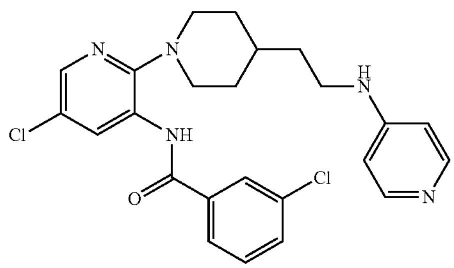 [SMILES: O=C(Nc1cc(Cl)cnc1N1CCC(CCNc2ccncc2)CC1)c1cccc(Cl)c1] | 3-Chloro-N-{5'-chloro-4-[2-(pyridin-4-ylamino)-ethyl]-3,4,5,6-tetrahydro-2H-[1,2']bipyridinyl-3'-yl}-benzamide |
| 35 | 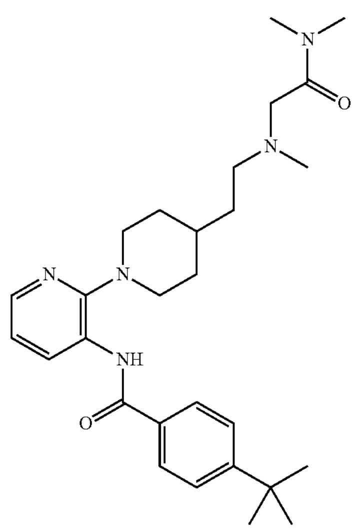 [SMILES: CN(CCC1CCN(c2ncccc2NC(=O)c2ccc(C(C)(C)C)cc2)CC1)CC(=O)N(C)C] | 4-tert-Butyl-N-{4-[2-(dimethylcarbamoylmethyl-methyl-amino)-ethyl]-3,4,5,6-tetrahydro-2H-[1,2']bipyridinyl-3'-yl}-benzamide |
| 36 | 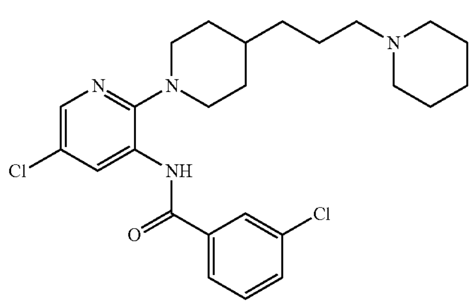 [SMILES: O=C(Nc1cc(Cl)cnc1N1CCC(CCCN2CCCCC2)CC1)c1cccc(Cl)c1] | 3-Chloro-N-[5'-chloro-4-(3-piperidin-1-yl-propyl)-3,4,5,6-tetrahydro-2H-[1,2']bipyridinyl-3'-yl]-benzamide |

TABLE 1-continued

| Cpd # | Structure | Name |
|---|---|---|
| 37 | 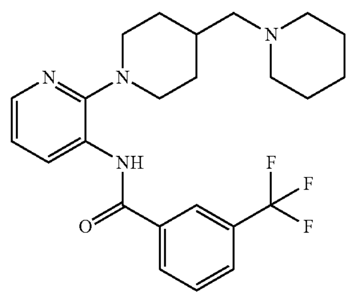 [SMILES: O=C(Nc1cccnc1N1CCC(CN2CCCCC2)CC1)c1cccc(C(F)(F)F)c1] | N-(4-Piperidin-1-ylmethyl-3,4,5,6-tetrahydro-2H-[1,2']bipyridinyl-3'-yl)-3-trifluoromethyl-benzamide |
| 38 | 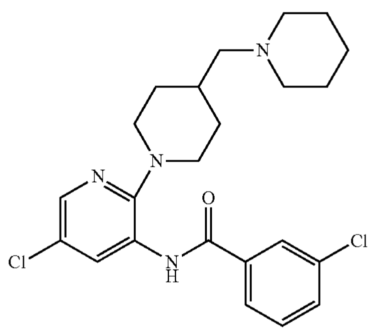 [SMILES: O=C(Nc1cc(Cl)cnc1N1CCC(CN2CCCCC2)CC1)c1cccc(Cl)c1] | 3-Chloro-N-(5'-chloro-4-piperidin-1-ylmethyl-3,4,5,6-tetrahydro-2H-[1,2']bipyridinyl-3'-yl)-benzamide |
| 39 | 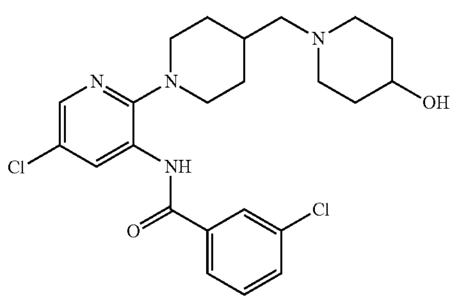 [SMILES: O=C(Nc1cc(Cl)cnc1N1CCC(CN2CCC(O)CC2)CC1)c1cccc(Cl)c1] | 3-Chloro-N-[5'-chloro-4-(4-hydroxy-piperidin-1-ylmethyl)-3,4,5,6-tetrahydro-2H-[1,2']bipyridinyl-3'-yl]-benzamide |
| 40 | 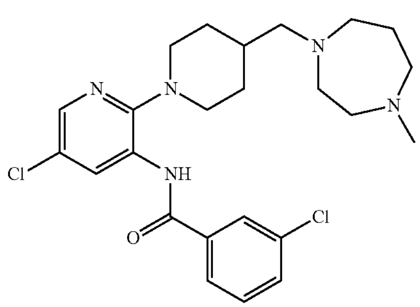 [SMILES: CN1CCCN(CC2CCN(c3ncc(Cl)cc3NC(=O)c3cccc(Cl)c3)CC2)CC1] | 3-Chloro-N-[5'-chloro-4-(4-methyl-[1,4]diazepan-1-ylmethyl)-3,4,5,6-tetrahydro-2H-[1,2']bipyridinyl-3'-yl]-benzamide |
| 41 | 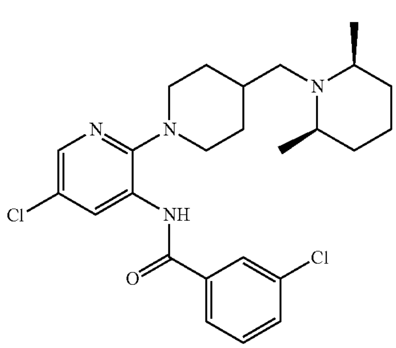 [SMILES: C[C@@H]1CCC[C@H](C)N1CC1CCN(c2ncc(Cl)cc2NC(=O)c2cccc(Cl)c2)CC1] | 3-Chloro-N-[5'-chloro-4-((2S,6R)-2,6-dimethyl-piperidin-1-ylmethyl)-3,4,5,6-tetrahydro-2H-[1,2']bipyridinyl-3'-yl]-benzamide |

TABLE 1-continued

| Cpd # | Structure | Name |
|---|---|---|
| 42 | 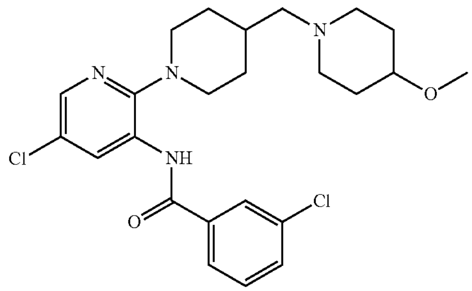 [SMILES: COC1CCN(CC2CCN(c3ncc(Cl)cc3NC(=O)c3cccc(Cl)c3)CC2)CC1] | 3-Chloro-N-[5'-chloro-4-(4-methoxy-piperidin-1-ylmethyl)-3,4,5,6-tetrahydro-2H-[1,2']bipyridinyl-3'-yl]-benzamide |
| 43 | 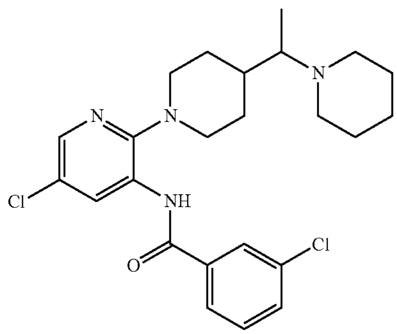 [SMILES: CC(C1CCN(c2ncc(Cl)cc2NC(=O)c2cccc(Cl)c2)CC1)N1CCCCC1] | 3-Chloro-N-[5'-chloro-4-(1-piperidin-1-yl-ethyl)-3,4,5,6-tetrahydro-2H-[1,2']bipyridinyl-3'-yl]-benzamide |
| 44 | 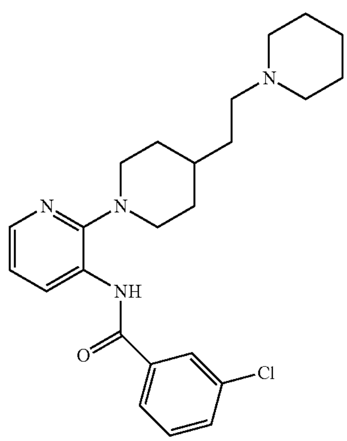 [SMILES: O=C(Nc1cccnc1N1CCC(CCN2CCCCC2)CC1)c1cccc(Cl)c1] | 3-Chloro-N-[4-(2-piperidin-1-yl-ethyl)-3,4,5,6-tetrahydro-2H-[1,2']bipyridinyl-3'-yl]-benzamide |
| 45 | 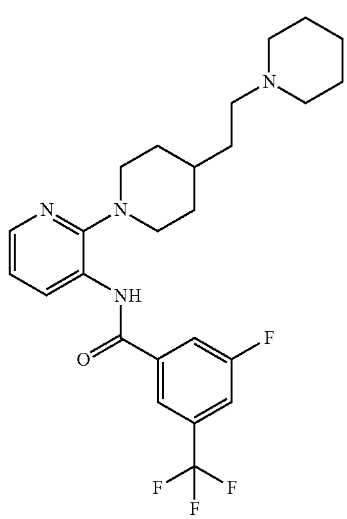 [SMILES: O=C(Nc1cccnc1N1CCC(CCN2CCCCC2)CC1)c1cc(F)cc(C(F)(F)F)c1] | 3-Fluoro-N-[4-(2-piperidin-1-yl-ethyl)-3,4,5,6-tetrahydro-2H-[1,2']bipyridinyl-3'-yl]-5-trifluoromethyl-benzamide |

TABLE 1-continued

| Cpd # | Structure | Name |
|---|---|---|
| 46 | 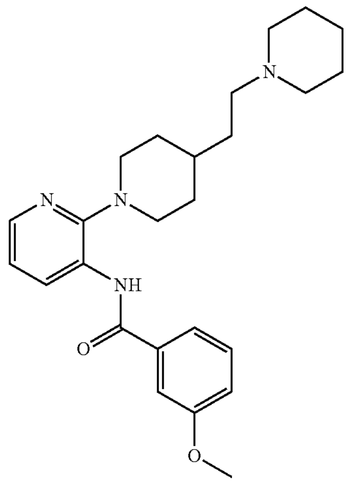 [SMILES: COc1cccc(C(=O)Nc2cccnc2N2CCC(CCN3CCCCC3)CC2)c1] | 3-Methoxy-N-[4-(2-piperidin-1-yl-ethyl)-3,4,5,6-tetrahydro-2H-[1,2']bipyridinyl-3'-yl]-benzamide |
| 47 | 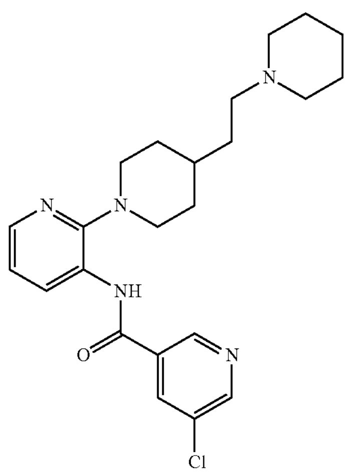 [SMILES: O=C(Nc1cccnc1N1CCC(CCN2CCCCC2)CC1)c1cncc(Cl)c1] | 5-Chloro-N-[4-(2-piperidin-1-yl-ethyl)-3,4,5,6-tetrahydro-2H-[1,2']bipyridinyl-3'-yl]-nicotinamide |
| 48 | 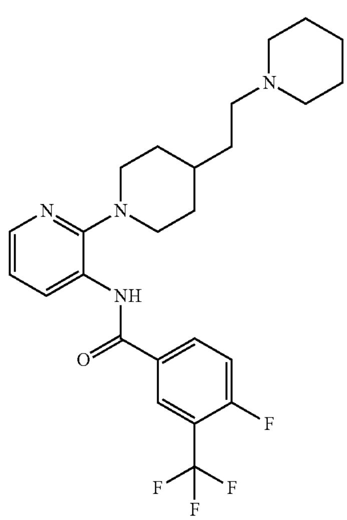 [SMILES: O=C(Nc1cccnc1N1CCC(CCN2CCCCC2)CC1)c1ccc(F)c(C(F)(F)F)c1] | 4-Fluoro-N-[4-(2-piperidin-1-yl-ethyl)-3,4,5,6-tetrahydro-2H-[1,2']bipyridinyl-3'-yl]-3-trifluoromethyl-benzamide |

TABLE 1-continued

| Cpd # | Structure | Name |
|---|---|---|
| 49 | 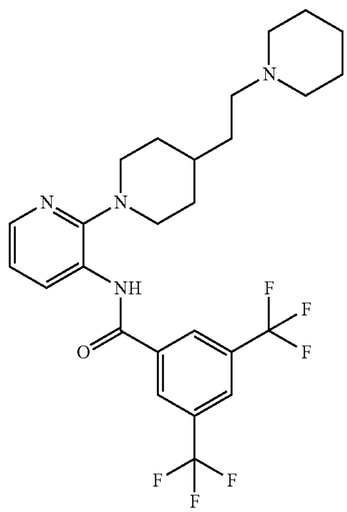 [SMILES: O=C(Nc1cccnc1N1CCC(CCN2CCCCC2)CC1)c1cc(C(F)(F)F)cc(C(F)(F)F)c1] | N-[4-(2-Piperidin-1-yl-ethyl)-3,4,5,6-tetrahydro-2H-[1,2']bipyridinyl-3'-yl]-3,5-bis-trifluoromethyl-benzamide |
| 50 | 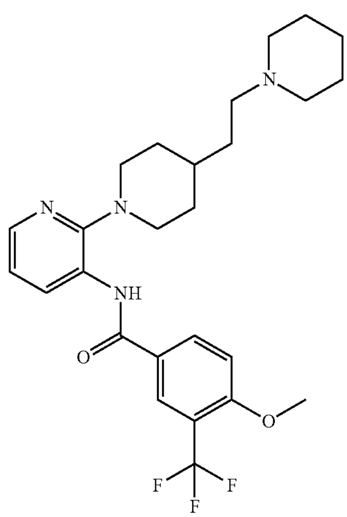 [SMILES: COc1ccc(C(=O)Nc2cccnc2N2CCC(CCN3CCCCC3)CC2)cc1C(F)(F)F] | 4-Methoxy-N-[4-(2-piperidin-1-yl-ethyl)-3,4,5,6-tetrahydro-2H-[1,2']bipyridinyl-3'-yl]-3-trifluoromethyl-benzamide |
| 51 | 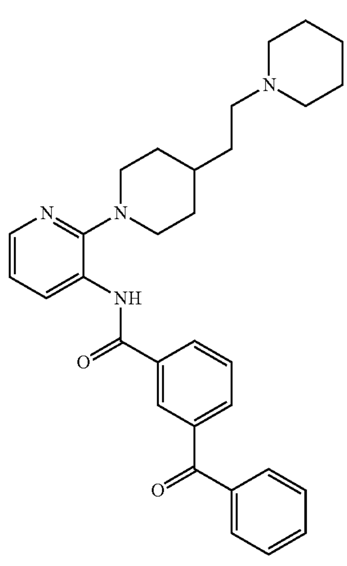 [SMILES: O=C(Nc1cccnc1N1CCC(CCN2CCCCC2)CC1)c1cccc(C(=O)c2ccccc2)c1] | 3-Benzoyl-N-[4-(2-piperidin-1-yl-ethyl)-3,4,5,6-tetrahydro-2H-[1,2']bipyridinyl-3'-yl]-benzamide |

TABLE 1-continued

| Cpd # | Structure | Name |
|---|---|---|
| 52 | 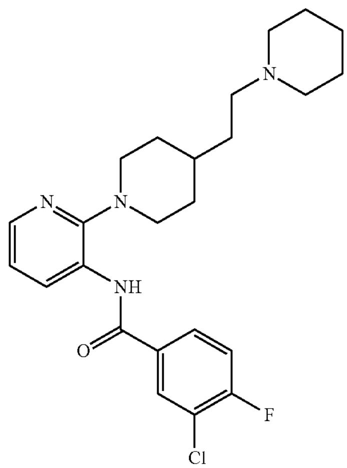 [SMILES: O=C(Nc1cccnc1N1CCC(CCN2CCCCC2)CC1)c1ccc(F)c(Cl)c1] | 3-Chloro-4-fluoro-N-[4-(2-piperidin-1-yl-ethyl)-3,4,5,6-tetrahydro-2H-[1,2']bipyridinyl-3'-yl]-benzamide |
| 53 | 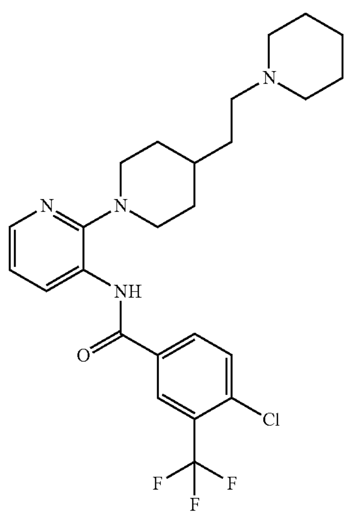 [SMILES: O=C(Nc1cccnc1N1CCC(CCN2CCCCC2)CC1)c1ccc(Cl)c(C(F)(F)F)c1] | 4-Chloro-N-[4-(2-piperidin-1-yl-ethyl)-3,4,5,6-tetrahydro-2H-[1,2']bipyridinyl-3'-yl]-3-trifluoromethyl-benzamide |
| 54 | 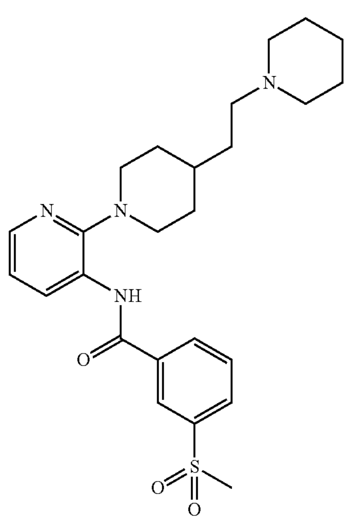 [SMILES: CS(=O)(=O)c1cccc(C(=O)Nc2cccnc2N2CCC(CCN3CCCCC3)CC2)c1] | 3-Methanesulfonyl-N-[4-(2-piperidin-1-yl-ethyl)-3,4,5,6-tetrahydro-2H-[1,2']bipyridinyl-3'-yl]-benzamide |

TABLE 1-continued

| Cpd # | Structure | Name |
|---|---|---|
| 55 | 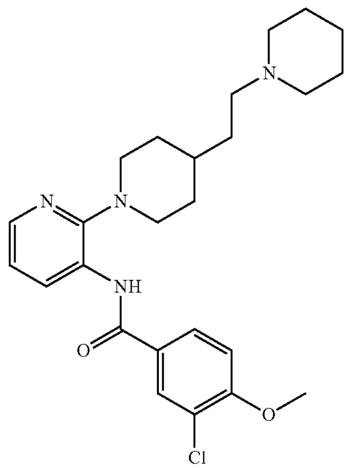 [SMILES: COc1ccc(C(=O)Nc2cccnc2N2CCC(CCN3CCCCC3)CC2)cc1Cl] | 3-Chloro-4-methoxy-N-[4-(2-piperidin-1-yl-ethyl)-3,4,5,6-tetrahydro-2H-[1,2']bipyridinyl-3'-yl]-benzamide |
| 56 | 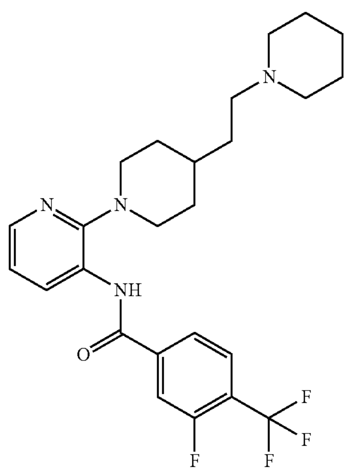 [SMILES: O=C(Nc1cccnc1N1CCC(CCN2CCCCC2)CC1)c1ccc(C(F)(F)F)c(F)c1] | 3-Fluoro-N-[4-(2-piperidin-1-yl-ethyl)-3,4,5,6-tetrahydro-2H-[1,2']bipyridinyl-3'-yl]-4-trifluoromethyl-benzamide |
| 57 | 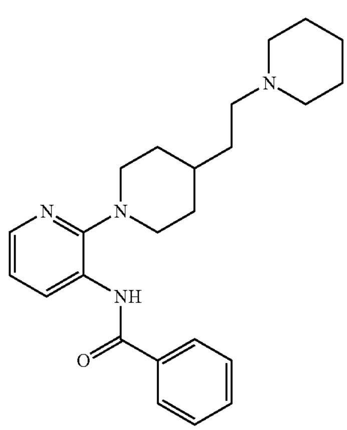 [SMILES: O=C(Nc1cccnc1N1CCC(CCN2CCCCC2)CC1)c1ccccc1] | N-[4-(2-Piperidin-1-yl-ethyl)-3,4,5,6-tetrahydro-2H-[1,2']bipyridinyl-3'-yl]-benzamide |

TABLE 1-continued
| Cpd # | Structure | Name |
|---|---|---|
| 58 | 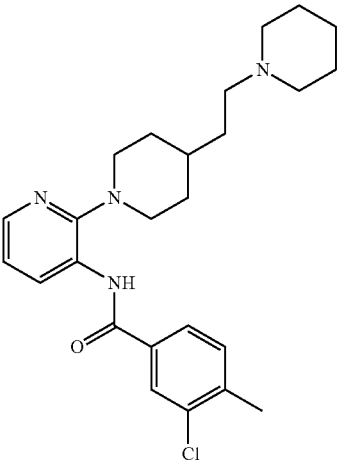 [SMILES: Cc1ccc(C(=O)Nc2cccnc2N2CCC(CCN3CCCCC3)CC2)cc1Cl] | 3-Chloro-4-methyl-N-[4-(2-piperidin-1-yl-ethyl)-3,4,5,6-tetrahydro-2H-[1,2']bipyridinyl-3'-yl]-benzamide |
| 59 | 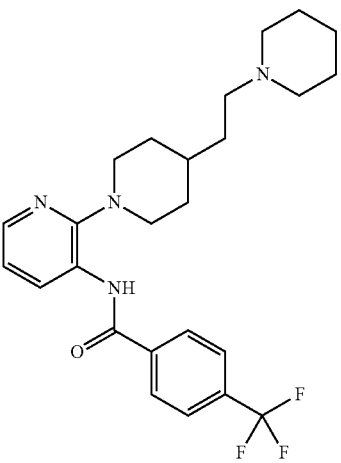 [SMILES: O=C(Nc1cccnc1N1CCC(CCN2CCCCC2)CC1)c1ccc(C(F)(F)F)cc1] | N-[4-(2-Piperidin-1-yl-ethyl)-3,4,5,6-tetrahydro-2H-[1,2']bipyridinyl-3'-yl]-4-trifluoromethyl-benzamide |
| 60 | 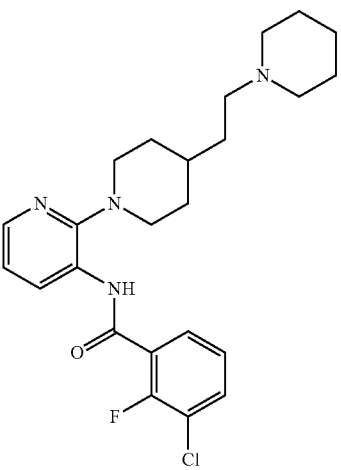 [SMILES: O=C(Nc1cccnc1N1CCC(CCN2CCCCC2)CC1)c1cccc(Cl)c1F] | 3-Chloro-2-fluoro-N-[4-(2-piperidin-1-yl-ethyl)-3,4,5,6-tetrahydro-2H-[1,2']bipyridinyl-3'-yl]-benzamide |

TABLE 1-continued

| Cpd # | Structure | Name |
|---|---|---|
| 61 | 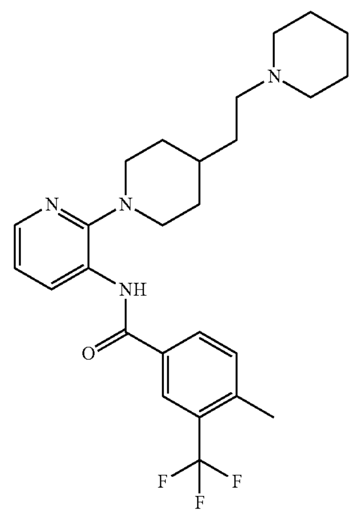 [SMILES: Cc1ccc(C(=O)Nc2cccnc2N2CCC(CCN3CCCCC3)CC2)cc1C(F)(F)F] | 4-Methyl-N-[4-(2-piperidin-1-yl-ethyl)-3,4,5,6-tetrahydro-2H-[1,2']bipyridinyl-3'-yl]-3-trifluoromethyl-benzamide |
| 62 | 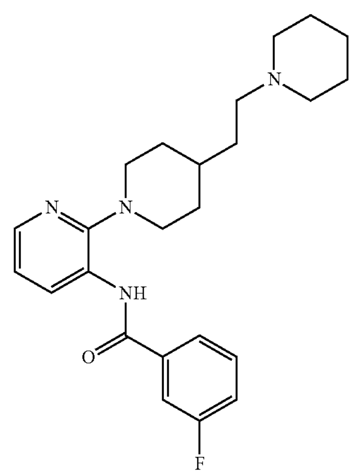 [SMILES: O=C(Nc1cccnc1N1CCC(CCN2CCCCC2)CC1)c1cccc(F)c1] | 3-Fluoro-N-[4-(2-piperidin-1-yl-ethyl)-3,4,5,6-tetrahydro-2H-[1,2']bipyridinyl-3'-yl]-benzamide |
| 63 | 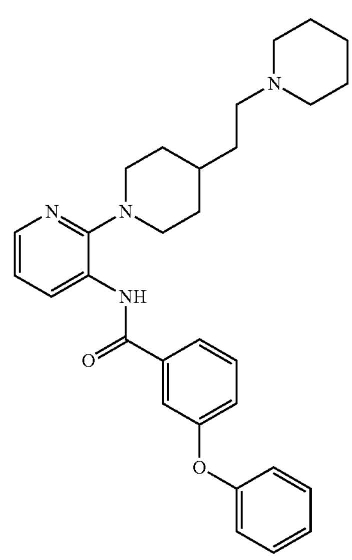 [SMILES: O=C(Nc1cccnc1N1CCC(CCN2CCCCC2)CC1)c1cccc(Oc2ccccc2)c1] | 3-Phenoxy-N-[4-(2-piperidin-1-yl-ethyl)-3,4,5,6-tetrahydro-2H-[1,2']bipyridinyl-3'-yl]-benzamide |

TABLE 1-continued

| Cpd # | Structure | Name |
|---|---|---|
| 64 | 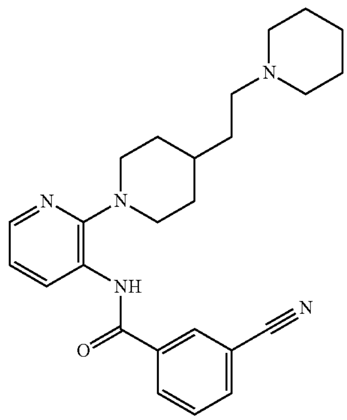 [SMILES: N#Cc1cccc(C(=O)Nc2cccnc2N2CCC(CCN3CCCCC3)CC2)c1] | 3-Cyano-N-[4-(2-piperidin-1-yl-ethyl)-3,4,5,6-tetrahydro-2H-[1,2']bipyridinyl-3'-yl]-benzamide |
| 65 | 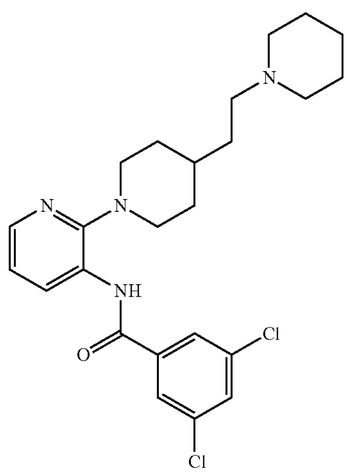 [SMILES: O=C(Nc1cccnc1N1CCC(CCN2CCCCC2)CC1)c1cc(Cl)cc(Cl)c1] | 3,5-Dichloro-N-[4-(2-piperidin-1-yl-ethyl)-3,4,5,6-tetrahydro-2H-[1,2']bipyridinyl-3'-yl]-benzamide |
| 66 | 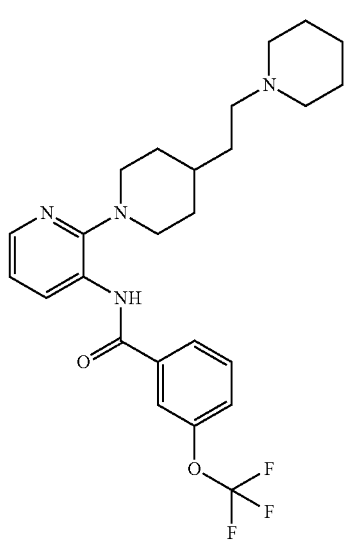 [SMILES: O=C(Nc1cccnc1N1CCC(CCN2CCCCC2)CC1)c1cccc(OC(F)(F)F)c1] | N-[4-(2-Piperidin-1-yl-ethyl)-3,4,5,6-tetrahydro-2H-[1,2']bipyridinyl-3'-yl]-3-trifluoromethoxy-benzamide |

TABLE 1-continued

| Cpd # | Structure | Name |
|---|---|---|
| 67 | 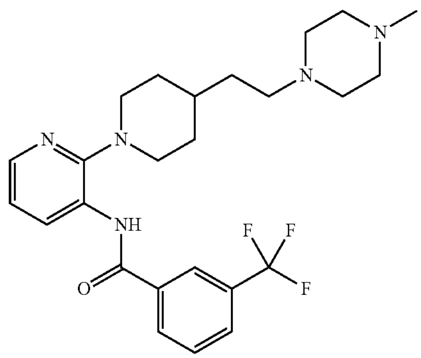 [SMILES: CN1CCN(CCC2CCN(c3ncccc3NC(=O)c3cccc(C(F)(F)F)c3)CC2)CC1] | N-{4-[2-(4-Methyl-piperazin-1-yl)-ethyl]-3,4,5,6-tetrahydro-2H-[1,2']bipyridinyl-3'-yl}-3-trifluoromethyl-benzamide |
| 68 | 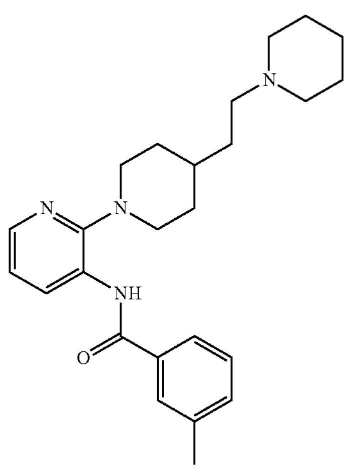 [SMILES: Cc1cccc(C(=O)Nc2cccnc2N2CCC(CCN3CCCCC3)CC2)c1] | 3-Methyl-N-[4-(2-piperidin-1-yl-ethyl)-3,4,5,6-tetrahydro-2H-[1,2']bipyridinyl-3'-yl]-benzamide |
| 69 | 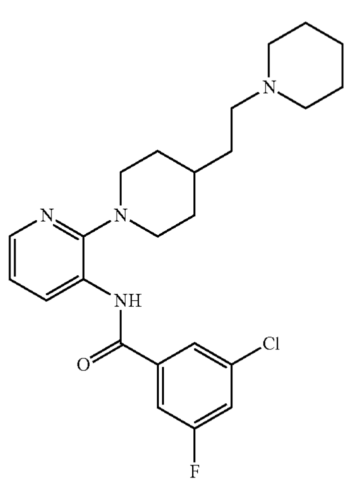 [SMILES: O=C(Nc1cccnc1N1CCC(CCN2CCCCC2)CC1)c1cc(F)cc(Cl)c1] | 3-Chloro-5-fluoro-N-[4-(2-piperidin-1-yl-ethyl)-3,4,5,6-tetrahydro-2H-[1,2']bipyridinyl-3'-yl]-benzamide |

TABLE 1-continued

| Cpd # | Structure | Name |
|---|---|---|
| 70 | 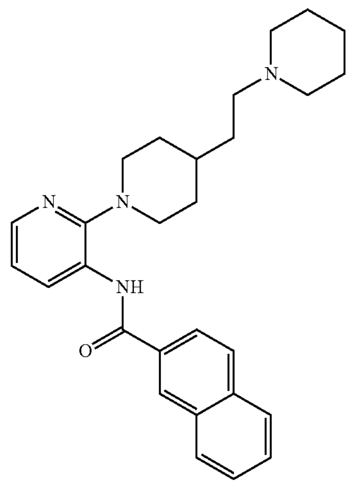 [SMILES: O=C(Nc1cccnc1N1CCC(CCN2CCCCC2)CC1)c1ccc2ccccc2c1] | Naphthalene-2-carboxylic acid [4-(2-piperidin-1-yl-ethyl)-3,4,5,6-tetrahydro-2H-[1,2']bipyridinyl-3'-yl]-amide |
| 71 | 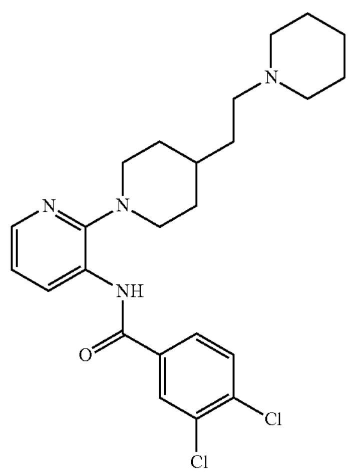 | 3,4-Dichloro-N-[4-(2-piperidin-1-yl-ethyl)-3,4,5,6-tetrahydro-2H-[1,2']bipyridinyl-3'-yl]-benzamide |
| 72 | 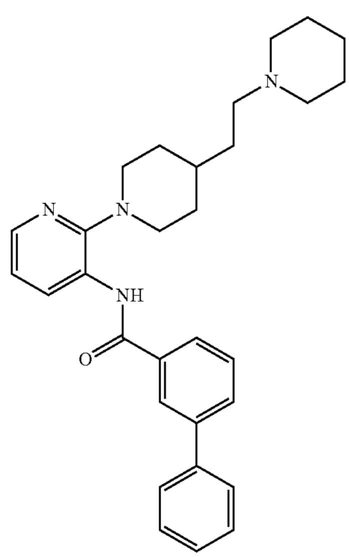 [SMILES: O=C(Nc1cccnc1N1CCC(CCN2CCCCC2)CC1)c1cccc(-c2ccccc2)c1] | Biphenyl-3-carboxylic acid [4-(2-piperidin-1-yl-ethyl)-3,4,5,6-tetrahydro-2H-[1,2']bipyridinyl-3'-yl]-amide |

TABLE 1-continued

| Cpd # | Structure | Name |
|---|---|---|
| 73 | 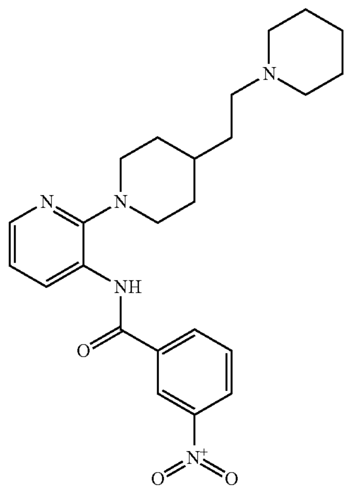 | 3-Nitro-N-[4-(2-piperidin-1-yl-ethyl)-3,4,5,6-tetrahydro-2H-[1,2']bipyridinyl-3'-yl]-benzamide |
| 74 | 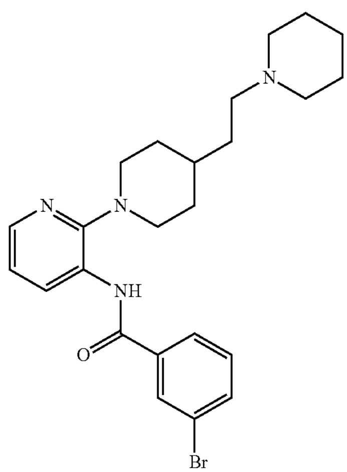 [SMILES: O=C(Nc1cccnc1N1CCC(CCN2CCCCC2)CC1)c1cccc(Br)c1] | 3-Bromo-N-[4-(2-piperidin-1-yl-ethyl)-3,4,5,6-tetrahydro-2H-[1,2']bipyridinyl-3'-yl]-benzamide |
| 75 | 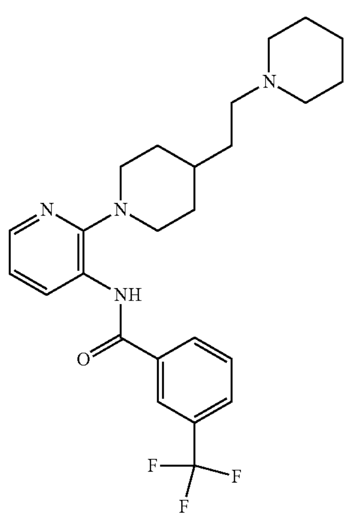 [SMILES: O=C(Nc1cccnc1N1CCC(CCN2CCCCC2)CC1)c1cccc(C(F)(F)F)c1] | N-[4-(2-Piperidin-1-yl-ethyl)-3,4,5,6-tetrahydro-2H-[1,2']bipyridinyl-3'-yl]-3-trifluoromethyl-benzamide |

TABLE 1-continued

| Cpd # | Structure | Name |
|---|---|---|
| 76 | 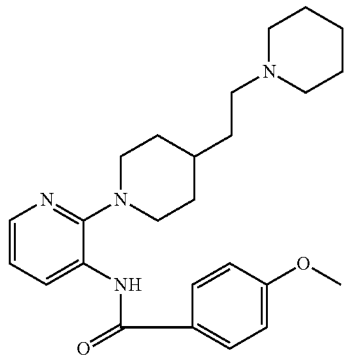 [SMILES: COc1ccc(C(=O)Nc2cccnc2N2CCC(CCN3CCCCC3)CC2)cc1] | 4-Methoxy-N-[4-(2-piperidin-1-yl-ethyl)-3,4,5,6-tetrahydro-2H-[1,2']bipyridinyl-3'-yl]-benzamide |
| 77 | 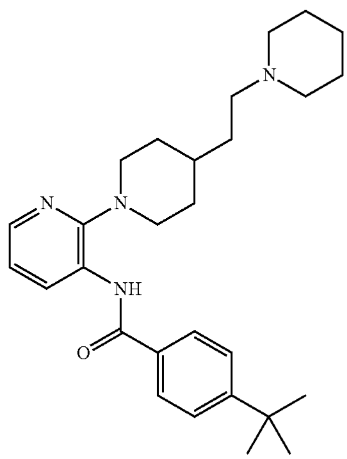 [SMILES: CC(C)(C)c1ccc(C(=O)Nc2cccnc2N2CCC(CCN3CCCCC3)CC2)cc1] | 4-tert-Butyl-N-[4-(2-piperidin-1-yl-ethyl)-3,4,5,6-tetrahydro-2H-[1,2']bipyridinyl-3'-yl]-benzamide |
| 78 | 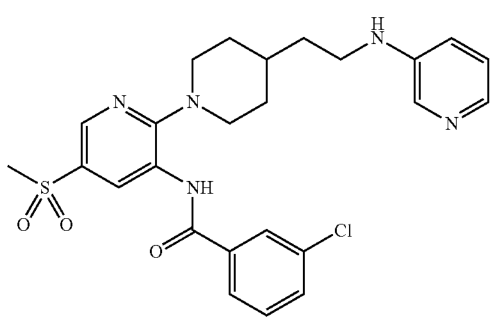 [SMILES: CS(=O)(=O)c1cnc(N2CCC(CCNc3cccnc3)CC2)c(NC(=O)c2cccc(Cl)c2)c1] | 3-Chloro-N-{5'-methanesulfonyl-4-[2-(pyridin-3-ylamino)-ethyl]-3,4,5,6-tetrahydro-2H-[1,2']bipyridinyl-3'-yl}-benzamide |
| 79 | 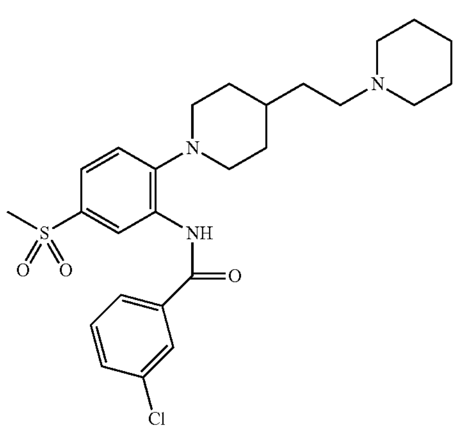 [SMILES: CS(=O)(=O)c1ccc(N2CCC(CCN3CCCCC3)CC2)c(NC(=O)c2cccc(Cl)c2)c1] | 3-Chloro-N-{5-methanesulfonyl-2-[4-(2-piperidin-1-yl-ethyl)-piperidin-1-yl]-phenyl}-benzamide |

TABLE 1-continued

| Cpd # | Structure | Name |
|---|---|---|
| 80 | 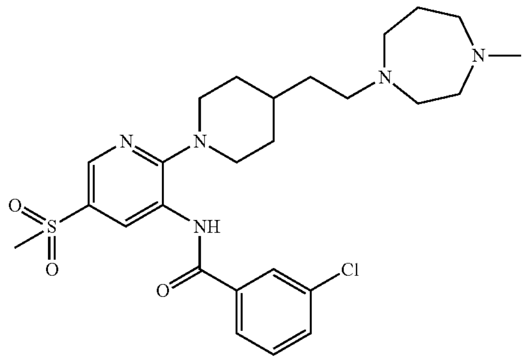 [SMILES: CN1CCCN(CCC2CCN(c3ncc(S(C)(=O)=O)cc3NC(=O)c3cccc(Cl)c3)CC2)CC1] | 3-Chloro-N-{5'-methanesulfonyl-4-[2-(4-methyl-[1,4]diazepan-1-yl)-ethyl]-3,4,5,6-tetrahydro-2H-[1,2']bipyridinyl-3'-yl}-benzamide |
| 81 | 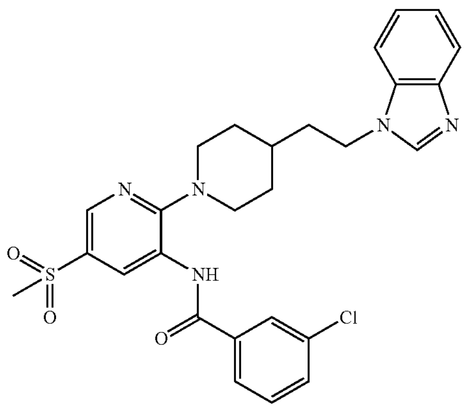 [SMILES: CS(=O)(=O)c1cnc(N2CCC(CCn3cnc4ccccc43)CC2)c(NC(=O)c2cccc(Cl)c2)c1] | N-[4-(2-Benzoimidazol-1-yl-ethyl)-5-methanesulfonyl-3,4,5,6-tetrahydro-2H-[1,2']bipyridinyl-3'-yl]-3-chloro-benzamide |
| 82 | 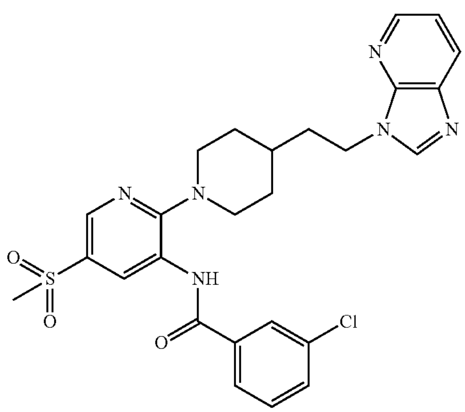 [SMILES: CS(=O)(=O)c1cnc(N2CCC(CCn3cnc4cccnc43)CC2)c(NC(=O)c2cccc(Cl)c2)c1] | 3-Chloro-N-[4-(2-imidazo[4,5-b]pyridin-3-yl-ethyl)-5'-methanesulfonyl-3,4,5,6-tetrahydro-2H-[1,2']bipyridinyl-3'-yl]-benzamide |
| 83 | 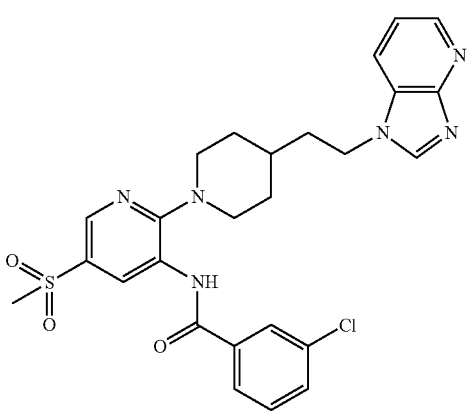 [SMILES: CS(=O)(=O)c1cnc(N2CCC(CCn3cnc4ncccc43)CC2)c(NC(=O)c2cccc(Cl)c2)c1] | 3-Chloro-N-[4-(2-imidazo[4,5-b]pyridin-1-yl-ethyl)-5'-methanesulfonyl-3,4,5,6-tetrahydro-2H-[1,2']bipyridinyl-3'-yl]-benzamide |

TABLE 1-continued

| Cpd # | Structure | Name |
|---|---|---|
| 84 | 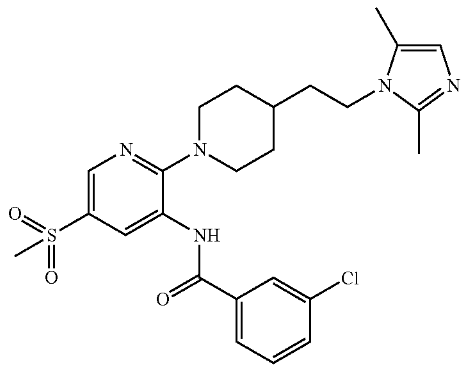 [SMILES: Cc1cnc(C)n1CCC1CCN(c2ncc(S(C)(=O)=O)cc2NC(=O)c2cccc(Cl)c2)CC1] | 3-Chloro-N-{4-[2-(2,5-dimethyl-imidazol-1-yl)-ethyl]-5'-methanesulfonyl-3,4,5,6-tetrahydro-2H-[1,2']bipyridinyl-3'-yl}-benzamide |
| 85 | 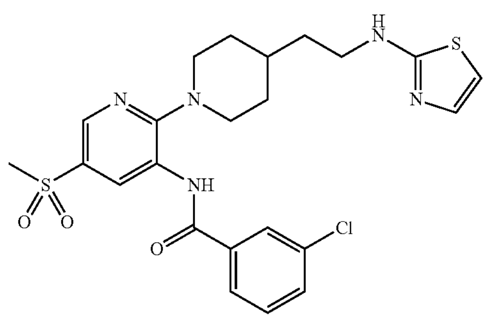 [SMILES: CS(=O)(=O)c1cnc(N2CCC(CCNc3nccs3)CC2)c(NC(=O)c2cccc(Cl)c2)c1] | 3-Chloro-N-{5'-methanesulfonyl-4-[2-(thiazol-2-ylamino)-ethyl]-3,4,5,6-tetrahydro-2H-[1,2']bipyridinyl-3'-yl}-benzamide |
| 86 | 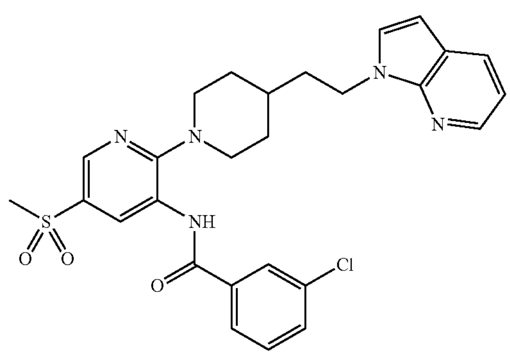 [SMILES: CS(=O)(=O)c1cnc(N2CCC(CCn3ccc4cccnc43)CC2)c(NC(=O)c2cccc(Cl)c2)c1] | 3-Chloro-N-[5'-methanesulfonyl-4-(2-pyrrolo[2,3-b]pyridin-1-yl-ethyl)-3,4,5,6-tetrahydro-2H-[1,2']bipyridinyl-3'-yl]-benzamide |
| 87 | 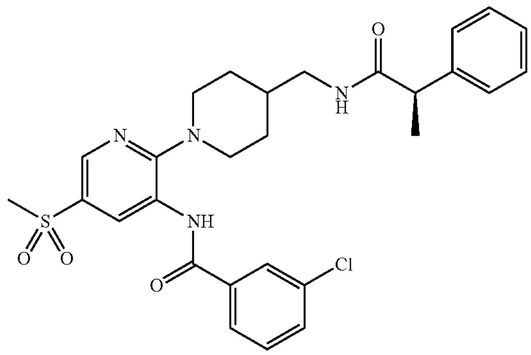 [SMILES: C[C@@H](C(=O)NCC1CCN(c2ncc(S(C)(=O)=O)cc2NC(=O)c2cccc(Cl)c2)CC1)c1ccccc1] | 3-Chloro-N-{5'-methanesulfonyl-4-[((R)-2-phenyl-propionylamino)-methyl]-3,4,5,6-tetrahydro-2H-[1,2']bipyridinyl-3'-yl}-benzamide |

TABLE 1-continued

| Cpd # | Structure | Name |
|---|---|---|
| 88 | 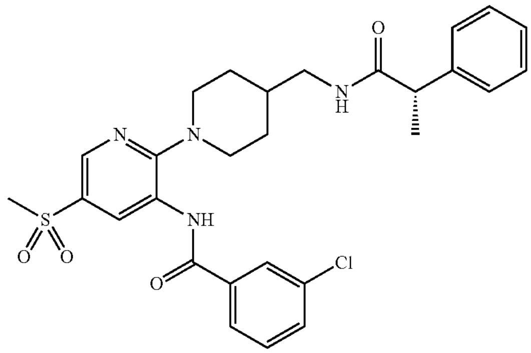 [SMILES: C[C@H](C(=O)NCC1CCN(c2ncc(S(C)(=O)=O)cc2NC(=O)c2cccc(Cl)c2)CC1)c1ccccc1] | 3-Chloro-N-{5'-methanesulfonyl-4-[((S)-2-phenyl-propionylamino)-methyl]-3,4,5,6-tetrahydro-2H-[1,2']bipyridinyl-3'-yl}-benzamide |
| 89 | 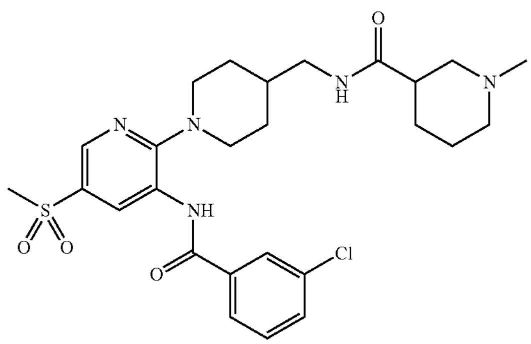 | 1-Methyl-piperidine-3-carboxylic acid [3'-(3-chloro-benzoylamino)-5'-methanesulfonyl-3,4,5,6-tetrahydro-2H-[1,2']bipyridinyl-4-ylmethyl]-amide |
| 90 | 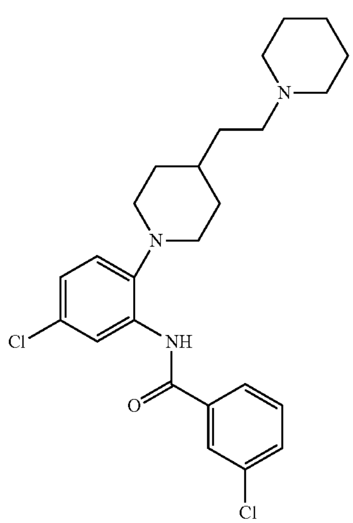 [SMILES: O=C(Nc1cc(Cl)ccc1N1CCC(CCN2CCCCC2)CC1)c1cccc(Cl)c1] | 3-Chloro-N-{5-chloro-2-[4-(2-piperidin-1-yl-ethyl)-piperidin-1-yl]-phenyl}-benzamide |

TABLE 1-continued

| Cpd # | Structure | Name |
|---|---|---|
| 91 | 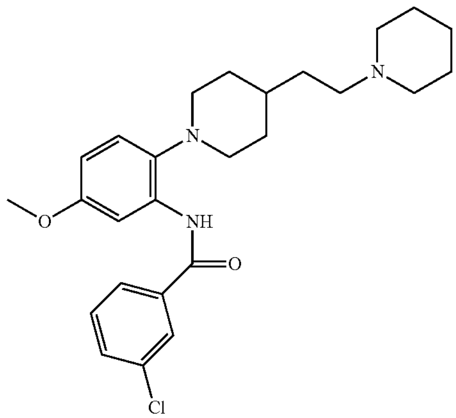 [SMILES: COc1ccc(N2CCC(CCN3CCCCC3)CC2)c(NC(=O)c2cccc(Cl)c2)c1] | 3-Chloro-N-{5-methoxy-2-[4-(2-piperidin-1-yl-ethyl)-piperidin-1-yl]-phenyl}-benzamide |
| 92 | 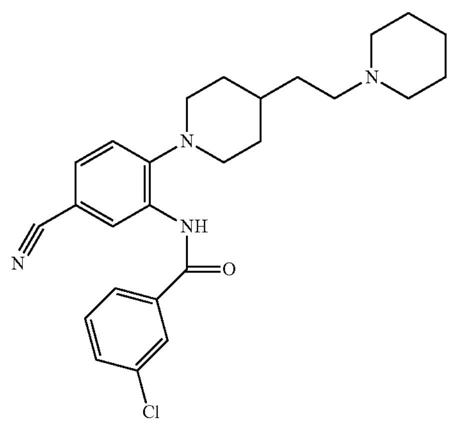 [SMILES: N#Cc1ccc(N2CCC(CCN3CCCCC3)CC2)c(NC(=O)c2cccc(Cl)c2)c1] | 3-Chloro-N-{5-cyano-2-[4-(2-piperidin-1-yl-ethyl)-piperidin-1-yl]-phenyl}-benzamide |
| 93 | 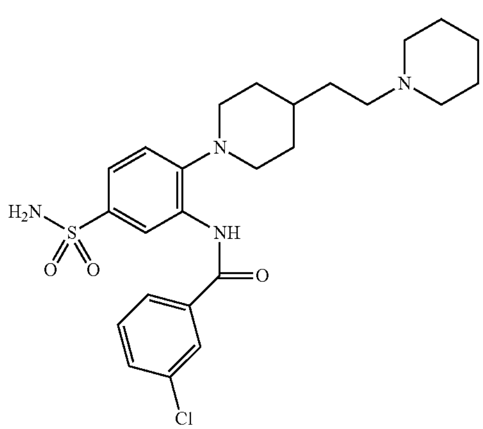 [SMILES: NS(=O)(=O)c1ccc(N2CCC(CCN3CCCCC3)CC2)c(NC(=O)c2cccc(Cl)c2)c1] | 3-Chloro-N-{2-[4-(2-piperidin-1-yl-ethyl)-piperidin-1-yl]-5-sulfamoyl-phenyl}-benzamide |

TABLE 1-continued

| Cpd # | Structure | Name |
|---|---|---|
| 94 | 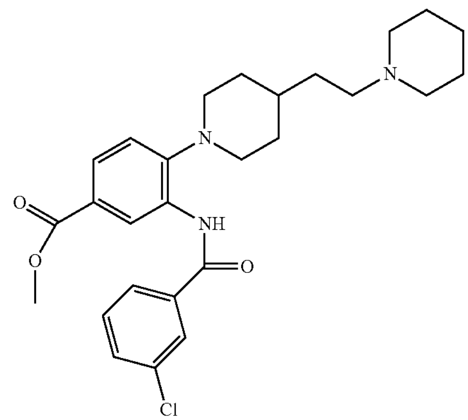 [SMILES: COC(=O)c1ccc(N2CCC(CCN3CCCCC3)CC2)c(NC(=O)c2cccc(Cl)c2)c1] | 3-(3-Chloro-benzoylamino)-4-[4-(2-piperidin-1-yl-ethyl)-piperidin-1-yl]-benzoic acid methyl ester |
| 95 | 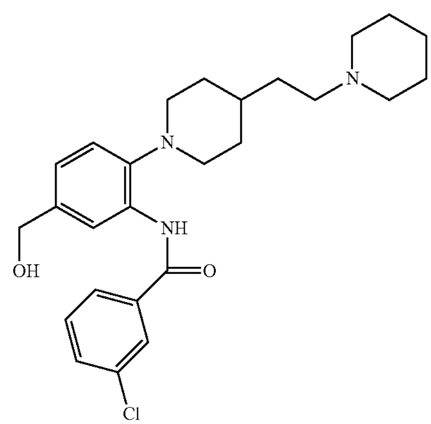 [SMILES: O=C(Nc1cc(CO)ccc1N1CCC(CCN2CCCCC2)CC1)c1cccc(Cl)c1] | 3-Chloro-N-{5-hydroxymethyl-2-[4-(2-piperidin-1-yl-ethyl)-piperidin-1-yl]-phenyl}-benzamide |
| 96 | 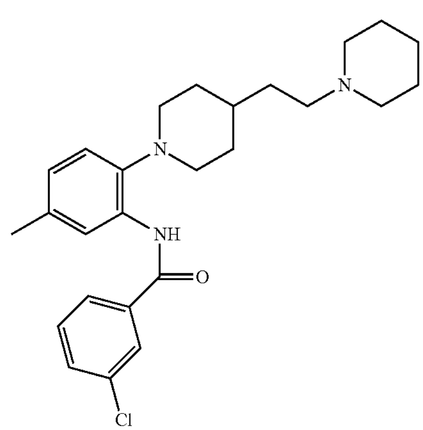 [SMILES: Cc1ccc(N2CCC(CCN3CCCCC3)CC2)c(NC(=O)c2cccc(Cl)c2)c1] | 3-Chloro-N-{5-methyl-2-[4-(2-piperidin-1-yl-ethyl)-piperidin-1-yl]-phenyl}-benzamide |

TABLE 1-continued

| Cpd # | Structure | Name |
|---|---|---|
| 97 | 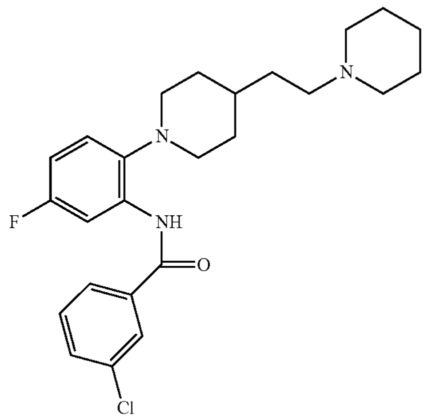 [SMILES: O=C(Nc1cc(F)ccc1N1CCC(CCN2CCCCC2)CC1)c1cccc(Cl)c1] | 3-Chloro-N-{5-fluoro-2-[4-(2-piperidin-1-yl-ethyl)-piperidin-1-yl]-phenyl}-benzamide |
| 98 | 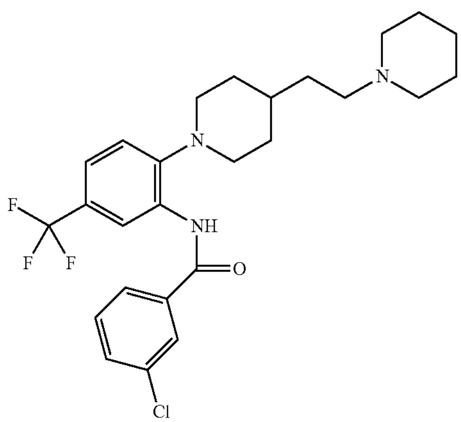 [SMILES: O=C(Nc1cc(C(F)(F)F)ccc1N1CCC(CCN2CCCCC2)CC1)c1cccc(Cl)c1] | 3-Chloro-N-{2-[4-(2-piperidin-1-yl-ethyl)-piperidin-1-yl]-5-trifluoromethyl-phenyl}-benzamide |
| 99 | 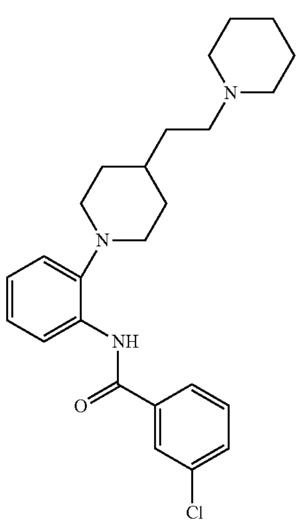 [SMILES: O=C(Nc1ccccc1N1CCC(CCN2CCCCC2)CC1)c1cccc(Cl)c1] | 3-Chloro-N-{2-[4-(2-piperidin-1-yl-ethyl)-piperidin-1-yl]-phenyl}-benzamide |

TABLE 1-continued

| Cpd # | Structure | Name |
|---|---|---|
| 100 | 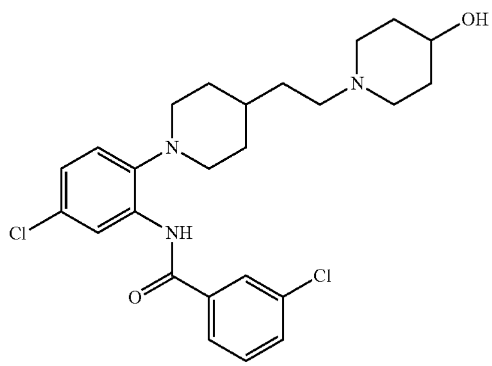 [SMILES: O=C(Nc1cc(Cl)ccc1N1CCC(CCN2CCC(O)CC2)CC1)c1cccc(Cl)c1] | 3-Chloro-N-(5-chloro-2-{4-[2-(4-hydroxy-piperidin-1-yl)-ethyl]-piperidin-1-yl}-phenyl)-benzamide |
| 101 | 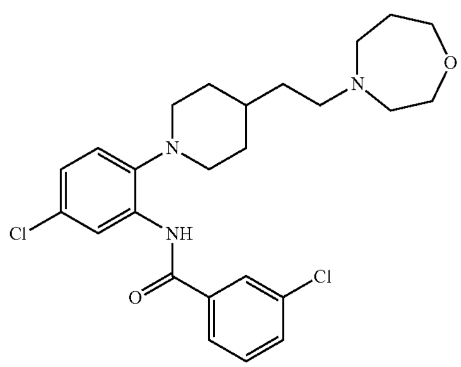 [SMILES: O=C(Nc1cc(Cl)ccc1N1CCC(CCN2CCCOCC2)CC1)c1cccc(Cl)c1] | 3-Chloro-N-{5-chloro-2-[4-(2-[1,4]oxazepan-4-yl-ethyl)-piperidin-1-yl]-phenyl}-benzamide |
| 102 | 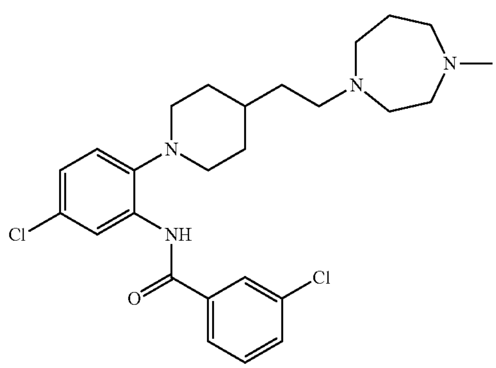 [SMILES: CN1CCCN(CCC2CCN(c3ccc(Cl)cc3NC(=O)c3cccc(Cl)c3)CC2)CC1] | 3-Chloro-N-(5-chloro-2-{4-[2-(4-methyl-[1,4]diazepan-1-yl)-ethyl]-piperidin-1-yl}-phenyl)-benzamide |
| 103 | 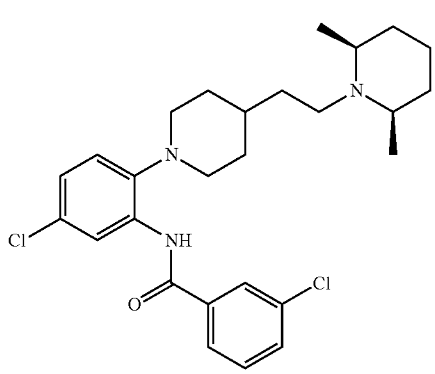 [SMILES: C[C@@H]1CCC[C@H](C)N1CCC1CCN(c2ccc(Cl)cc2NC(=O)c2cccc(Cl)c2)CC1] | 3-Chloro-N-(5-chloro-2-{4-[2-((2S,6R)-2,6-dimethyl-piperidin-1-yl)-ethyl]-piperidin-1-yl}-phenyl)-benzamide |

TABLE 1-continued

| Cpd # | Structure | Name |
|---|---|---|
| 104 | 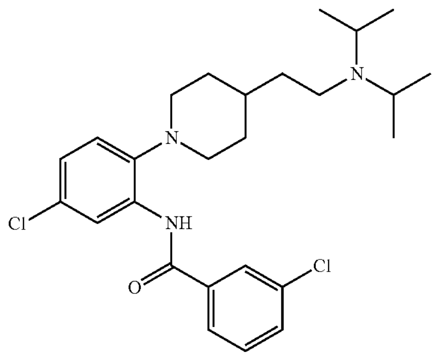 [SMILES: CC(C)N(CCC1CCN(c2ccc(Cl)cc2NC(=O)c2cccc(Cl)c2)CC1)C(C)C] | 3-Chloro-N-{5-chloro-2-[4-(2-diisopropylamino-ethyl)-piperidin-1-yl]-phenyl}-benzamide |
| 105 | 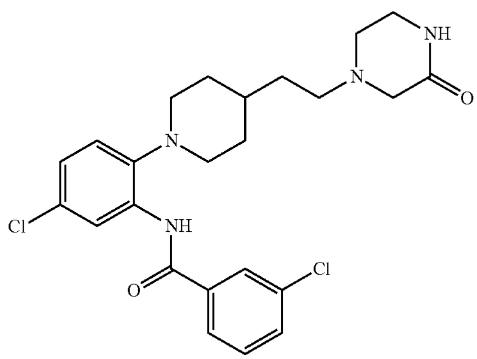 [SMILES: O=C1CN(CCC2CCN(c3ccc(Cl)cc3NC(=O)c3cccc(Cl)c3)CC2)CCN1] | 3-Chloro-N-(5-chloro-2-{4-[2-(3-oxo-piperazin-1-yl)-ethyl]-piperidin-1-yl}-phenyl)-benzamide |
| 106 | 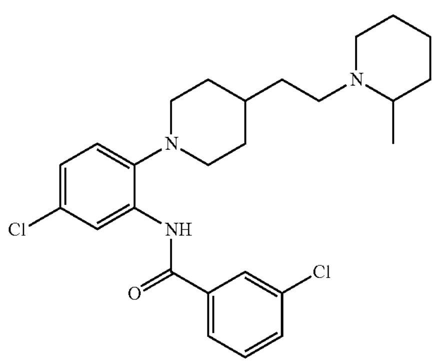 [SMILES: CC1CCCCN1CCC1CCN(c2ccc(Cl)cc2NC(=O)c2cccc(Cl)c2)CC1] | 3-Chloro-N-(5-chloro-2-{4-[2-(2-methyl-piperidin-1-yl)-ethyl]-piperidin-1-yl}-phenyl)-benzamide |
| 107 | 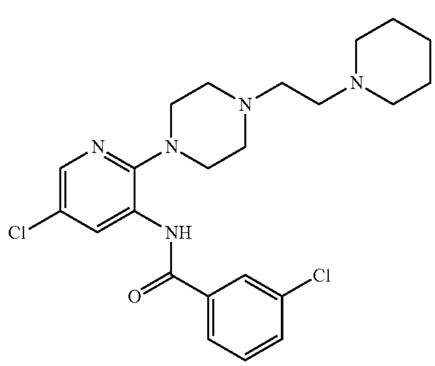 [SMILES: O=C(Nc1cc(Cl)cnc1N1CCN(CCN2CCCCC2)CC1)c1cccc(Cl)c1] | 3-Chloro-N-{5-chloro-2-[4-(2-piperidin-1-yl-ethyl)-piperazin-1-yl]-pyridin-3-yl}-benzamide |

TABLE 1-continued

| Cpd # | Structure | Name |
|---|---|---|
| 108 | 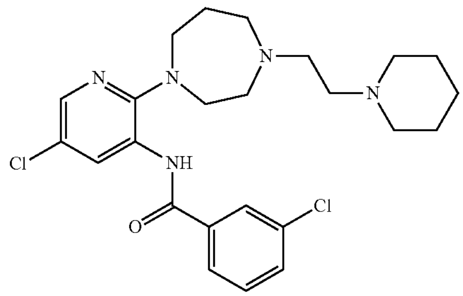 [SMILES: O=C(Nc1cc(Cl)cnc1N1CCCN(CCN2CCCCC2)CC1)c1cccc(Cl)c1] | 3-Chloro-N-{5-chloro-2-[4-(2-piperidin-1-yl-ethyl)-[1,4]diazepan-1-yl]-pyridin-3-yl}-benzamide |
| 109 | 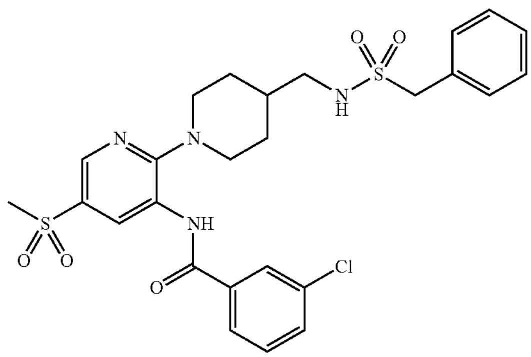 [SMILES: CS(=O)(=O)c1cnc(N2CCC(CNS(=O)(=O)Cc3ccccc3)CC2)c(NC(=O)c2cccc(Cl)c2)c1] | 3-Chloro-N-[5'-methanesulfonyl-4-(phenylmethanesulfonylamino-methyl)-3,4,5,6-tetrahydro-2H-[1,2']bipyridinyl-3'-yl]-benzamide |
| 110 | 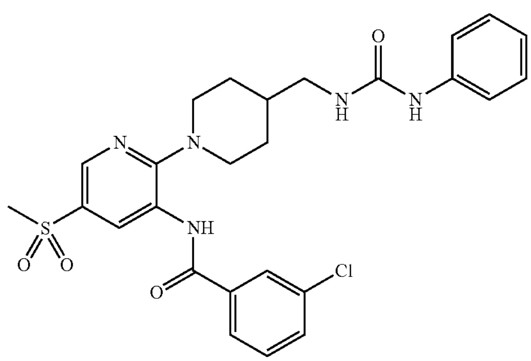 [SMILES: CS(=O)(=O)c1cnc(N2CCC(CNC(=O)Nc3ccccc3)CC2)c(NC(=O)c2cccc(Cl)c2)c1] | 3-Chloro-N-{5'-methanesulfonyl-4-[(3-phenyl-ureido)-methyl]-3,4,5,6-tetrahydro-2H-[1,2']bipyridinyl-3'-yl}-benzamide |
| 111 | 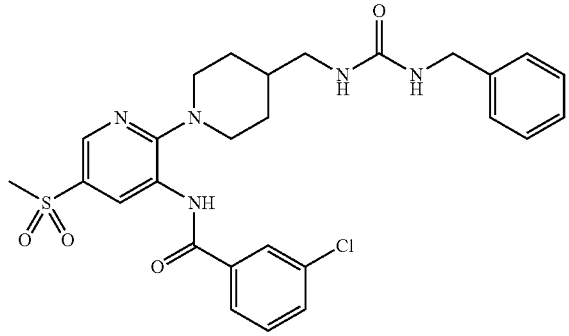 [SMILES: CS(=O)(=O)c1cnc(N2CCC(CNC(=O)NCc3ccccc3)CC2)c(NC(=O)c2cccc(Cl)c2)c1] | N-[4-(3-Benzyl-ureidomethyl)-5'-methanesulfonyl-3,4,5,6-tetrahydro-2H-[1,2']bipyridinyl-3'-yl]-3-chloro-benzamide |

TABLE 1-continued

| Cpd # | Structure | Name |
|---|---|---|
| 112 | 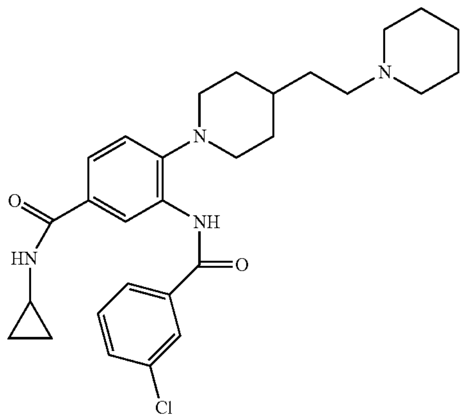 [SMILES: O=C(Nc1cc(C(=O)NC2CC2)ccc1N1CCC(CCN2CCCCC2)CC1)c1cccc(Cl)c1] | 3-(3-Chloro-benzoylamino)-N-cyclopropyl-4-[4-(2-piperidin-1-yl-ethyl)-piperidin-1-yl]-benzamide |
| 113 | 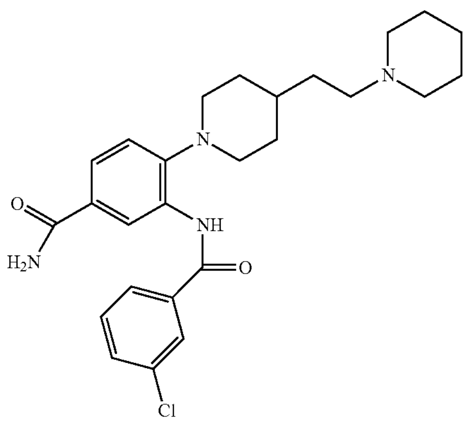 [SMILES: NC(=O)c1ccc(N2CCC(CCN3CCCCC3)CC2)c(NC(=O)c2cccc(Cl)c2)c1] | 3-(3-Chloro-benzoylamino)-4-[4-(2-piperidin-1-yl-ethyl)-piperidin-1-yl]-benzamide |
| 114 | 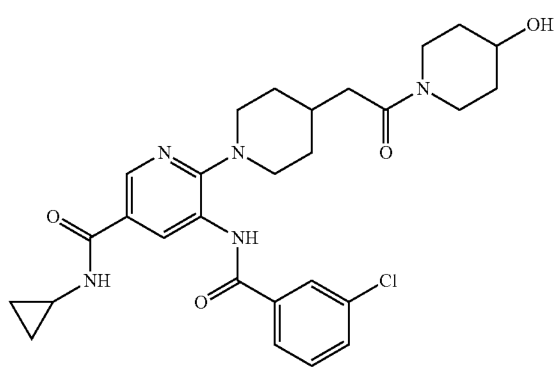 [SMILES: O=C(Nc1cc(C(=O)NC2CC2)cnc1N1CCC(CC(=O)N2CCC(O)CC2)CC1)c1cccc(Cl)c1] | 3'-(3-Chloro-benzoylamino)-4-[2-(4-hydroxy-piperidin-1-yl)-2-oxo-ethyl]-3,4,5,6-tetrahydro-2H-[1,2']bipyridinyl-5'-carboxylic acid cyclopropylamide |
| 115 | 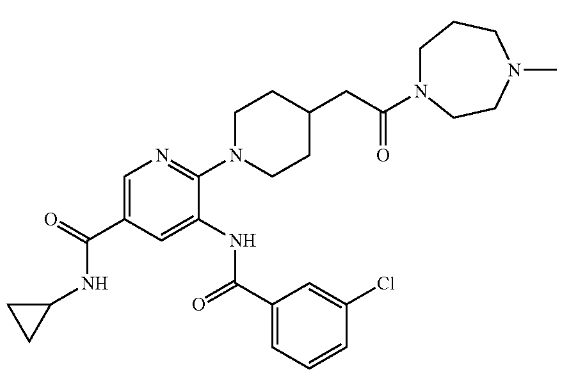 [SMILES: CN1CCCN(C(=O)CC2CCN(c3ncc(C(=O)NC4CC4)cc3NC(=O)c3cccc(Cl)c3)CC2)CC1] | 3'-(3-Chloro-benzoylamino)-4-[2-(4-methyl-[1,4]diazepan-1-yl)-2-oxo-ethyl]-3,4,5,6-tetrahydro-2H-[1,2']bipyridinyl-5'-carboxylic acid cyclopropylamide |

TABLE 1-continued

| Cpd # | Structure | Name |
|---|---|---|
| 116 | 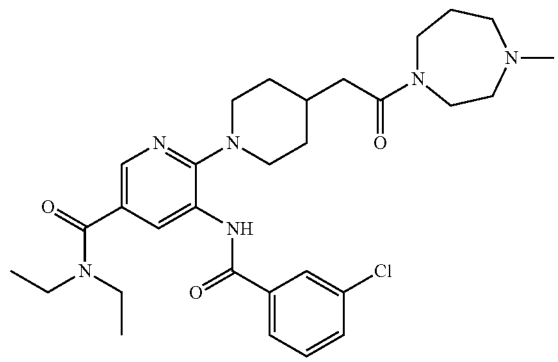 [SMILES: CCN(CC)C(=O)c1cnc(N2CCC(CC(=O)N3CCCN(C)CC3)CC2)c(NC(=O)c2cccc(Cl)c2)c1] | 3'-(3-Chloro-benzoylamino)-4-[2-(4-methyl-[1,4]diazepan-1-yl)-2-oxo-ethyl]-3,4,5,6-tetrahydro-2H-[1,2']bipyridinyl-5'-carboxylic acid diethylamide |
| 117 | 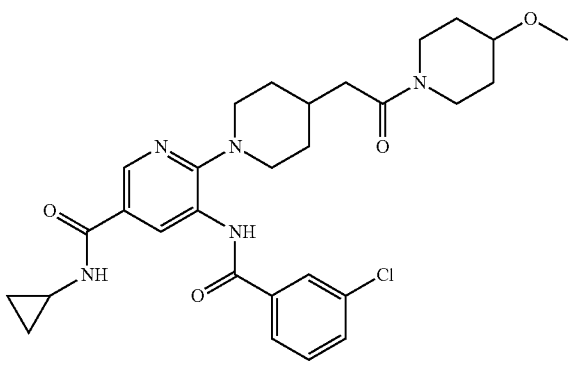 [SMILES: COC1CCN(C(=O)CC2CCN(c3ncc(C(=O)NC4CC4)cc3NC(=O)c3cccc(Cl)c3)CC2)CC1] | 3'-(3-Chloro-benzoylamino)-4-[2-(4-methoxy-piperidin-1-yl)-2-oxo-ethyl]-3,4,5,6-tetrahydro-2H-[1,2']bipyridinyl-5'-carboxylic acid cyclopropylamide |
| 118 | 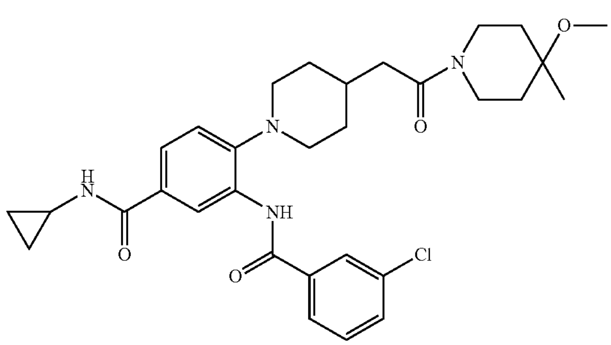 [SMILES: COC1(C)CCN(C(=O)CC2CCN(c3ccc(C(=O)NC4CC4)cc3NC(=O)c3cccc(Cl)c3)CC2)CC1] | 3-(3-Chloro-benzoylamino)-N-cyclopropyl-4-{4-[2-(4-methoxy-4-methyl-piperidin-1-yl)-2-oxo-ethyl]-piperidin-1-yl}-benzamide |
| 119 | 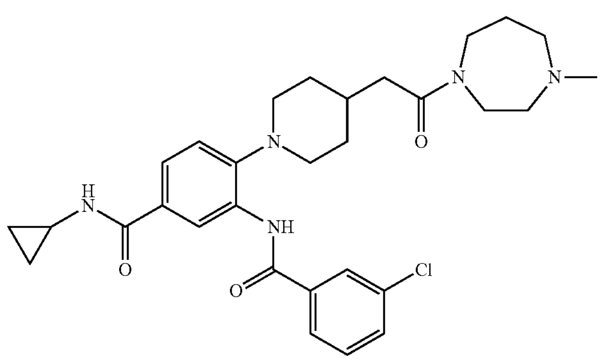 [SMILES: CN1CCCN(C(=O)CC2CCN(c3ccc(C(=O)NC4CC4)cc3NC(=O)c3cccc(Cl)c3)CC2)CC1] | 3-(3-Chloro-benzoylamino)-N-cyclopropyl-4-{4-[2-(4-methyl-[1,4]diazepan-1-yl)-2-oxo-ethyl]-piperidin-1-yl}-benzamide |

TABLE 1-continued

| Cpd # | Structure | Name |
|---|---|---|
| 120 | 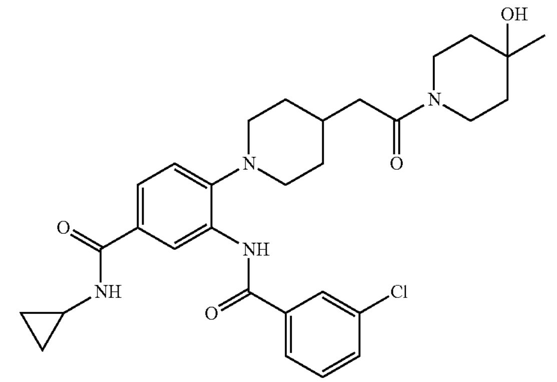 [SMILES: CC1(O)CCN(C(=O)CC2CCN(c3ccc(C(=O)NC4CC4)cc3NC(=O)c3cccc(Cl)c3)CC2)CC1] | 3-(3-Chloro-benzoylamino)-N-cyclopropyl-4-{4-[2-(4-hydroxy-4-methyl-piperidin-1-yl)-2-oxo-ethyl]-piperidin-1-yl}-benzamide |
| 121 | 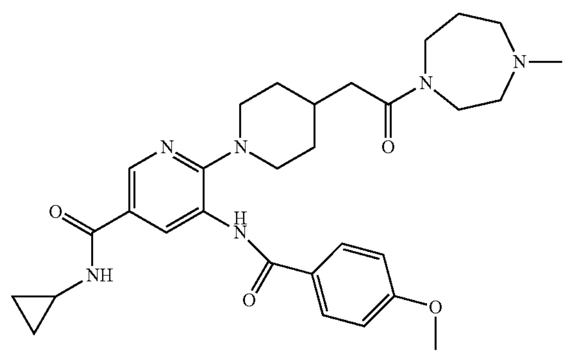 [SMILES: COc1ccc(C(=O)Nc2cc(C(=O)NC3CC3)cnc2N2CCC(CC(=O)N3CCCN(C)CC3)CC2)cc1] | 3'-(4-Methoxy-benzoylamino)-4-[2-(4-methyl-[1,4]diazepan-1-yl)-2-oxo-ethyl]-3,4,5,6-tetrahydro-2H-[1,2']bipyridinyl-5'-carboxylic acid cyclopropylamide |
| 122 | 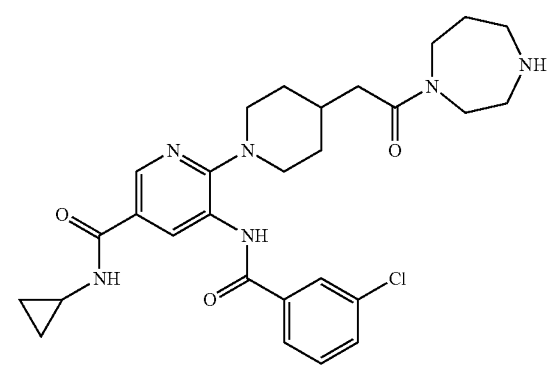 [SMILES: O=C(Nc1cc(C(=O)NC2CC2)cnc1N1CCC(CC(=O)N2CCCNCC2)CC1)c1cccc(Cl)c1] | 3'-(3-Chloro-benzoylamino)-4-(2-[1,4]diazepan-1-yl-2-oxo-ethyl)-3,4,5,6-tetrahydro-2H-[1,2']bipyridinyl-5'-carboxylic acid cyclopropylamide |
| 123 | 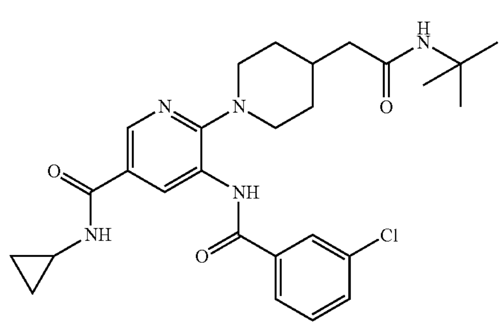 [SMILES: CC(C)(C)NC(=O)CC1CCN(c2ncc(C(=O)NC3CC3)cc2NC(=O)c2cccc(Cl)c2)CC1] | 4-(tert-Butylcarbamoyl-methyl)-3'-(3-chloro-benzoylamino)-3,4,5,6-tetrahydro-2H-[1,2']bipyridinyl-5'-carboxylic acid cyclopropylamide |

TABLE 1-continued

| Cpd # | Structure | Name |
|---|---|---|
| 124 | 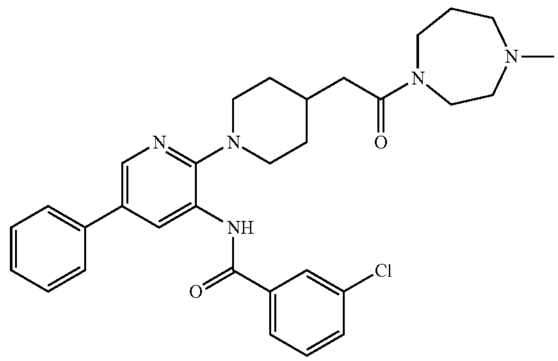 [SMILES: CN1CCCN(C(=O)CC2CCN(c3ncc(-c4ccccc4)cc3NC(=O)c3cccc(Cl)c3)CC2)CC1] | 3-Chloro-N-{4-[2-(4-methyl-[1,4]diazepan-1-yl)-2-oxo-ethyl]-5'-phenyl-3,4,5,6-tetrahydro-2H-[1,2']bipyridinyl-3'-yl}-benzamide |
| 125 | 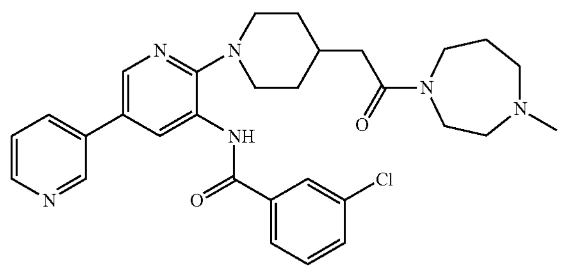 [SMILES: CN1CCCN(C(=O)CC2CCN(c3ncc(-c4cccnc4)cc3NC(=O)c3cccc(Cl)c3)CC2)CC1] | 3-Chloro-N-{4-[2-(4-methyl-[1,4]diazepan-1-yl)-2-oxo-ethyl]-3,4,5,6-tetrahydro-2H-[1,2';5',3'']terpyridin-3'-yl}-benzamide |
| 126 | 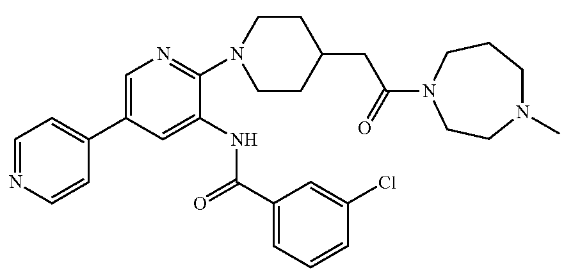 [SMILES: CN1CCCN(C(=O)CC2CCN(c3ncc(-c4ccncc4)cc3NC(=O)c3cccc(Cl)c3)CC2)CC1] | 3-Chloro-N-{4-[2-(4-methyl-[1,4]diazepan-1-yl)-2-oxo-ethyl]-3,4,5,6-tetrahydro-2H-[1,2';5',4'']terpyridin-3'-yl}-benzamide |
| 127 | 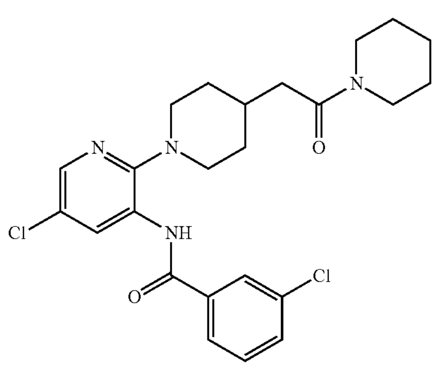 [SMILES: O=C(Nc1cc(Cl)cnc1N1CCC(CC(=O)N2CCCCC2)CC1)c1cccc(Cl)c1] | 3-Chloro-N-[5'-chloro-4-(2-oxo-2-piperidin-1-yl-ethyl)-3,4,5,6-tetrahydro-2H-[1,2']bipyridinyl-3'-yl]-benzamide |

TABLE 1-continued

| Cpd # | Structure | Name |
|---|---|---|
| 128 | 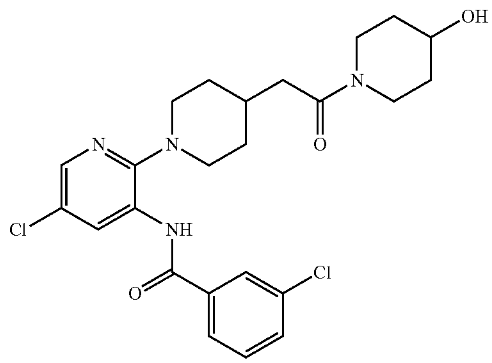 [SMILES: O=C(Nc1cc(Cl)cnc1N1CCC(CC(=O)N2CCC(O)CC2)CC1)c1cccc(Cl)c1] | 3-Chloro-N-{5'-chloro-4-[2-(4-hydroxy-piperidin-1-yl)-2-oxo-ethyl]-3,4,5,6-tetrahydro-2H-[1,2']bipyridinyl-3'-yl}-benzamide |
| 129 | 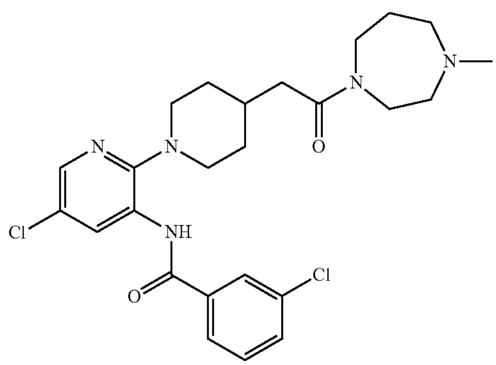 [SMILES: CN1CCCN(C(=O)CC2CCN(c3ncc(Cl)cc3NC(=O)c3cccc(Cl)c3)CC2)CC1] | 3-Chloro-N-{5'-chloro-4-[2-(4-methyl-[1,4]diazepan-1-yl)-2-oxo-ethyl]-3,4,5,6-tetrahydro-2H-[1,2']bipyridinyl-3'-yl}-benzamide |
| 130 | 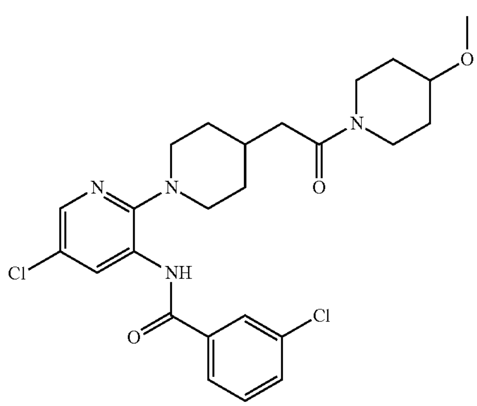 [SMILES: COC1CCN(C(=O)CC2CCN(c3ncc(Cl)cc3NC(=O)c3cccc(Cl)c3)CC2)CC1] | 3-Chloro-N-{5'-chloro-4-[2-(4-methoxy-piperidin-1-yl)-2-oxo-ethyl]-3,4,5,6-tetrahydro-2H-[1,2']bipyridinyl-3'-yl}-benzamide |
| 131 | 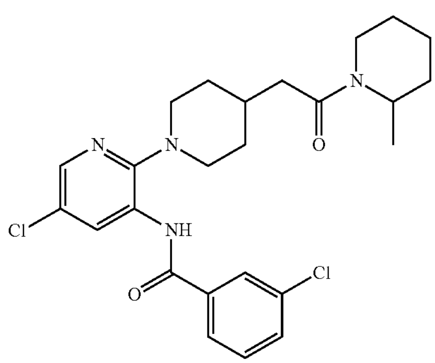 [SMILES: CC1CCCCN1C(=O)CC1CCN(c2ncc(Cl)cc2NC(=O)c2cccc(Cl)c2)CC1] | 3-Chloro-N-{5'-chloro-4-[2-(2-methyl-piperidin-1-yl)-2-oxo-ethyl]-3,4,5,6-tetrahydro-2H-[1,2']bipyridinyl-3'-yl}-benzamide |

TABLE 1-continued

| Cpd # | Structure | Name |
|---|---|---|
| 132 | 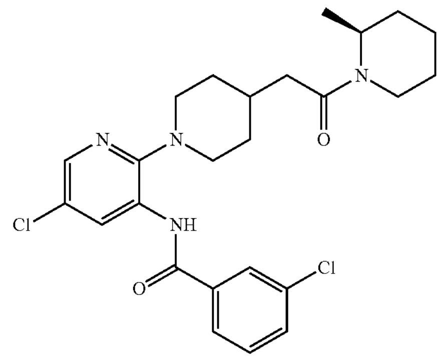 [SMILES: C[C@H]1CCCCN1C(=O)CC1CCN(c2ncc(Cl)cc2NC(=O)c2cccc(Cl)c2)CC1] | 3-Chloro-N-{5'-chloro-4-[2-((S)-2-methyl-piperidin-1-yl)-2-oxo-ethyl]-3,4,5,6-tetrahydro-2H-[1,2']bipyridinyl-3'-yl}-benzamide |
| 133 | 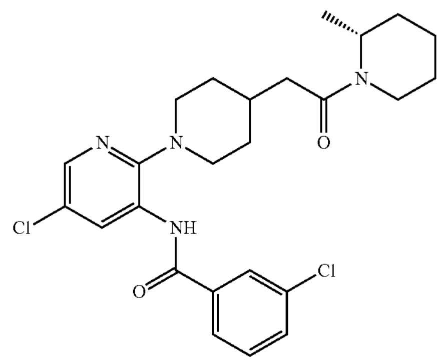 [SMILES: C[C@@H]1CCCCN1C(=O)CC1CCN(c2ncc(Cl)cc2NC(=O)c2cccc(Cl)c2)CC1] | 3-Chloro-N-{5'-chloro-4-[2-((R)-2-methyl-piperidin-1-yl)-2-oxo-ethyl]-3,4,5,6-tetrahydro-2H-[1,2']bipyridinyl-3'-yl}-benzamide |
| 134 | 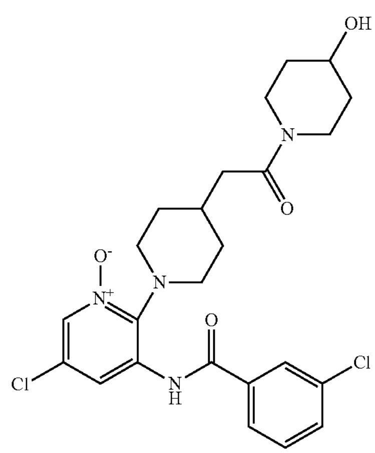 [SMILES: O=C(Nc1cc(Cl)c[n+]([O-])c1N1CCC(CC(=O)N2CCC(O)CC2)CC1)c1cccc(Cl)c1] | 3-Chloro-N-{5'-chloro-4-[2-(4-hydroxy-piperidin-1-yl)-2-oxo-ethyl]-1'-oxy-3,4,5,6-tetrahydro-2H-[1,2']bipyridinyl-3'-yl}-benzamide |
| 135 | 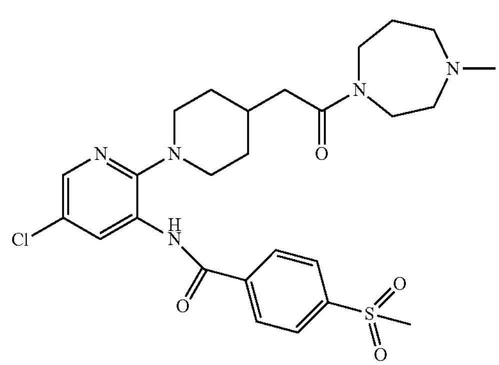 [SMILES: CN1CCCN(C(=O)CC2CCN(c3ncc(Cl)cc3NC(=O)c3ccc(S(C)(=O)=O)cc3)CC2)CC1] | N-{5'-Chloro-4-[2-(4-methyl-[1,4]diazepan-1-yl)-2-oxo-ethyl]-3,4,5,6-tetrahydro-2H-[1,2']bipyridinyl-3'-yl}-4-methanesulfonyl-benzamide |

TABLE 1-continued

| Cpd # | Structure | Name |
|---|---|---|
| 136 | 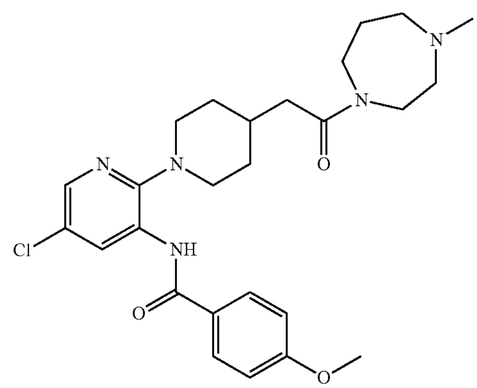 [SMILES: COc1ccc(C(=O)Nc2cc(Cl)cnc2N2CCC(CC(=O)N3CCCN(C)CC3)CC2)cc1] | N-{5'-Chloro-4-[2-(4-methyl-[1,4]diazepan-1-yl)-2-oxo-ethyl]-3,4,5,6-tetrahydro-2H-[1,2']bipyridinyl-3'-yl}-4-methoxy-benzamide |
| 137 | 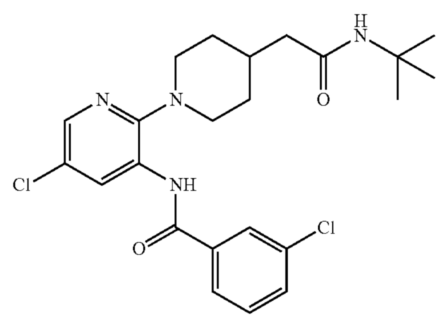 [SMILES: CC(C)(C)NC(=O)CC1CCN(c2ncc(Cl)cc2NC(=O)c2cccc(Cl)c2)CC1] | N-[4-(tert-Butylcarbamoyl-methyl)-5'-chloro-3,4,5,6-tetrahydro-2H-[1,2']bipyridinyl-3'-yl]-3-chloro-benzamide |
| 138 | 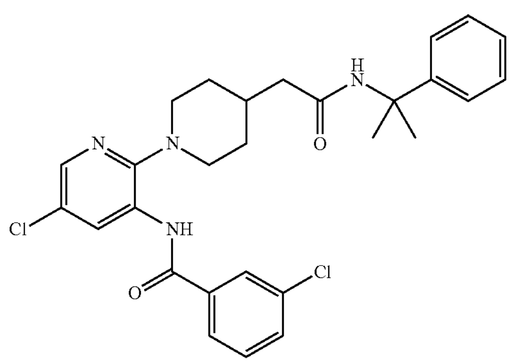 [SMILES: CC(C)(NC(=O)CC1CCN(c2ncc(Cl)cc2NC(=O)c2cccc(Cl)c2)CC1)c1ccccc1] | 3-Chloro-N-{5'-chloro-4-[(1-methyl-1-phenyl-ethylcarbamoyl)-methyl]-3,4,5,6-tetrahydro-2H-[1,2']bipyridinyl-3'-yl}-benzamide |
| 139 | 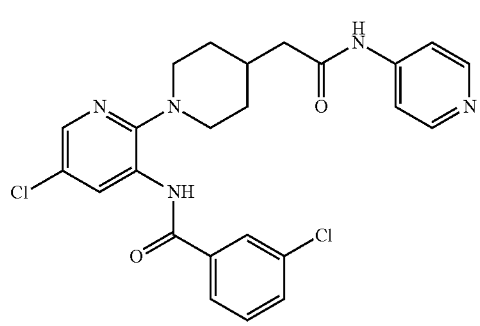 [SMILES: O=C(CC1CCN(c2ncc(Cl)cc2NC(=O)c2cccc(Cl)c2)CC1)Nc1ccncc1] | 3-Chloro-N-[5'-chloro-4-(pyridin-4-ylcarbamoylmethyl)-3,4,5,6-tetrahydro-2H-[1,2']bipyridinyl-3'-yl]-benzamide |

TABLE 1-continued

| Cpd # | Structure | Name |
|---|---|---|
| 140 | 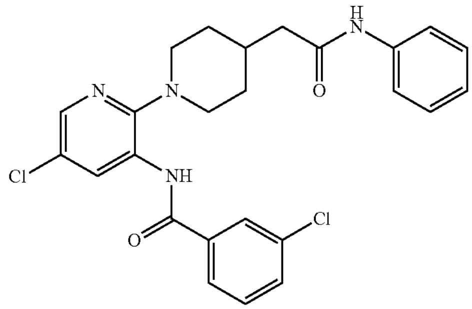 [SMILES: O=C(CC1CCN(c2ncc(Cl)cc2NC(=O)c2cccc(Cl)c2)CC1)Nc1ccccc1] | 3-Chloro-N-(5'-chloro-4-phenylcarbamoylmethyl-3,4,5,6-tetrahydro-2H-[1,2']bipyridinyl-3'-yl)-benzamide |
| 141 | 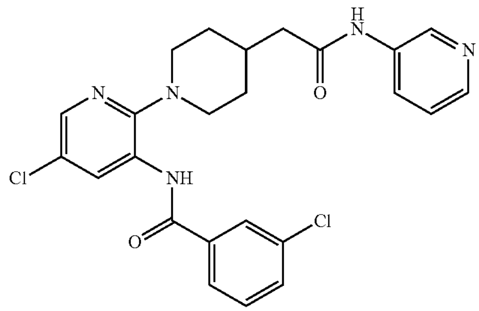 [SMILES: O=C(CC1CCN(c2ncc(Cl)cc2NC(=O)c2cccc(Cl)c2)CC1)Nc1cccnc1] | 3-Chloro-N-[5'-chloro-4-(pyridin-3-ylcarbamoylmethyl)-3,4,5,6-tetrahydro-2H-[1,2']bipyridinyl-3'-yl]-benzamide |
| 142 | 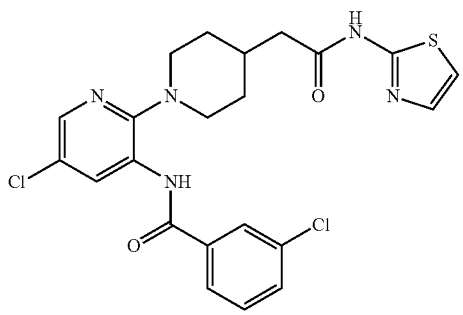 [SMILES: O=C(CC1CCN(c2ncc(Cl)cc2NC(=O)c2cccc(Cl)c2)CC1)Nc1nccs1] | 3-Chloro-N-[5'-chloro-4-(thiazol-2-ylcarbamoylmethyl)-3,4,5,6-tetrahydro-2H-[1,2']bipyridinyl-3'-yl]-benzamide |
| 143 | 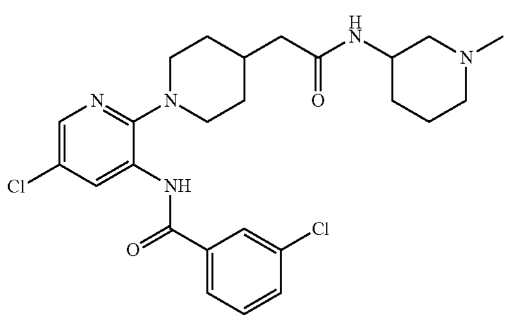 [SMILES: CN1CCCC(NC(=O)CC2CCN(c3ncc(Cl)cc3NC(=O)c3cccc(Cl)c3)CC2)C1] | 3-Chloro-N-{5'-chloro-4-[(1-methyl-piperidin-3-ylcarbamoyl)-methyl]-3,4,5,6-tetrahydro-2H-[1,2']bipyridinyl-3'-yl}-benzamide |
| 144 | 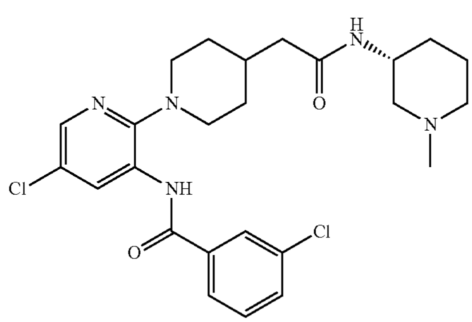 [SMILES: CN1CCC[C@@H](NC(=O)CC2CCN(c3ncc(Cl)cc3NC(=O)c3cccc(Cl)c3)CC2)C1] | 3-Chloro-N-{5'-chloro-4-[((R)-1-methyl-piperidin-3-ylcarbamoyl)-methyl]-3,4,5,6-tetrahydro-2H-[1,2']bipyridinyl-3'-yl}-benzamide |

TABLE 1-continued

| Cpd # | Structure | Name |
|---|---|---|
| 145 | 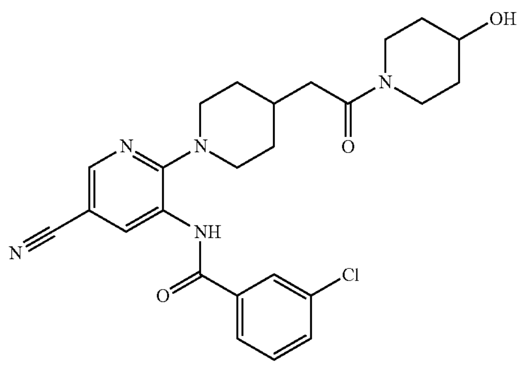 [SMILES: N#Cc1cnc(N2CCC(CC(=O)N3CCC(O)CC3)CC2)c(NC(=O)c2cccc(Cl)c2)c1] | 3-Chloro-N-{5'-cyano-4-[2-(4-hydroxy-piperidin-1-yl)-2-oxo-ethyl]-3,4,5,6-tetrahydro-2H-[1,2']bipyridinyl-3'-yl}-benzamide |
| 146 | 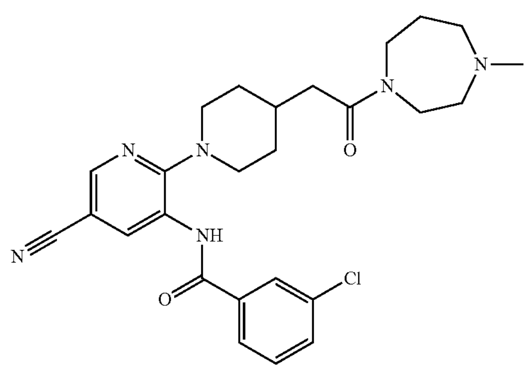 [SMILES: CN1CCCN(C(=O)CC2CCN(c3ncc(C#N)cc3NC(=O)c3cccc(Cl)c3)CC2)CC1] | 3-Chloro-N-{5'-cyano-4-[2-(4-methyl-[1,4]diazepan-1-yl)-2-oxo-ethyl]-3,4,5,6-tetrahydro-2H-[1,2']bipyridinyl-3'-yl}-benzamide |
| 147 | 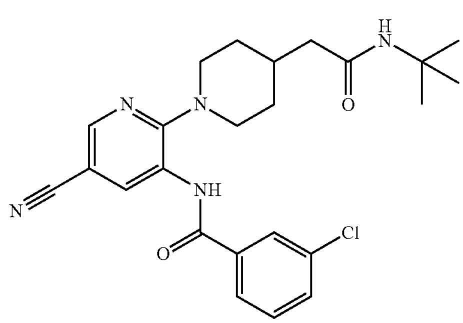 [SMILES: CC(C)(C)NC(=O)CC1CCN(c2ncc(C#N)cc2NC(=O)c2cccc(Cl)c2)CC1] | N-[4-(tert-Butylcarbamoyl-methyl)-5'-cyano-3,4,5,6-tetrahydro-2H-[1,2']bipyridinyl-3'-yl]-3-chloro-benzamide |
| 148 | 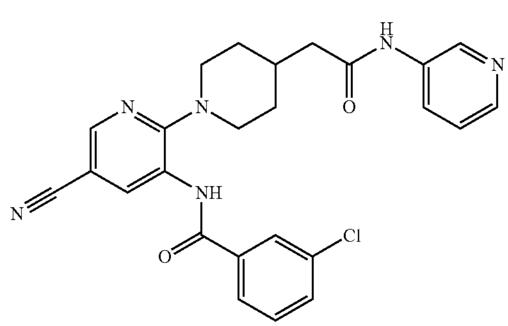 [SMILES: N#Cc1cnc(N2CCC(CC(=O)Nc3cccnc3)CC2)c(NC(=O)c2cccc(Cl)c2)c1] | 3-Chloro-N-[5'-cyano-4-(pyridin-3-ylcarbamoylmethyl)-3,4,5,6-tetrahydro-2H-[1,2']bipyridinyl-3'-yl]-benzamide |

TABLE 1-continued

| Cpd # | Structure | Name |
|---|---|---|
| 149 | 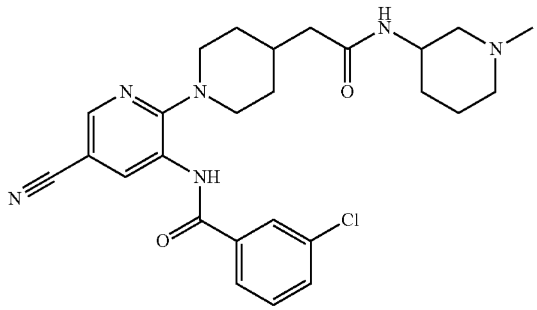 [SMILES: CN1CCCC(NC(=O)CC2CCN(c3ncc(C#N)cc3NC(=O)c3cccc(Cl)c3)CC2)C1] | 3-Chloro-N-{5'-cyano-4-[(1-methyl-piperidin-3-ylcarbamoyl)-methyl]-3,4,5,6-tetrahydro-2H-[1,2']bipyridinyl-3'-yl}-benzamide |
| 150 | 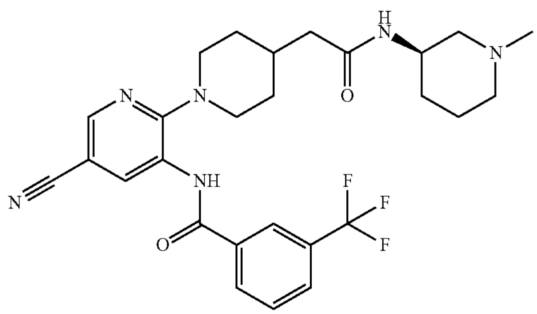 [SMILES: CN1CCC[C@@H](NC(=O)CC2CCN(c3ncc(C#N)cc3NC(=O)c3cccc(C(F)(F)F)c3)CC2)C1] | N-{5'-Cyano-4-[((R)-1-methyl-piperidin-3-ylcarbamoyl)-methyl]-3,4,5,6-tetrahydro-2H-[1,2']bipyridinyl-3'-yl}-3-trifluoromethyl-benzamide |
| 151 | 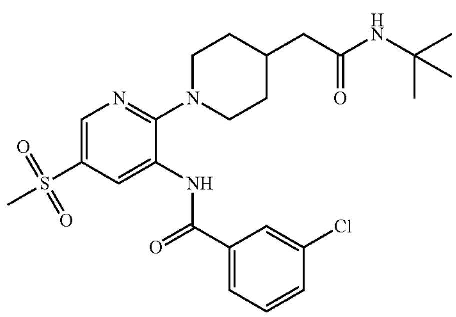 [SMILES: CC(C)(C)NC(=O)CC1CCN(c2ncc(S(C)(=O)=O)cc2NC(=O)c2cccc(Cl)c2)CC1] | N-[4-(tert-Butylcarbamoyl-methyl)-5'-methanesulfonyl-3,4,5,6-tetrahydro-2H-[1,2']bipyridinyl-3'-yl]-3-chloro-benzamide |
| 152 | 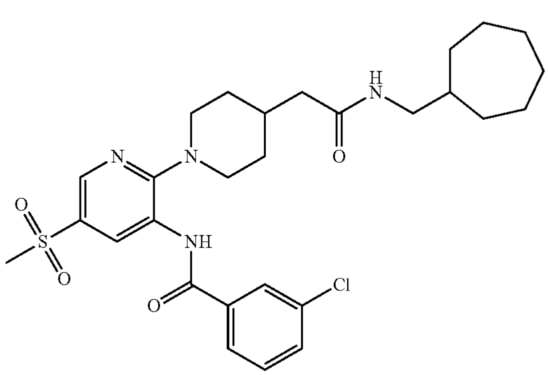 [SMILES: CS(=O)(=O)c1cnc(N2CCC(CC(=O)NCC3CCCCCC3)CC2)c(NC(=O)c2cccc(Cl)c2)c1] | 3-Chloro-N-{4-[(cycloheptylmethyl-carbamoyl)-methyl]-5'-methanesulfonyl-3,4,5,6-tetrahydro-2H-[1,2']bipyridinyl-3'-yl}-benzamide |

TABLE 1-continued

| Cpd # | Structure | Name |
|---|---|---|
| 153 | 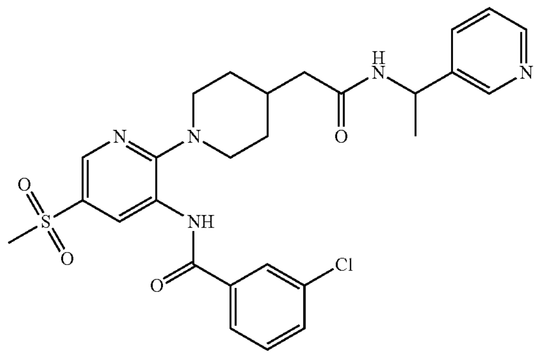 [SMILES: CC(NC(=O)CC1CCN(c2ncc(S(C)(=O)=O)cc2NC(=O)c2cccc(Cl)c2)CC1)c1cccnc1] | 3-Chloro-N-{5'-methanesulfonyl-4-[(1-pyridin-3-yl-ethylcarbamoyl)-methyl]-3,4,5,6-tetrahydro-2H-[1,2']bipyridinyl-3'-yl}-benzamide |
| 154 | 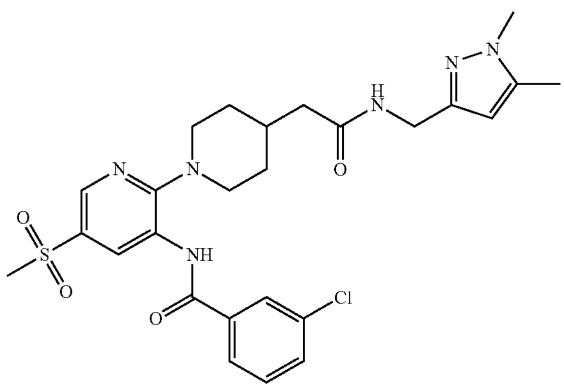 | 3-Chloro-N-(4-{[(1,5-dimethyl-1H-pyrazol-3-ylmethyl)-carbamoyl]-methyl}-5'-methanesulfonyl-3,4,5,6-tetrahydro-2H-[1,2']bipyridinyl-3'-yl)-benzamide |
| 155 | 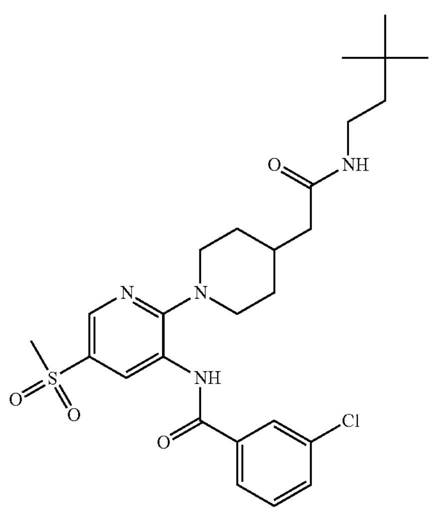 [SMILES: CC(C)(C)CCNC(=O)CC1CCN(c2ncc(S(C)(=O)=O)cc2NC(=O)c2cccc(Cl)c2)CC1] | 3-Chloro-N-{4-[(3,3-dimethyl-butylcarbamoyl)-methyl]-5'-methanesulfonyl-3,4,5,6-tetrahydro-2H-[1,2']bipyridinyl-3'-yl}-benzamide |
| 156 | 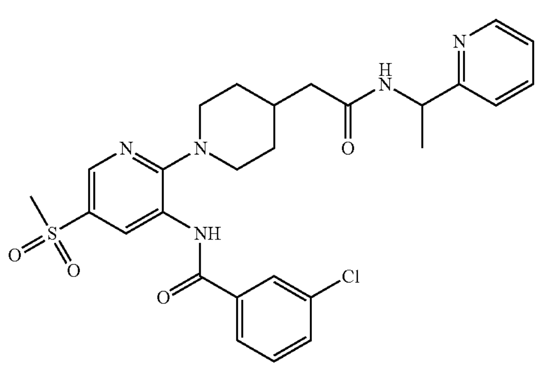 [SMILES: CC(NC(=O)CC1CCN(c2ncc(S(C)(=O)=O)cc2NC(=O)c2cccc(Cl)c2)CC1)c1ccccn1] | 3-Chloro-N-{5'-methanesulfonyl-4-[(1-pyridin-2-yl-ethylcarbamoyl)-methyl]-3,4,5,6-tetrahydro-2H-[1,2']bipyridinyl-3'-yl}-benzamide |

TABLE 1-continued

| Cpd # | Structure | Name |
|---|---|---|
| 157 | 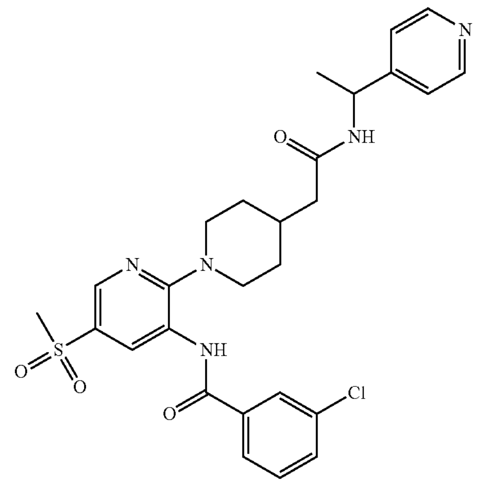 [SMILES: CC(NC(=O)CC1CCN(c2ncc(S(C)(=O)=O)cc2NC(=O)c2cccc(Cl)c2)CC1)c1ccncc1] | 3-Chloro-N-{5'-methanesulfonyl-4-[(1-pyridin-4-yl-ethylcarbamoyl)-methyl]-3,4,5,6-tetrahydro-2H-[1,2']bipyridinyl-3'-yl}-benzamide |
| 158 | 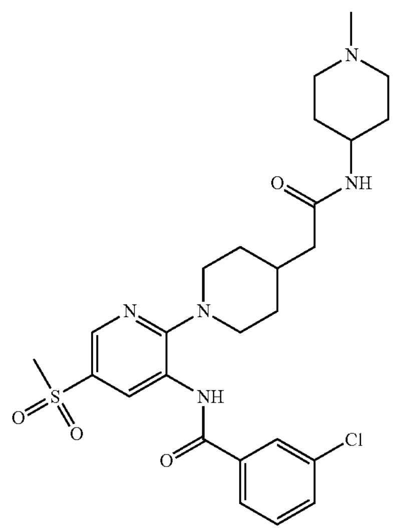 [SMILES: CN1CCC(NC(=O)CC2CCN(c3ncc(S(C)(=O)=O)cc3NC(=O)c3cccc(Cl)c3)CC2)CC1] | 3-Chloro-N-{5'-methanesulfonyl-4-[(1-methyl-piperidin-4-ylcarbamoyl)-methyl]-3,4,5,6-tetrahydro-2H-[1,2']bipyridinyl-3'-yl}-benzamide |
| 159 | 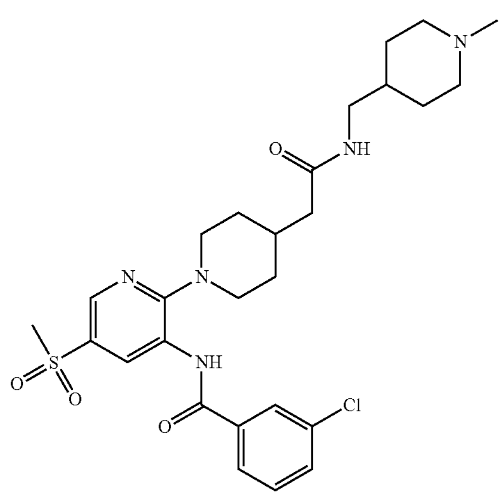 [SMILES: CN1CCC(CNC(=O)CC2CCN(c3ncc(S(C)(=O)=O)cc3NC(=O)c3cccc(Cl)c3)CC2)CC1] | 3-Chloro-N-(5'-methanesulfonyl-4-{[(1-methyl-piperidin-4-ylmethyl)-carbamoyl]-methyl}-3,4,5,6-tetrahydro-2H-[1,2']bipyridinyl-3'-yl)-benzamide |

US 8,952,004 B2

TABLE 1-continued

| Cpd # | Structure | Name |
|---|---|---|
| 160 | 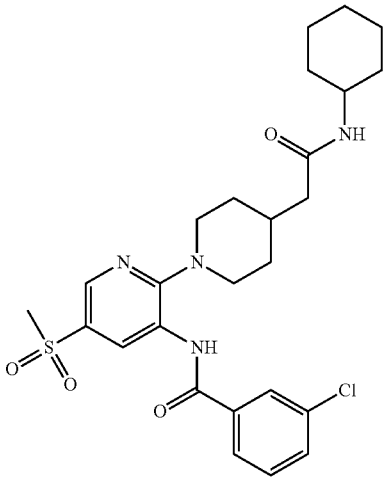 [SMILES: CS(=O)(=O)c1cnc(N2CCC(CC(=O)NC3CCCCC3)CC2)c(NC(=O)c2cccc(Cl)c2)c1] | 3-Chloro-N-(4-cyclohexylcarbamoylmethyl-5'-methanesulfonyl-3,4,5,6-tetrahydro-2H-[1,2']bipyridinyl-3'-yl)-benzamide |
| 161 | 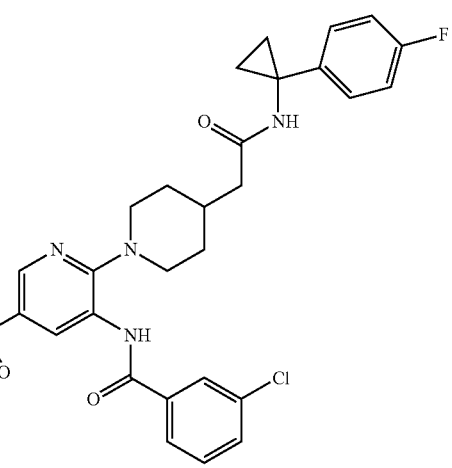 | 3-Chloro-N-(4-{[1-(4-fluoro-phenyl)-cyclopropylcarbamoyl]-methyl}-5'-methanesulfonyl-3,4,5,6-tetrahydro-2H-[1,2']bipyridinyl-3'-yl)-benzamide |
| 162 | 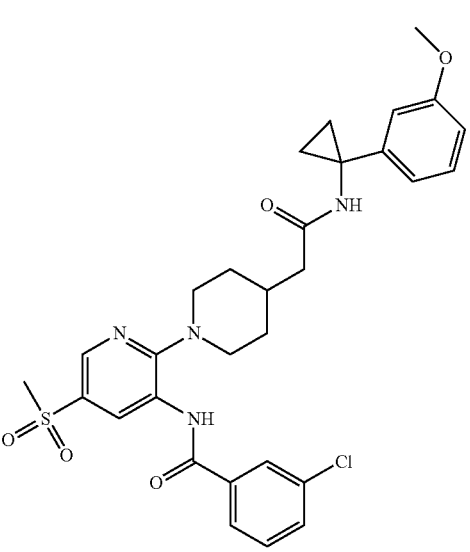 [SMILES: COc1cccc(C2(NC(=O)CC3CCN(c4ncc(S(C)(=O)=O)cc4NC(=O)c4cccc(Cl)c4)CC3)CC2)c1] | 3-Chloro-N-(5'-methanesulfonyl-4-{[1-(3-methoxy-phenyl)-cyclopropylcarbamoyl]-methyl}-3,4,5,6-tetrahydro-2H-[1,2']bipyridinyl-3'-yl)-benzamide |

TABLE 1-continued

| Cpd # | Structure | Name |
|---|---|---|
| 163 | 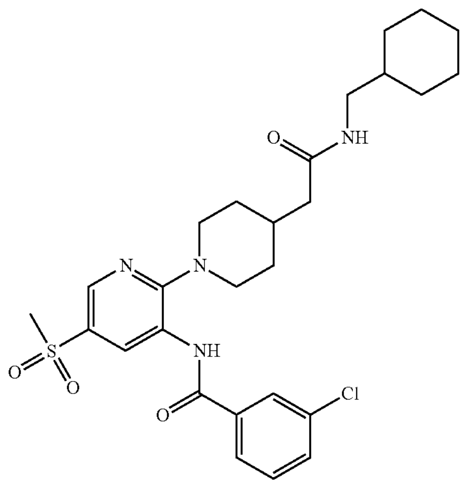 [SMILES: CS(=O)(=O)c1cnc(N2CCC(CC(=O)NCC3CCCCC3)CC2)c(NC(=O)c2cccc(Cl)c2)c1] | 3-Chloro-N-{4-[(cyclohexylmethyl-carbamoyl)-methyl]-5'-methanesulfonyl-3,4,5,6-tetrahydro-2H-[1,2']bipyridinyl-3'-yl}-benzamide |
| 164 | 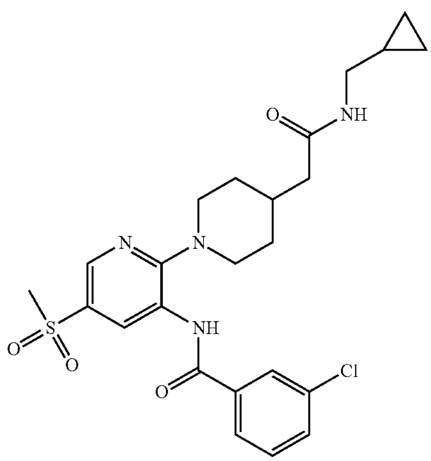 [SMILES: CS(=O)(=O)c1cnc(N2CCC(CC(=O)NCC3CC3)CC2)c(NC(=O)c2cccc(Cl)c2)c1] | 3-Chloro-N-{4-[(cyclopropylmethyl-carbamoyl)-methyl]-5'-methanesulfonyl-3,4,5,6-tetrahydro-2H-[1,2']bipyridinyl-3'-yl}-benzamide |
| 165 | 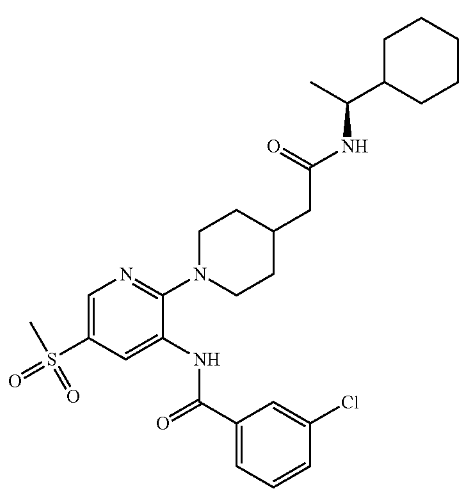 [SMILES: C[C@H](NC(=O)CC1CCN(c2ncc(S(C)(=O)=O)cc2NC(=O)c2cccc(Cl)c2)CC1)C1CCCCC1] | 3-Chloro-N-{4-[((S)-1-cyclohexyl-ethylcarbamoyl)-methyl]-5'-methanesulfonyl-3,4,5,6-tetrahydro-2H-[1,2']bipyridinyl-3'-yl}-benzamide |

TABLE 1-continued

| Cpd # | Structure | Name |
|---|---|---|
| 166 | 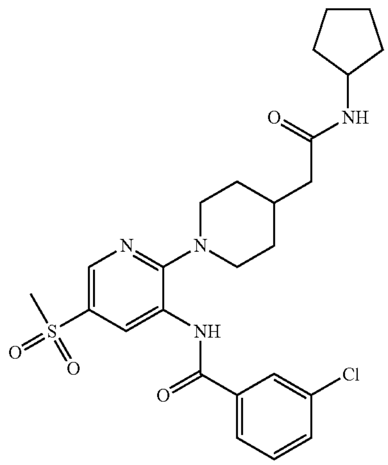 [SMILES: CS(=O)(=O)c1cnc(N2CCC(CC(=O)NC3CCCC3)CC2)c(NC(=O)c2cccc(Cl)c2)c1] | 3-Chloro-N-(4-cyclopentylcarbamoylmethyl-5'-methanesulfonyl-3,4,5,6-tetrahydro-2H-[1,2']bipyridinyl-3'-yl)-benzamide |
| 167 | 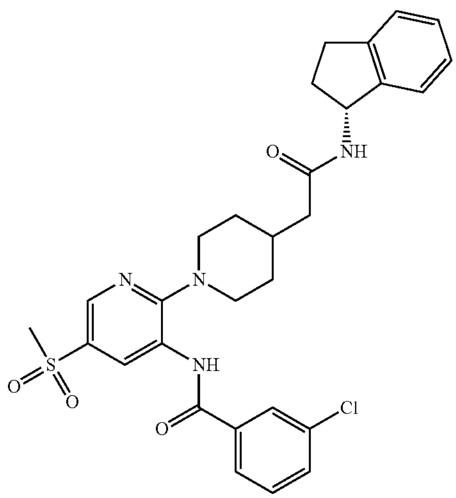 [SMILES: CS(=O)(=O)c1cnc(N2CCC(CC(=O)N[C@@H]3CCc4ccccc43)CC2)c(NC(=O)c2cccc(Cl)c2)c1] | 3-Chloro-N-[4-((R)-indan-1-ylcarbamoylmethyl)-5'-methanesulfonyl-3,4,5,6-tetrahydro-2H-[1,2']bipyridinyl-3'-yl]-benzamide |
| 168 | 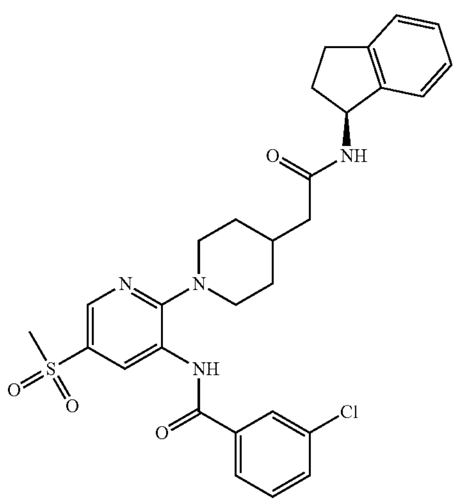 [SMILES: CS(=O)(=O)c1cnc(N2CCC(CC(=O)N[C@H]3CCc4ccccc43)CC2)c(NC(=O)c2cccc(Cl)c2)c1] | 3-Chloro-N-[4-((S)-indan-1-ylcarbamoylmethyl)-5'-methanesulfonyl-3,4,5,6-tetrahydro-2H-[1,2']bipyridinyl-3'-yl]-benzamide |

TABLE 1-continued

| Cpd # | Structure | Name |
|---|---|---|
| 169 | 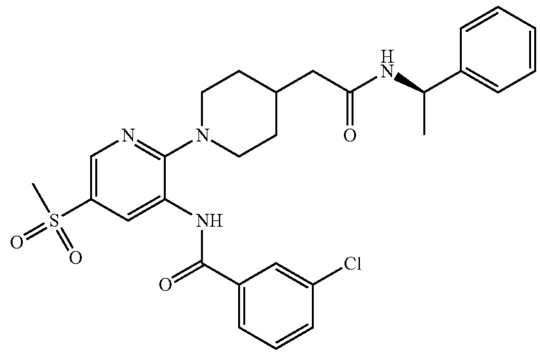 [SMILES: C[C@@H](NC(=O)CC1CCN(c2ncc(S(C)(=O)=O)cc2NC(=O)c2cccc(Cl)c2)CC1)c1ccccc1] | 3-Chloro-N-{5'-methanesulfonyl-4-[((R)-1-phenyl-ethylcarbamoyl)-methyl]-3,4,5,6-tetrahydro-2H-[1,2']bipyridinyl-3'-yl}-benzamide |
| 170 | 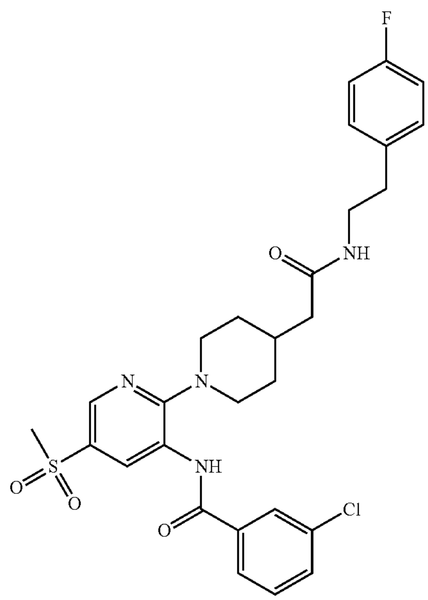 [SMILES: CS(=O)(=O)c1cnc(N2CCC(CC(=O)NCCc3ccc(F)cc3)CC2)c(NC(=O)c2cccc(Cl)c2)c1] | 3-Chloro-N-(4-{[2-(4-fluoro-phenyl)-ethylcarbamoyl]-methyl}-5'-methanesulfonyl-3,4,5,6-tetrahydro-2H-[1,2']bipyridinyl-3'-yl)-benzamide |
| 171 | 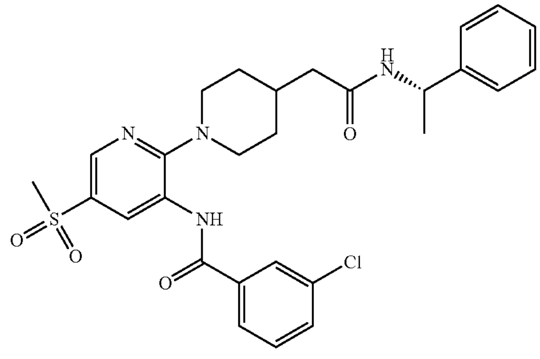 [SMILES: C[C@H](NC(=O)CC1CCN(c2ncc(S(C)(=O)=O)cc2NC(=O)c2cccc(Cl)c2)CC1)c1ccccc1] | 3-Chloro-N-{5'-methanesulfonyl-4-[((S)-1-phenyl-ethylcarbamoyl)-methyl]-3,4,5,6-tetrahydro-2H-[1,2']bipyridinyl-3'-yl}-benzamide |

TABLE 1-continued

| Cpd # | Structure | Name |
|---|---|---|
| 172 | 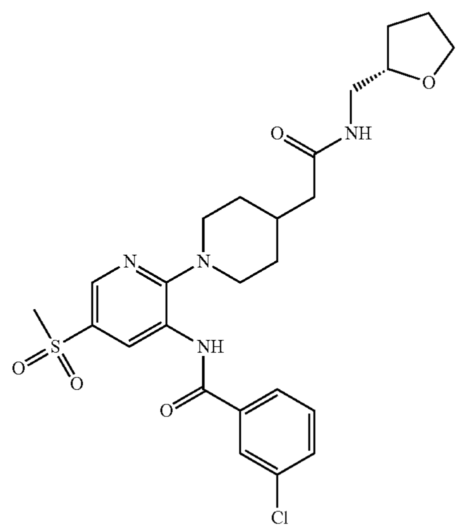 [SMILES: CS(=O)(=O)c1cnc(N2CCC(CC(=O)NC[C@@H]3CCCO3)CC2)c(NC(=O)c2cccc(Cl)c2)c1] | 3-Chloro-N-[5'-methanesulfonyl-4-({[(S)-1-(tetrahydro-furan-2-yl)methyl]-carbamoyl}-methyl)-3,4,5,6-tetrahydro-2H-[1,2']bipyridinyl-3'-yl]-benzamide |
| 173 | 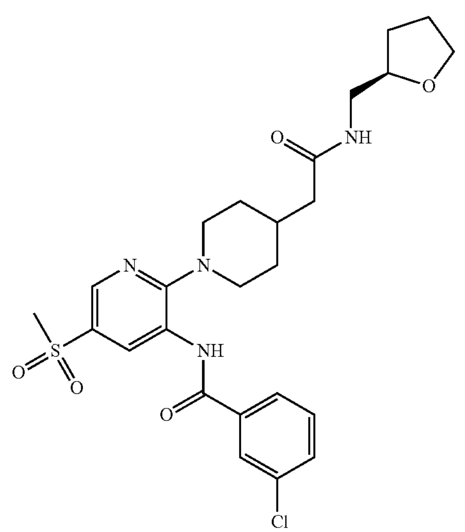 [SMILES: CS(=O)(=O)c1cnc(N2CCC(CC(=O)NC[C@H]3CCCO3)CC2)c(NC(=O)c2cccc(Cl)c2)c1] | 3-Chloro-N-[5'-methanesulfonyl-4-({[(R)-1-(tetrahydro-furan-2-yl)methyl]-carbamoyl}-methyl)-3,4,5,6-tetrahydro-2H-[1,2']bipyridinyl-3'-yl]-benzamide |
| 174 | 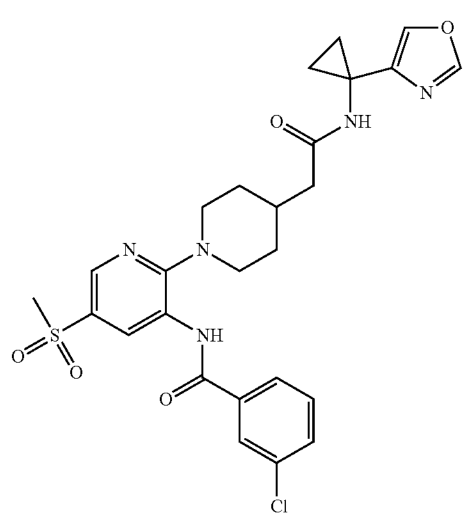 [SMILES: CS(=O)(=O)c1cnc(N2CCC(CC(=O)NC3(c4cocn4)CC3)CC2)c(NC(=O)c2cccc(Cl)c2)c1] | 3-Chloro-N-{5'-methanesulfonyl-4-[(1-oxazol-4-yl-cyclopropylcarbamoyl)-methyl]-3,4,5,6-tetrahydro-2H-[1,2']bipyridinyl-3'-yl}-benzamide |

TABLE 1-continued

| Cpd # | Structure | Name |
|---|---|---|
| 175 | 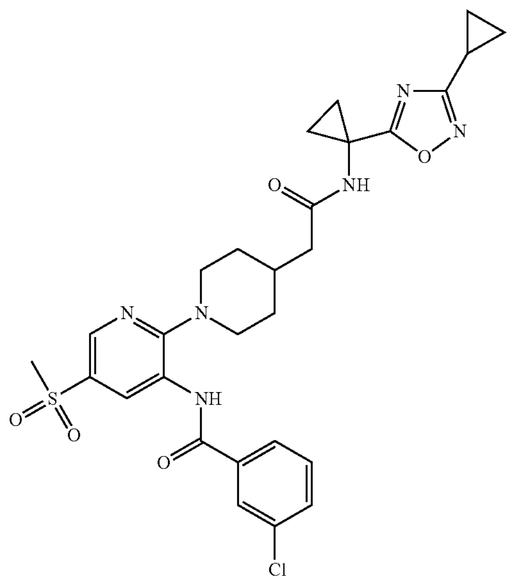 [SMILES: CS(=O)(=O)c1cnc(N2CCC(CC(=O)NC3(c4nc(C5CC5)no4)CC3)CC2)c(NC(=O)c2cccc(Cl)c2)c1] | 3-Chloro-N-(4-{[1-(3-cyclopropyl-[1,2,4]oxadiazol-5-yl)-cyclopropylcarbamoyl]-methyl}-5'-methanesulfonyl-3,4,5,6-tetrahydro-2H-[1,2']bipyridinyl-3'-yl)-benzamide |
| 176 | 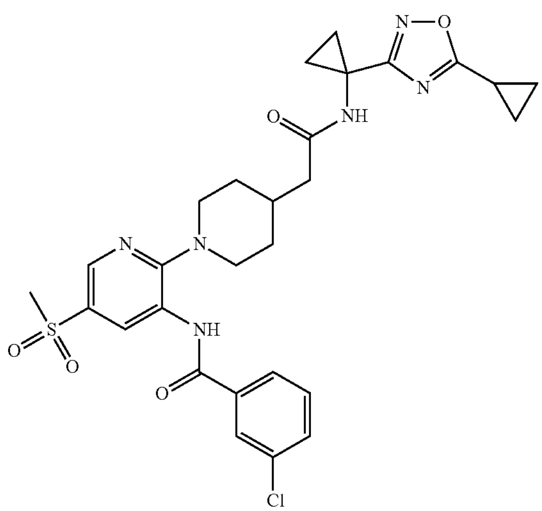 [SMILES: CS(=O)(=O)c1cnc(N2CCC(CC(=O)NC3(c4noc(C5CC5)n4)CC3)CC2)c(NC(=O)c2cccc(Cl)c2)c1] | 3-Chloro-N-(4-{[1-(5-cyclopropyl-[1,2,4]oxadiazol-3-yl)-cyclopropylcarbamoyl]-methyl}-5'-methanesulfonyl-3,4,5,6-tetrahydro-2H-[1,2']bipyridinyl-3'-yl)-benzamide |
| 177 | 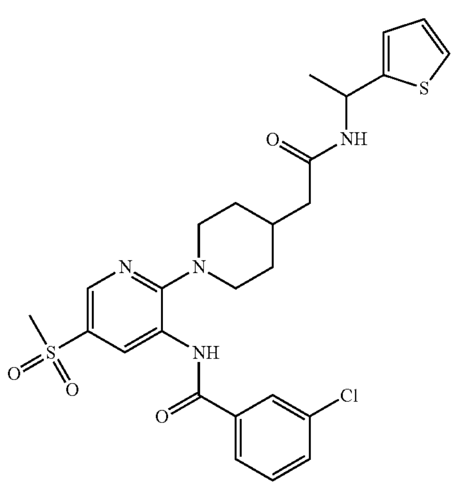 [SMILES: CC(NC(=O)CC1CCN(c2ncc(S(C)(=O)=O)cc2NC(=O)c2cccc(Cl)c2)CC1)c1cccs1] | 3-Chloro-N-{5'-methanesulfonyl-4-[(1-thiophen-2-yl-ethylcarbamoyl)-methyl]-3,4,5,6-tetrahydro-2H-[1,2']bipyridinyl-3'-yl}-benzamide |

TABLE 1-continued

| Cpd # | Structure | Name |
|---|---|---|
| 178 | 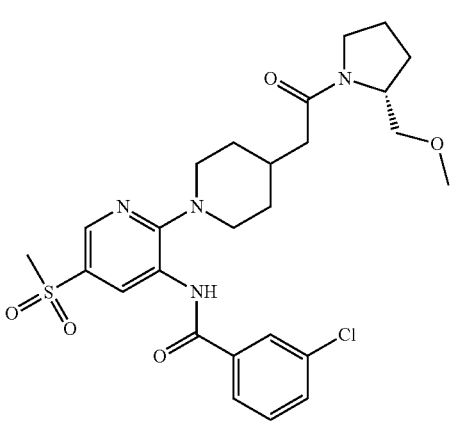 [SMILES: COC[C@H]1CCCN1C(=O)CC1CCN(c2ncc(S(C)(=O)=O)cc2NC(=O)c2cccc(Cl)c2)CC1] | 3-Chloro-N-{5'-methanesulfonyl-4-[2-((R)-2-methoxymethyl-pyrrolidin-1-yl)-2-oxo-ethyl]-3,4,5,6-tetrahydro-2H-[1,2']bipyridinyl-3'-yl}-benzamide |
| 179 | 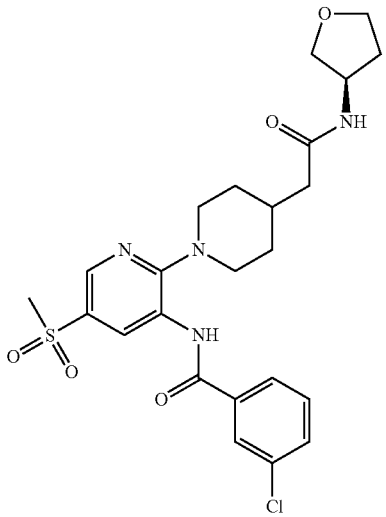 [SMILES: CS(=O)(=O)c1cnc(N2CCC(CC(=O)N[C@@H]3CCOC3)CC2)c(NC(=O)c2cccc(Cl)c2)c1] | 3-Chloro-N-(5'-methanesulfonyl-4-{[(R)-(tetrahydro-furan-3-yl)carbamoyl]-methyl}-3,4,5,6-tetrahydro-2H-[1,2']bipyridinyl-3'-yl)-benzamide |
| 180 | 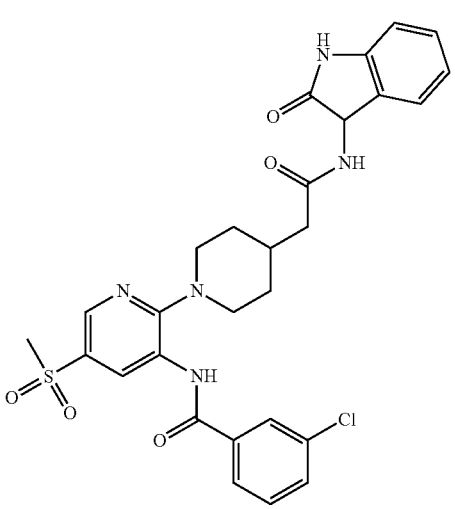 [SMILES: CS(=O)(=O)c1cnc(N2CCC(CC(=O)NC3C(=O)Nc4ccccc43)CC2)c(NC(=O)c2cccc(Cl)c2)c1] | 3-Chloro-N-{5'-methanesulfonyl-4-[(2-oxo-2,3-dihydro-1H-indol-3-ylcarbamoyl)-methyl]-3,4,5,6-tetrahydro-2H-[1,2']bipyridinyl-3'-yl}-benzamide |

TABLE 1-continued

| Cpd # | Structure | Name |
|---|---|---|
| 181 | 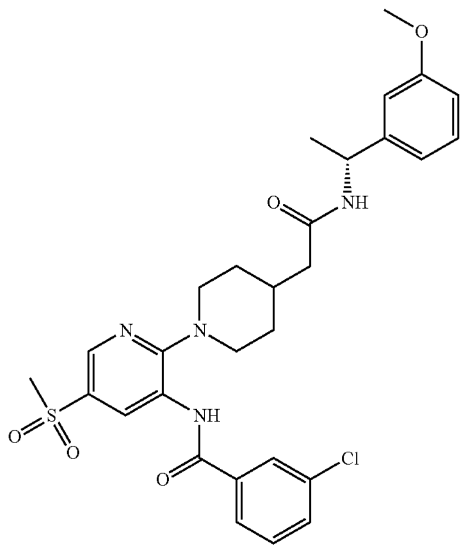 [SMILES: COc1cccc([C@@H](C)NC(=O)CC2CCN(c3ncc(S(C)(=O)=O)cc3NC(=O)c3cccc(Cl)c3)CC2)c1] | 3-Chloro-N-(5'-methanesulfonyl-4-{[(R)-1-(3-methoxy-phenyl)-ethylcarbamoyl]-methyl}-3,4,5,6-tetrahydro-2H-[1,2']bipyridinyl-3'-yl)-benzamide |
| 182 | 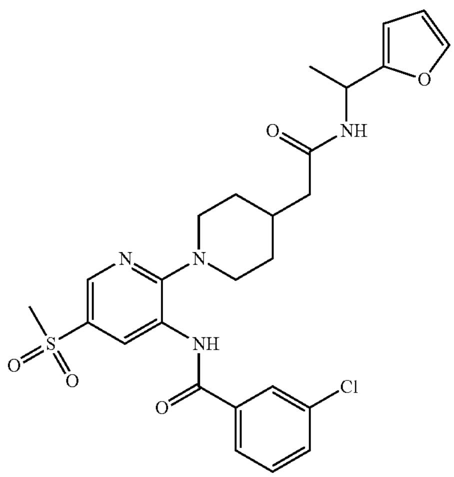 [SMILES: CC(NC(=O)CC1CCN(c2ncc(S(C)(=O)=O)cc2NC(=O)c2cccc(Cl)c2)CC1)c1ccco1] | 3-Chloro-N-{4-[(1-furan-2-yl-ethylcarbamoyl)-methyl]-5'-methanesulfonyl-3,4,5,6-tetrahydro-2H-[1,2']bipyridinyl-3'-yl}-benzamide |
| 183 | 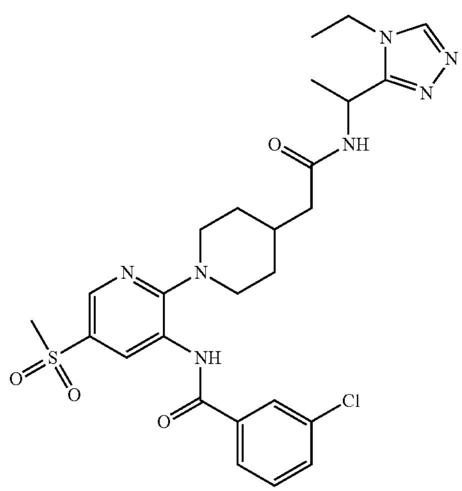 [SMILES: CCn1cnnc1C(C)NC(=O)CC1CCN(c2ncc(S(C)(=O)=O)cc2NC(=O)c2cccc(Cl)c2)CC1] | 3-Chloro-N-(4-{[1-(4-ethyl-4H-[1,2,4]triazol-3-yl)-ethylcarbamoyl]-methyl}-5'-methanesulfonyl-3,4,5,6-tetrahydro-2H-[1,2']bipyridinyl-3'-yl)-benzamide |

TABLE 1-continued
| Cpd # | Structure | Name |
|---|---|---|
| 184 | 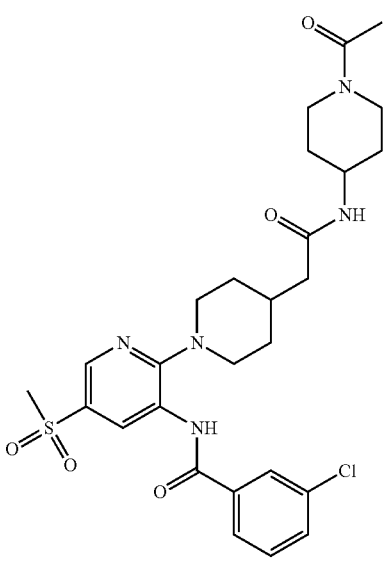 [SMILES: CC(=O)N1CCC(NC(=O)CC2CCN(c3ncc(S(C)(=O)=O)cc3NC(=O)c3cccc(Cl)c3)CC2)CC1] | N-{4-[(1-Acetyl-piperidin-4-ylcarbamoyl)-methyl]-5'-methanesulfonyl-3,4,5,6-tetrahydro-2H-[1,2']bipyridinyl-3'-yl}-3-chloro-benzamide |
| 185 | 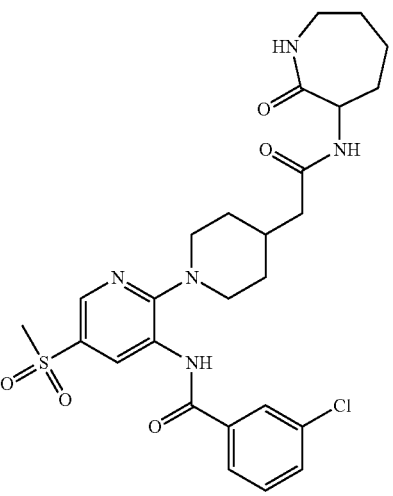 [SMILES: CS(=O)(=O)c1cnc(N2CCC(CC(=O)NC3CCCCNC3=O)CC2)c(NC(=O)c2cccc(Cl)c2)c1] | 3-Chloro-N-{5'-methanesulfonyl-4-[(2-oxo-azepan-3-ylcarbamoyl)-methyl]-3,4,5,6-tetrahydro-2H-[1,2']bipyridinyl-3'-yl}-benzamide |
| 186 | 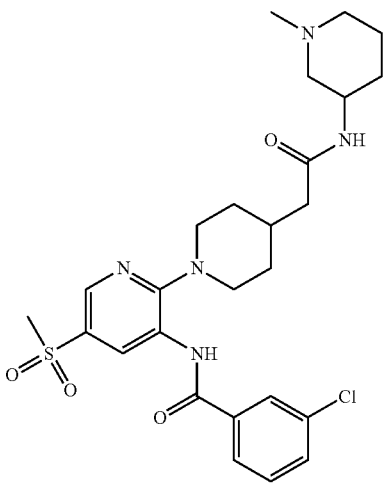 [SMILES: CN1CCCC(NC(=O)CC2CCN(c3ncc(S(C)(=O)=O)cc3NC(=O)c3cccc(Cl)c3)CC2)C1] | 3-Chloro-N-{5'-methanesulfonyl-4-[(1-methyl-piperidin-3-ylcarbamoyl)-methyl]-3,4,5,6-tetrahydro-2H-[1,2']bipyridinyl-3'-yl}-benzamide |

TABLE 1-continued
| Cpd # | Structure | Name |
|---|---|---|
| 187 | 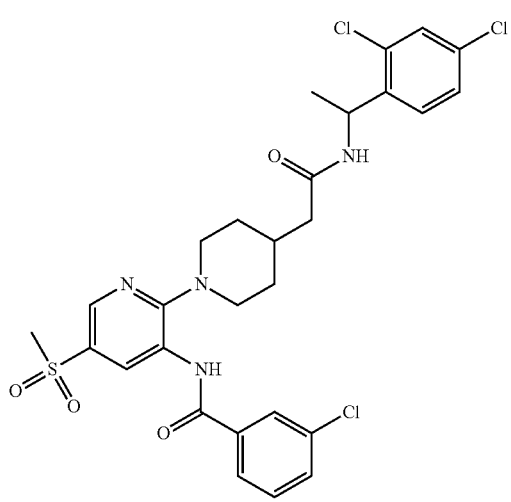 [SMILES: CC(NC(=O)CC1CCN(c2ncc(S(C)(=O)=O)cc2NC(=O)c2cccc(Cl)c2)CC1)c1ccc(Cl)cc1Cl] | 3-Chloro-N-(4-{[1-(2,4-dichloro-phenyl)-ethylcarbamoyl]-methyl}-5'-methanesulfonyl-3,4,5,6-tetrahydro-2H-[1,2']bipyridinyl-3'-yl)-benzamide |
| 188 | 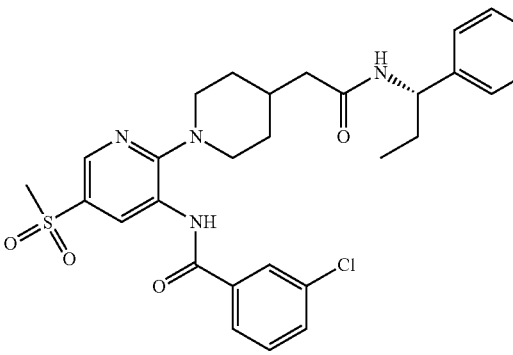 | 3-Chloro-N-{5'-methanesulfonyl-4-[((S)-1-phenyl-propylcarbamoyl)-methyl]-3,4,5,6-tetrahydro-2H-[1,2']bipyridinyl-3'-yl}-benzamide |
| 189 | 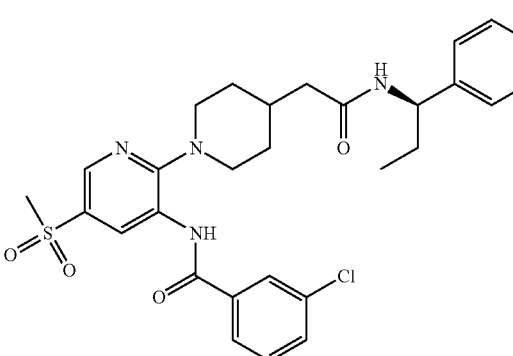 | 3-Chloro-N-{5'-methanesulfonyl-4-[((R)-1-phenyl-propylcarbamoyl)-methyl]-3,4,5,6-tetrahydro-2H-[1,2']bipyridinyl-3'-yl)-benzamide |

TABLE 1-continued

| Cpd # | Structure | Name |
|---|---|---|
| 190 | 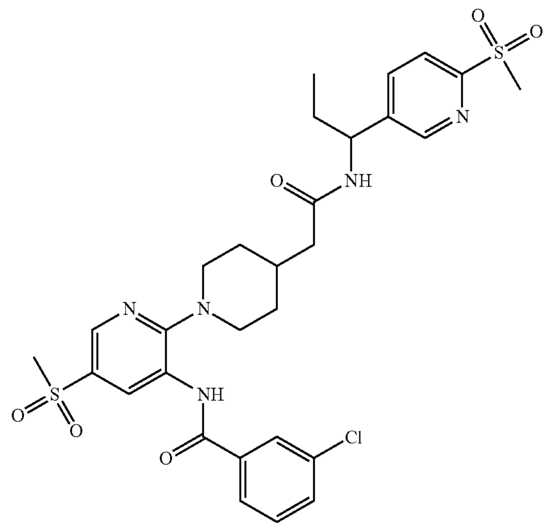 [SMILES: CCC(NC(=O)CC1CCN(c2ncc(S(C)(=O)=O)cc2NC(=O)c2cccc(Cl)c2)CC1)c1ccc(S(C)(=O)=O)nc1] | 3-Chloro-N-(5'-methanesulfonyl-4-{[1-(6-methanesulfonyl-pyridin-3-yl)-propylcarbamoyl]-methyl}-3,4,5,6-tetrahydro-2H-[1,2']bipyridinyl-3'-yl)-benzamide |
| 191 | 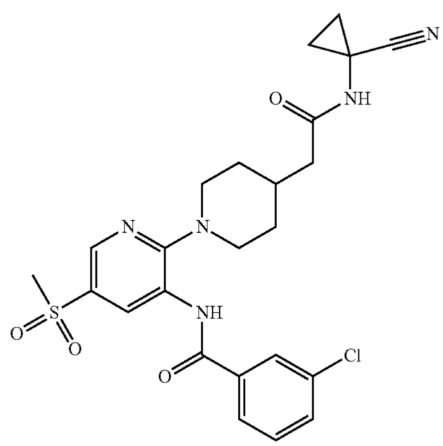 [SMILES: CS(=O)(=O)c1cnc(N2CCC(CC(=O)NC3(C#N)CC3)CC2)c(NC(=O)c2cccc(Cl)c2)c1] | 3-Chloro-N-{4-[(1-cyano-cyclopropylcarbamoyl)-methyl]-5'-methanesulfonyl-3,4,5,6-tetrahydro-2H-[1,2']bipyridinyl-3'-yl}-benzamide |
| 192 | 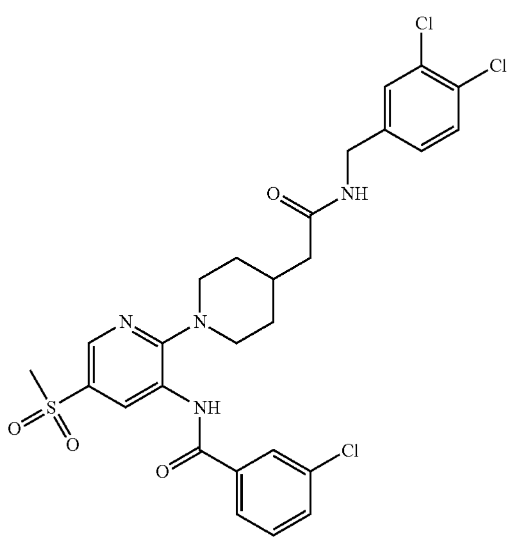 [SMILES: CS(=O)(=O)c1cnc(N2CCC(CC(=O)NCc3ccc(Cl)c(Cl)c3)CC2)c(NC(=O)c2cccc(Cl)c2)c1] | 3-Chloro-N-{4-[(3,4-dichloro-benzylcarbamoyl)-methyl]-5'-methanesulfonyl-3,4,5,6-tetrahydro-2H-[1,2']bipyridinyl-3'-yl}-benzamide |

TABLE 1-continued
| Cpd # | Structure | Name |
|---|---|---|
| 193 | 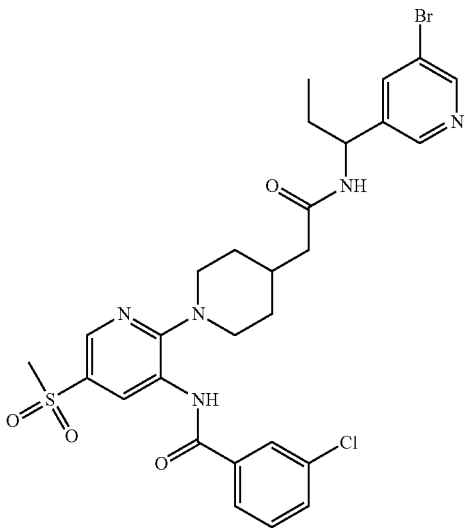 [SMILES: CCC(NC(=O)CC1CCN(c2ncc(S(C)(=O)=O)cc2NC(=O)c2cccc(Cl)c2)CC1)c1cncc(Br)c1] | N-(4-{[1-(5-Bromo-pyridin-3-yl)-propylcarbamoyl]-methyl}-5'-methanesulfonyl-3,4,5,6-tetrahydro-2H-[1,2']bipyridinyl-3'-yl)-3-chloro-benzamide |
| 194 | 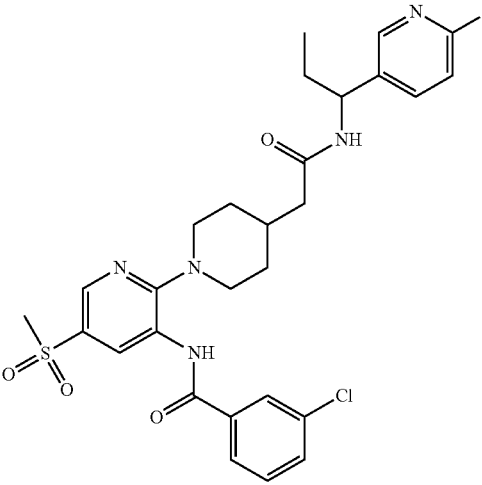 | N-(4-{[1-(6-Bromo-pyridin-3-yl)-propylcarbamoyl]-methyl}-5'-methanesulfonyl-3,4,5,6-tetrahydro-2H-[1,2']bipyridinyl-3'-yl)-3-chloro-benzamide |
| 195 | 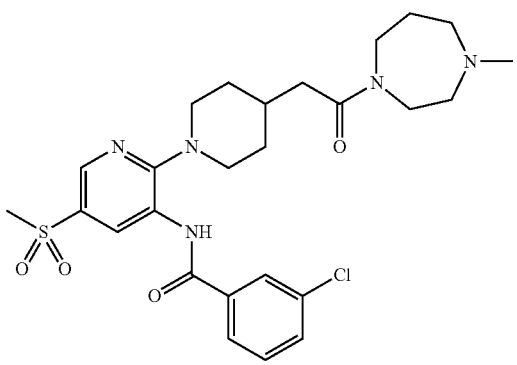 | 3-Chloro-N-{5'-methanesulfonyl-4-[2-(4-methyl-[1,4]diazepan-1-yl)-2-oxo-ethyl]-3,4,5,6-tetrahydro-2H-[1,2']bipyridinyl-3'-yl}-benzamide |

TABLE 1-continued

| Cpd # | Structure | Name |
|---|---|---|
| 196 | 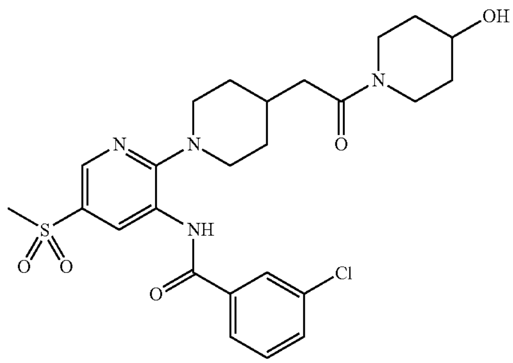 [SMILES: CS(=O)(=O)c1cnc(N2CCC(CC(=O)N3CCC(O)CC3)CC2)c(NC(=O)c2cccc(Cl)c2)c1] | 3-Chloro-N-{4-[2-(4-hydroxy-piperidin-1-yl)-2-oxo-ethyl]-5'-methanesulfonyl-3,4,5,6-tetrahydro-2H-[1,2']bipyridinyl-3'-yl}-benzamide |
| 197 | 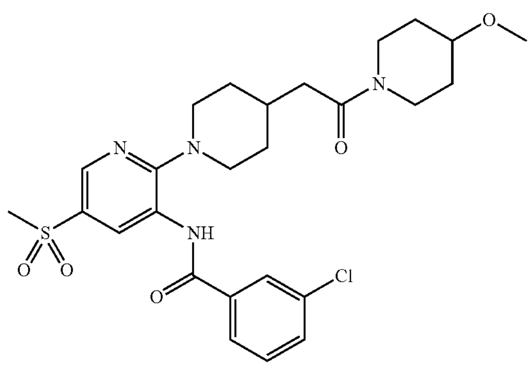 | 3-Chloro-N-{5'-methanesulfonyl-4-[2-(4-methoxy-piperidin-1-yl)-2-oxo-ethyl]-3,4,5,6-tetrahydro-2H-[1,2']bipyridinyl-3'-yl}-benzamide |
| 198 | 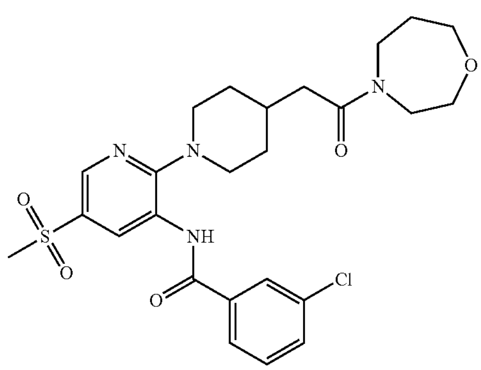 [SMILES: CS(=O)(=O)c1cnc(N2CCC(CC(=O)N3CCCOCC3)CC2)c(NC(=O)c2cccc(Cl)c2)c1] | 3-Chloro-N-[5'-methanesulfonyl-4-(2-[1,4]oxazepan-4-yl-2-oxo-ethyl)-3,4,5,6-tetrahydro-2H-[1,2']bipyridinyl-3'-yl]-benzamide |
| 199 | 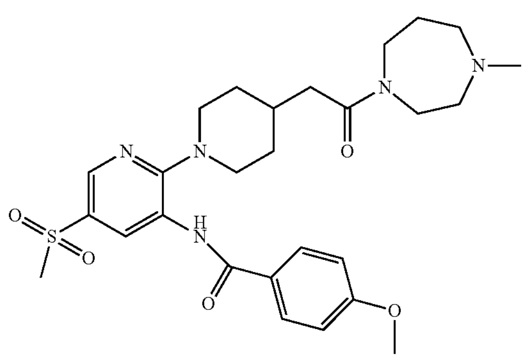 [SMILES: COc1ccc(C(=O)Nc2cc(S(C)(=O)=O)cnc2N2CCC(CC(=O)N3CCCN(C)CC3)CC2)cc1] | N-{5'-Methanesulfonyl-4-[2-(4-methyl-[1,4]diazepan-1-yl)-2-oxo-ethyl]-3,4,5,6-tetrahydro-2H-[1,2']bipyridinyl-3'-yl}-4-methoxy-benzamide |

TABLE 1-continued

| Cpd # | Structure | Name |
|---|---|---|
| 200 | 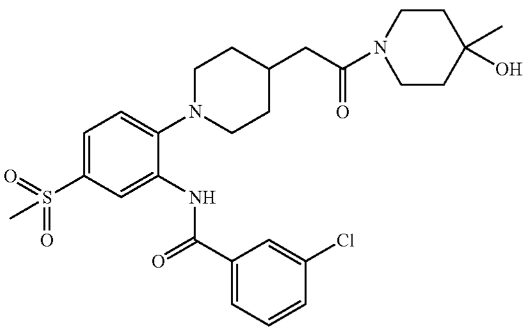 [SMILES: CC1(O)CCN(C(=O)CC2CCN(c3ccc(S(C)(=O)=O)cc3NC(=O)c3cccc(Cl)c3)CC2)CC1] | 3-Chloro-N-(2-{4-[2-(4-hydroxy-4-methyl-piperidin-1-yl)-2-oxo-ethyl]-piperidin-1-yl}-5-methanesulfonyl-phenyl)-benzamide |
| 201 | 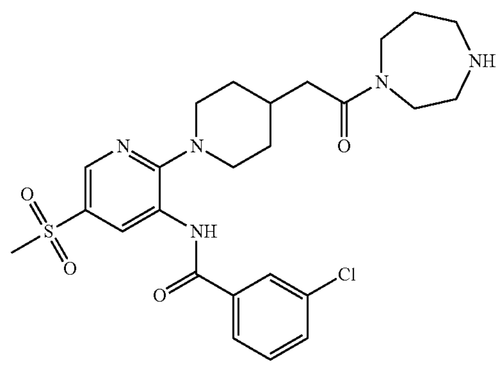 [SMILES: CS(=O)(=O)c1cnc(N2CCC(CC(=O)N3CCCNCC3)CC2)c(NC(=O)c2cccc(Cl)c2)c1] | 3-Chloro-N-[4-(2-[1,4]diazepan-1-yl-2-oxo-ethyl)-5'-methanesulfonyl-3,4,5,6-tetrahydro-2H-[1,2']bipyridinyl-3'-yl]-benzamide |
| 202 | 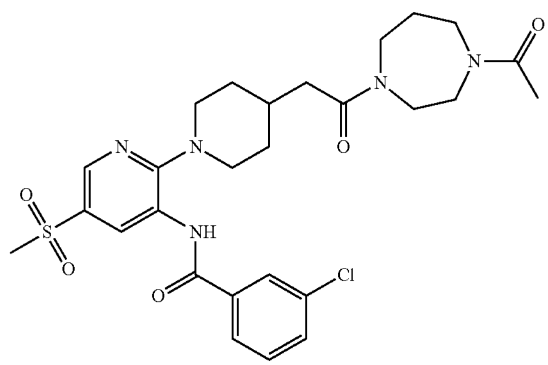 [SMILES: CC(=O)N1CCCN(C(=O)CC2CCN(c3ncc(S(C)(=O)=O)cc3NC(=O)c3cccc(Cl)c3)CC2)CC1] | N-{4-[2-(4-Acetyl-[1,4]diazepan-1-yl)-2-oxo-ethyl]-5'-methanesulfonyl-3,4,5,6-tetrahydro-2H-[1,2']bipyridinyl-3'-yl}-3-chloro-benzamide |
| 203 | 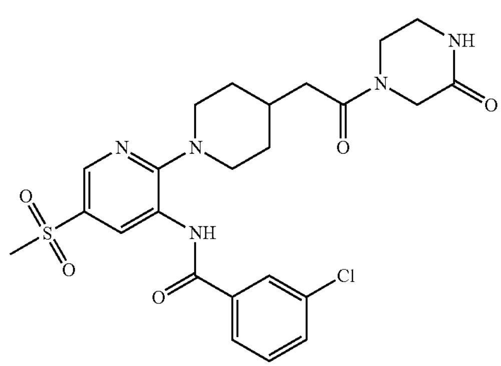 [SMILES: CS(=O)(=O)c1cnc(N2CCC(CC(=O)N3CCNC(=O)C3)CC2)c(NC(=O)c2cccc(Cl)c2)c1] | 3-Chloro-N-{5'-methanesulfonyl-4-[2-oxo-2-(3-oxo-piperazin-1-yl)-ethyl]-3,4,5,6-tetrahydro-2H-[1,2']bipyridinyl-3'-yl}-benzamide |

TABLE 1-continued

| Cpd # | Structure | Name |
|---|---|---|
| 204 | 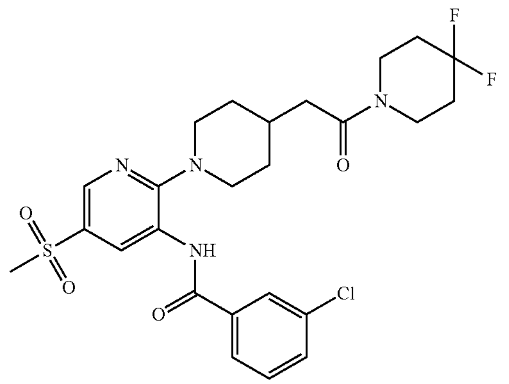 [SMILES: CS(=O)(=O)c1cnc(N2CCC(CC(=O)N3CCC(F)(F)CC3)CC2)c(NC(=O)c2cccc(Cl)c2)c1] | 3-Chloro-N-{4-[2-(4,4-difluoro-piperidin-1-yl)-2-oxo-ethyl]-5'-methanesulfonyl-3,4,5,6-tetrahydro-2H-[1,2']bipyridinyl-3'-yl}-benzamide |
| 205 | 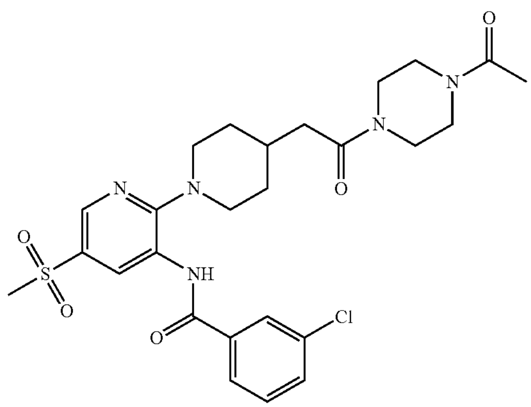 [SMILES: CC(=O)N1CCN(C(=O)CC2CCN(c3ncc(S(C)(=O)=O)cc3NC(=O)c3cccc(Cl)c3)CC2)CC1] | N-{4-[2-(4-Acetyl-piperazin-1-yl)-2-oxo-ethyl]-5'-methanesulfonyl-3,4,5,6-tetrahydro-2H-[1,2']bipyridinyl-3'-yl}-3-chloro-benzamide |
| 206 | 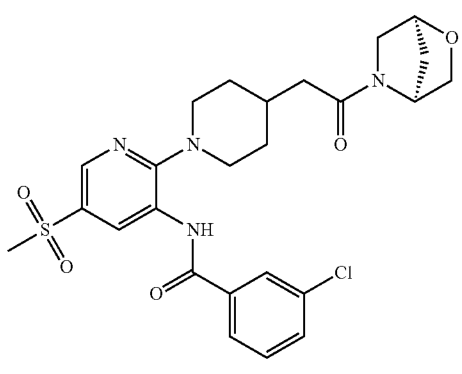 [SMILES: CS(=O)(=O)c1cnc(N2CCC(CC(=O)N3C[C@@H]4C[C@H]3CO4)CC2)c(NC(=O)c2cccc(Cl)c2)c1] | 3-Chloro-N-[5'-methanesulfonyl-4-((1S,4S)-2-2-oxa-5-aza-bicyclo[2.2.1]hept-5-yl-2-oxo-ethyl)-3,4,5,6-tetrahydro-2H-[1,2']bipyridinyl-3'-yl]-benzamide |
| 207 | 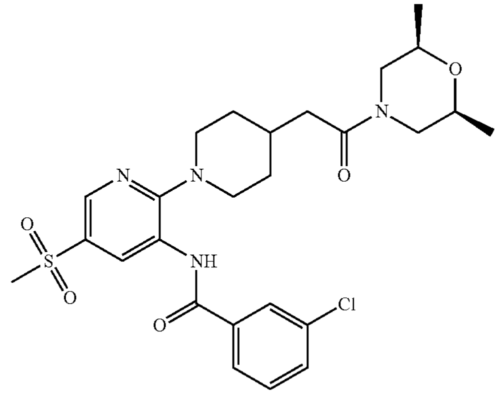 | 3-Chloro-N-{4-[2-((2R,6S)-2,6-dimethyl-morpholin-4-yl)-2-oxo-ethyl]-5'-methanesulfonyl-3,4,5,6-tetrahydro-2H-[1,2']bipyridinyl-3'-yl}-benzamide |

| Cpd # | Structure | Name |
|---|---|---|
| 208 | 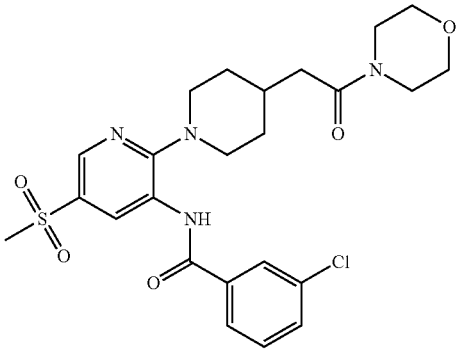 [SMILES: CS(=O)(=O)c1cnc(N2CCC(CC(=O)N3CCOCC3)CC2)c(NC(=O)c2cccc(Cl)c2)c1] | 3-Chloro-N-[5'-methanesulfonyl-4-(2-morpholin-4-yl-2-oxo-ethyl)-3,4,5,6-tetrahydro-2H-[1,2']bipyridinyl-3'-yl]-benzamide |
| 209 | 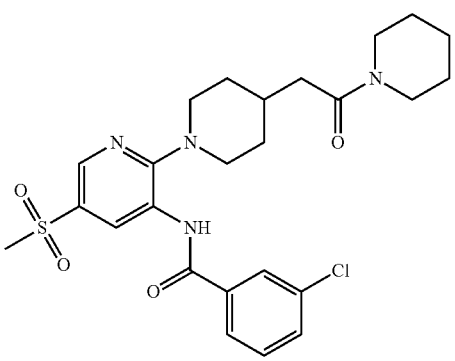 [SMILES: CS(=O)(=O)c1cnc(N2CCC(CC(=O)N3CCCCC3)CC2)c(NC(=O)c2cccc(Cl)c2)c1] | 3-Chloro-N-[5'-methanesulfonyl-4-(2-oxo-2-piperidin-1-yl-ethyl)-3,4,5,6-tetrahydro-2H-[1,2']bipyridinyl-3'-yl]-benzamide |
| 210 | 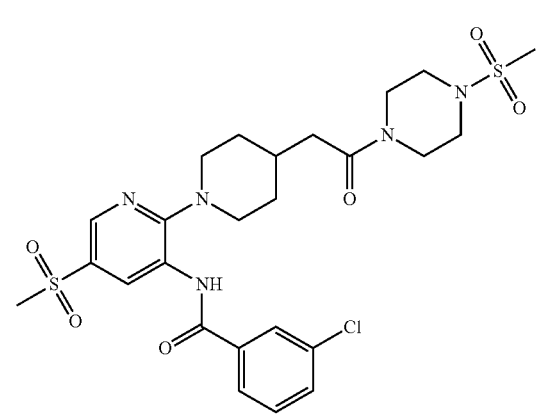 | 3-Chloro-N-{5'-methanesulfonyl-4-[2-(4-methanesulfonyl-piperazin-1-yl)-2-oxo-ethyl]-3,4,5,6-tetrahydro-2H-[1,2']bipyridinyl-3'-yl}-benzamide |
| 211 | 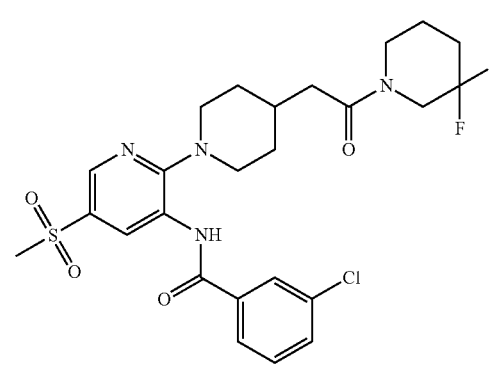 | 3-Chloro-N-{4-[2-(3,3-difluoro-piperidin-1-yl)-2-oxo-ethyl]-5'-methanesulfonyl-3,4,5,6-tetrahydro-2H-[1,2']bipyridinyl-3'-yl}-benzamide |

TABLE 1-continued

| Cpd # | Structure | Name |
|---|---|---|
| 212 | 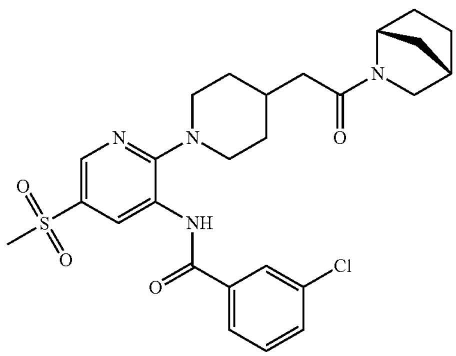 [SMILES: CS(=O)(=O)c1cnc(N2CCC(CC(=O)N3C[C@H]4CC[C@@H]3C4)CC2)c(NC(=O)c2cccc(Cl)c2)c1] | N-[4-((1R,4S)-2-2-Aza-bicyclo[2.2.1]hept-2-yl-2-oxo-ethyl)-5'-methanesulfonyl-3,4,5,6-tetrahydro-2H-[1,2']bipyridinyl-3'-yl]-3-chloro-benzamide |
| 213 | 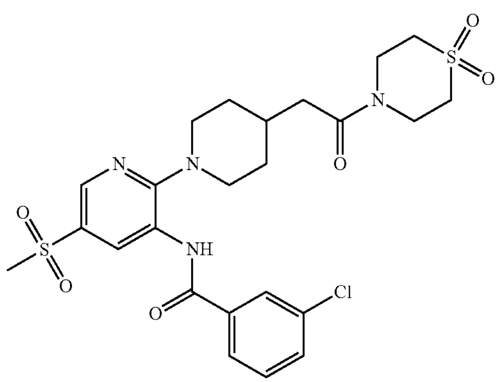 [SMILES: CS(=O)(=O)c1cnc(N2CCC(CC(=O)N3CCS(=O)(=O)CC3)CC2)c(NC(=O)c2cccc(Cl)c2)c1] | 3-Chloro-N-{4-[2-(1,1-dioxo-1lambda*6*-thiomorpholin-4-yl)-2-oxo-ethyl]-5'-methanesulfonyl-3,4,5,6-tetrahydro-2H-[1,2']bipyridinyl-3'-yl}-benzamide |
| 214 | 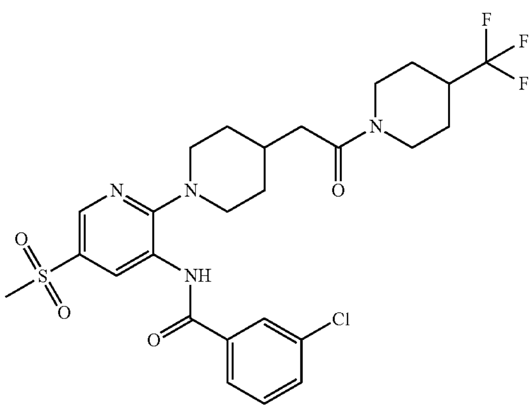 [SMILES: CS(=O)(=O)c1cnc(N2CCC(CC(=O)N3CCC(C(F)(F)F)CC3)CC2)c(NC(=O)c2cccc(Cl)c2)c1] | 3-Chloro-N-{5'-methanesulfonyl-4-[2-oxo-2-(4-trifluoromethyl-piperidin-1-yl)-ethyl]-3,4,5,6-tetrahydro-2H-[1,2']bipyridinyl-3'-yl}-benzamide |
| 215 | 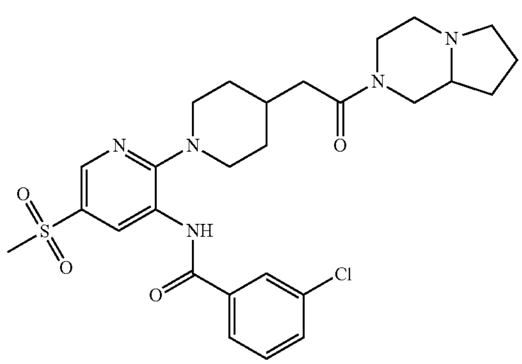 [SMILES: CS(=O)(=O)c1cnc(N2CCC(CC(=O)N3CCN4CCCC4C3)CC2)c(NC(=O)c2cccc(Cl)c2)c1] | 3-Chloro-N-{4-[2-(hexahydro-pyrrolo[1,2-a]pyrazin-2-yl)-2-oxo-ethyl]-5'-methanesulfonyl-3,4,5,6-tetrahydro-2H-[1,2']bipyridinyl-3'-yl}-benzamide |

TABLE 1-continued

| Cpd # | Structure | Name |
|---|---|---|
| 216 | 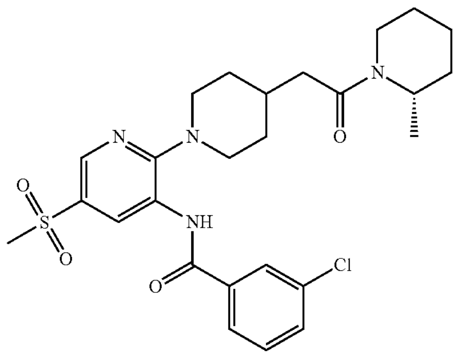 | 3-Chloro-N-{5'-methanesulfonyl-4-[2-((S)-2-methyl-piperidin-1-yl)-2-oxo-ethyl]-3,4,5,6-tetrahydro-2H-[1,2']bipyridinyl-3'-yl}-benzamide |
| 217 | 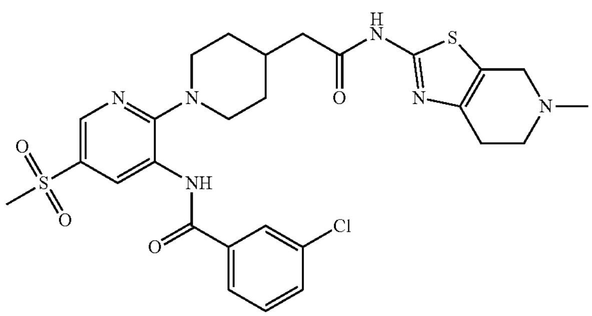 | 3-Chloro-N-{5'-methanesulfonyl-4-[(5-methyl-4,5,6,7-tetrahydro-thiazolo[5,4-c]pyridin-2-ylcarbamoyl)-methyl]-3,4,5,6-tetrahydro-2H-[1,2']bipyridinyl-3'-yl}-benzamide |
| 218 | 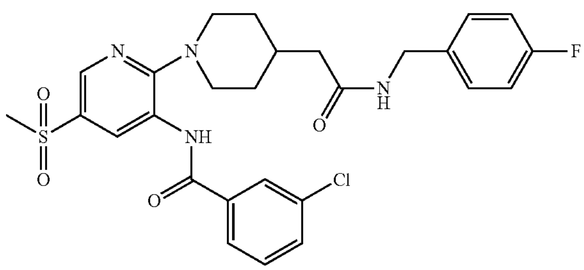 [SMILES: CS(=O)(=O)c1cnc(N2CCC(CC(=O)NCc3ccc(F)cc3)CC2)c(NC(=O)c2cccc(Cl)c2)c1] | 3-Chloro-N-{4-[(4-fluoro-benzylcarbamoyl)-methyl]-5'-methanesulfonyl-3,4,5,6-tetrahydro-2H-[1,2']bipyridinyl-3'-yl}-benzamide |
| 219 | 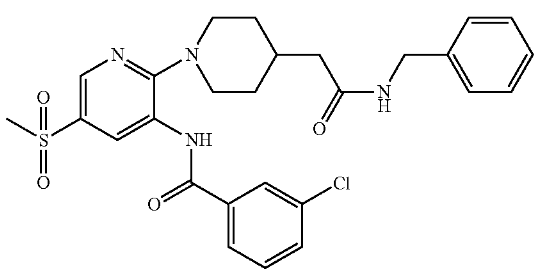 [SMILES: CS(=O)(=O)c1cnc(N2CCC(CC(=O)NCc3ccccc3)CC2)c(NC(=O)c2cccc(Cl)c2)c1] | N-[4-(Benzylcarbamoyl-methyl)-5'-methanesulfonyl-3,4,5,6-tetrahydro-2H-[1,2']bipyridinyl-3'-yl]-3-chloro-benzamide |
| 220 | 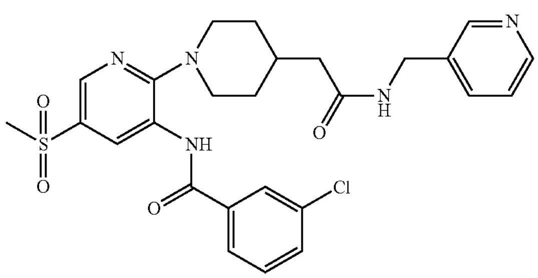 [SMILES: CS(=O)(=O)c1cnc(N2CCC(CC(=O)NCc3cccnc3)CC2)c(NC(=O)c2cccc(Cl)c2)c1] | 3-Chloro-N-(5'-methanesulfonyl-4-{[(pyridin-3-ylmethyl)-carbamoyl]-methyl}-3,4,5,6-tetrahydro-2H-[1,2']bipyridinyl-3'-yl)-benzamide |

TABLE 1-continued

| Cpd # | Structure | Name |
|---|---|---|
| 221 | 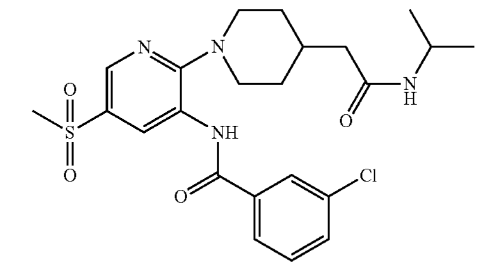 [SMILES: CC(C)NC(=O)CC1CCN(c2ncc(S(C)(=O)=O)cc2NC(=O)c2cccc(Cl)c2)CC1] | 3-Chloro-N-[4-(isopropylcarbamoyl-methyl)-5'-methanesulfonyl-3,4,5,6-tetrahydro-2H-[1,2']bipyridinyl-3'-yl]-benzamide |
| 222 | 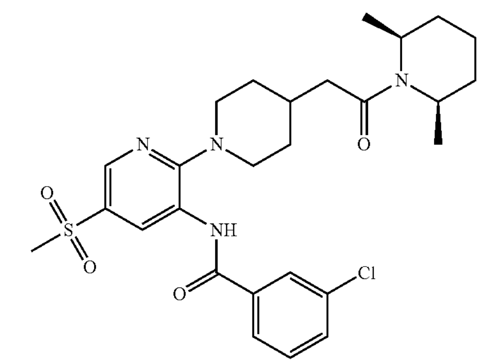 [SMILES: C[C@@H]1CCC[C@H](C)N1C(=O)CC1CCN(c2ncc(S(C)(=O)=O)cc2NC(=O)c2cccc(Cl)c2)CC1] | 3-Chloro-N-{4-[2-((2S,6R)-2,6-dimethyl-piperidin-1-yl)-2-oxo-ethyl]-5'-methanesulfonyl-3,4,5,6-tetrahydro-2H-[1,2']bipyridinyl-3'-yl}-benzamide |
| 223 | 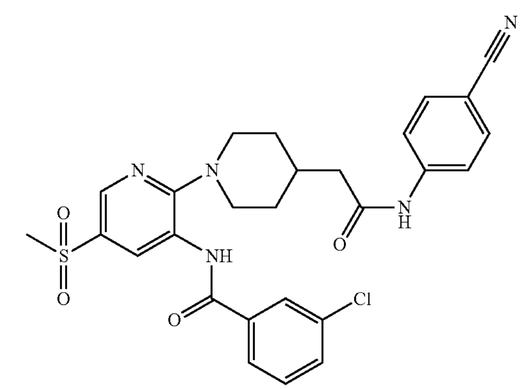 [SMILES: CS(=O)(=O)c1cnc(N2CCC(CC(=O)Nc3ccc(C#N)cc3)CC2)c(NC(=O)c2cccc(Cl)c2)c1] | 3-Chloro-N-{4-[(4-cyano-phenylcarbamoyl)-methyl]-5'-methanesulfonyl-3,4,5,6-tetrahydro-2H-[1,2']bipyridinyl-3'-yl}-benzamide |
| 224 | 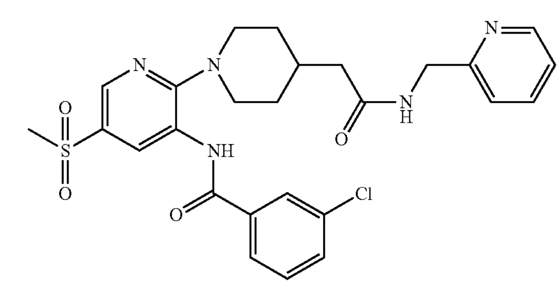 [SMILES: CS(=O)(=O)c1cnc(N2CCC(CC(=O)NCc3ccccn3)CC2)c(NC(=O)c2cccc(Cl)c2)c1] | 3-Chloro-N-(5'-methanesulfonyl-4-{[(pyridin-2-ylmethyl)-carbamoyl]-methyl}-3,4,5,6-tetrahydro-2H-[1,2']bipyridinyl-3'-yl)-benzamide |
| 225 | 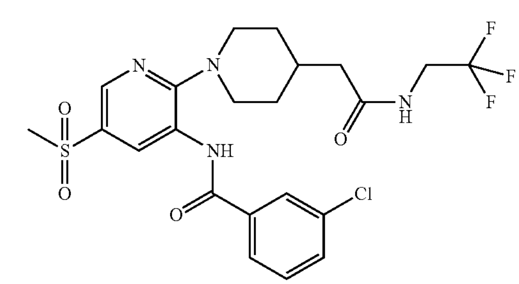 [SMILES: CS(=O)(=O)c1cnc(N2CCC(CC(=O)NCC(F)(F)F)CC2)c(NC(=O)c2cccc(Cl)c2)c1] | 3-Chloro-N-{5'-methanesulfonyl-4-[(2,2,2-trifluoro-ethylcarbamoyl)-methyl]-3,4,5,6-tetrahydro-2H-[1,2']bipyridinyl-3'-yl}-benzamide |

TABLE 1-continued

| Cpd # | Structure | Name |
|---|---|---|
| 226 | 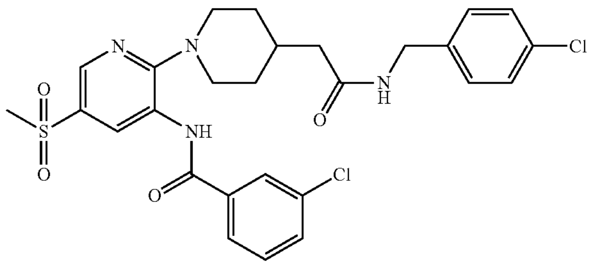 [SMILES: CS(=O)(=O)c1cnc(N2CCC(CC(=O)NCc3ccc(Cl)cc3)CC2)c(NC(=O)c2cccc(Cl)c2)c1] | 3-Chloro-N-{4-[(4-chloro-benzylcarbamoyl)-methyl]-5'-methanesulfonyl-3,4,5,6-tetrahydro-2H-[1,2']bipyridinyl-3'-yl}-benzamide |
| 227 | 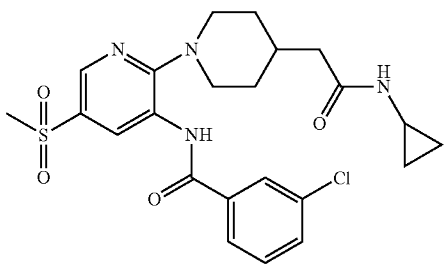 [SMILES: CS(=O)(=O)c1cnc(N2CCC(CC(=O)NC3CC3)CC2)c(NC(=O)c2cccc(Cl)c2)c1] | 3-Chloro-N-(4-cyclopropylcarbamoylmethyl-5'-methanesulfonyl-3,4,5,6-tetrahydro-2H-[1,2']bipyridinyl-3'-yl)-benzamide |
| 228 | 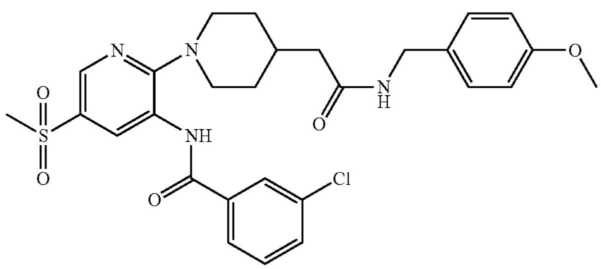 | 3-Chloro-N-{5'-methanesulfonyl-4-[(4-methoxy-benzylcarbamoyl)-methyl]-3,4,5,6-tetrahydro-2H-[1,2']bipyridinyl-3'-yl}-benzamide |
| 229 | 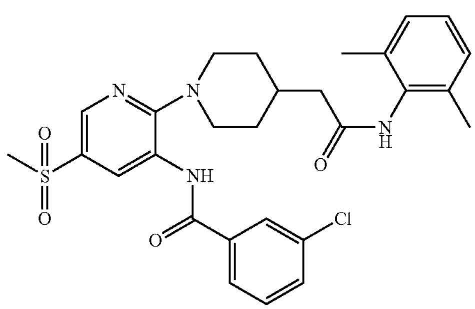 | 3-Chloro-N-{4-[(2,6-dimethyl-phenylcarbamoyl)-methyl]-5'-methanesulfonyl-3,4,5,6-tetrahydro-2H-[1,2']bipyridinyl-3'-yl}-benzamide |
| 230 | 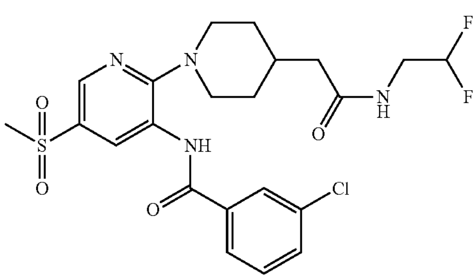 [SMILES: CS(=O)(=O)c1cnc(N2CCC(CC(=O)NCC(F)F)CC2)c(NC(=O)c2cccc(Cl)c2)c1] | 3-Chloro-N-{4-[(2,2-difluoro-ethylcarbamoyl)-methyl]-5'-methanesulfonyl-3,4,5,6-tetrahydro-2H-[1,2']bipyridinyl-3'-yl}-benzamide |

| Cpd # | Structure | Name |
|---|---|---|
| 231 | 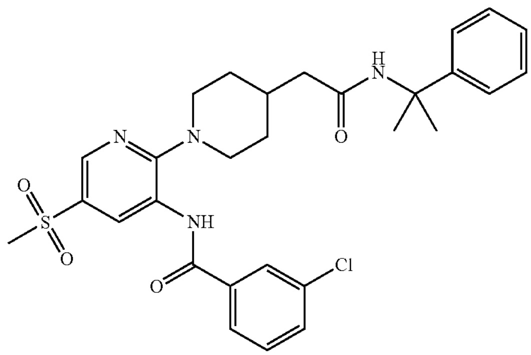 [SMILES: CC(C)(NC(=O)CC1CCN(c2ncc(S(C)(=O)=O)cc2NC(=O)c2cccc(Cl)c2)CC1)c1ccccc1] | 3-Chloro-N-{5'-methanesulfonyl-4-[(1-methyl-1-phenyl-ethylcarbamoyl)-methyl]-3,4,5,6-tetrahydro-2H-[1,2']bipyridinyl-3'-yl}-benzamide |
| 232 | 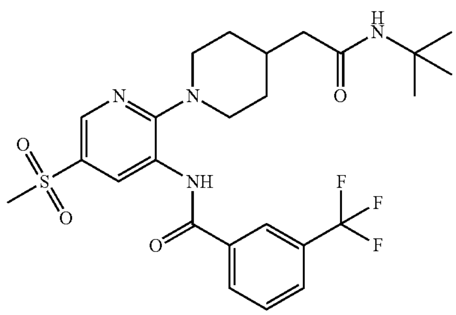 [SMILES: CC(C)(C)NC(=O)CC1CCN(c2ncc(S(C)(=O)=O)cc2NC(=O)c2cccc(C(F)(F)F)c2)CC1] | N-[4-(tert-Butylcarbamoyl-methyl)-5'-methanesulfonyl-3,4,5,6-tetrahydro-2H-[1,2']bipyridinyl-3'-yl]-3-trifluoromethyl-benzamide |
| 233 | 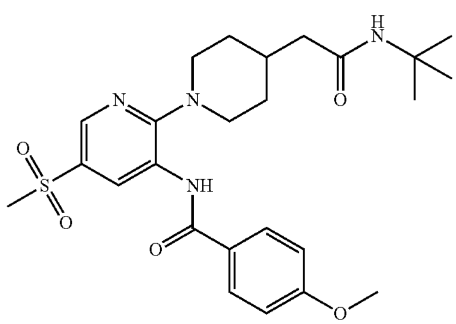 [SMILES: COc1ccc(C(=O)Nc2cc(S(C)(=O)=O)cnc2N2CCC(CC(=O)NC(C)(C)C)CC2)cc1] | N-[4-(tert-Butylcarbamoyl-methyl)-5'-methanesulfonyl-3,4,5,6-tetrahydro-2H-[1,2']bipyridinyl-3'-yl]-4-methoxy-benzamide |
| 234 | 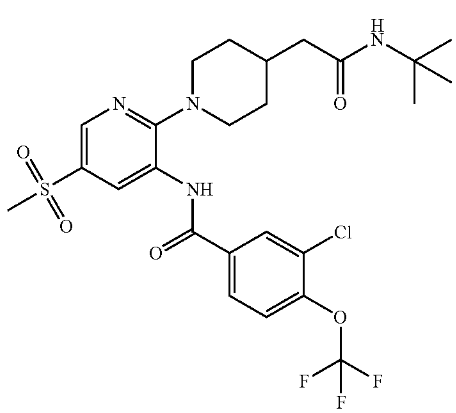 [SMILES: CC(C)(C)NC(=O)CC1CCN(c2ncc(S(C)(=O)=O)cc2NC(=O)c2ccc(OC(F)(F)F)c(Cl)c2)CC1] | N-[4-(tert-Butylcarbamoyl-methyl)-5'-methanesulfonyl-3,4,5,6-tetrahydro-2H-[1,2']bipyridinyl-3'-yl]-3-chloro-4-trifluoromethoxy-benzamide |

TABLE 1-continued

| Cpd # | Structure | Name |
|---|---|---|
| 235 | 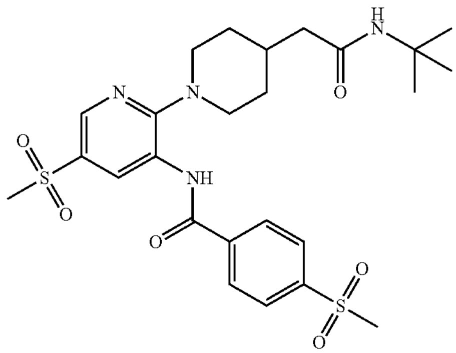 [SMILES: CC(C)(C)NC(=O)CC1CCN(c2ncc(S(C)(=O)=O)cc2NC(=O)c2ccc(S(C)(=O)=O)cc2)CC1] | N-[4-(tert-Butylcarbamoyl-methyl)-5'-methanesulfonyl-3,4,5,6-tetrahydro-2H-[1,2']bipyridinyl-3'-yl]-4-methanesulfonyl-benzamide |
| 236 | 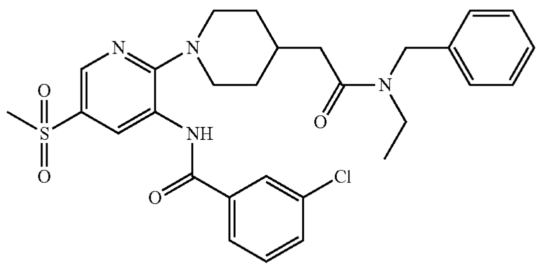 [SMILES: CCN(Cc1ccccc1)C(=O)CC1CCN(c2ncc(S(C)(=O)=O)cc2NC(=O)c2cccc(Cl)c2)CC1] | N-{4-[(Benzyl-ethyl-carbamoyl)-methyl]-5'-methanesulfonyl-3,4,5,6-tetrahydro-2H-[1,2']bipyridinyl-3'-yl}-3-chloro-benzamide |
| 237 | 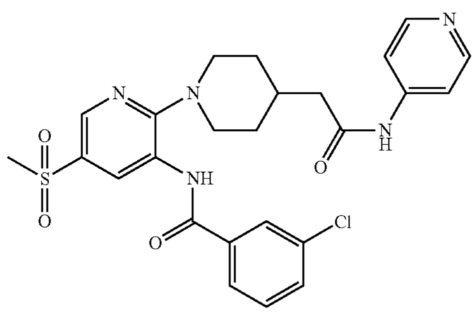 [SMILES: CS(=O)(=O)c1cnc(N2CCC(CC(=O)Nc3ccncc3)CC2)c(NC(=O)c2cccc(Cl)c2)c1] | 3-Chloro-N-[5'-methanesulfonyl-4-(pyridin-4-ylcarbamoylmethyl)-3,4,5,6-tetrahydro-2H-[1,2']bipyridinyl-3'-yl]-benzamide |
| 238 | 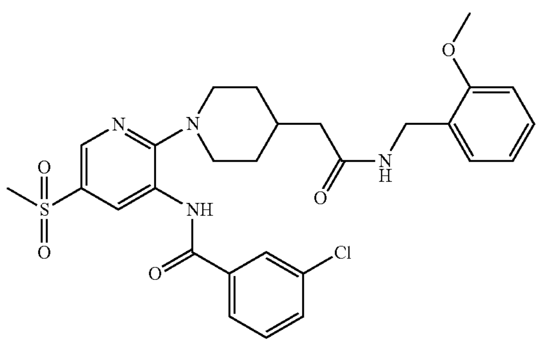 [SMILES: COc1ccccc1CNC(=O)CC1CCN(c2ncc(S(C)(=O)=O)cc2NC(=O)c2cccc(Cl)c2)CC1] | 3-Chloro-N-{5'-methanesulfonyl-4-[(2-methoxy-benzylcarbamoyl)-methyl]-3,4,5,6-tetrahydro-2H-[1,2']bipyridinyl-3'-yl}-benzamide |
| 239 | 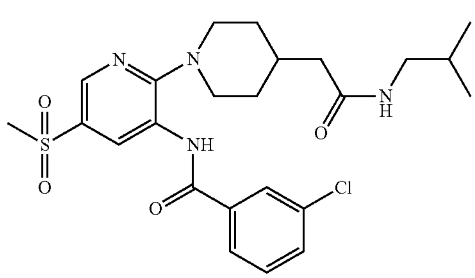 [SMILES: CC(C)CNC(=O)CC1CCN(c2ncc(S(C)(=O)=O)cc2NC(=O)c2cccc(Cl)c2)CC1] | 3-Chloro-N-[4-(isobutylcarbamoyl-methyl)-5'-methanesulfonyl-3,4,5,6-tetrahydro-2H-[1,2']bipyridinyl-3'-yl]-benzamide |

TABLE 1-continued

| Cpd # | Structure | Name |
|---|---|---|
| 240 | 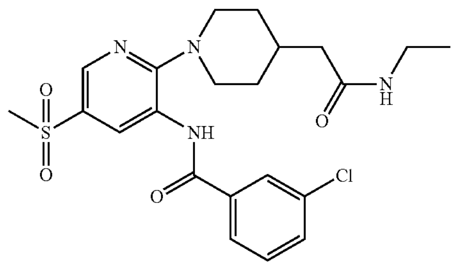 [SMILES: CCNC(=O)CC1CCN(c2ncc(S(C)(=O)=O)cc2NC(=O)c2cccc(Cl)c2)CC1] | 3-Chloro-N-(4-ethylcarbamoylmethyl-5'-methanesulfonyl-3,4,5,6-tetrahydro-2H-[1,2']bipyridinyl-3'-yl)-benzamide |
| 241 | 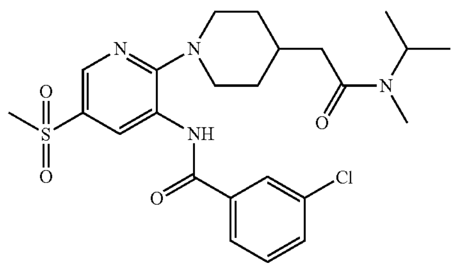 [SMILES: CC(C)N(C)C(=O)CC1CCN(c2ncc(S(C)(=O)=O)cc2NC(=O)c2cccc(Cl)c2)CC1] | 3-Chloro-N-{4-[(isopropyl-methyl-carbamoyl)-methyl]-5'-methanesulfonyl-3,4,5,6-tetrahydro-2H-[1,2']bipyridinyl-3'-yl}-benzamide |
| 242 | 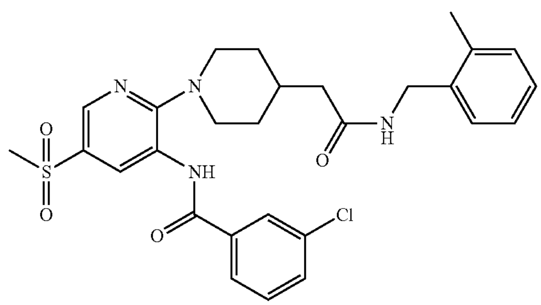 [SMILES: Cc1ccccc1CNC(=O)CC1CCN(c2ncc(S(C)(=O)=O)cc2NC(=O)c2cccc(Cl)c2)CC1] | 3-Chloro-N-{5'-methanesulfonyl-4-[(2-methyl-benzylcarbamoyl)-methyl]-3,4,5,6-tetrahydro-2H-[1,2']bipyridinyl-3'-yl}-benzamide |
| 243 | 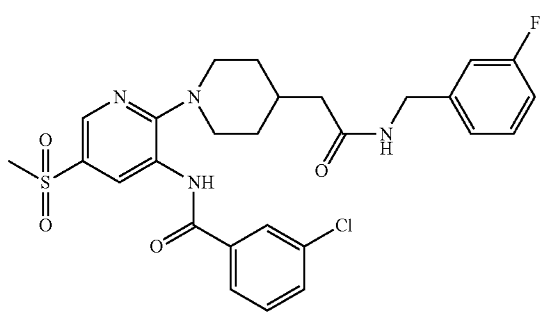 [SMILES: CS(=O)(=O)c1cnc(N2CCC(CC(=O)NCc3cccc(F)c3)CC2)c(NC(=O)c2cccc(Cl)c2)c1] | 3-Chloro-N-{4-[(3-fluoro-benzylcarbamoyl)-methyl]-5'-methanesulfonyl-3,4,5,6-tetrahydro-2H-[1,2']bipyridinyl-3'-yl}-benzamide |
| 244 | 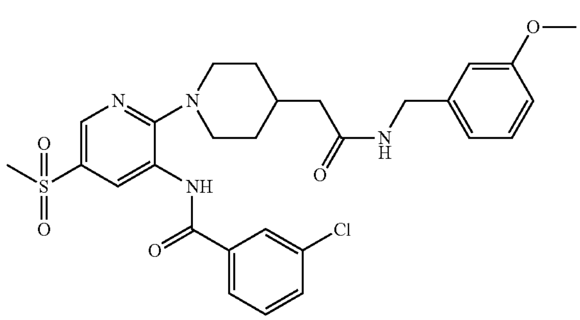 | 3-Chloro-N-{5'-methanesulfonyl-4-[(3-methoxy-benzylcarbamoyl)-methyl]-3,4,5,6-tetrahydro-2H-[1,2']bipyridinyl-3'-yl)-benzamide |

TABLE 1-continued

| Cpd # | Structure | Name |
|---|---|---|
| 245 | 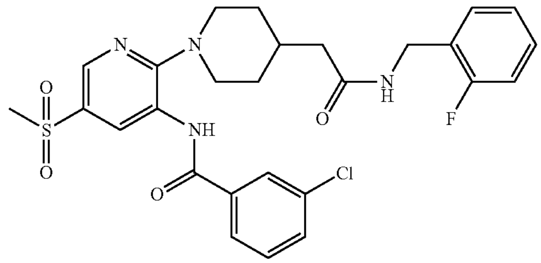 [SMILES: CS(=O)(=O)c1cnc(N2CCC(CC(=O)NCc3ccccc3F)CC2)c(NC(=O)c2cccc(Cl)c2)c1] | 3-Chloro-N-{4-[(2-fluoro-benzylcarbamoyl)-methyl]-5'-methanesulfonyl-3,4,5,6-tetrahydro-2H-[1,2']bipyridinyl-3'-yl}-benzamide |
| 246 | 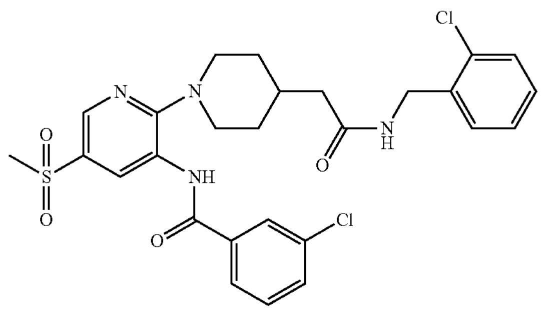 [SMILES: CS(=O)(=O)c1cnc(N2CCC(CC(=O)NCc3ccccc3Cl)CC2)c(NC(=O)c2cccc(Cl)c2)c1] | 3-Chloro-N-{4-[(2-chloro-benzylcarbamoyl)-methyl]-5'-methanesulfonyl-3,4,5,6-tetrahydro-2H-[1,2']bipyridinyl-3'-yl}-benzamide |
| 247 | 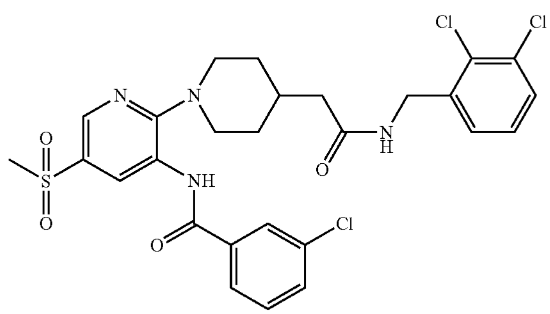 [SMILES: CS(=O)(=O)c1cnc(N2CCC(CC(=O)NCc3cccc(Cl)c3Cl)CC2)c(NC(=O)c2cccc(Cl)c2)c1] | 3-Chloro-N-{4-[(2,3-dichloro-benzylcarbamoyl)-methyl]-5'-methanesulfonyl-3,4,5,6-tetrahydro-2H-[1,2']bipyridinyl-3'-yl}-benzamide |
| 248 | 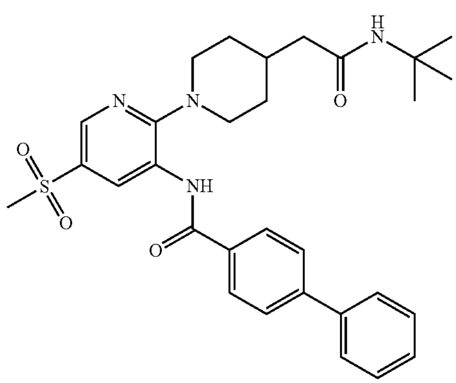 [SMILES: CC(C)(C)NC(=O)CC1CCN(c2ncc(S(C)(=O)=O)cc2NC(=O)c2ccc(-c3ccccc3)cc2)CC1] | Biphenyl-4-carboxylic acid [4-(tert-butylcarbamoyl-methyl)-5'-methanesulfonyl-3,4,5,6-tetrahydro-2H-[1,2']bipyridinyl-3'-yl]-amide |
| 249 | 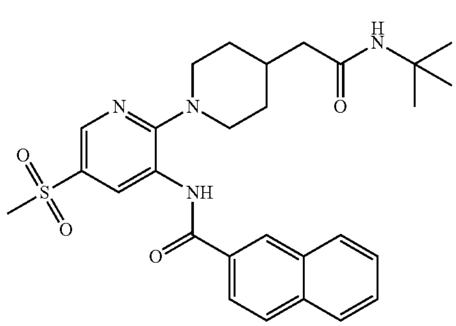 [SMILES: CC(C)(C)NC(=O)CC1CCN(c2ncc(S(C)(=O)=O)cc2NC(=O)c2ccc3ccccc3c2)CC1] | Naphthalene-2-carboxylic acid [4-(tert-butylcarbamoyl-methyl)-5'-methanesulfonyl-3,4,5,6-tetrahydro-2H-[1,2']bipyridinyl-3'-yl]-amide |

TABLE 1-continued

| Cpd # | Structure | Name |
|---|---|---|
| 250 | 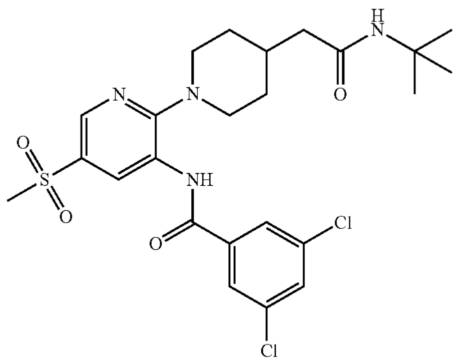 [SMILES: CC(C)(C)NC(=O)CC1CCN(c2ncc(S(C)(=O)=O)cc2NC(=O)c2cc(Cl)cc(Cl)c2)CC1] | N-[4-(tert-Butylcarbamoyl-methyl)-5'-methanesulfonyl-3,4,5,6-tetrahydro-2H-[1,2']bipyridinyl-3'-yl]-3,5-dichloro-benzamide |
| 251 | 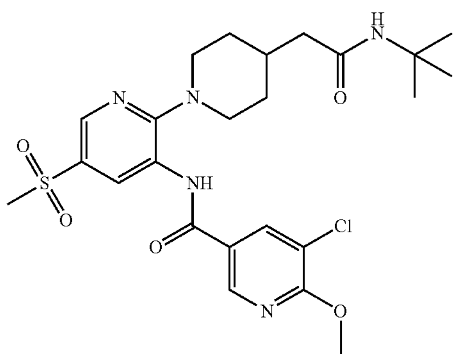 [SMILES: COc1ncc(C(=O)Nc2cc(S(C)(=O)=O)cnc2N2CCC(CC(=O)NC(C)(C)C)CC2)cc1Cl] | N-[4-(tert-Butylcarbamoyl-methyl)-5'-methanesulfonyl-3,4,5,6-tetrahydro-2H-[1,2']bipyridinyl-3'-yl]-5-chloro-6-methoxy-nicotinamide |
| 252 | 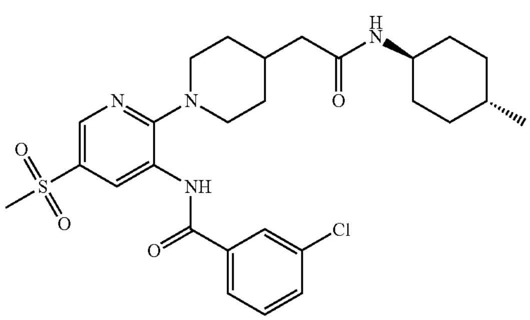 | 3-Chloro-N-{5'-methanesulfonyl-4-[(4-methyl-cyclohexylcarbamoyl)-methyl]-3,4,5,6-tetrahydro-2H-[1,2']bipyridinyl-3'-yl}-benzamide |
| 253 | 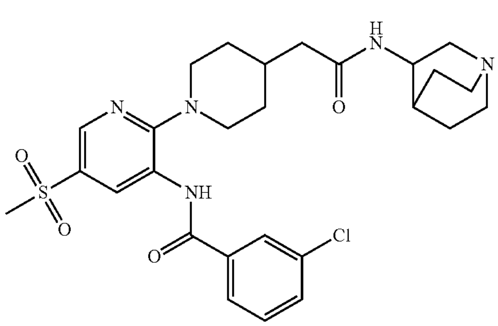 [SMILES: CS(=O)(=O)c1cnc(N2CCC(CC(=O)NC3CN4CCC3CC4)CC2)c(NC(=O)c2cccc(Cl)c2)c1] | N-{4-[(1-Aza-bicyclo[2.2.2]oct-3-ylcarbamoyl)-methyl]-5'-methanesulfonyl-3,4,5,6-tetrahydro-2H-[1,2']bipyridinyl-3'-yl}-3-chloro-benzamide |

TABLE 1-continued

| Cpd # | Structure | Name |
|---|---|---|
| 254 | 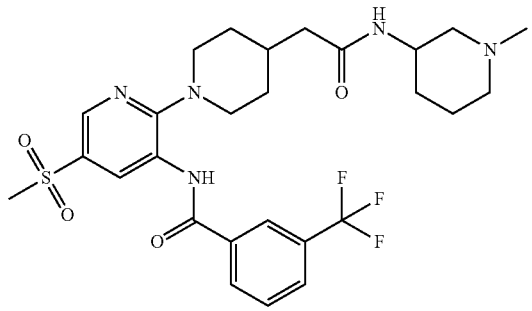 | N-{5'-Methanesulfonyl-4-[(1-methyl-piperidin-3-ylcarbamoyl)-methyl]-3,4,5,6-tetrahydro-2H-[1,2']bipyridinyl-3'-yl}-3-trifluoromethyl-benzamide |
| 255 | 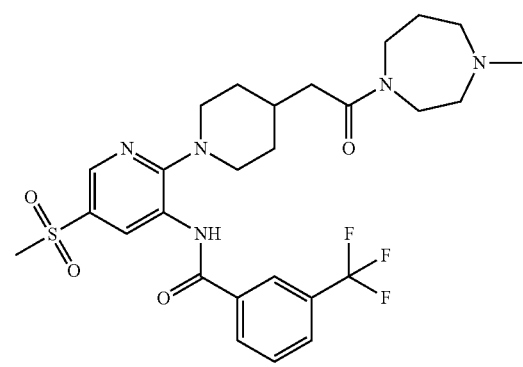 | N-{5'-Methanesulfonyl-4-[2-(4-methyl-[1,4]diazepan-1-yl)-2-oxo-ethyl]-3,4,5,6-tetrahydro-2H-[1,2']bipyridinyl-3'-yl}-3-trifluoromethyl-benzamide |
| 256 | 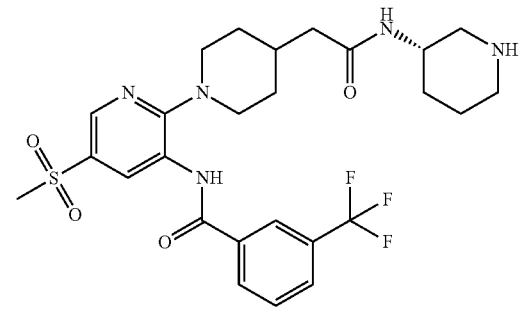 [SMILES: CS(=O)(=O)c1cnc(N2CCC(CC(=O)N[C@H]3CCCNC3)CC2)c(NC(=O)c2cccc(C(F)(F)F)c2)c1] | N-[5'-Methanesulfonyl-4-((S)-piperidin-3-ylcarbamoylmethyl)-3,4,5,6-tetrahydro-2H-[1,2']bipyridinyl-3'-yl]-3-trifluoromethyl-benzamide |
| 257 | 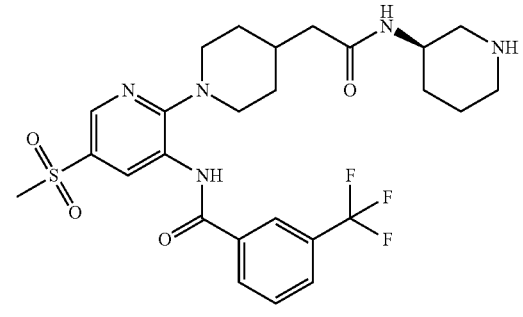 [SMILES: CS(=O)(=O)c1cnc(N2CCC(CC(=O)N[C@@H]3CCCNC3)CC2)c(NC(=O)c2cccc(C(F)(F)F)c2)c1] | N-[5'-Methanesulfonyl-4-((R)-piperidin-3-ylcarbamoylmethyl)-3,4,5,6-tetrahydro-2H-[1,2']bipyridinyl-3'-yl]-3-trifluoromethyl-benzamide |

TABLE 1-continued

| Cpd # | Structure | Name |
|---|---|---|
| 258 | 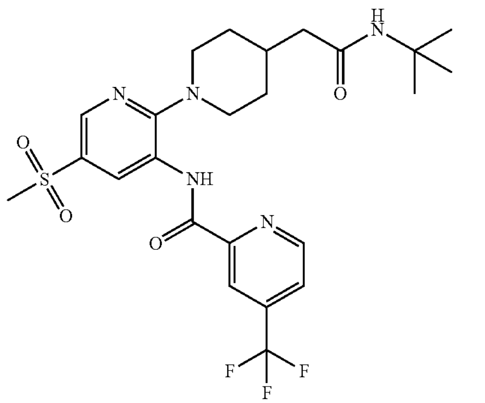 [SMILES: CC(C)(C)NC(=O)CC1CCN(c2ncc(S(C)(=O)=O)cc2NC(=O)c2cc(C(F)(F)F)ccn2)CC1] | 4-Trifluoromethyl-pyridine-2-carboxylic acid [4-(tert-butylcarbamoyl-methyl)-5'-methanesulfonyl-3,4,5,6-tetrahydro-2H-[1,2']bipyridinyl-3'-yl]-amide |
| 259 | 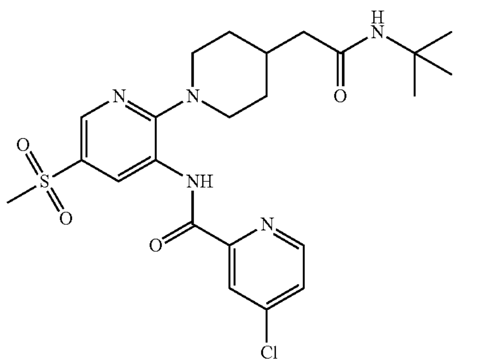 [SMILES: CC(C)(C)NC(=O)CC1CCN(c2ncc(S(C)(=O)=O)cc2NC(=O)c2cc(Cl)ccn2)CC1] | 4-Chloro-pyridine-2-carboxylic acid [4-(tert-butylcarbamoyl-methyl)-5'-methanesulfonyl-3,4,5,6-tetrahydro-2H-[1,2']bipyridinyl-3'-yl]-amide |
| 260 | 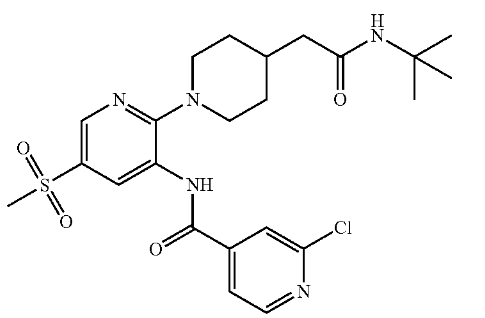 [SMILES: CC(C)(C)NC(=O)CC1CCN(c2ncc(S(C)(=O)=O)cc2NC(=O)c2ccnc(Cl)c2)CC1] | N-[4-(tert-Butylcarbamoyl-methyl)-5'-methanesulfonyl-3,4,5,6-tetrahydro-2H-[1,2']bipyridinyl-3'-yl]-2-chloro-isonicotinamide |
| 261 | 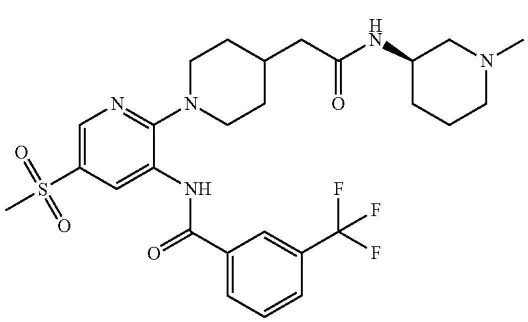 | N-{5'-Methanesulfonyl-4-[((R)-1-methyl-piperidin-3-ylcarbamoyl)-methyl]-3,4,5,6-tetrahydro-2H-[1,2']bipyridinyl-3'-yl}-3-trifluoromethyl-benzamide |

| Cpd # | Structure | Name |
|---|---|---|
| 262 | 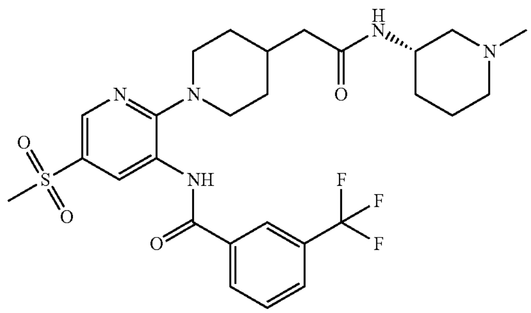 | N-{5'-Methanesulfonyl-4-[((S)-1-methyl-piperidin-3-ylcarbamoyl)-methyl]-3,4,5,6-tetrahydro-2H-[1,2']bipyridinyl-3'-yl}-3-trifluoromethyl-benzamide |
| 263 | 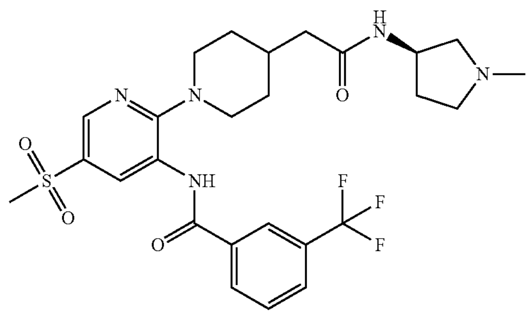 | N-{5'-Methanesulfonyl-4-[((R)-1-methyl-pyrrolidin-3-ylcarbamoyl)-methyl]-3,4,5,6-tetrahydro-2H-[1,2']bipyridinyl-3'-yl}-3-trifluoromethyl-benzamide |
| 264 | 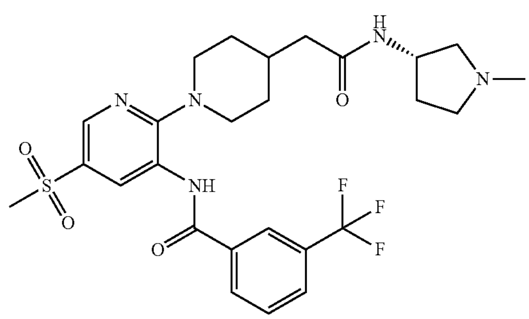 | N-{5'-Methanesulfonyl-4-[((S)-1-methyl-pyrrolidin-3-ylcarbamoyl)-methyl]-3,4,5,6-tetrahydro-2H-[1,2']bipyridinyl-3'-yl}-3-trifluoromethyl-benzamide |
| 265 | 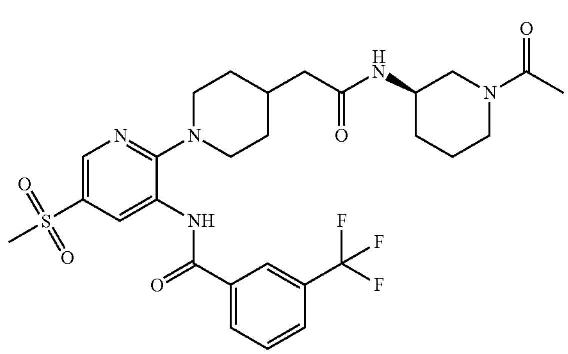 [SMILES: CC(=O)N1CCC[C@@H](NC(=O)CC2CCN(c3ncc(S(C)(=O)=O)cc3NC(=O)c3cccc(C(F)(F)F)c3)CC2)C1] | N-{4-[((R)-1-Acetyl-piperidin-3-ylcarbamoyl)-methyl]-5'-methanesulfonyl-3,4,5,6-tetrahydro-2H-[1,2']bipyridinyl-3'-yl}-3-trifluoromethyl-benzamide |

TABLE 1-continued

| Cpd # | Structure | Name |
|---|---|---|
| 266 | 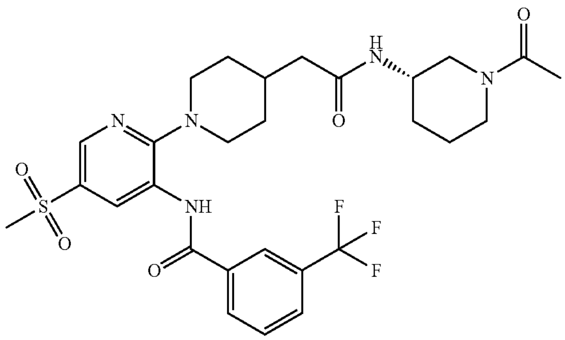 [SMILES: CC(=O)N1CCC[C@H](NC(=O)CC2CCN(c3ncc(S(C)(=O)=O)cc3NC(=O)c3cccc(C(F)(F)F)c3)CC2)C1] | N-{4-[((S)-1-Acetyl-piperidin-3-ylcarbamoyl)-methyl]-5'-methanesulfonyl-3,4,5,6-tetrahydro-2H-[1,2']bipyridinyl-3'-yl}-3-trifluoromethyl-benzamide |
| 267 | 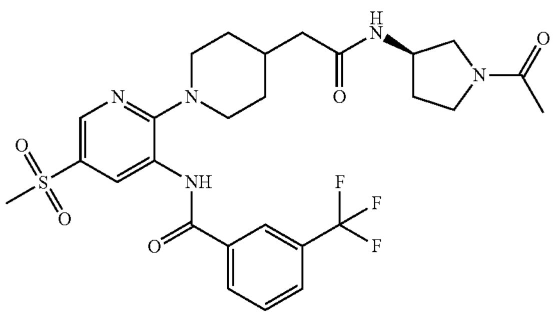 [SMILES: CC(=O)N1CC[C@@H](NC(=O)CC2CCN(c3ncc(S(C)(=O)=O)cc3NC(=O)c3cccc(C(F)(F)F)c3)CC2)C1] | N-{4-[((R)-1-Acetyl-pyrrolidin-3-ylcarbamoyl)-methyl]-5'-methanesulfonyl-3,4,5,6-tetrahydro-2H-[1,2']bipyridinyl-3'-yl}-3-trifluoromethyl-benzamide |
| 268 | 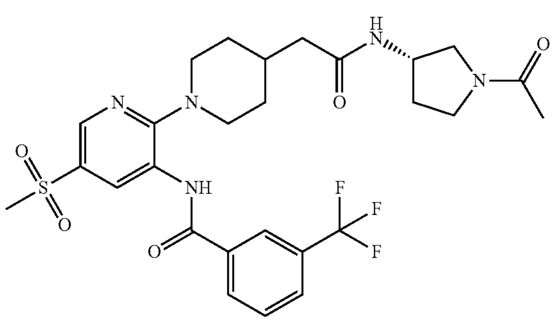 [SMILES: CC(=O)N1CC[C@H](NC(=O)CC2CCN(c3ncc(S(C)(=O)=O)cc3NC(=O)c3cccc(C(F)(F)F)c3)CC2)C1] | N-{4-[((S)-1-Acetyl-pyrrolidin-3-ylcarbamoyl)-methyl]-5'-methanesulfonyl-3,4,5,6-tetrahydro-2H-[1,2']bipyridinyl-3'-yl}-3-trifluoromethyl-benzamide |
| 269 | 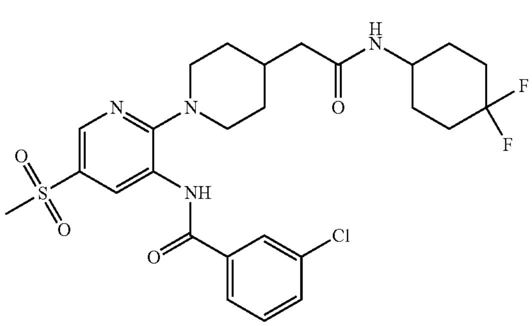 [SMILES: CS(=O)(=O)c1cnc(N2CCC(CC(=O)NC3CCC(F)(F)CC3)CC2)c(NC(=O)c2cccc(Cl)c2)c1] | 3-Chloro-N-{4-[(4,4-difluoro-cyclohexylcarbamoyl)-methyl]-5'-methanesulfonyl-3,4,5,6-tetrahydro-2H-[1,2']bipyridinyl-3'-yl}-benzamide |

TABLE 1-continued

| Cpd # | Structure | Name |
|---|---|---|
| 270 | 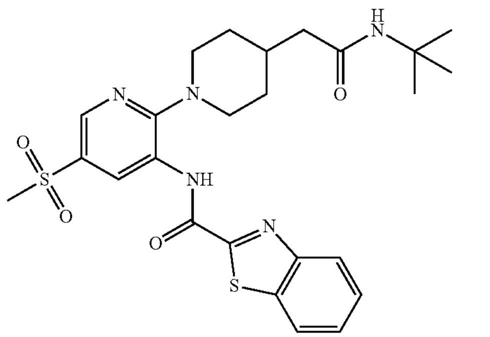 [SMILES: CC(C)(C)NC(=O)CC1CCN(c2ncc(S(C)(=O)=O)cc2NC(=O)c2nc3ccccc3s2)CC1] | Benzothiazole-2-carboxylic acid [4-(tert-butylcarbamoyl-methyl)-5'-methanesulfonyl-3,4,5,6-tetrahydro-2H-[1,2']bipyridinyl-3'-yl]-amide |
| 271 | 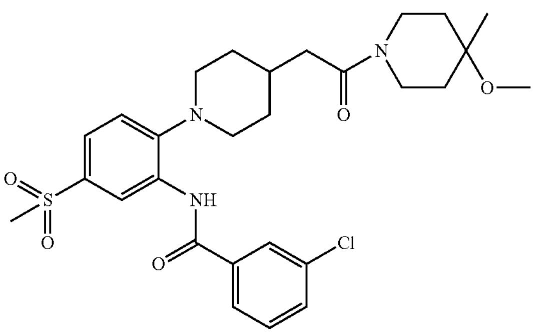 [SMILES: COC1(C)CCN(C(=O)CC2CCN(c3ccc(S(C)(=O)=O)cc3NC(=O)c3cccc(Cl)c3)CC2)CC1] | 3-Chloro-N-(5-methanesulfonyl-2-{4-[2-(4-methoxy-4-methyl-piperidin-1-yl)-2-oxo-ethyl]-piperidin-1-yl}-phenyl)-benzamide |
| 272 | 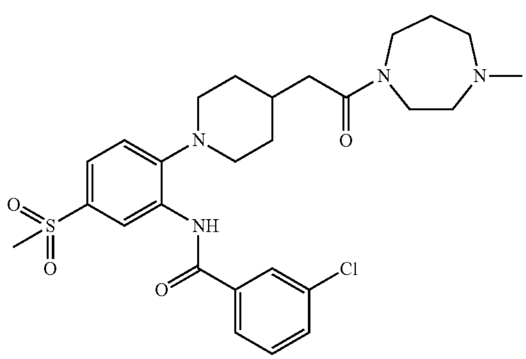 [SMILES: CN1CCCN(C(=O)CC2CCN(c3ccc(S(C)(=O)=O)cc3NC(=O)c3cccc(Cl)c3)CC2)CC1] | 3-Chloro-N-(5-methanesulfonyl-2-{4-[2-(4-methyl-[1,4]diazepan-1-yl)-2-oxo-ethyl]-piperidin-1-yl}-phenyl)-benzamide |
| 273 | 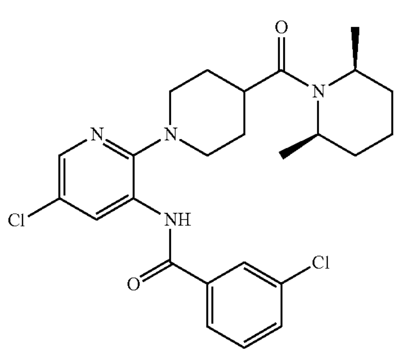 [SMILES: C[C@@H]1CCC[C@H](C)N1C(=O)C1CCN(c2ncc(Cl)cc2NC(=O)c2cccc(Cl)c2)CC1] | 3-Chloro-N-[5'-chloro-4-((2S,6R)-2,6-dimethyl-piperidine-1-carbonyl)-3,4,5,6-tetrahydro-2H-[1,2']bipyridinyl-3'-yl]-benzamide |

TABLE 1-continued

| Cpd # | Structure | Name |
|---|---|---|
| 274 | 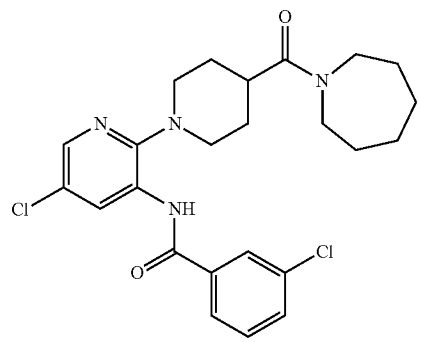 [SMILES: O=C(Nc1cc(Cl)cnc1N1CCC(C(=O)N2CCCCCC2)CC1)c1cccc(Cl)c1] | N-[4-(Azepane-1-carbonyl)-5'-chloro-3,4,5,6-tetrahydro-2H-[1,2']bipyridinyl-3'-yl]-3-chloro-benzamide |
| 275 | 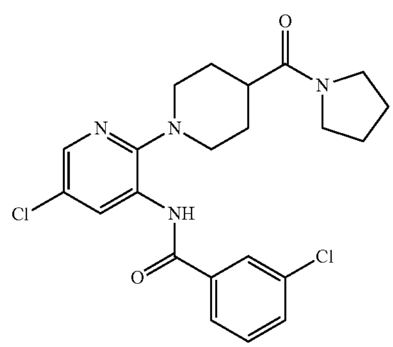 [SMILES: O=C(Nc1cc(Cl)cnc1N1CCC(C(=O)N2CCCC2)CC1)c1cccc(Cl)c1] | 3-Chloro-N-[5'-chloro-4-(pyrrolidine-1-carbonyl)-3,4,5,6-tetrahydro-2H-[1,2']bipyridinyl-3'-yl]-benzamide |
| 276 | 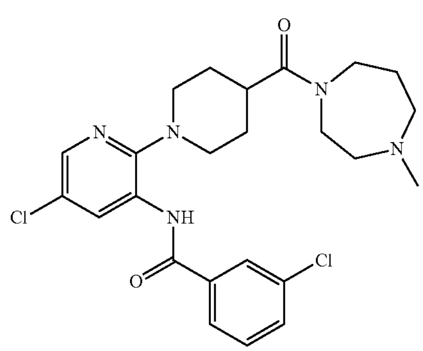 [SMILES: CN1CCCN(C(=O)C2CCN(c3ncc(Cl)cc3NC(=O)c3cccc(Cl)c3)CC2)CC1] | 3-Chloro-N-[5'-chloro-4-(4-methyl-[1,4]diazepane-1-carbonyl)-3,4,5,6-tetrahydro-2H-[1,2']bipyridinyl-3'-yl]-benzamide |
| 277 | 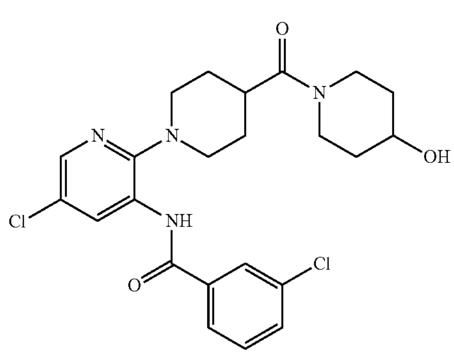 [SMILES: O=C(Nc1cc(Cl)cnc1N1CCC(C(=O)N2CCC(O)CC2)CC1)c1cccc(Cl)c1] | 3-Chloro-N-[5'-chloro-4-(4-hydroxy-piperidine-1-carbonyl)-3,4,5,6-tetrahydro-2H-[1,2']bipyridinyl-3'-yl]-benzamide |

TABLE 1-continued

| Cpd # | Structure | Name |
|---|---|---|
| 278 | 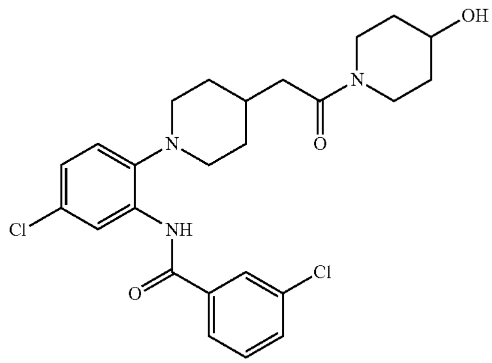 [SMILES: O=C(Nc1cc(Cl)ccc1N1CCC(CC(=O)N2CCC(O)CC2)CC1)c1cccc(Cl)c1] | 3-Chloro-N-(5-chloro-2-{4-[2-(4-hydroxy-piperidin-1-yl)-2-oxo-ethyl]-piperidin-1-yl}-phenyl)-benzamide |
| 279 | 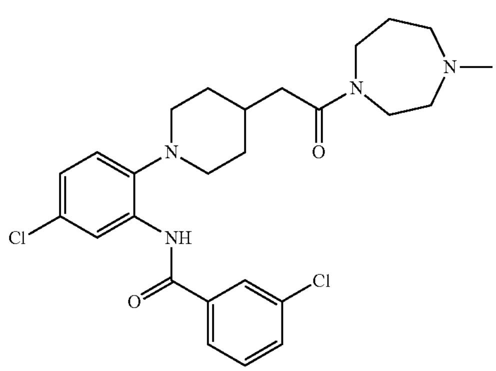 [SMILES: CN1CCCN(C(=O)CC2CCN(c3ccc(Cl)cc3NC(=O)c3cccc(Cl)c3)CC2)CC1] | 3-Chloro-N-(5-chloro-2-{4-[2-(4-methyl-[1,4]diazepan-1-yl)-2-oxo-ethyl]-piperidin-1-yl}-phenyl)-benzamide |
| 280 | 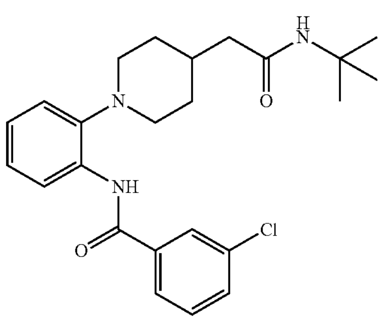 [SMILES: CC(C)(C)NC(=O)CC1CCN(c2ccccc2NC(=O)c2cccc(Cl)c2)CC1] | N-{2-[4-(tert-Butylcarbamoyl-methyl)-piperidin-1-yl]-phenyl}-3-chloro-benzamide |
| 281 | 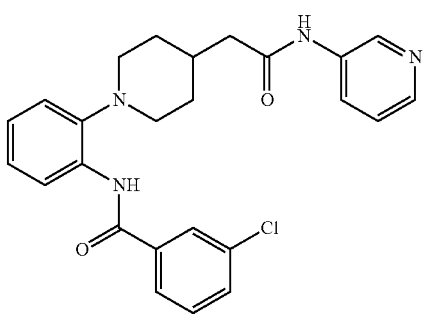 [SMILES: O=C(CC1CCN(c2ccccc2NC(=O)c2cccc(Cl)c2)CC1)Nc1cccnc1] | 3-Chloro-N-{2-[4-(pyridin-3-ylcarbamoylmethyl)-piperidin-1-yl]-phenyl}-benzamide |

TABLE 1-continued

| Cpd # | Structure | Name |
|---|---|---|
| 282 | 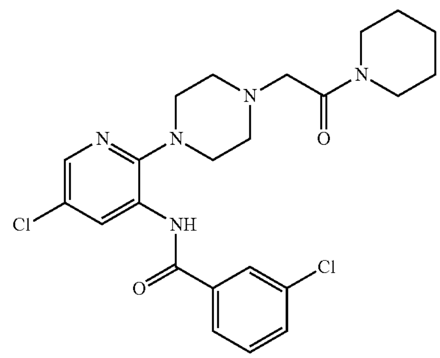 [SMILES: O=C(Nc1cc(Cl)cnc1N1CCN(CC(=O)N2CCCCC2)CC1)c1cccc(Cl)c1] | 3-Chloro-N-{5-chloro-2-[4-(2-oxo-2-piperidin-1-yl-ethyl)-piperazin-1-yl]-pyridin-3-yl}-benzamide |
| 283 | 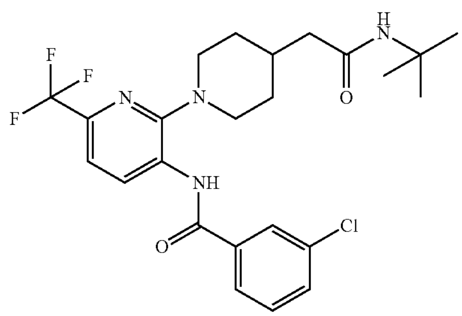 [SMILES: CC(C)(C)NC(=O)CC1CCN(c2nc(C(F)(F)F)ccc2NC(=O)c2cccc(Cl)c2)CC1] | N-[4-(tert-Butylcarbamoyl-methyl)-6'-trifluoromethyl-3,4,5,6-tetrahydro-2H-[1,2']bipyridinyl-3'-yl]-3-chloro-benzamide |
| 284 | 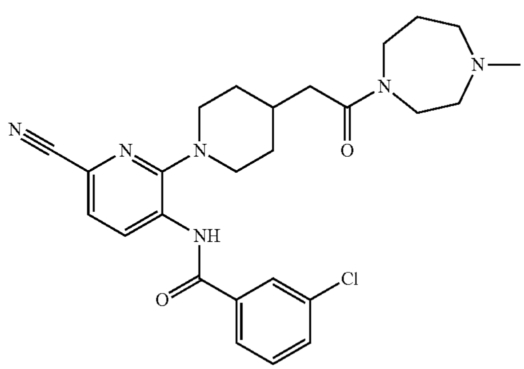 [SMILES: CN1CCCN(C(=O)CC2CCN(c3nc(C#N)ccc3NC(=O)c3cccc(Cl)c3)CC2)CC1] | 3-Chloro-N-{6'-cyano-4-[2-(4-methyl-[1,4]diazepan-1-yl)-2-oxo-ethyl]-3,4,5,6-tetrahydro-2H-[1,2']bipyridinyl-3'-yl}-benzamide |
| 285 | 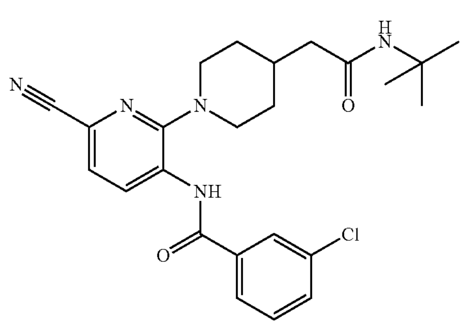 [SMILES: CC(C)(C)NC(=O)CC1CCN(c2nc(C#N)ccc2NC(=O)c2cccc(Cl)c2)CC1] | N-[4-(tert-Butylcarbamoyl-methyl)-6'-cyano-3,4,5,6-tetrahydro-2H-[1,2']bipyridinyl-3'-yl]-3-chloro-benzamide |

TABLE 1-continued

| Cpd # | Structure | Name |
|---|---|---|
| 286 | 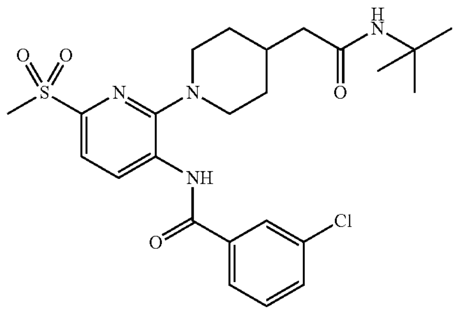 [SMILES: CC(C)(C)NC(=O)CC1CCN(c2nc(S(C)(=O)=O)ccc2NC(=O)c2cccc(Cl)c2)CC1] | N-[4-(tert-Butylcarbamoyl-methyl)-6'-methanesulfonyl-3,4,5,6-tetrahydro-2H-[1,2']bipyridinyl-3'-yl]-3-chloro-benzamide |

In another embodiment, the invention relates to a compound selected from compounds described in Table 1, or the pharmaceutically acceptable salts thereof.

In another embodiment, the invention relates to a compound selected from compounds 6, 17-19, 25, 36, 39-43, 78, 79, 82, 86, 90, 92, 97, 103, 112, 115, 118-120, 124, 127-133, 135-138, 141, 143, 144, 146, 149-152, 155, 160-163, 166-169, 174, 177, 181, 182, 186, 189, 193, 197, 199, 200, 214-216, 219, 231, 236, 239, 242-247, 252, 254, 261, 262, 266, 269, 271, 272 and 278 in Table 1, or the pharmaceutically acceptable salts thereof.

For all compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$C_{3-10}$ cycloalkyl" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ cycloakyl may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

As used herein, the term "aryl" refers to an aromatic hydrocarbon rings containing from six to ten carbon ring atoms (e.g., a $C_{6-10}$ aryl). The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "heterocyclyl" refers to a "5 to 11-membered heterocycle" and includes stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-$1\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-azaspiro[3,4]octanyl.

As used herein, the term "heteroaryl" refers to a "5 to 11-membered heteroaryl" and includes aromatic 5 to 6-membered monocyclic heteroaryls and aromatic 7 to 11-membered heteroaryl bicyclic rings where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl. It will be understood that when a heterocyclyl or heteroaryl contains a S ring atom, such S ring atom can be present in the ring in its divalent, tetravalent, or hexavalent form, i.e., —S—, —S(O)— or —S(O)$_2$—.

Each aryl or heteroaryl unless otherwise specified includes it's partially or fully hydrogenated derivatives. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art. It will be understood that one to three carbon ring moieties in the each of the $C_{3-10}$ carbocyclic rings, the 5 to 11-membered heterocyclic rings, the nonaromatic portion of the bicyclic aryl or heteroaryl rings, and the nonaromatic portion of the bicyclic heterocyclic rings can independently be replaced with a carbonyl, thiocarbonyl, or iminyl moiety, i.e., —C(═O)—, —C(═S)— and —C(═NR$^8$)—, respectively, where R$^8$ is as defined above. The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$-C$_4$ alkyl)$_4$$^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula (I) may be made using the general synthetic methods described below, which also constitute part of the invention.

General Synthetic Methods

The compounds of the invention may be prepared by the methods described below. In each of the schemes below, the groups R$^1$ to R$^3$, A, B, X, and n are as defined above for general formula (I) unless noted otherwise. Optimum reaction conditions and reaction times may vary depending on the particular reactants used. Unless otherwise specified, solvents, temperatures, pressures and other reaction conditions may be readily selected by one of ordinary skill in the art. Amide bond formations may be carried out by standard coupling conditions well-known in the art (see, for example, M. Bodanszky, *The Practice of Peptide Synthesis* (Springer-Verlag: 1984), which is hereby incorporated by reference in its entirety), for example, by reacting a carboxylic acid and an amine in the presence of 1-(3-dimethylaminopropyl)-3-ethylcarbodiimide (EDC) and 1-hydroxybenzotriazole. Specific procedures are provided in the Synthetic Examples section. Typically, reaction progress may be monitored by thin layer chromatography (TLC) or HPLC-MS if desired. Intermediates and products may be purified by chromatography on silica gel, recrystallization, HPLC and/or reverse phase HPLC.

Starting materials and reagents are either commercially available or may be prepared by one skilled in the art using methods described in the chemical literature. Initial products of formula (I) may be modified further by methods known in the art to produce additional compounds of formula (I).

Compounds of formula (I) having B=N may be prepared as described in Scheme 1.

Compounds of formula (I) having B=N or C may be prepared as illustrated in Scheme 2.

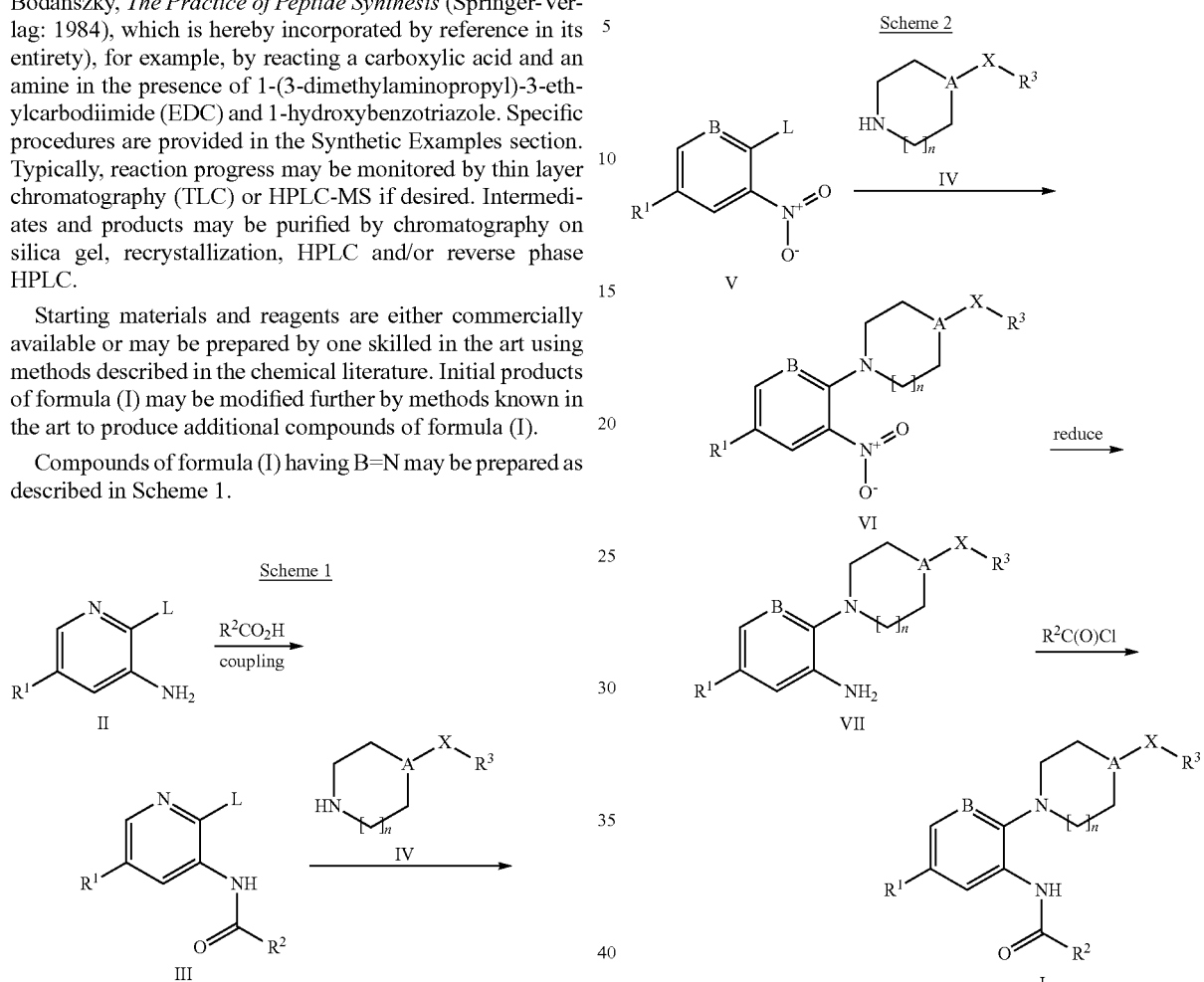

As illustrated in Scheme 1, intermediate II, where L is a halogen, preferably Cl, is coupled with $R^2CO_2H$, for example by stirring together in a suitable solvent such as acetonitrile or using other coupling conditions well known in the art to form III. Alternatively the acid chloride $R^2C(O)Cl$ may be used instead of the acid and reacted with intermediate II in the presence of a suitable base such as triethylamine in a suitable solvent such as methylene chloride to provide III. Intermediate IV is then reacted with III, for example by heating together in a suitable solvent such as acetonitrile in a microwave reactor at about 100-200° C. to provide the desired compound of formula I As illustrated in Scheme 2, intermediate IV is reacted with V, where L is a halogen, preferably Cl, by heating in a suitable solvent such as acetonitrile at about 75-200° C., optionally in a microwave reactor, to form VI. Intermediate VI is then reduced by methods known in the art, for example by treatment with hydrogen in the presence of a catalyst such as Pd on carbon in a suitable solvent such as EtOH or acetonitrile to provide VII. Intermediate VII may then be coupled with $R^2C(O)Cl$ or $R^2CO_2H$ as described above in Scheme I to provide the desired compound of formula (I).

Scheme 3 illustrates another method for preparing compounds of formula (I) having $X=(CH_2)_{2-3}$, B=N and $R^3$=—N$(R^4)(R^5)$ or a N-containing heterocycle.

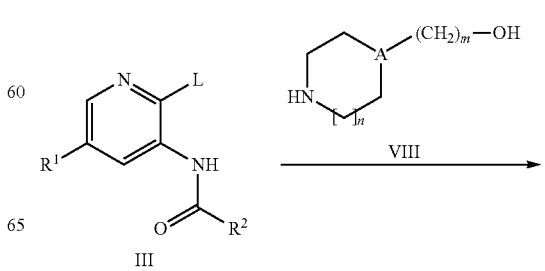

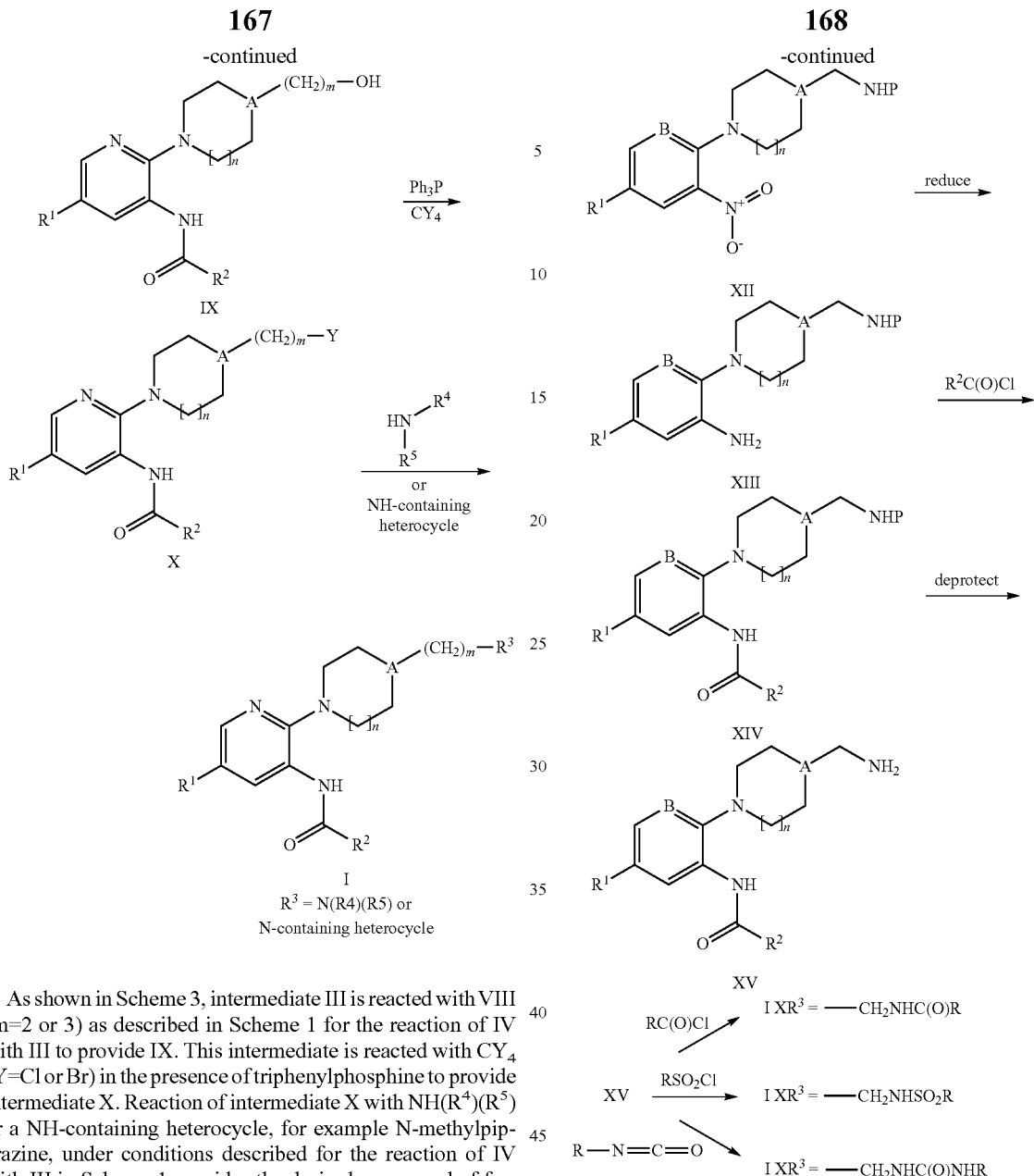

As shown in Scheme 3, intermediate III is reacted with VIII (m=2 or 3) as described in Scheme 1 for the reaction of IV with III to provide IX. This intermediate is reacted with $CY_4$ (Y=Cl or Br) in the presence of triphenylphosphine to provide intermediate X. Reaction of intermediate X with $NH(R^4)(R^5)$ or a NH-containing heterocycle, for example N-methylpiperazine, under conditions described for the reaction of IV with III in Scheme 1 provides the desired compound of formula (I) with $R^3$ being $—N(R^4)(R^5)$ or a N-containing heterocycle.

Compounds of formula (I) containing an amide, sulfonamide or urea in the X—$R^3$ side chain may be prepared as illustrated in Scheme 4.

Scheme 4

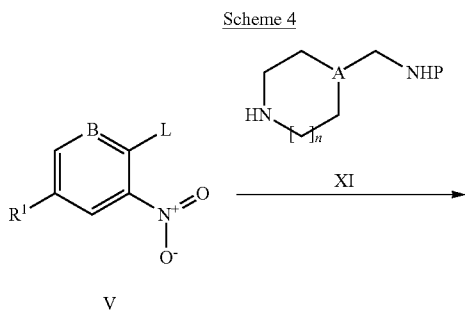

As described in Scheme 4, intermediate V is reacted with XI (P is an amine protecting group) in the presence of a suitable base such as potassium carbonate in a solvent such as DMF or the reaction may be conducted in the same manner as described for reaction of V with IV in Scheme 2 to provide XII. Subsequent reduction of XII to amine XII and reaction of XIII with $R^2C(O)Cl$ as described in Scheme 2 with intermediate VII provides intermediate XIV. Deprotection of the amine by methods known in the art, for example by treatment with acid if P is a t-BOC group, provides the amine XV. Intermediate XV may then be converted to the desired amine derivative by methods known in the art. For example, treatment with an acid chloride, R(O)Cl in the presence of a suitable base such as triethylamine in a solvent such as methylene chloride provides compounds of formula (I) having $XR^3$=—$CH_2NHC(O)R$. In a similar manner, reaction with $RSO_2Cl$ provides the sulfonamide ($XR^3$=—$CH_2NHSO_2R$) and reaction with R—N=C=O provides the urea ($XR^3$=—$CH_2NHC(O)NHR$).

Compounds of formula (I) having X=—CH$_2$C(O)— and R$^3$=an N-containing heterocyclyl or —N(R$^4$)(R$^5$) may be prepared as described in Scheme 5.

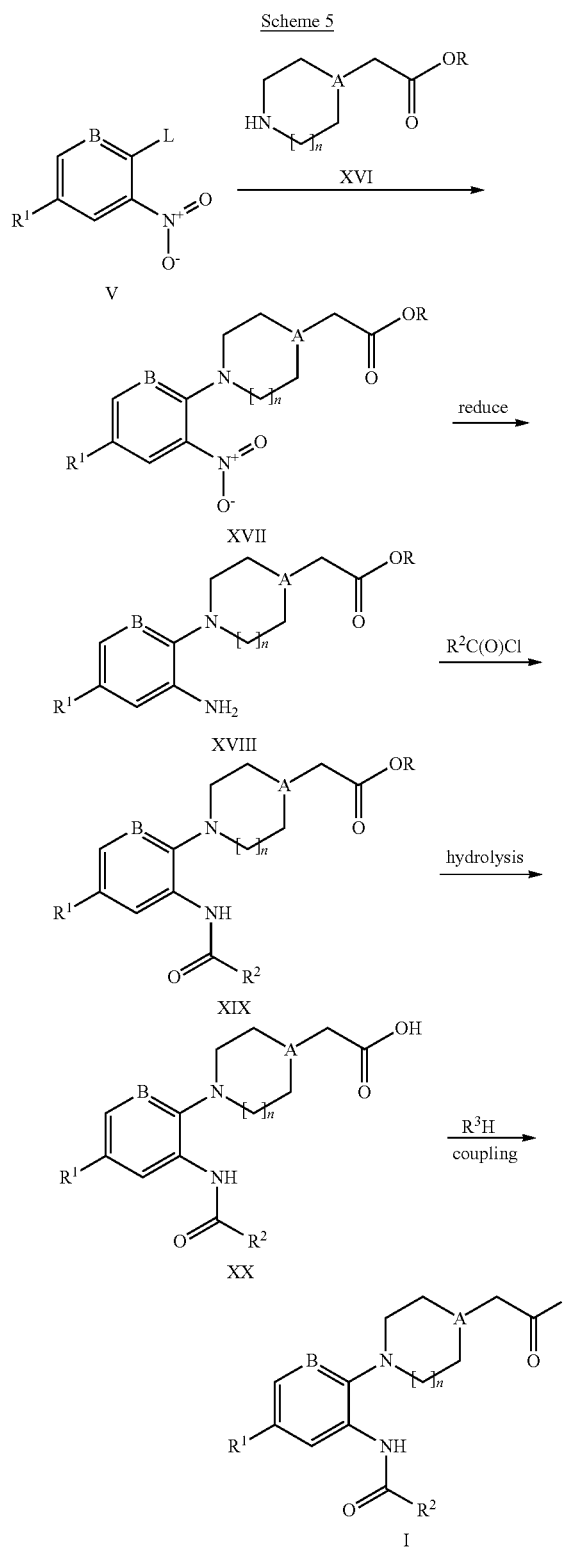

Scheme 5

As illustrated above, intermediate V is reacted with ester XVI where R is a C$_{1-6}$alkyl, preferably methyl or ethyl, by heating in a suitable solvent such as DMF or acetonitrile at about 75-200° C., optionally in a microwave reactor to provide XVII. Intermediate XVII is reduced as described for the conversion of VI to VII in Scheme 2 to provide XVIII. Coupling of XVIII with R$^2$C(O)Cl as described in Scheme I for conversion of II to III provides XIX which is hydrolyzed, for example by treatment with a base such as LiOH in a suitable aqueous solvent such as THF with water to provide the carboxylic acid XX. Coupling of XX with R$^3$H, where R$^3$ is an optionally substituted N-containing heterocycle such as piperidine or piperazine or R$^3$ is —N(R$^4$)(R$^5$), under standard coupling conditions known in the art, for example treatment with O-(benzotriazol-1-yl)-N,N,N',N'-tetramethyluronium tetrafluoroborate (TBTU) in the presence of a suitable base such as triethylamine in a suitable solvent such as DMF, provides the desired compound of formula (I).

All of the compounds in Table I were prepared by the methods illustrated above and in the Synthetic Examples section below.

SYNTHETIC EXAMPLES

Example 1

Synthesis of 3-chloro-N-[5'-chloro-4-(2-piperidin-1-yl-ethyl)-3,4,5,6-tetrahydro-2H-[1,2']bipyridinyl-3'-yl]-benzamide (1)

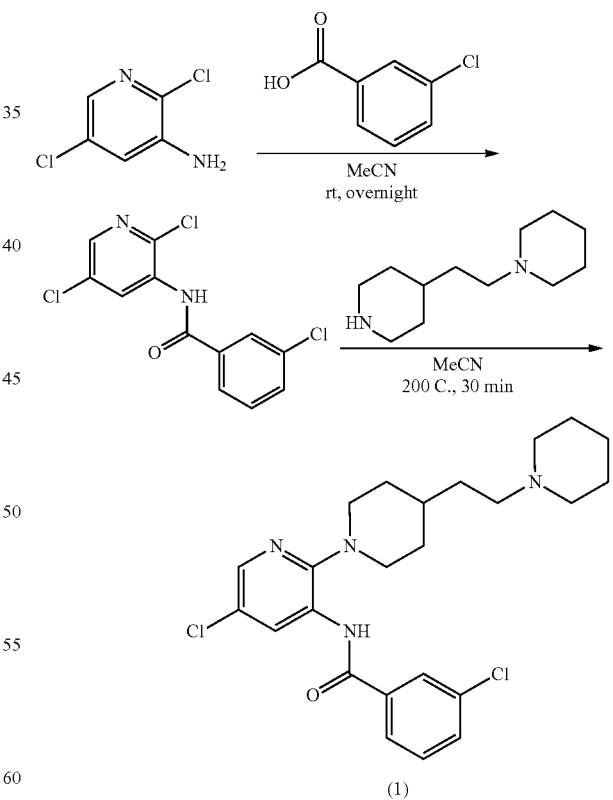

To a solution of 3.26 g (20.0 mmol) of 2,5-dichloro-pyridin-3-ylamine in acetonitrile (50 mL) is added 3.50 g (20.0 mmol) of 3-chlorobenzoic acid. The mixture is stirred overnight at room temperature during which time a precipitate forms. The formed solid is collected by filtration, washed with cold diethyl ether and dried to give 5.43 g (90%) of 2,5-dichloro-N-(3-chloro-phenyl)-nicotinamide as a white solid.

To a solution of 0.15 g (0.50 mmol) of the above amide in acetonitrile (5 mL) is added 0.098 g (0.50 mmol) of 1-(2-piperidin-4-yl-ethyl)-piperidine. The mixture is heated in a microwave reactor at 200° C. for 30 minutes. The mixture is cooled to room temperature and the mixture is purified by preparative reverse phase HPLC to give the title compound (1). [M+H]$^+$=462.4

The following compound can be prepared analogously:
N-[5'-Chloro-4-(2-piperidin-1-yl-ethyl)-3,4,5,6-tetrahydro-2H-[1,2']bipyridinyl-3'-yl]-4-methoxy-benzamide, $C_{25}H_{33}ClN_4O_2$, [M+H]$^+$=457.4.

Example 2

Synthesis of 3-chloro-N-[5'-methyl-4-(2-piperidin-1-yl-ethyl)-3,4,5,6-tetrahydro-2H-[1,2']bipyridinyl-3'-yl]-benzamide (3)

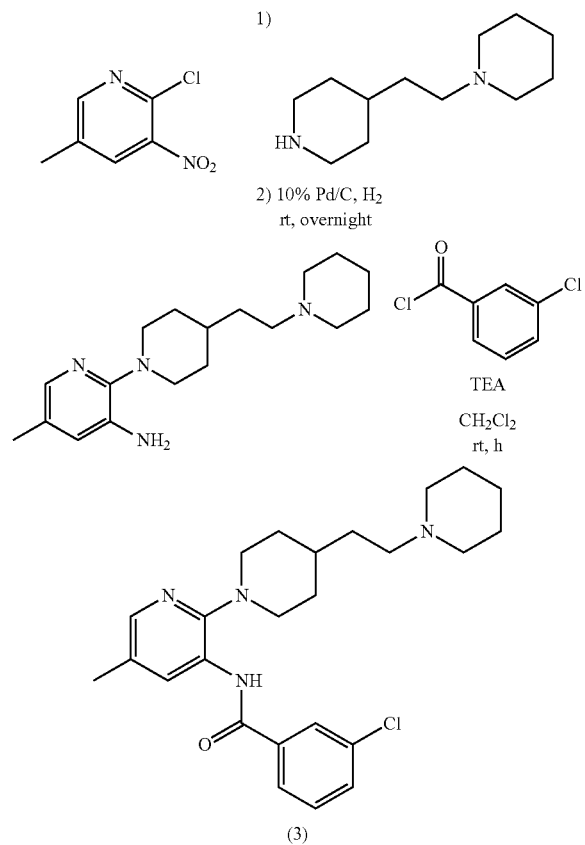

To a stirred solution of 0.086 g (0.50 mmol) of 2-chloro-5-methyl-3-nitro-pyridine in acetonitrile (5 mL) is added 0.098 g (0.50 mmol) of 1-(2-piperidin-4-yl-ethyl)-piperidine. The mixture is heated in a microwave reactor at 100° C. for 10 minutes then cooled to room temperature. To this solution is added 0.010 g (0.009 mmol) of 10% palladium on carbon. The mixture is placed under an atmosphere of hydrogen and stirred overnight at room temperature. The mixture is filtered and concentrated under reduced pressure to give 0.151 g (quant.) of 5'-methyl-4-(2-piperidin-1-yl-ethyl)-3,4,5,6-tetrahydro-2H-[1,2']bipyridinyl-3'-ylamine.

To a solution of 0.075 g (0.25 mmol) of 5'-methyl-4-(2-piperidin-1-yl-ethyl)-3,4,5,6-tetrahydro-2H-[1,2']bipyridinyl-3'-ylamine in methylene chloride (5 mL) is added 0.050 mL (0.30 mmol) of triethylamine followed by 0.044 g (0.25 mmol) of 3-chlorobenzoyl chloride. The mixture is stirred overnight at room temperature then purified by preparative reverse phase HPLC to give 0.033 g (30%) of the title compound (3) as a white solid. [M+H]$^+$=441.3.

The following compound can be prepared analogously:
N-[5'-Bromo-4-(2-piperidin-1-yl-ethyl)-3,4,5,6-tetrahydro-2H-[1,2']bipyridinyl-3'-yl]-3-chloro-benzamide, $C_{24}H_{30}BrClN_4O$, [M+H]$^+$=475.1.

Example 3

Synthesis of 3-chloro-N-{5'-chloro-4-[2-(4-methyl-piperazin-1-yl)-ethyl]-3,4,5,6-tetrahydro-2H-[1,2']bipyridinyl-3'-yl}-benzamide (5)

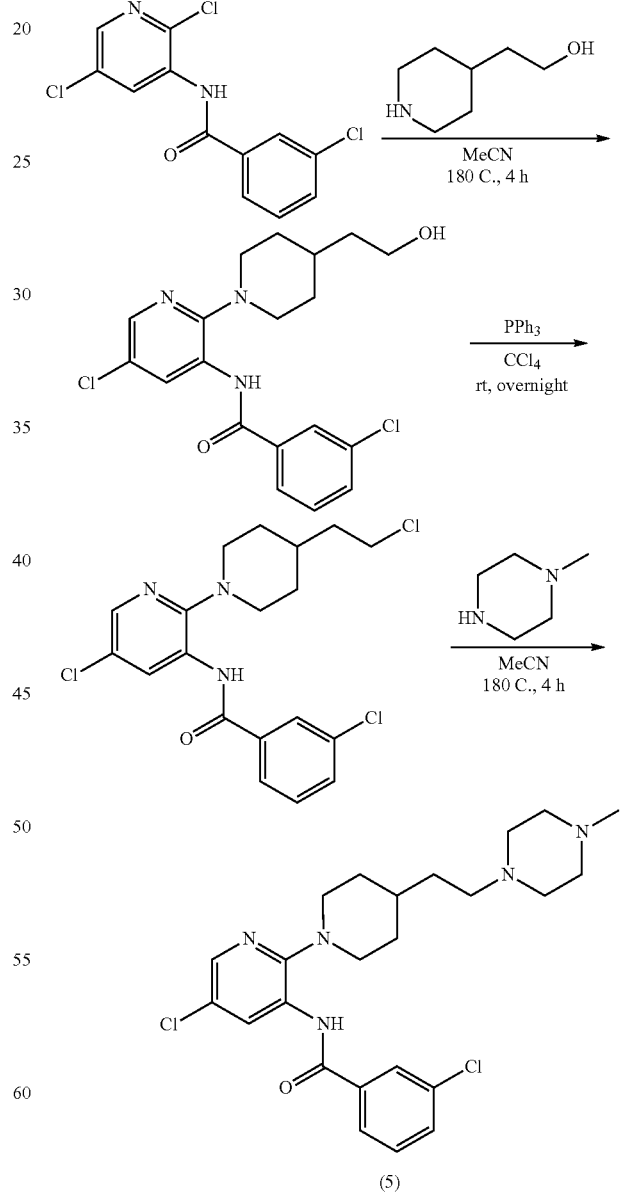

A mixture of 1.06 g (5.00 mmol) of 3-chloro-N-(2,5-dichloro-pyridin-3-yl)-benzamide and 0.646 g (5.00 mmol)

of 4-piperidine ethanol in acetonitrile (25 mL) is heated in a microwave reactor at 180° C. for 4 hours. Upon standing at room temperature a solid precipitates from solution. The solid is collected by filtration, washed with cold acetonitrile, and dried on the filter pad to provide 1.97 g (76%) of 3-chloro-N-[5'-chloro-4-(2-hydroxy-ethyl)-3,4,5,6-tetrahydro-2H-[1,2']bipyridinyl-3'-yl]-benzamide as a clear solid.

A mixture of 0.76 g (10 mmol) of triphenylphosphine and 1.97 g (5.00 mmol) of the above amide in carbon tetrachloride (50 mL) is stirred overnight at room temperature. The solvent is concentrated, and the residue is purified by flash silica gel chromatography to provide 1.24 g (30%) of 3-chloro-N-[5'-chloro-4-(2-chloro-ethyl)-3,4,5,6-tetrahydro-2H-[1,2']bipyridinyl-3'-yl]-benzamide as a white solid.

To a solution of 0.041 g (0.10 mmol) of 3-chloro-N-[5'-chloro-4-(2-chloromethyl)-3,4,5,6-tetrahydro-2H-[1,2']bipyridinyl-3'-yl]-benzamide in acetonitrile (2 mL) is added 0.10 g (1.0 mmol) of N-methylpiperazine. The mixture is heated at 200° C. in a microwave reactor for 15 minutes then cooled to room temperature and purified by preparative reverse phase HPLC to give 0.010 g (21%) of 3-chloro-N-{5'-chloro-4-[2-(4-methyl-piperazin-1-yl)-ethyl]-3,4,5,6-tetrahydro-2H-[1,2']bipyridinyl-3'-yl}-benzamide (5) as a white solid. $[M+H]^+=476.2$.

The following compounds can be prepared analogously:
3-Chloro-N-{5'-chloro-4-[2-(pyridin-3-ylamino)-ethyl]-3,4,5,6-tetrahydro-2H-[1,2']bipyridinyl-3'-yl}-benzamide, $C_{24}H_{25}Cl_2N_5O$, $[M+H]^+=552.3$;
N-[4-(2-Azepan-1-yl-ethyl)-3,4,5,6-tetrahydro-2H-[1,2']bipyridinyl-3'-yl]-3-trifluoromethyl-benzamide, $C_{26}H_{33}F_3N_4O$, $[M+H]^+=421.4$;
N-[4-(2-Diethylamino-ethyl)-3,4,5,6-tetrahydro-2H[1,2']bipyridinyl-3'-yl]-3-trifluoromethyl-benzamide, $C_{24}H_{31}F_3N_4O$, $[M+H]^+=497.2$;
N-[4-(2-Dimethylamino-ethyl)-3,4,5,6-tetrahydro-2H-[1,2']bipyridinyl-3'-yl]-3-trifluoromethyl-benzamide, $C_{22}H_{27}F_3N_4O$, $[M+H]^+=494.2$;
N-[4-(2-Morpholin-4-yl-ethyl)-3,4,5,6-tetrahydro-2H-[1,2']bipyridinyl-3'-yl]-3-trifluoromethyl-benzamide, $C_{24}H_{29}F_3N_4O_2$, $[M+H]^+=461.3$;
3-Chloro-N-[5'-chloro-4-(2-diisopropylamino-ethyl)-3,4,5,6-tetrahydro-2H-[1,2']bipyridinyl-3'-yl]-benzamide, $C_{25}H_{34}Cl_2N_4O$, $[M+H]=500.3$;
N-[4-(2-Pyrrolidin-1-yl-ethyl)-3,4,5,6-tetrahydro-2H-[1,2']bipyridinyl-3'-yl]-3-trifluoromethyl-benzamide, $C_{24}H_{29}F_3N_4O$, $[M+H]^+=491.1$;
N-{4-[2-(4-Methyl-piperidin-1-yl)-ethyl]-3,4,5,6-tetrahydro-2H-[1,2']bipyridinyl-3'-yl}-3-trifluoromethyl-benzamide, $C_{26}H_{33}F_3N_4O$, $[M+H]^+=463.3$;
3-Chloro-N-{5'-chloro-4-[2-(2,6-dimethyl-morpholin-4-yl)-ethyl]-3,4,5,6-tetrahydro-2H-[1,2']bipyridinyl-3'-yl}-benzamide, $C_{25}H_{32}Cl_2N_4O_2$, $[M+H]_+=491.2$;
3-Chloro-N-[5'-chloro-4-(2-[1,4]oxazepan-4-yl-ethyl)-3,4,5,6-tetrahydro-2H-[1,2']bipyridinyl-3'-yl]-benzamide, $C_{24}H_{30}Cl_2N_4O_2$, $[M+H]^+=477.2$;
3-Chloro-N-{5'-chloro-4-[2-(4-hydroxy-piperidin-1-yl)-ethyl]-3,4,5,6-tetrahydro-2H-[1,2']bipyridinyl-3'-yl}-benzamide, $C_{24}H_{30}Cl_2N_4O_2$, $[M+H]^+=477.2$;
3-Chloro-N-{5'-chloro-4-[2-(4-methyl-piperidin-1-yl)-ethyl]-3,4,5,6-tetrahydro-2H-[1,2']bipyridinyl-3'-yl}-benzamide, $C_{25}H_{32}Cl_2N_4O$, $[M+H]^+=475.3$;
N-[4-(2-Azepan-1-yl-ethyl)-5'-chloro-3,4,5,6-tetrahydro-2H-[1,2']bipyridinyl-3'-yl]-3-chloro-benzamide, $C_{25}H_{32}Cl_2N_4O$, $[M+H]^+=475.2$;
3-Chloro-N-{5'-chloro-4-[2-((2S,6R)-2,6-dimethyl-piperidin-1-yl)-ethyl]-3,4,5,6-tetrahydro-2H-[1,2']bipyridinyl-3'-yl}-benzamide, $C_{26}H_{34}Cl_2N_4O$, $[M+H]^+=489.3$;
3-Chloro-N-[5'-chloro-4-(2-morpholin-4-yl-ethyl)-3,4,5,6-tetrahydro-2H-[1,2']bipyridinyl-3'-yl]-benzamide, $C_{23}H_{28}Cl_2N_4O_2$, $[M+H]^+=463.2$;
3-Chloro-N-{5'-chloro-4-[2-(4-formyl-[1,4]diazepan-1-yl)-ethyl]-3,4,5,6-tetrahydro-2H-[1,2']bipyridinyl-3'-yl}-benzamide, $C_{25}H_{31}Cl_2N_5O_2$, $[M+H]^+=504.3$;
3-Chloro-N-{5'-chloro-4-[2-(1,1-dioxo-1lambda*6*-thiomorpholin-4-yl)-ethyl]-3,4,5,6-tetrahydro-2H-[1,2']bipyridinyl-3'-yl}-benzamide, $C_{23}H_{28}Cl_2N_4O_3S$, $[M+H]^+=511.2$.
3-Chloro-N-{5'-chloro-4-[2-(4,4-difluoro-piperidin-1-yl)-ethyl]-3,4,5,6-tetrahydro-2H-[1,2']bipyridinyl-3'-yl}-benzamide, $C_{24}H_{28}Cl_2F_2N_4O$, $[M+H]^+=497.2$;
3-Chloro-N-{5'-chloro-4-[2-(4-methyl-[1,4]diazepan-1-yl)-ethyl]-3,4,5,6-tetrahydro-2H-[1,2']bipyridinyl-3'-yl}-benzamide, $C_{25}H_{33}Cl_2N_5O$, $[M+H]^+=490.3$;
3-Chloro-N-{5'-chloro-4-[2-(4-methoxy-piperidin-1-yl)-ethyl]-3,4,5,6-tetrahydro-2H-[1,2']bipyridinyl-3'-yl}-benzamide, $C_{25}H_{32}Cl_2N_4O_2$, $[M+H]^+=493.2$;
3-Chloro-N-{5'-chloro-4-[2-(3,5-dimethyl-pyrazol-1-yl)-ethyl]-3,4,5,6-tetrahydro-2H-[1,2']bipyridinyl-3'-yl}-benzamide, $C_{24}H_{27}Cl_2N_5O$, $[M+H]^+=472.3$;
3-Chloro-N-{5'-chloro-4-[2-(2,4-dimethyl-imidazol-1-yl)-ethyl]-3,4,5,6-tetrahydro-2H-[1,2']bipyridinyl-3'-yl}-benzamide, $C_{24}H_{27}Cl_2N_5O$, $[M+H]^+=472.3$;
3-Chloro-N-{5'-chloro-4-[2-(2-methyl-benzoimidazol-1-yl)-ethyl]-3,4,5,6-tetrahydro-2H-[1,2']bipyridinyl-3'-yl}-benzamide, $C_{27}H_{27}Cl_2N_5O$, $[M+H]^+=508.3$;
3-Chloro-N-{5'-chloro-4-[2-(4-methanesulfonyl-piperidin-1-yl)-ethyl]-3,4,5,6-tetrahydro-2H-[1,2']bipyridinyl-3'-yl}-benzamide, $C_{25}H_{32}Cl_2N_4O_3S$, $[M+H]^+=539.3$;
3-Chloro-N-[5'-chloro-4-(2-piperidin-1-yl-ethyl)-3,4,5,6-tetrahydro-2H-[1,2']bipyridinyl-3'-yl]-4-methoxy-benzamide, $C_{25}H_{32}Cl_2N_4O_2$, $[M+H]^+=491.2$;
3-Chloro-N-{5'-chloro-4-[2-(4-trifluoromethyl-piperidin-1-yl)-ethyl]-3,4,5,6-tetrahydro-2H-[1,2']bipyridinyl-3'-yl}-benzamide, $C_{25}H_{29}Cl_2F_3N_4O$, $[M+H]^+=529.7$;
3-Chloro-N-{5'-chloro-4-[2-(3,3,3-trifluoro-2-hydroxy-propylamino)-ethyl]-3,4,5,6-tetrahydro-2H-[1,2']bipyridinyl-3'-yl}-benzamide, $C_{22}H_{25}Cl_2F_3N_4O_2$, $[M+H]^+=505.7$;
3-Chloro-N-{5'-chloro-4-[2-(2-cyano-ethylamino)-ethyl]-3,4,5,6-tetrahydro-2H-[1,2']bipyridinyl-3'-yl}-benzamide, $C_{22}H_{25}Cl_2N_5O$, $[M+H]^+=446.7$;
3-Chloro-N-{5'-chloro-4-[2-(pyridin-4-ylamino)-ethyl]-3,4,5,6-tetrahydro-2H-[1,2']bipyridinyl-3'-yl}-benzamide, $C_{24}H_{25}Cl_2N_5O$, $[M+H]^+=470.7$; and 4-tert-Butyl-N-{4-[2-(dimethylcarbamoylmethyl-methyl-amino)-ethyl]-3,4,5,6-tetrahydro-2H-[1,2']bipyridinyl-3'-yl}-benzamide, $C_{28}H_{41}N_5O_2$, $[M+H]^+=480.2$.

Example 4

Synthesis of 3-chloro-N-[5'-chloro-4-(3-piperidin-1-yl-propyl)-3,4,5,6-tetrahydro-2H-[1,2']bipyridinyl-3'-yl]-benzamide (36)

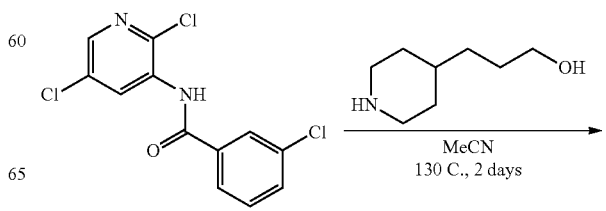

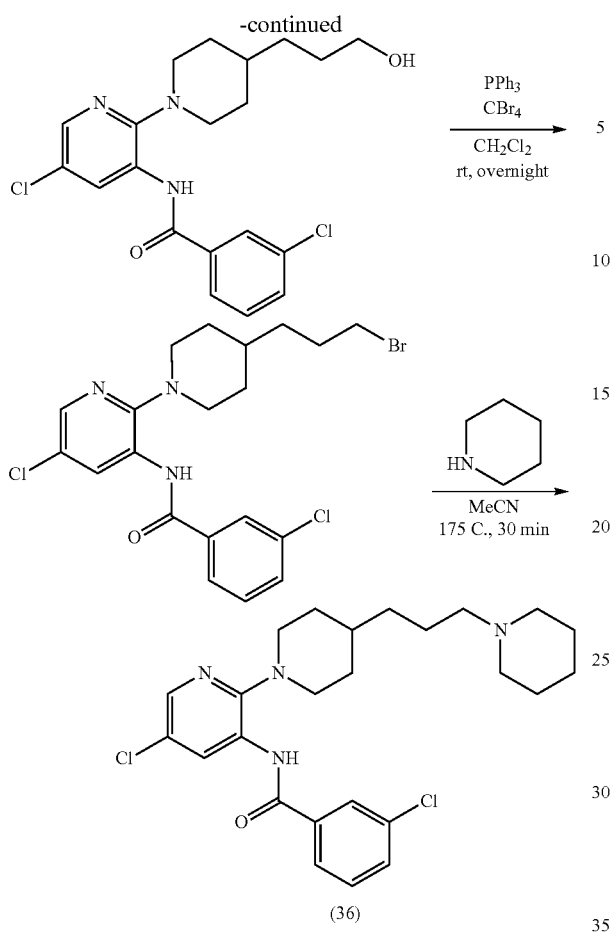

(36)

A mixture of 0.200 g (0.663 mmol) of 3-chloro-N-(2,5-dichloro-pyridin-3-yl)-benzamide and 0.190 g (1.33 mmol) of 3-piperdin-4-yl-propan-1-ol in N,N-dimethylformamide (5 mL) is heated to 130° C. and stirred for 2 days. The mixture is cooled to room temperature, diluted with water, and extracted with ethyl acetate. The combined organic phase is washed with brine, dried over anhydrous sodium sulfate, and concentrated under reduced pressure. The residue is purified by flash silica gel chromatography to provide 0.130 g (47%) of 3-chloro-N-[5'-chloro-4-(3-hydroxy-propyl)-3,4,5,6-tetrahydro-2H-[1,2']bipyridinyl-3'-yl]-benzamide as a light brown foam.

A mixture of 0.080 g (0.20 mmol) of the above amide and 0.056 g (0.22 mmol) of triphenylphosphine in anhydrous methylene chloride (10 mL), under an atmosphere of nitrogen, is stirred at room temperature for 20 minutes. To this mixture is added 0.071 g (0.22 mmol) of carbon tetrabromide and the resulting mixture is stirred overnight at room temperature. The reaction mixture is concentrated under reduced pressure and the residue is purified by flash silica gel chromatography to give 0.037 g (40%) of N-[4-(3-bromo-propyl)-5'-chloro-3,4,5,6-tetrahydro-2H-[1,2']bipyridinyl-3'-yl]-3-chloro-benzamide.

A mixture of 0.032 g (0.068 mmol) of N-[4-(3-bromo-propyl)-5'-chloro-3,4,5,6-tetrahydro-2H-[1,2']bipyridinyl-3'-yl]-3-chloro-benzamide, 0.029 g (0.34 mmol) of piperdine, and 0.50 mL (2.8 mmol) in acetonitrile (1 mL) is heated at 175° C. in a microwave reactor for 30 minutes. The mixture is cooled to room temperature and purified by preparative reverse phase HPLC to give 0.030 g (93%) of the title compound (36) as a colorless foam. [M+H]$^+$=475.3.

The following compounds can be prepared analogously:
N-(4-Piperidin-1-ylmethyl-3,4,5,6-tetrahydro-2H-[1,2']bipyridinyl-3'-yl)-3-trifluoromethyl-benzamide, $C_{24}H_{29}F_3N_4O$, [M+H]$^+$=461.1;
3-Chloro-N-(5'-chloro-4-piperidin-1-ylmethyl-3,4,5,6-tetrahydro-2H-[1,2']bipyridinyl-3'-yl)-benzamide, $C_{23}H_{28}Cl_2N_4O$, [M+H]$^+$=447.0;
3-Chloro-N-[5'-chloro-4-(4-hydroxy-piperidin-1-ylmethyl)-3,4,5,6-tetrahydro-2H-[1,2']bipyridinyl-3'-yl]-benzamide, $C_{23}H_{28}Cl_2N_4O_2$, [M+H]$^+$=465.2;
3-Chloro-N-[5'-chloro-4-(4-methyl-[1,4]diazepan-1-ylmethyl)-3,4,5,6-tetrahydro-2H-[1,2']bipyridinyl-3'-yl]-benzamide, $C_{24}H_3Cl_2N_5O$, [M+H]$^+$=476.2;
3-Chloro-N-[5'-chloro-4-((2S,6R)-2,6-dimethyl-piperidin-1-ylmethyl)-3,4,5,6-tetrahydro-2H-[1,2']bipyridinyl-3'-yl]-benzamide, $C_{25}H_{32}Cl_2N_4O$, [M+H]$^+$=475.2; and
3-Chloro-N-[5'-chloro-4-(4-methoxy-piperidin-1-ylmethyl)-3,4,5,6-tetrahydro-2H-[1,2']bipyridinyl-3'-yl]-benzamide, $C_{24}H_{30}Cl_2N_4O_2$, [M+H]$^+$=479.2.

Example 5

Synthesis of 3-chloro-N-[5'-chloro-4-(1-piperidin-1-yl-ethyl)-3,4,5,6-tetrahydro-2H-[1,2']bipyridinyl-3'-yl]-benzamide (43)

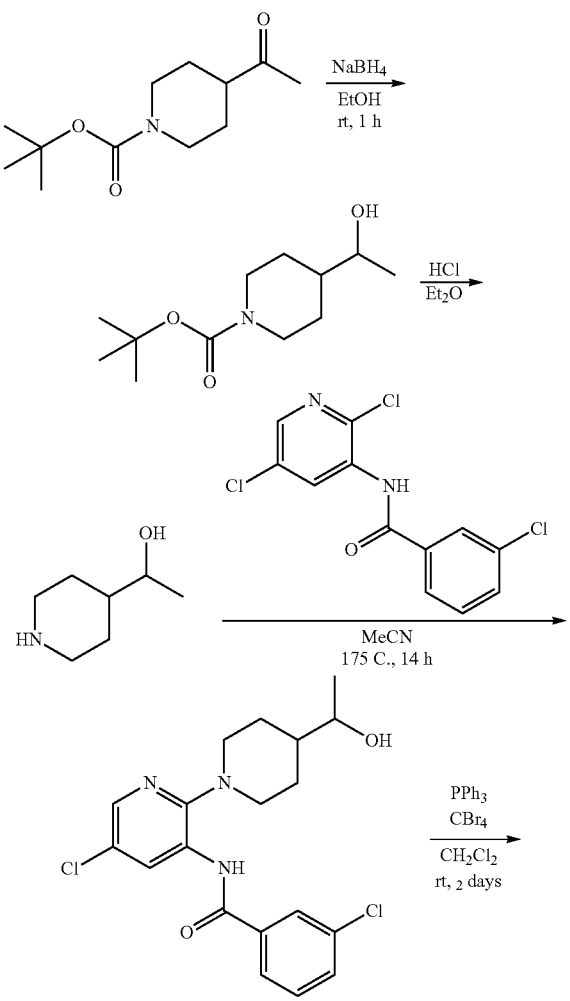

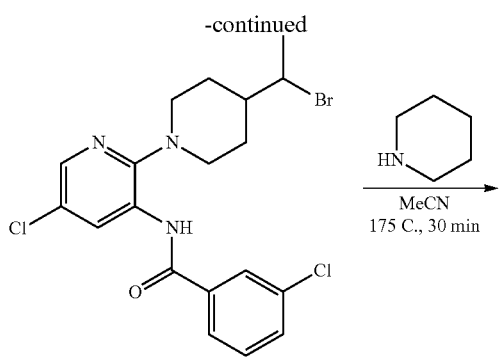

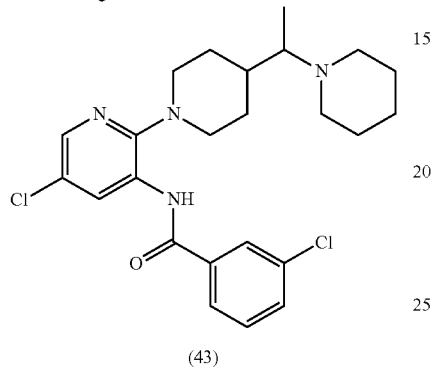

(43)

To a solution of 0.400 g (1.76 mmol) of 4-acetyl-piperidine-1-carboxylic acid tert-butyl ester in ethanol (3 mL) is added 0.134 g (3.52 mmol) of sodium borohydride. The mixture is stirred at room temperature for 1 hour then a saturated aqueous solution of ammonium chloride is added to consume excess reactants. The mixture is washed with ethyl acetate and the combined organic phase is dried over anhydrous sodium sulfate and concentrated under reduced pressure to provide 0.390 g (96.6%) of 4-(1-hydroxy-ethyl)-piperidine-1-carboxylic acid tert-butyl ester as a colorless oil.

To 0.390 g (1.70 mmol) of the above ester is added 5.0 mL (5.0 mmol) of hydrogen chloride as a 1.0 M solution in diethyl ether followed by several drops of methanol to generate a homogeneous mixture. To resulting mixture is stirred at room temperature for 2 hours then an excess of sodium hydroxide is added to make the pH alkaline. The mixture is extracted with ethyl acetate and the combined organic phase is dried over anhydrous sodium sulfate and concentrated under reduced pressure to provide 0.200 g (88.7%) of 1-piperidin-4-yl-ethanol as a light yellow oil.

A mixture of 0.200 g (1.55 mmol) of 1-piperidin-4-yl-ethanol and 0.200 g (0.663 mmol) of 3-chloro-N-(2,5-dichloro-pyridin-3-yl)-benzamide in acetonitrile (10 mL) is heated at 175 C in a microwave reactor for 14 hours. The mixture is cooled to room temperature and concentrated under reduced pressure. The residue is purified by flash silica gel chromatography to give 0.170 g (65.0%) of 3-chloro-N-[5'-chloro-4-(1-hydroxy-ethyl)-3,4,5,6-tetrahydro-2H-[1,2']bipyridinyl-3'-yl]-benzamide as a yellow oil.

A mixture of 0.170 g (0.431 mmol) of 3-chloro-N-[5'-chloro-4-(1-hydroxy-ethyl)-3,4,5,6-tetrahydro-2H-[1,2']bipyridinyl-3'-yl]-benzamide and 0.135 g (0.517 mmol) of triphenylphosphine in methylene chloride (15 mL) is stirred under an atmosphere of nitrogen at 0 C for 5 minutes. To this is added 0.171 g (0.517 mmol) of carbon tetrabromide in several portions. The mixture is stirred at 0 C for 30 minutes and then warmed to room temperature and stirred for 2 days. The mixture is concentrated under reduced pressure and purified by flash silica gel chromatography to give 0.030 g (15%) of N-(4-bromomethyl-5'-chloro-3,4,5,6-tetrahydro-2H-[1,2'] bipyridinyl-3'-yl)-3-chloro-benzamide as a colorless oil.

A mixture of 0.030 g (0.066 mmol) of N-(4-bromomethyl-5'-chloro-3,4,5,6-tetrahydro-2H-[1,2']bipyridinyl-3'-yl)-3-chloro-benzamide, 0.028 g (0.033 mmol) of piperidine, and 0.10 mL (0.58 mmol) of N,N-diisopropylethylamine in acetonitrile (1 mL) is heated at 175 C in a microwave reactor for 30 minutes. The mixture is cooled to room temperature and purified by preparative reverse phase HPLC to give 0.001 g (3%) of the title compound (43) as a colorless solid. $[M+H]^+=461.2$.

Example 6

Synthesis of 3-chloro-N-[4-(2-piperidin-1-yl-ethyl)-3,4,5,6-tetrahydro-2H-[1,2']bipyridinyl-3'-yl]-benzamide (44)

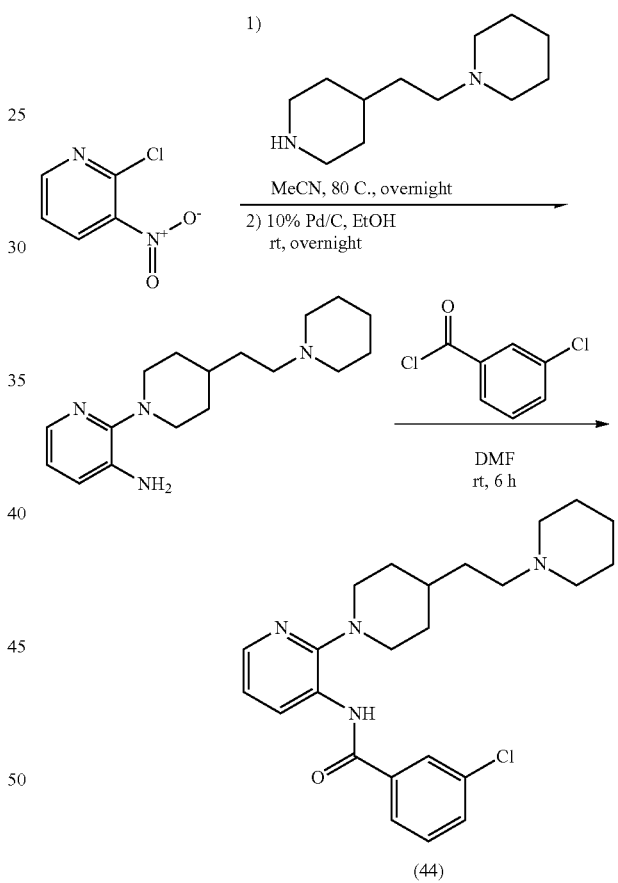

To a solution of 0.317 g (2.00 mmol) of 2-chloro-3-nitropyridine in acetonitrile (10 mL) is added 0.393 g (2.00 mmol) of 1-(2-piperdin-4-yl-ethyl)-piperidine. The mixture is heated to 80° C. and stirred overnight. The mixture is cooled to room temperature and concentrated under reduced pressure. The crude residue is dissolved in ethanol (10 mL) and treated with 0.050 g (0.05 mmol) of 10% palladium on carbon. The mixture is placed under an atmosphere of hydrogen and stirred overnight at room temperature. The mixture is concentrated under reduced pressure to provide 0.577 g (quant.) of 4-(2-piperidin-1-yl-ethyl)-3,4,5,6-tetrahydro-2H-[1,2']bipyridinyl-3'-ylamine.

To a solution of 0.029 g (0.10 mmol) of 4-(2-piperidin-1-yl-ethyl)-3,4,5,6-tetrahydro-2H-[1,2']bipyridinyl-3'-ylamine in N,N-dimethylformamide (1 mL) is added 0.017 g (0.10 mmol) of 3-chlorobenzoyl chloride. The mixture is stirred at room temperature for 6 hours and then purified by preparative reverse phase HPLC to provide 0.015 g (35%) of the title compound (44) as a colorless solid. [M+H]$^+$=427.1.

The following compounds can be prepared analogously:

3-Fluoro-N-[4-(2-piperidin-1-yl-ethyl)-3,4,5,6-tetrahydro-2H-[1,2']bipyridinyl-3'-yl]-5-trifluoromethyl-benzamide, $C_{25}H_{30}F_4N_4O$, [M+H]$^+$=469.5;

3-Methoxy-N-[4-(2-piperidin-1-yl-ethyl)-3,4,5,6-tetrahydro-2H-[1,2']bipyridinyl-3'-yl]-benzamide, $C_{25}H_{34}N_4O_2$, [M+H]$^+$=456.5;

5-Chloro-N-[4-(2-piperidin-1-yl-ethyl)-3,4,5,6-tetrahydro-2H-[1,2']bipyridinyl-3'-yl]-nicotinamide, $C_{23}H_{30}ClN_5O$, [M+H]$^+$=484.4;

4-Fluoro-N-[4-(2-piperidin-1-yl-ethyl)-3,4,5,6-tetrahydro-2H-[1,2']bipyridinyl-3'-yl]-3-trifluoromethyl-benzamide, $C_{25}H_{30}F_4N_4O$, [M+H]$^+$=445.3;

N-[4-(2-Piperidin-1-yl-ethyl)-3,4,5,6-tetrahydro-2H-[1,2']bipyridinyl-3'-yl]-3,5-bis-trifluoromethyl-benzamide, $C_{26}H_{30}F_6N_4O$, [M+H]$^+$=495.3;

4-Methoxy-N-[4-(2-piperidin-1-yl-ethyl)-3,4,5,6-tetrahydro-2H-[1,2']bipyridinyl-3'-yl]-3-trifluoromethyl-benzamide, $C_{26}H_{33}F_3N_4O_2$, [M+H]$^+$=475.5;

3-Benzoyl-N-[4-(2-piperidin-1-yl-ethyl)-3,4,5,6-tetrahydro-2H-[1,2']bipyridinyl-3'-yl]-benzamide, $C_{31}H_{36}N_4O_2$, [M+H]$^+$=423.2;

3-Chloro-4-fluoro-N-[4-(2-piperidin-1-yl-ethyl)-3,4,5,6-tetrahydro-2H-[1,2']bipyridinyl-3'-yl]-benzamide, $C_{24}H_{30}ClFN_4O$, [M+H]$^+$=485.1;

4-Chloro-N-[4-(2-piperidin-1-yl-ethyl)-3,4,5,6-tetrahydro-2H-[1,2']bipyridinyl-3'-yl]-3-trifluoromethyl-benzamide, $C_{25}H_{30}ClF_3N_4O$, [M+H]$^+$=457.1;

3-Methanesulfonyl-N-[4-(2-piperidin-1-yl-ethyl)-3,4,5,6-tetrahydro-2H-[1,2']bipyridinyl-3'-yl]-benzamide, $C_{25}H_{34}N_4O_3S$, [M+H]$^+$=469.4;

3-Chloro-4-methoxy-N-[4-(2-piperidin-1-yl-ethyl)-3,4,5,6-tetrahydro-2H-[1,2']bipyridinyl-3'-yl]-benzamide, $C_{25}H_{33}ClN_4O_2$, [M+H]$^+$=529.5;

3-Fluoro-N-[4-(2-piperidin-1-yl-ethyl)-3,4,5,6-tetrahydro-2H-[1,2']bipyridinyl-3'-yl]-4-trifluoromethyl-benzamide, $C_{25}H_{30}F_4N_4O$, [M+H]$^+$=471.5;

N-[4-(2-Piperidin-1-yl-ethyl)-3,4,5,6-tetrahydro-2H-[1,2']bipyridinyl-3'-yl]-benzamide, $C_{24}H_{32}N_4O$, [M+H]$^+$=456.6;

3-Chloro-4-methyl-N-[4-(2-piperidin-1-yl-ethyl)-3,4,5,6-tetrahydro-2H-[1,2']bipyridinyl-3'-yl]-benzamide, $C_{25}H_{33}ClN_4O$, [M+H]$^+$=418.3;

N-[4-(2-Piperidin-1-yl-ethyl)-3,4,5,6-tetrahydro-2H-[1,2']bipyridinyl-3'-yl]-4-trifluoromethyl-benzamide, $C_{25}H_{31}F_3N_4O$, [M+H]$^+$=475.2;

3-Chloro-2-fluoro-N-[4-(2-piperidin-1-yl-ethyl)-3,4,5,6-tetrahydro-2H-[1,2']bipyridinyl-3'-yl]-benzamide, $C_{24}H_{30}ClFN_4O$, [M+H]$^+$=451.2;

4-Methyl-N-[4-(2-piperidin-1-yl-ethyl)-3,4,5,6-tetrahydro-2H-[1,2']bipyridinyl-3'-yl]-3-trifluoromethyl-benzamide, $C_{26}H_{33}F_3N_4O$, [M+H]$^+$=447.1;

3-Fluoro-N-[4-(2-piperidin-1-yl-ethyl)-3,4,5,6-tetrahydro-2H-[1,2']bipyridinyl-3'-yl]-benzamide, $C_{24}H_{31}FN_4O$, [M+H]$^+$=477.2;

3-Phenoxy-N-[4-(2-piperidin-1-yl-ethyl)-3,4,5,6-tetrahydro-2H-[1,2']bipyridinyl-3'-yl]-benzamide, $C_{30}H_{36}N_4O_2$, [M+H]$^+$=441.2;

3-Cyano-N-[4-(2-piperidin-1-yl-ethyl)-3,4,5,6-tetrahydro-2H-[1,2']bipyridinyl-3'-yl]-benzamide, $C_{25}H_{31}N_5O$, [M+H]$^+$=440.2;

3,5-Dichloro-N-[4-(2-piperidin-1-yl-ethyl)-3,4,5,6-tetrahydro-2H-[1,2']bipyridinyl-3'-yl]-benzamide, $C_{24}H_{30}Cl_2N_4O$, [M+H]$^+$=438.3;

N-[4-(2-Piperidin-1-yl-ethyl)-3,4,5,6-tetrahydro-2H-[1,2']bipyridinyl-3'-yl]-3-trifluoromethoxy-benzamide, $C_{25}H_{31}F_3N_4O_2$, [M+H]$^+$=445.3;

N-{4-[2-(4-Methyl-piperazin-1-yl)-ethyl]-3,4,5,6-tetrahydro-2H-[1,2']bipyridinyl-3'-yl}-3-trifluoromethyl-benzamide, $C_{25}H_{32}F_3N_5O$, [M+H]$^+$=428.3;

3-Methyl-N-[4-(2-piperidin-1-yl-ethyl)-3,4,5,6-tetrahydro-2H-[1,2']bipyridinyl-3'-yl]-benzamide, $C_{25}H_{34}N_4O$, [M+H]$^+$=407.1;

3-Chloro-5-fluoro-N-[4-(2-piperidin-1-yl-ethyl)-3,4,5,6-tetrahydro-2H-[1,2']bipyridinyl-3'-yl]-benzamide, $C_{24}H_{30}ClFN_4O$, [M+H]$^+$=445.1;

Naphthalene-2-carboxylic acid [4-(2-piperidin-1-yl-ethyl)-3,4,5,6-tetrahydro-2H-[1,2']bipyridinyl-3'-yl]-amide, $C_{28}H_{34}N_4O$, [M+H]$^+$=411.4;

3,4-Dichloro-N-[4-(2-piperidin-1-yl-ethyl)-3,4,5,6-tetrahydro-2H-[1,2']bipyridinyl-3'-yl]-benzamide, $C_{24}H_{30}Cl_2N_4O$, [M+H]$^+$=471.2;

Biphenyl-3-carboxylic acid [4-(2-piperidin-1-yl-ethyl)-3,4,5,6-tetrahydro-2H-[1,2']bipyridinyl-3'-yl]-amide, $C_{30}H_{36}N_4O$, [M+H]$^+$=443.3;

3-Nitro-N-[4-(2-piperidin-1-yl-ethyl)-3,4,5,6-tetrahydro-2H-[1,2']bipyridinyl-3'-yl]-benzamide, $C_{24}H_{31}N_5O_3$, [M+H]$^+$=479.3;

3-Bromo-N-[4-(2-piperidin-1-yl-ethyl)-3,4,5,6-tetrahydro-2H-[1,2']bipyridinyl-3'-yl]-benzamide, $C_{24}H_{31}BrN_4O$, [M+H]$^+$=461.0;

N-[4-(2-Piperidin-1-yl-ethyl)-3,4,5,6-tetrahydro-2H-[1,2']bipyridinyl-3'-yl]-3-trifluoromethyl-benzamide, $C_{25}H_{31}F_3N_4O$, [M+H]$^+$=461.1;

4-Methoxy-N-[4-(2-piperidin-1-yl-ethyl)-3,4,5,6-tetrahydro-2H-[1,2']bipyridinyl-3'-yl]-benzamide, $C_{25}H_{34}N_4O_2$, [M+H]$^+$=423.2;

4-tert-Butyl-N-[4-(2-piperidin-1-yl-ethyl)-3,4,5,6-tetrahydro-2H-[1,2']bipyridinyl-3'-yl]-benzamide, $C_{28}H_{40}N_4O$, [M+H]$^+$=449.3;

Example 7

Synthesis of 3-chloro-N-{5'-methanesulfonyl-4-[2-(pyridin-3-ylamino)-ethyl]-3,4,5,6-tetrahydro-2H-[1,2']bipyridinyl-3'-yl}-benzamide (78)

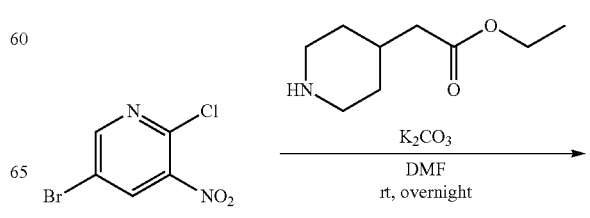

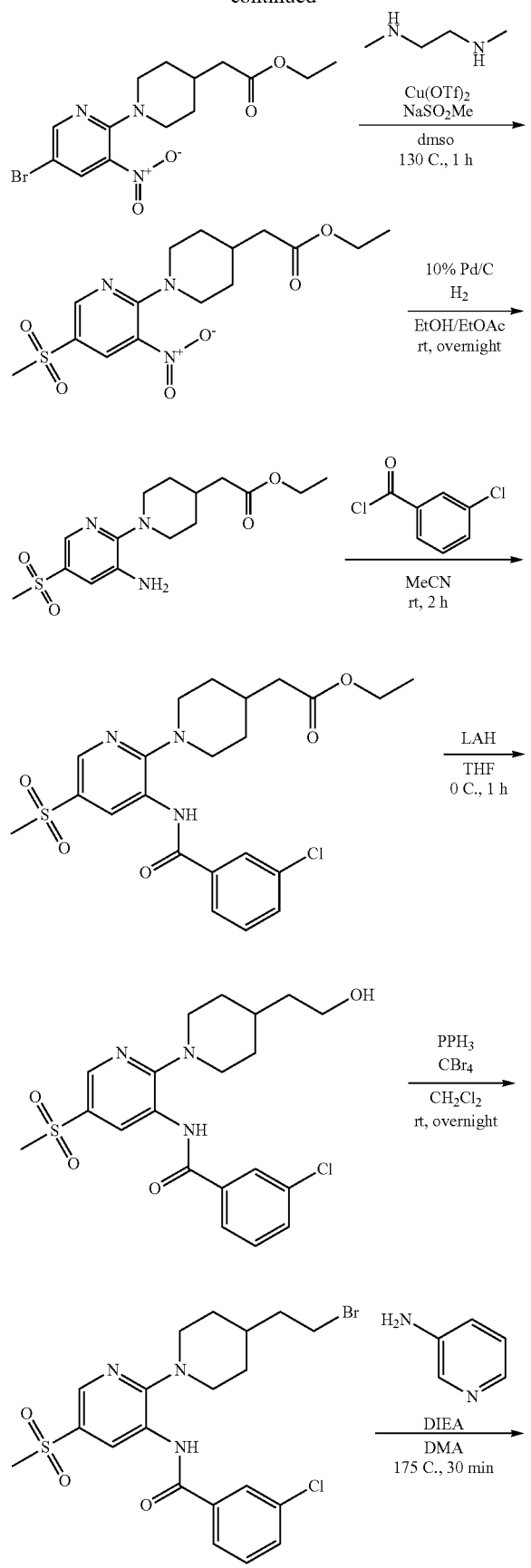

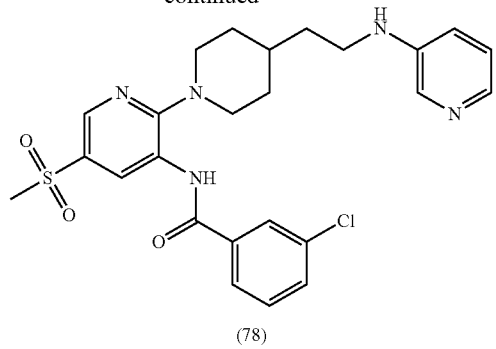

(78)

To a solution of 4.80 g (20.2 mmol) of 5-bromo-3-nitro-2-chloropyridine in N,N-dimethylformamide (100 mL) is added 3.6 g (21 mmol) of 2-(piperdin-4-yl) acetic acid ethyl ester followed by 14 g (100 mmol) of potassium carbonate. The mixture is stirred at room temperature overnight then diluted with water and extracted with ethyl acetate. The combined organic phase is washed with water followed by brine then dried over anhydrous sodium sulfate and concentrated under reduced pressure to provide 6.90 g (91.7%) of 5'-bromo-3'-nitro-3,4,5,6-tetrahydro-2H-[1,2']bipyridinyl-4-yl)-acetic acid ethyl ester as an orange oil.

To a solution of 6.90 g (18.5 mmol) of 5'-bromo-3'-nitro-3,4,5,6-tetrahydro-2H-[1,2']bipyridinyl-4-yl)-acetic acid in dimethylsulfoxide (100 mL) is added 4.5 mL (41 mmol) of dimethylethylenediamine followed by 4.0 g (39 mmol) of sodium methanesulfinate and 5.5 g (19 mmol) of copper (II) triflate. The mixture is heated to 130° C. for 1 hour then cooled to room temperature. The mixture is diluted with water and stirred overnight during which time a solid precipitates from solution. The yellow solid is collected by filtration, washed with water and dried on the filter pad to provide 5.00 g (72.6%) of (5'-methanesulfonyl-3'-nitro-3,4,5,6-tetrahydro-2H-[1,2']bipyridinyl-4-yl)-acetic acid ethyl ester.

A solution of 1.75 g (4.71 mmol) of (5'-methanesulfonyl-3'-nitro-3,4,5,6-tetrahydro-2H-[1,2']bipyridinyl-4-yl)-acetic acid ethyl ester in a 1:1 mixture of ethanol:ethyl acetate (150 mL) is shaken over 1.0 g (0.94 mmol) of 10% palladium on carbon under an atmosphere of hydrogen overnight. The mixture is filtered through a pad of diatomaceous earth and concentrated under reduced pressure to provide 1.65 g (100%) of (3'-amino-5'-methanesulfonyl-3,4,5,6-tetrahydro-2H-[1,2'] bipyridinyl-4-yl)-acetic acid ethyl ester as a brown solid.

To a solution of 1.65 g (4.83 mmol) of (3'-amino-5'-methanesulfonyl-3,4,5,6-tetrahydro-2H-[1,2']bipyridinyl-4-yl)-acetic acid ethyl ester in acetonitrile (100 mL) is added 0.64 mL (5.0 mmol) of 3-chlorobenzoyl chloride. After stirring at room temperature overnight the mixture is concentrated under reduced pressure. The residue is diluted with water and extracted with ethyl acetate. The combined organic phase is dried over anhydrous sodium sulfate, concentrated under reduced pressure, and purified by flash silica gel chromatography to provide 1.40 g (60.4%) of [3'-(3-chloro-benzoylamino)-5'-methanesulfonyl-3,4,5,6-tetrahydro-2H-[1,2']bipyridinyl-4-yl]-acetic acid ethyl ester as a white foam.

To a stirred mixture of 0.202 g (5.32 mmol) of lithium aluminum hydride in dry tetrahydrofuran (2 mL), cooled to 0° C., is added 1.70 g (3.54 mmol) of [3'-(3-chloro-benzoylamino)-5'-methanesulfonyl-3,4,5,6-tetrahydro-2H-[1,2']bipyridinyl-4-yl]-acetic acid ethyl ester as a solution in tetrahydrofuran (6 mL). The mixture is warmed to room temperature and stirred for 1 hour then cooled in an ice bath. Excess reactants are consumed by the dropwise addition of water (0.2 mL) followed by a 15% NaOH solution (0.2 mL) and additional water (0.4 mL). The mixture is stirred at room temperature for 30 minutes then filtered through a pad of diatomaceous earth. The filter pad is washed with tetrahydrofuran and the combined filtrate is concentrated under reduced pressure. The residue is purified by flash chromatography on neutral alumina to yield 1.3 g (86%) of 3-chloro-N-[4-(2-hydroxy-ethyl)-5'-methanesulfonyl-3,4,5,6-tetrahydro-2H-[1,2']bipyridinyl-3'-yl]-benzamide.

To a mixture of 0.300 g (1.14 mmol) of triphenylphosphine, and 0.500 g (1.14 mmol) of 3-chloro-N-[4-(2-hydroxy-ethyl)-5'-methanesulfonyl-3,4,5,6-tetrahydro-2H-[1,2']bipyridinyl-3'-yl]benzamide in methylene chloride (20 mL), cooled to 0° C., is added 0.380 g (1.14 mmol) of carbon tetrabromide in multiple portions. The mixture is warmed to room temperature and stirred overnight then concentrated under reduced pressure and the residue purified by flash silica gel chromatography to provide 0.285 g (50% yield) of N-[4-(2-bromo-ethyl)-5'-methanesulfonyl-3,4,5,6-tetrahydro-2H-[1,2']bipyridinyl-3'-yl]-3-chloro-benzamide.

A mixture of 0.040 g (0.080 mmol) of N-[4-(2-bromo-ethyl)-5'-methanesulfonyl-3,4,5,6-tetrahydro-2H-[1,2']bipyridinyl-3'-yl]-3-chloro-benzamide, 0.022 g (0.24 mmol) of 3-aminopyridine, and 0.20 mL (1.1 mmol) of N,N-diisopropylethylamine in N,N-dimethylacetamide (1 mL) is heated at 175° C. in a microwave reactor for 30 min. The mixture is cooled to room temperature, diluted with water, and purified by preparative reverse phase HPLC to provide, 0.031 g (75%) of the title compound (78) as a colorless foam. [M+H]$^+$=514.2.

The following compounds can be prepared analogously:

3-Chloro-N-{5-methanesulfonyl-2-[4-(2-piperidin-1-yl-ethyl)-piperidin-1-yl]-phenyl}-benzamide, $C_{26}H_{34}ClN_3O_3S$, [M+H]$^+$=544.4;

3-Chloro-N-{5'-methanesulfonyl-4-[2-(4-methyl-[1,4]diazepan-1-yl)-ethyl]-3,4,5,6-tetrahydro-2H-[1,2']bipyridinyl-3'-yl}-benzamide, $C_{26}H_{36}ClN_5O_3S$, [M+H]$^+$=470.4;

N-[4-(2-Benzoimidazol-1-yl-ethyl)-5'-methanesulfonyl-3,4,5,6-tetrahydro-2H-[1,2']bipyridinyl-3'-yl]-3-chloro-benzamide, $C_{27}H_{28}ClN_5O_3S$, [M+H]$^+$=477.4;

3-Chloro-N-[4-(2-imidazo[4,5-b]pyridin-3-yl-ethyl)-5'-methanesulfonyl-3,4,5,6-tetrahydro-2H-[1,2']bipyridinyl-3'-yl]-benzamide, $C_{26}H_{27}ClN_6O_3S$, [M+H]$^+$=504.2;

3-Chloro-N-[4-(2-imidazo[4,5-b]pyridin-1-yl-ethyl)-5'-methanesulfonyl-3,4,5,6-tetrahydro-2H-[1,2']bipyridinyl-3'-yl]-benzamide, $C_{26}H_{27}ClN_6O_3S$, [M+H]$^+$=524.2;

3-Chloro-N-{4-[2-(2,5-dimethyl-imidazol-1-yl)-ethyl]-5'-methanesulfonyl-3,4,5,6-tetrahydro-2H-[1,2']bipyridinyl-3'-yl}-benzamide, $C_{25}H_{30}ClN_5O_3S$, [M+H]$^+$=505.4;

3-Chloro-N-{5'-methanesulfonyl-4-[2-(thiazol-2-ylamino)-ethyl]-3,4,5,6-tetrahydro-2H-[1,2']bipyridinyl-3'-yl}-benzamide, $C_{23}H_{26}ClN_5O_3S_2$, [M+H]$^+$=520.2; and 3-Chloro-N-[5'-methanesulfonyl-4-(2-pyrrolo[2,3-b]pyridin-1-yl-ethyl)-3,4,5,6-tetrahydro-2H-[1,2']bipyridinyl-3'-yl]-benzamide, $C_{27}H_{28}ClN_5O_3S$, [M+H]$^+$=538.3.

Example 8

3-Chloro-N-{5'-methanesulfonyl-4-[((R)-2-phenyl-propionylamino)-methyl]-3,4,5,6-tetrahydro-2H-[1,2']bipyridinyl-3'-yl}-benzamide (87)

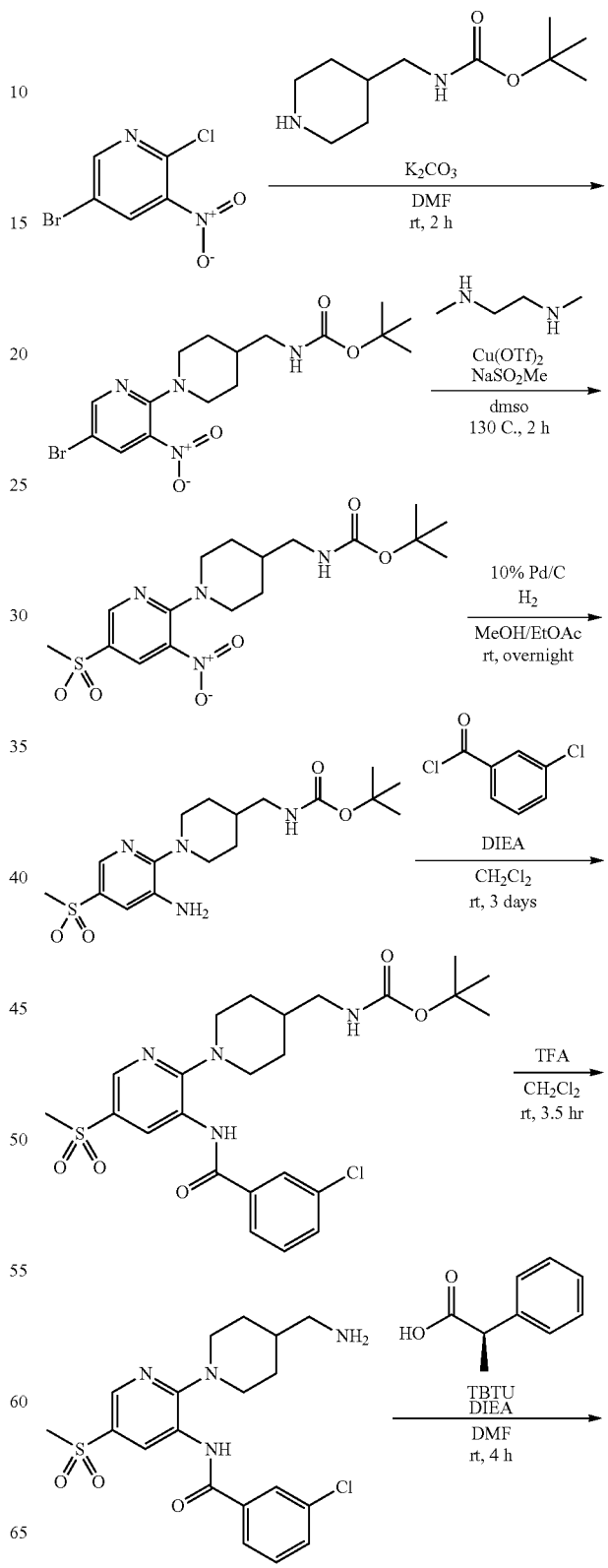

-continued

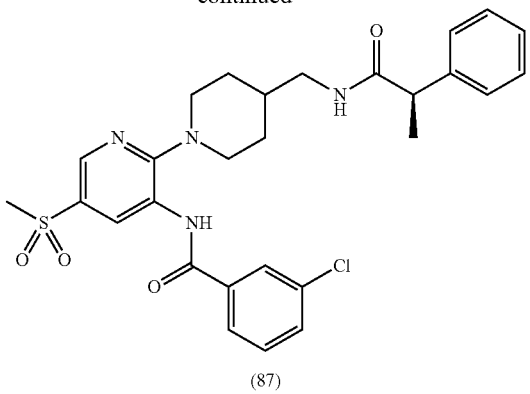

(87)

A suspension of 1.00 g (4.21 mmol) 5-bromo-2-chloro-3-nitro-pyridine, 0.993 g (4.63 mmol) of piperidin-4-ylmethyl-carbamic acid tert-butyl ester, and 1.16 g (8.42 mmol) of potassium carbonate in N,N-dimethylformamide (10 mL) is stirred for 2 hours under argon. The mixture is diluted with water which causes a solid to precipitate from solution. The formed solid is collected by filtration, washed with water, and dried for 1 hour under vacuum at 50° C. to give 1.57 g (90.0%) of (5'-bromo-3'-nitro-3,4,5,6-tetrahydro-2H-[1,2']bipyridinyl-4-ylmethyl)-carbamic acid tert-butyl ester as a yellow solid.

To a solution of 2.00 g (4.82 mmol) of the above tert-butyl ester in dimethylsulfoxide (15 mL) is added 1.10 mL (10.1 mmol) of dimethylethylenediamine followed by 0.983 g (9.64 mmol) of sodium methanesulfinate, and 1.74 g (4.82 mmol) of copper (II) triflate. The mixture is heated at 130° C. under argon for 2 hours. The mixture is cooled to room temperature and diluted with water causing a solid to precipitate from solution. The formed solid is collected by filtration, washed with water, and dried on the filter pad. The residue is purified by flash silica gel chromatography to give 1.03 g (52.0%) of (5'-methanesulfonyl-3'-nitro-3,4,5,6-tetrahydro-2H-[1,2']bipyridinyl-4-ylmethyl)-carbamic acid tert-butyl ester as a brown resin.

A mixture of 1.03 g (2.48 mmol) of (5'-methanesulfonyl-3'-nitro-3,4,5,6-tetrahydro-2H-[1,2']bipyridinyl-4-ylmethyl)-carbamic acid tert-butyl ester and 0.15 g (0.14 mmol) of 10% palladium on carbon in a 1:1 mixture of ethyl acetate:methanol (50 mL) is placed under an atmosphere of hydrogen and stirred overnight at room temperature. The mixture is filtered through diatomaceous earth and the filter pad is washed with methanol. The filtrate is concentrated under reduced pressure to provide 0.980 g (103%) of as a (3'-amino-5'-methanesulfonyl-3,4,5,6-tetrahydro-2H-[1,2']bipyridinyl-4-ylmethyl)-carbamic acid tert-butyl ester as a brown resin.

To a solution of 0.300 g (0.780 mmol) of (3'-amino-5'-methanesulfonyl-3,4,5,6-tetrahydro-2H-[1,2']bipyridinyl-4-ylmethyl)-carbamic acid tert-butyl ester in methylene chloride (3 mL) under argon, cooled to 0° C., is added 0.136 mL (0.780 mmol) of N,N-diisopropylethylamine followed by 0.110 mL (0.858 mmol) of 3-chlorobenzoyl chloride. The mixture is stirred at 0° C. for 15 min then warmed to room temperature and stirred for 2 days during which time the solvent evaporates. The residue is dissolved in methylene chloride (3 mL) and an additional 0.136 mL (0.780 mmol) of N,N-diisopropylethylamine and 0.110 mL (0.858 mmol) of 3-chlorobenzoyl chloride is added. The reaction is stirred overnight at room temperature. The mixture is diluted with ethyl acetate and washed with water followed by aqueous ammonium chloride and then aqueous sodium carbonate. The organic phase is dried over anhydrous sodium sulfate and concentrated under reduced pressure. The residue is purified by preparative thin layer chromatography to give 0.186 g (46.0%) of [3'-(3-chloro-benzoylamino)-5'-methanesulfonyl-3,4,5,6-tetrahydro-2H-[1,2']bipyridinyl-4-ylmethyl]-carbamic acid tert-butyl ester as a beige foam.

A solution of 0.612 g (1.17 mmol) of [3'-(3-chloro-benzoylamino)-5'-methanesulfonyl-3,4,5,6-tetrahydro-2H-[1,2']bipyridinyl-4-ylmethyl]-carbamic acid tert-butyl ester in a mixture of methylene chloride (2 mL) and trifluoroacetic acid (2 mL) is stirred for 3.5 hours in a capped flask. The reaction mixture is concentrated under reduced pressure, diluted with water, and washed with diethyl ether. The pH of the aqueous phase is adjusted to alkaline with an aqueous solution of sodium carbonate and extracted with ethyl acetate. The combined organic phase is washed with an aqueous solution of sodium carbonate followed by water then dried over anhydrous sodium sulfate and filtered to remove the drying agent. The aqueous phase is re-extracted with a 1:1 mixture of n-butanol:ethyl acetate followed by n-butanol. The organic phases from these extractions are washed with an aqueous solution of sodium carbonate followed by water. The organic phase is then concentrated under reduced pressure co-evaporating with toluene. The residue is dissolved in a mixture of methanol:methylene chloride, dried over anhydrous sodium sulfate and combined with the previous organic washings. The combined organic phase is concentrated under reduced pressure to give 0.422 g (85.0%) of N-(4-aminomethyl-5'-methanesulfonyl-3,4,5,6-tetrahydro-2H-[1,2']bipyridinyl-3'-yl)-3-chloro-benzamide as a resin.

To 0.028 g (0.066 mmol) of the above benzamide in N,N-dimethylformamide (0.5 mL) is added 0.010 g (0.066 mmol) of (R)-(−)-2-phenylpropionic acid followed by 0.032 g (0.099 mmol) of O-benzotriazol-1-yl-N,N,N',N'-tetramethyluronium tetrafluoroborate, and 0.034 mL (0.20 mmol) of N,N-diisopropylethyl amine. The mixture is stirred at room temperature for 4 hours then poured into water which causes a solid to precipitate from solution. The formed solid is collected by filtration, washed with water and dried overnight at room temperature then for 1 hour at 70° C. under vacuum to provide 0.023 g (63%) of the title compound (87) as a beige solid. [M+H]$^+$=555.7.

The following compounds can be prepared analogously:

3-Chloro-N-{5'-methanesulfonyl-4-[((S)-2-phenyl-propionylamino)-methyl]-3,4,5,6-tetrahydro-2H-[1,2']bipyridinyl-3'-yl}-benzamide, $C_{28}H_{31}ClN_4O_4S$ [M+H]$^+$=555.7; and 1-Methyl-piperidine-3-carboxylic acid [3'-(3-chloro-benzoylamino)-5'-methanesulfonyl-3,4,5,6-tetrahydro-2H-[1,2']bipyridinyl-4-ylmethyl]-amide, $C_{26}H_{34}ClN_5O_4S$, [M+H]$^+$=548.8.

Example 9

3-Chloro-N-{5-chloro-2-[4-(2-piperidin-1-yl-ethyl)-piperidin-1-yl]-phenyl}-benzamide (90)

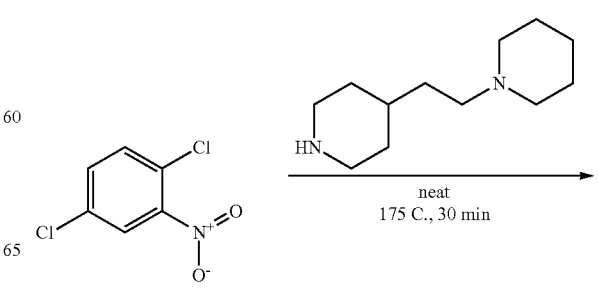

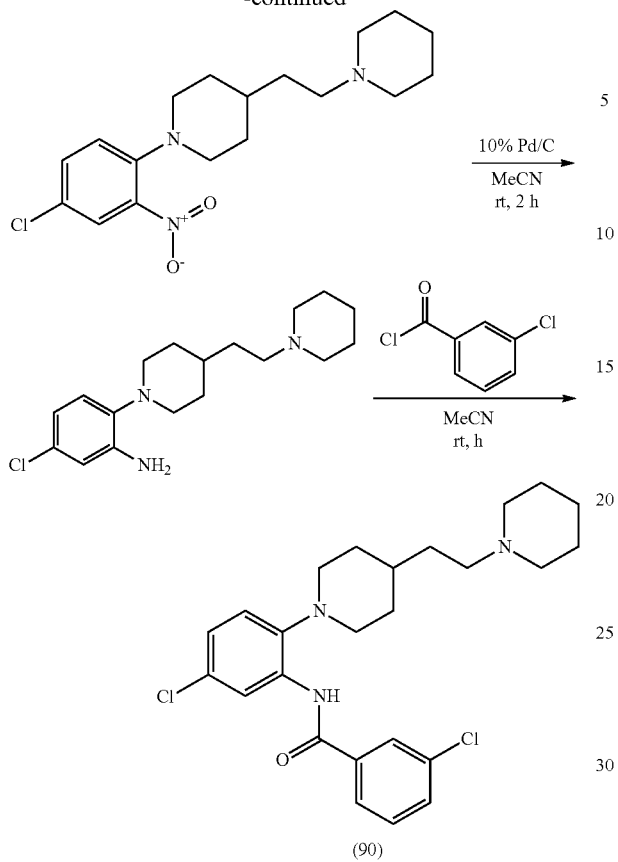

A mixture of 0.576 g (3.00 mmol) of 2,5-dichloronitrobezene and 0.589 g (3.00 mmol) of 1-(2-piperidin-4-yl-ethyl)-piperidine in acetonitrile (5 mL) are heated at 175° C. in a microwave reactor for 30 minutes. The mixture is cooled to room temperature and concentrated under reduced pressure to provide 0.95 g (90% yield) of 1-(4-chloro-2-nitro-phenyl)-4-(2-piperidin-1-yl-ethyl)-piperidine.

To a solution of 0.351 g (1.00 mmol) of 1-(4-chloro-2-nitro-phenyl)-4-(2-piperidin-1-yl-ethyl)-piperidine dissolved in acetonitrile (5 mL) is added 0.010 g (0.01 mmol) of 10% palladium on carbon. The mixture is placed under an atmosphere of hydrogen and stirred at room temperature for 2 hours. The mixture is concentrated under reduced pressure to provide 0.322 g (quant.) of 5-chloro-2-[4-(2-piperidin-1-yl-ethyl)-piperidin-1-yl]-phenylamine.

To a solution of 0.032 g, 0.10 mmol) acetonitrile (5 mL), cooled to 0° C., is treated with 0.018 g (0.10 mmol) of 3-chlorobenzoyl chloride. The mixture is stirred at room temperature overnight and then purified by preparative reverse phase HPLC to give 0.015 g (33% yield) of 3-chloro-N-(5-chloro-2-{4-[2-(piperidin-1-yl)ethyl]piperidin-1-yl}phenyl)benzamide (90) as a colorless solid. [M+H]$^+$=460.2

The following compounds can be prepared analogously:
3-Chloro-N-{5-methoxy-2-[4-(2-piperidin-1-yl-ethyl)-piperidin-1-yl]-phenyl}-benzamide, $C_{26}H_{34}ClN_3O_2$, [M+H]$^+$=476.4;
3-Chloro-N-{5-cyano-2-[4-(2-piperidin-1-yl-ethyl)-piperidin-1-yl]-phenyl}-benzamide, $C_{26}H_{31}ClN_4O$, [M+H]$^+$=534.1;
3-Chloro-N-{2-[4-(2-piperidin-1-yl-ethyl)-piperidin-1-yl]-5-sulfamoyl-phenyl}-benzamide, $C_{25}H_{33}ClN_4O_3S$, [M+H]$^+$=553.5;
3-(3-Chloro-benzoylamino)-4-[4-(2-piperidin-1-yl-ethyl)-piperidin-1-yl]-benzoic acid methyl ester, $C_{27}H_{34}ClN_3O_3$, [M+H]$^+$=427.4;
3-Chloro-N-{5-hydroxymethyl-2-[4-(2-piperidin-1-yl-ethyl)-piperidin-1-yl]-phenyl}-benzamide, $C_{26}H_{34}ClN_3O_2$, [M+H]$^+$=393.4;
3-Chloro-N-{5-methyl-2-[4-(2-piperidin-1-yl-ethyl)-piperidin-1-yl]-phenyl}-benzamide, $C_{26}H_{34}ClN_3O$, [M+H]$^+$=539.2;
3-Chloro-N-{5-fluoro-2-[4-(2-piperidin-1-yl-ethyl)-piperidin-1-yl]-phenyl}-benzamide, $C_{25}H_{31}ClFN_3O$, [M+H]$^+$=538.2;
3-Chloro-N-{2-[4-(2-piperidin-1-yl-ethyl)-piperidin-1-yl]-5-trifluoromethyl-phenyl}-benzamide, $C_{26}H_{31}ClF_3N_3O$, [M+H]$^+$=539.2; and
3-Chloro-N-{2-[4-(2-piperidin-1-yl-ethyl)-piperidin-1-yl]-phenyl}-benzamide, $C_{25}H_{32}ClN_3O$, [M+H]$^+$=426.2.

Example 10

Synthesis of 3-chloro-N-(5-chloro-2-{4-[2-(4-hydroxy-piperidin-1-yl)-ethyl]-piperidin-1-yl}-phenyl)-benzamide (100)

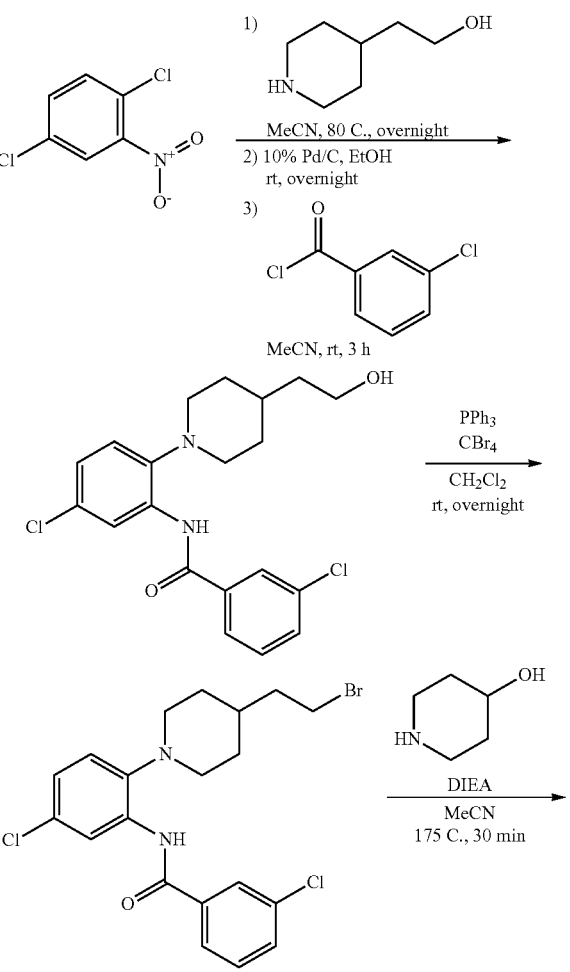

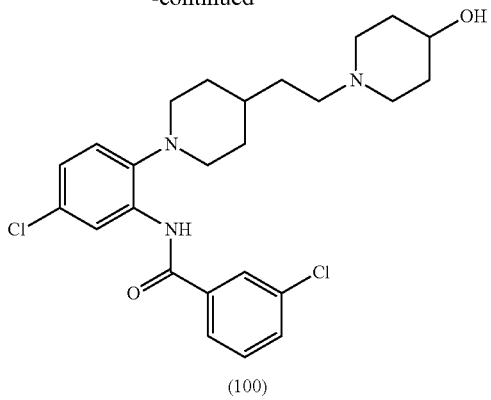

(100)

A mixture of 1.00 g (5.21 mmol) of 2,5-dichloronitrobenzene and 1.01 g (7.81 mmol) of 4-piperdineethanol in N,N-dimethylformamide (3 mL) is heated at 130° C. and stirred overnight. The mixture is cooled to room temperature, diluted with water and extracted with ethyl acetate. The combined organic phase is washed with brine, dried over anhydrous sodium sulfate and concentrated under reduced pressure to provide a red oil. The residue is dissolved in ethanol (15 mL) and 0.20 g (0.19 mmol) of 10% palladium on carbon is added followed by a drop of concentrated hydrochloric acid. The mixture is stirred at room temperature for 2 hours then filtered through a pad of diatomaceous earth and the filter pad is washed with methanol. The mixture is concentrated under reduced pressure to provide a black oil. The residue is dissolved in acetonitrile (50 mL) and treated with 1.03 g (5.89 mmol) of 3-chlorobenzoyl chloride. The mixture is stirred at room temperature for 3 hours then concentrated under reduced pressure. To the residue is slowly added a 2M solution of sodium bicarbonate. The mixture is extracted with ethyl acetate and the combined organic phase is washed with brine and dried over anhydrous sodium sulfate. The mixture is concentrated and the residue is purified by flash silica gel chromatography to give 0.800 g (39.0% overall) of 3-chloro-N-{5-chloro-2-[4-(2-hydroxy-ethyl)-piperidin-1-yl]-phenyl}-benzamide as a brown foam.

A mixture of 0.800 g (2.03 mmol) of 3-chloro-N-{5-chloro-2-[4-(2-hydroxy-ethyl)-piperidin-1-yl]-phenyl}-benzamide and 0.533 g (2.03 mmol) of triphenylphosphine in methylene chloride (20 mL), cooled to 0° C., is stirred for 20 minutes. To this is added 0.674 g (2.03 mmol) of carbon tetrabromide and the mixture is warmed to room temperature and stirred overnight. The mixture is concentrated under reduced pressure and the residue is purified by flash silica gel chromatography to provide 0.400 g (70.0%) of N-{2-[4-(2-bromo-ethyl)-piperidin-1-yl]-5-chloro-phenyl}-3-chloro-benzamide as a light red oil.

A mixture of 0.040 g (0.088 mmol) of N-{2-[4-(2-bromo-ethyl)-piperidin-1-yl]-5-chloro-phenyl}-3-chloro-benzamide, 0.044 g (0.44 mmol) of 4-hydoxypiperidine, and 0.50 mL (2.9 mmol) of N,N-diisopropylethylamine in acetonitrile (1 mL) is heated to 175° C. in a microwave reactor for 30 minutes. The mixture is cooled to room temperature and purified by preparative reverse phase HPLC to provide 0.023 g (55%) of the title compound (100) as a colorless solid. $[M+H]^+=476.3$.

The following compounds can be prepared analogously:

3-Chloro-N-{5-chloro-2-[4-(2-[1,4]oxazepan-4-yl-ethyl)-piperidin-1-yl]-phenyl}-benzamide, $C_{25}H_{31}Cl_2N_3O_2$, $[M+H]^+=476.3$;

3-Chloro-N-(5-chloro-2-{4-[2-(4-methyl-[1,4]diazepan-1-yl)-ethyl]-piperidin-1-yl}-phenyl)-benzamide, $C_{26}H_{34}Cl_2N_4O$, $[M+H]^+=489.3$;

3-Chloro-N-(5-chloro-2-{4-[2-((2S,6R)-2,6-dimethyl-piperidin-1-yl)-ethyl]-piperidin-1-yl}-phenyl)-benzamide, $C_{27}H_{35}Cl_2N_3O$, $[M+H]^+=488.3$;

3-Chloro-N-{5-chloro-2-[4-(2-diisopropylamino-ethyl)-piperidin-1-yl]-phenyl}-benzamide, $C_{26}H_{35}Cl_2N_3O$, $[M+H]^+=476.4$;

3-Chloro-N-(5-chloro-2-{4-[2-(3-oxo-piperazin-1-yl)-ethyl]-piperidin-1-yl}-phenyl)-benzamide, $C_{24}H_{28}Cl_2N_4O_2$, $[M+H]^+=475.3$; and 3-Chloro-N-(5-chloro-2-{4-[2-(2-methyl-piperidin-1-yl)-ethyl]-piperidin-1-yl}-phenyl)-benzamide, $C_{26}H_{33}Cl_2N_3O$, $[M+H]^+=474.3$.

Example 11

Synthesis of 3-chloro-N-{5-chloro-2-[4-(2-piperidin-1-yl-ethyl)-piperazin-1-yl]-pyridin-3-yl}-benzamide (107)

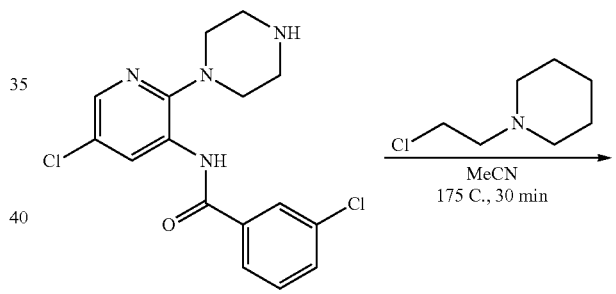

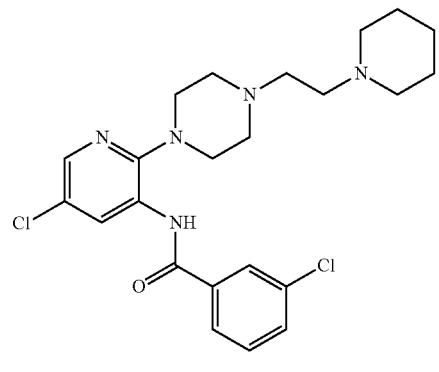

(107)

A mixture of 0.035 g (0.10 mmol) of 3-chloro-N-(5-chloro-2-piperazin-1-yl-pyridin-3-yl)-benzamide and 0.055 g (0.30 mmol) of 1-(2-chloroethyl)piperidine in acetonitrile (2 mL) is heated at 175° C. in a microwave reactor for 30 minutes. The mixture is cooled to room temperature and purified by preparative reverse phase HPLC to give 0.012 g (26%) of the title compound (107) as a brown oil. [M+H]+=464.2.

Example 12

Synthesis of 3-chloro-N-{5-chloro-2-[4-(2-piperidin-1-yl-ethyl)-[1,4]diazepan-1-yl]-pyridin-3-yl}-benzamide (108)

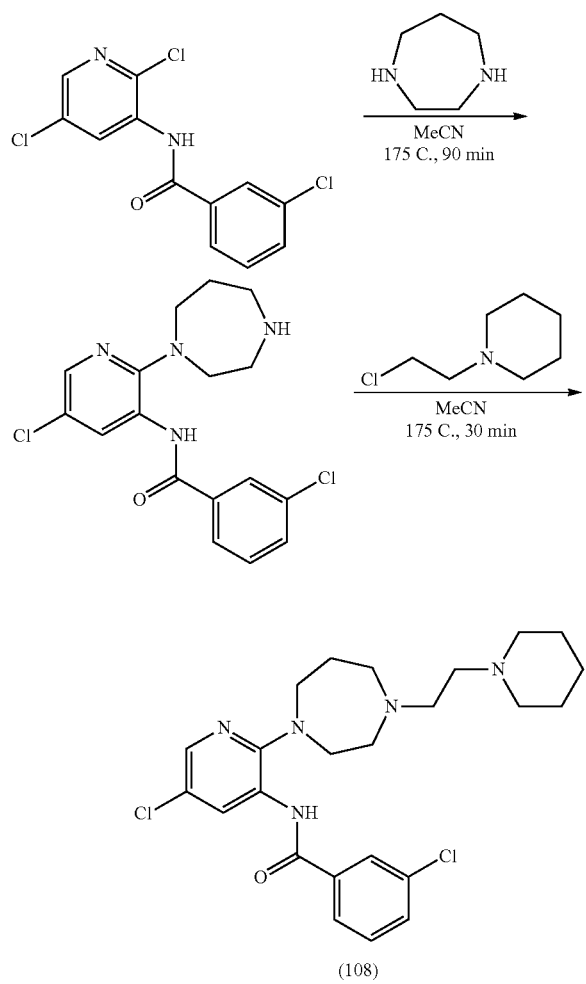

(108)

A mixture of 0.500 g (1.66 mmol) of 3-chloro-N-(2,5-dichloro-pyridin-3-yl)-benzamide and 0.498 g (4.97 mmol) of homopiperazine in acetonitrile (5 mL) is heated at 175° C. in a microwave reactor for 90 minutes. The mixture is cooled to room temperature and concentrated under reduced pressure. The residue is purified by flash silica gel chromatography to give 0.390 g (66.8%) of 3-chloro-N-(5-chloro-2-[1,4]diazepan-1-yl-pyridin-3-yl)-benzamide as a red oil.

A mixture of 0.035 g (0.096 mmol) of 3-chloro-N-(5-chloro-2-[1,4]diazepan-1-yl-pyridin-3-yl)-benzamide in 0.053 g (0.29 mmol) of 2-pyridino-1-ethylchloride hydrochloride in acetonitrile (2 mL) is heated at 175° C. in a microwave reactor for 30 minutes. The mixture is cooled to room temperature and concentrated under reduced pressure. The residue is purified by flash silica gel chromatography to provide 0.004 g (9%) of the title compound (108) as a red solid. [M+H]+=476.2.

Example 13

Synthesis of N-[2-(4-{[(benzylsulfonyl)amino]methyl}piperidin-1-yl)-5-(methylsulfonyl)pyridin-3-yl]-3-chlorobenzamide (109)

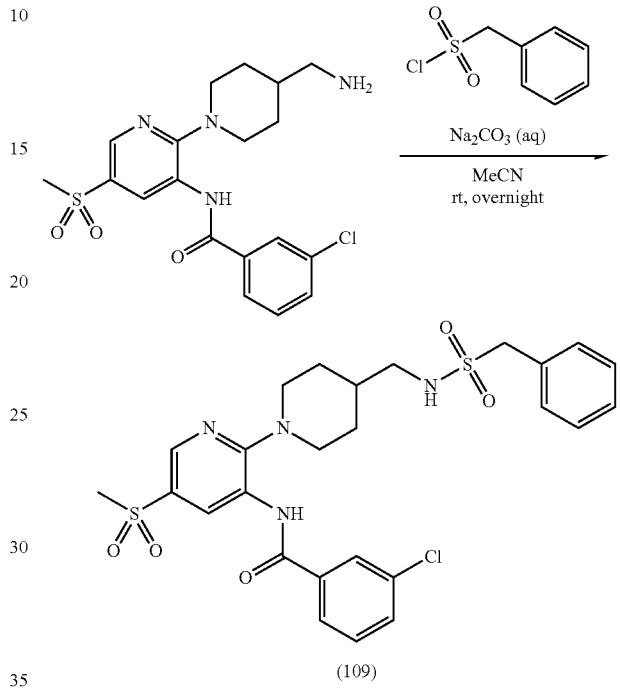

(109)

To 0.028 g (0.066 mmol) of N-(4-aminomethyl-5'-methanesulfonyl-3,4,5,6-tetrahydro-2H-[1,2']bipyridinyl-3'-yl)-3-chloro-benzamide in a mixture of acetonitrile (0.5 mL) and saturated aqueous sodium carbonate (0.5 mL) is added 0.015 mg (0.079 mmol) of phenylmethanesulfonyl chloride. The mixture is stirred overnight at room temperature then diluted with water and extracted with ethyl acetate. The combined organic phase is washed with water, dried over anhydrous sodium sulfate and concentrated under reduced pressure. The residue is purified by preparative thin layer chromatography to give 0.027 g (72%) of the title compound (109) as a clear resin. [M+H]+=577.7.

Example 14

Synthesis of 3-chloro-N-{5'-methanesulfonyl-4-[(3-phenyl-ureido)-methyl]-3,4,5,6-tetrahydro-2H-[1,2']bipyridinyl-3'-yl}-benzamide (110)

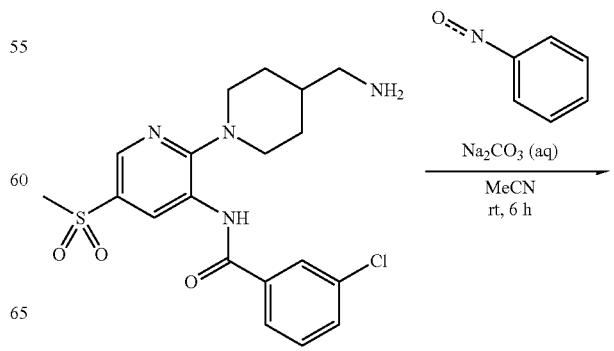

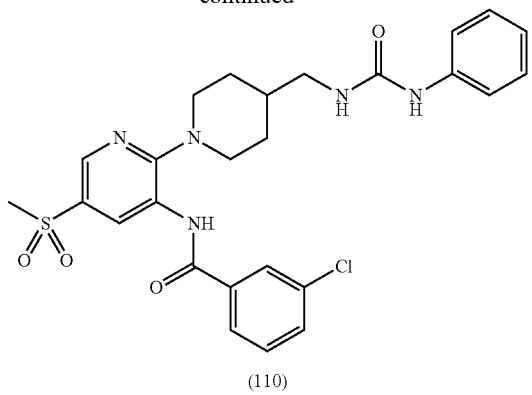

(110)

To 0.028 g (0.066 mmol) of N-(4-aminomethyl-5'-methanesulfonyl-3,4,5,6-tetrahydro-2H-[1,2']bipyridinyl-3'-yl)-3-chloro-benzamide in a mixture of acetonitrile (0.5 mL) and saturated aqueous sodium carbonate (0.5 mL) is added 0.0086 mL (0.11 mmol) of phenylisocyanate. The mixture is stirred at room temperature for 6 hours then concentrated under reduced pressure. The residue is diluted with water causing a gummy solid to form. The aqueous phase is decanted off and the solid is rinsed and decanted with water and then dried. The residue is purified by preparative thin layer chromatography to give 0.016 mg (44%) of the title compound (110) as a clear resin. $[M+H]^+=542.7$.

The following compound can be prepared analogously:
N-[4-(3-Benzyl-ureidomethyl)-5'-methanesulfonyl-3,4,5,6-tetrahydro-2H-[1,2']bipyridinyl-3'-yl]-3-chloro-benzamide, $C_{27}H_{30}ClN_5O_4S$, $[M+H]^+=556.6$.

Example 15

Synthesis of 3-(3-Chloro-benzoylamino)-N-cyclopropyl-4-[4-(2-piperidin-1-yl-ethyl)-piperidin-1-yl]-benzamide (112)

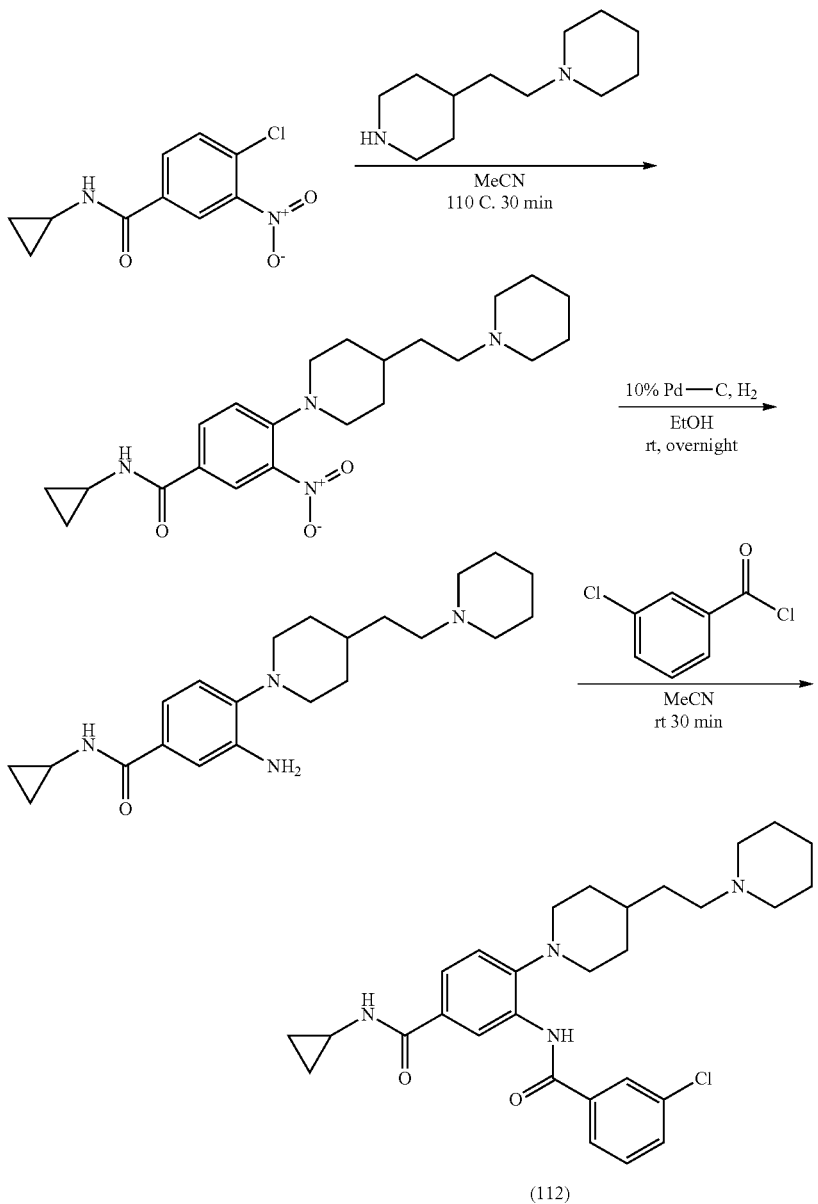

(112)

A mixture of 0.612 g (2.51 mmol) of 4-chloro-N-cyclopropyl-3-nitro-benzamide and 0.50 g (2.5 mmol) of 1-(2-piperidin-4-yl-ethyl)-piperidine in acetonitrile (0.5 mL) are heated at 110° C. for 30 minutes in a microwave reactor. The mixture is cooled to room temperature and concentrated under reduced pressure. The residue is purified by flash silica gel chromatography to provide 0.80 g (79%) of N-cyclopropyl-3-nitro-4-[4-(2-piperidin-1-yl-ethyl)-piperidin-1-yl]-benzamide.

To a stirred solution of 0.80 g (2.0 mmol) of N-cyclopropyl-3-nitro-4-[4-(2-piperidin-1-yl-ethyl)-piperidin-1-yl]-benzamide in ethanol (20 mL) is added 0.080 g (0.07 mmol) of 10% palladium on carbon. The reaction mixture is shaken overnight under 3 bar of a hydrogen atmosphere. The mixture is then filtered through a pad of diatomaceous earth and the filter pad is washed with ethanol. The mixture is concentrated under reduced pressure to give amine 0.50 g (68%) of 3-amino-N-cyclopropyl-4-[4-(2-piperidin-1-yl-ethyl)-piperidin-1-yl]-benzamide.

To a stirred solution of compound 0.20 g (0.53 mmol) of 3-amino-N-cyclopropyl-4-[4-(2-piperidin-1-yl-ethyl)-piperidin-1-yl]-benzamide in acetonitrile (5 mL) is added 0.04 mL (0.31 mmol) 3-chlorobenzoyl chloride. The mixture is stirred at room temperature for 30 minutes then volatiles are removed under reduced pressure. The residue is dissolved in dichloromethane and the mixture is washed with 5% aqueous NaOH solution followed by water and then dried over anhydrous magnesium sulfate. The mixture is concentrated under reduced pressure and the crude mass purified by flash silica gel chromatography to yield 0.040 g (15%) of 3-(3-Chloro-benzoylamino)-N-cyclopropyl-4-[4-(2-piperidin-1-yl-ethyl)-piperidin-1-yl]-benzamide (112). [M+H]$^+$=479.4

The following compound can be prepared analogously 3-(3-Chloro-benzoylamino)-4-[4-(2-piperidin-1-yl-ethyl)-piperidin-1-yl]-benzamide, $C_{26}H_{33}ClN_4O_2$, [M+H]$^+$=449.4.

Example 16

Synthesis of 3'-(3-chloro-benzoylamino)-4-[2-(4-hydroxy-piperidin-1-yl)-2-oxo-ethyl]-3,4,5,6-tetrahydro-2H-[1,2']bipyridinyl-5'-carboxylic acid (114)

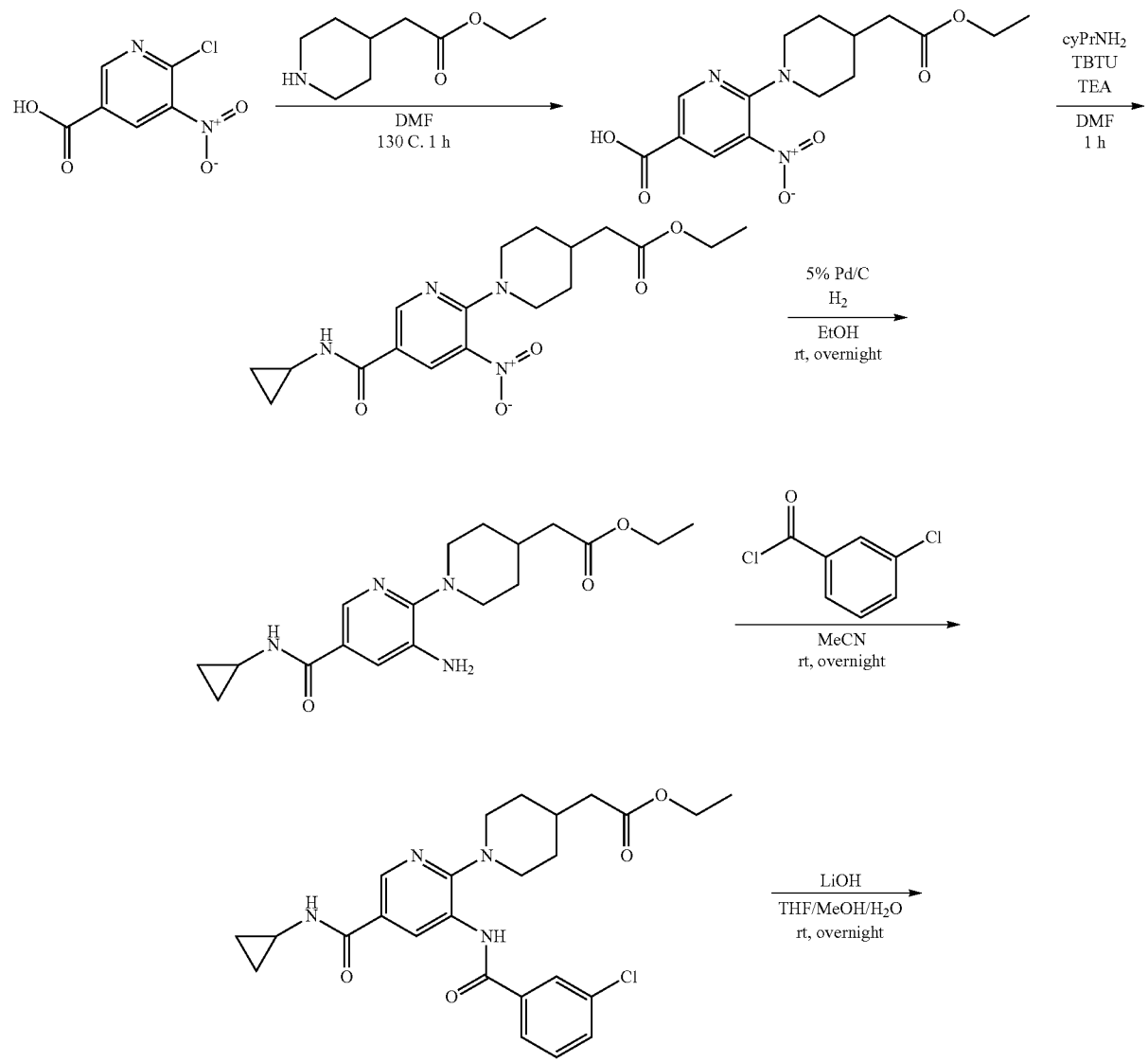

-continued

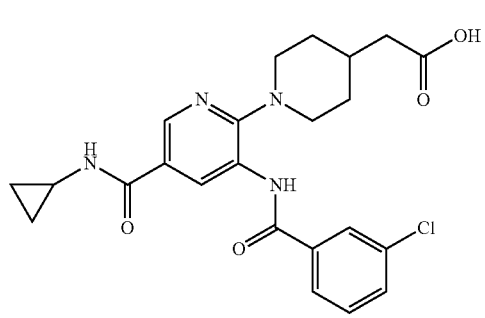
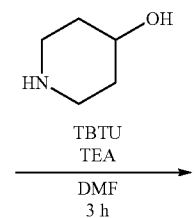

TBTU
TEA
DMF
3 h

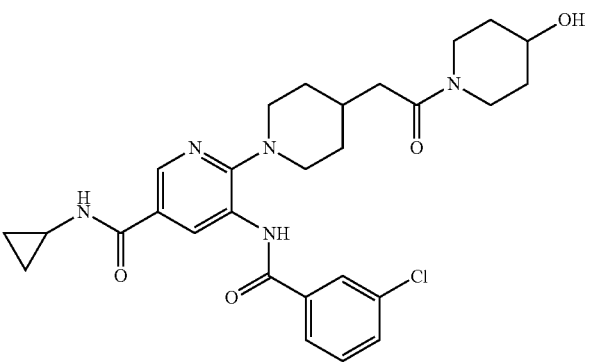

(114)

A mixture of 2.00 g (9.87 mmol) of 6-chloro-5-nitro-nicotinic acid and 2.03 g (11.8 mmol) of piperazin-1-yl-acetic acid ethyl ester in N,N-dimethylformamide (10 mL) are heated to 130° C. in a microwave reactor for 1 hour. The resulting dark mixture is poured into water which forms a precipitate. The pH of the mixture is adjusted to approximately pH 2 by adding concentrated hydrochloric acid. The precipitated solid is collected by filtration, washed with water, and dried under reduced pressure to give 2.70 g (81.1%) of 4-ethoxycarbonylmethyl-3'-nitro-3,4,5,6-tetrahydro-2H-[1,2']bipyridinyl-5'-carboxylic acid as a yellow solid.

A mixture of 0.300 g (0.889 mmol) of 4-ethoxycarbonylmethyl-3'-nitro-3,4,5,6-tetrahydro-2H-[1,2']bipyridinyl-5'-carboxylic acid, 0.254 g (4.45 mmol) of cyclopropylamine, 0.371 g (1.16 mmol) of O-(benzotriazol-1-yl)-N,N,N',N'-tetramethyluronium tetrafluoroborate, and 0.269 g (2.69 mmol) of triethylamine in N,N-dimethylformamide (5 mL) is stirred at room temperature for 1 hour. The mixture is poured to water and extracted with ethyl acetate. The combined organic phase is washed with water followed by brine and then dried over anhydrous sodium sulfate. The mixture is concentrated under reduced pressure to give 0.33 g (99%) of [4-(5-cyclopropylcarbamoyl-3-nitro-pyridin-2-yl)-piperazin-1-yl]-acetic acid ethyl ester as an orange solid.

To a solution of 0.33 g (0.93 mmol) of [4-(5-cyclopropylcarbamoyl-3-nitro-pyridin-2-yl)-piperazin-1-yl]-acetic acid ethyl ester in ethanol is added 0.050 g (0.023 mmol) of 5% palladium on carbon. The mixture is placed under an atmosphere of hydrogen and stirred overnight. The mixture is filtered through a pad of diatomaceous earth and concentrated under reduced pressure to provide 0.39 g (97%) of (3'-amino-5'-cyclopropylcarbamoyl-3,4,5,6-tetrahydro-2H-[1,2']bipyridinyl-4-yl)-acetic acid ethyl ester as a red oil.

A mixture of 0.39 g (0.90 mmol) of (3'-amino-5'-cyclopropylcarbamoyl-3,4,5,6-tetrahydro-2H-[1,2']bipyridinyl-4-yl)-acetic acid ethyl ester in acetonitrile (5 mL) is treated with 0.14 mL (1.1 mmol) of 3-chlorobenzoyl chloride. The mixture is stirred overnight and then concentrated under reduced pressure. The residue is taken up into water and extracted with ethyl acetate. The combined organic phase is washed with brine, dried over anhydrous sodium sulfate, and concentrated under reduced pressure. The residue is purified by flash silica gel chromatography to provide 0.23 g (52%) of [3'-(3-chlorobenzoylamino)-5'-cyclopropylcarbamoyl-3,4,5,6-tetrahydro-2H-[1,2']bipyridinyl-4-yl]-acetic acid ethyl ester as a colorless foam.

To a solution of 0.23 g (0.47 mmol) of [3'-(3-chloro-benzoylamino)-5'-cyclopropylcarbamoyl-3,4,5,6-tetrahydro-2H-[1,2']bipyridinyl-4-yl]-acetic acid ethyl ester in a 5:2 mixture of tetrahydrofuran:methanol is added a solution of 0.056 g (2.3 mmol) of lithium hydroxide in water (1 mL). The reaction mixture is stirred overnight and then concentrated under reduced pressure to remove volatile organics. The pH of the mixture is adjusted to approximately pH 2 by the addition of concentrated hydrochloric acid causing a solid to precipitate. The formed colorless solid is collected by filtration and dried under vacuum to provide 0.14 g (66%) of [3'-(3-chloro-benzoylamino)-5'-cyclopropylcarbamoyl-3,4,5,6-tetrahydro-2H-[1,2']bipyridinyl-4-yl]-acetic acid.

A mixture of 0.035 g (0.077 mmol) of 3'-(3-chloro-benzoylamino)-5'-cyclopropylcarbamoyl-3,4,5,6-tetrahydro-2H-[1,2']bipyridinyl-4-yl]-acetic acid, 0.039 g (0.38 mmol) of 4-hydroxypiperdine, 0.032 g (0.10 mmol) of O-(benzotriazol-1-yl)-N,N,N',N'-tetramethyluronium tetrafluoroborate, and 0.032 mL (0.23 mmol) of triethylamine in N,N-dimethylformamide (2 mL) are stirred at room temperature for 3 hours. The mixture is concentrated under reduced pressure and the residue is purified by preparative reverse phase HPLC to provide 0.014 g (41%) of the title compound (114) as a colorless solid. [M+H]$^+$=540.3

The following compounds can be prepared analogously:

3'-(3-Chloro-benzoylamino)-4-[2-(4-methyl-[1,4]diazepan-1-yl)-2-oxo-ethyl]-3,4,5,6-tetrahydro-2H-[1,2']bipyridinyl-5'-carboxylic acid cyclopropylamide, $C_{29}H_{37}ClN_6O_3$, $[M+H]^+=553.3$;

3'-(3-Chloro-benzoylamino)-4-[2-(4-methyl-[1,4]diazepan-1-yl)-2-oxo-ethyl]-3,4,5,6-tetrahydro-2H-[1,2']bipyridinyl-5'-carboxylic acid diethylamide, $C_{30}H_{41}ClN_6O_3$, $[M+H]^+=569.3$;

3'-(3-Chloro-benzoylamino)-4-[2-(4-methoxy-piperidin-1-yl)-2-oxo-ethyl]-3,4,5,6-tetrahydro-2H-[1,2']bipyridinyl-5'-carboxylic acid cyclopropylamide, $C_{29}H_{36}ClN_5O_4$, $[M+H]^+=554.3$;

3-(3-Chloro-benzoylamino)-N-cyclopropyl-4-{4-[2-(4-methoxy-4-methyl-piperidin-1-yl)-2-oxo-ethyl]-piperidin-1-yl}-benzamide, $C_{31}H_{39}ClN_4O_4$, $[M+H]^+=549.3$;

3-(3-Chloro-benzoylamino)-N-cyclopropyl-4-{4-[2-(4-methyl-[1,4]diazepan-1-yl)-2-oxo-ethyl]-piperidin-1-yl}-benzamide, $C_{30}H_{38}ClN_5O_3$, $[M+H]^+=562.2$;

3-(3-Chloro-benzoylamino)-N-cyclopropyl-4-{4-[2-(4-hydroxy-4-methyl-piperidin-1-yl)-2-oxo-ethyl]-piperidin-1-yl}-benzamide, $C_{30}H_{37}ClN_4O_4$, $[M+H]^+=567.3$;

3'-(4-Methoxy-benzoylamino)-4-[2-(4-methyl-[1,4]diazepan-1-yl)-2-oxo-ethyl]-3,4,5,6-tetrahydro-2H-[1,2']bipyridinyl-5'-carboxylic acid cyclopropylamide, $C_{30}H_{40}N_6O_4$, $[M+H]^+=505.4$;

3'-(3-Chloro-benzoylamino)-4-(2-[1,4]diazepan-1-yl-2-oxo-ethyl)-3,4,5,6-tetrahydro-2H-[1,2']bipyridinyl-5'-carboxylic acid cyclopropylamide, $C_{28}H_{35}ClN_6O_3$, $[M+H]^+=539.3$; and 4-(tert-Butylcarbamoyl-methyl)-3'-(3-chloro-benzoylamino)-3,4,5,6-tetrahydro-2H-[1,2']bipyridinyl-5'-carboxylic acid cyclopropylamide, $C_{27}H_{34}ClN_5O_3$, $[M+H]^+=512.3$.

Example 17

Synthesis of 3-chloro-N-{4-[2-(4-methyl-[1,4]diazepan-1-yl)-2-oxo-ethyl]-5'-phenyl-3,4,5,6-tetrahydro-2H-[1,2']bipyridinyl-3'-yl}-benzamide (124)

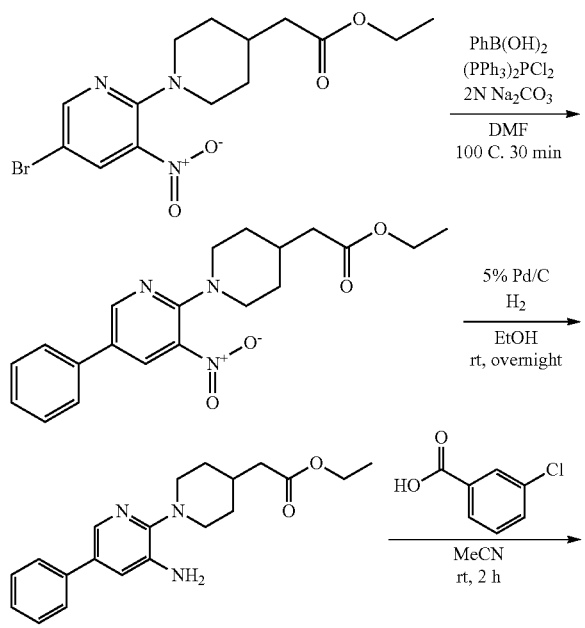

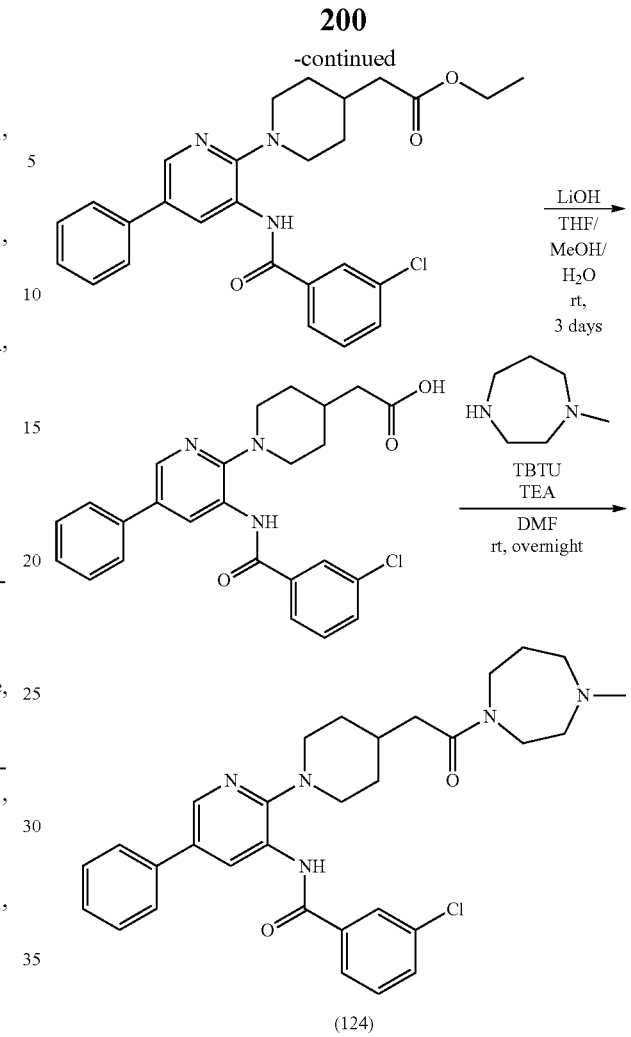

A mixture of 0.200 g (0.54 mmol) of (5'-bromo-3'-nitro-3,4,5,6-tetrahydro-2H-[1,2']bipyridinyl-4-yl)-acetic acid ethyl ester, 0.137 g (1.07 mmol) of phenylboronic acid, 0.028 g (0.054 mmol) of bis(triphenylphosphine)palladium(II) chloride, 1.34 mL (2.69 mmol) of a 2N sodium carbonate solution, and N,N-dimethylformamide (5 mL) are heated in a microwave to 100° C. for 30 minutes. The resulting dark mixture is poured into water and extracted with ethyl acetate. The organic phase is washed with water followed by brine. The mixture is dried over anhydrous sodium sulfate and concentrated under reduced pressure. The crude residue is purified by flash silica gel chromatography. Removal of the eluent under reduced pressure gives 0.11 g (55%) of [4-(3-nitro-5-phenyl-pyridin-2-yl)-piperazin-1-yl]-acetic acid ethyl ester as a yellow oil.

To a solution of 0.11 g (0.30 mmol) of [4-(3-nitro-5-phenyl-pyridin-2-yl)-piperazin-1-yl]-acetic acid ethyl ester in ethanol (10 mL) is added 0.020 g (0.009 mmol) of 5% palladium on carbon. The mixture is placed under an atmosphere of hydrogen and stirred overnight. The mixture is filtered through a pad of diatomaceous earth and concentrated under reduced pressure to provide 0.10 g (99%) of (3'-Amino-5'-phenyl-3,4,5,6-tetrahydro-2H-[1,2']bipyridinyl-4-yl)-acetic acid ethyl ester as a red oil.

To a solution of 0.10 g (0.29 mmol) of (3'-amino-5'-phenyl-3,4,5,6-tetrahydro-2H-[1,2']bipyridinyl-4-yl)-acetic acid ethyl ester in acetonitrile (5 mL) is added 0.041 mL (0.32 mmol) of 3-chlorobenzoyl chloride. The mixture is stirred at room temperature for 2 hours then concentrated under reduced pressure. A saturated aqueous solution of ammonium chloride is added and the mixture is extracted with ethyl acetate. The combined organic phase is dried over anhydrous sodium sulfate and concentrated under reduced pressure. The residue is purified by flash silica gel chromatography to provide 0.115 g (81%) of [3'-(3-chloro-benzoylamino)-5'-phenyl-3,4,5,6-tetrahydro-2H-[1,2']bipyridinyl-4-yl]-acetic acid ethyl ester as a colorless foam.

To a solution of 0.115 g (0.241 mmol) of [3'-(3-chloro-benzoylamino)-5'-phenyl-3,4,5,6-tetrahydro-2H-[1,2']bipyridinyl-4-yl]-acetic acid ethyl ester in a 5:2 mixture of tetrahydrofuran:methanol (7 mL) is added a solution of 0.028 g (1.2 mmol) of lithium hydroxide in water (1 mL). The reaction mixture is stirred at room temperature for 3 days and then concentrated under reduced pressure to remove volatile organics. The residue is diluted with water and the pH of the mixture is adjusted to approximately pH 2 by the addition of concentrated hydrochloric acid causing a solid to precipitate. The formed yellow solid is collected by filtration and dried under vacuum to provide 0.090 g (83%) of [3'-(3-chloro-benzoylamino)-5'-phenyl-3,4,5,6-tetrahydro-2H-[1,2']bipyridinyl-4-yl]-acetic acid.

A mixture of 0.035 g (0.078 mmol) of [3'-(3-chloro-benzoylamino)-5'-phenyl-3,4,5,6-tetrahydro-2H-[1,2']bipyridinyl-4-yl]-acetic acid, 0.044 g (0.39 mmol) of 1-methyl homopiperazine, 0.032 g (0.10 mmol) of O-(benzotriazol-1-yl)-N,N,N',N'-tetramethyluronium tetrafluoroborate, and 0.032 mL (0.23 mmol) of triethylamine in N,N-dimethylformamide (2 mL) are stirred overnight at room temperature. The mixture is concentrated under reduced pressure and the residue is diluted with water which causes a solid to precipitate from solution. The colorless solid is collected by filtration, washed with water and dried to provide 0.032 g (75%) of 3-chloro-N-(2-{4-[2-(4-methyl-1,4-diazepan-1-yl)-2-oxoethyl]piperidin-1-yl}-5-phenylpyridin-3-yl)benzamide (124) as a colorless solid. [M+H]$^+$=546.3.

Example 18

Synthesis of 3-chloro-N-{4-[2-(4-methyl-[1,4]diazepan-1-yl)-2-oxo-ethyl]-3,4,5,6-tetrahydro-2H-[1,2';5',3"]terpyridin-3'-yl}-benzamide (125)

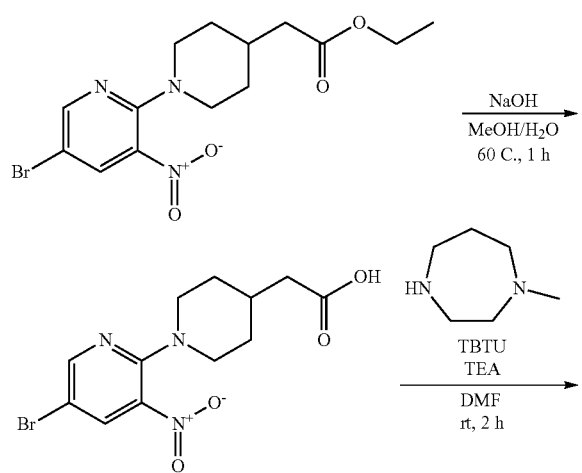

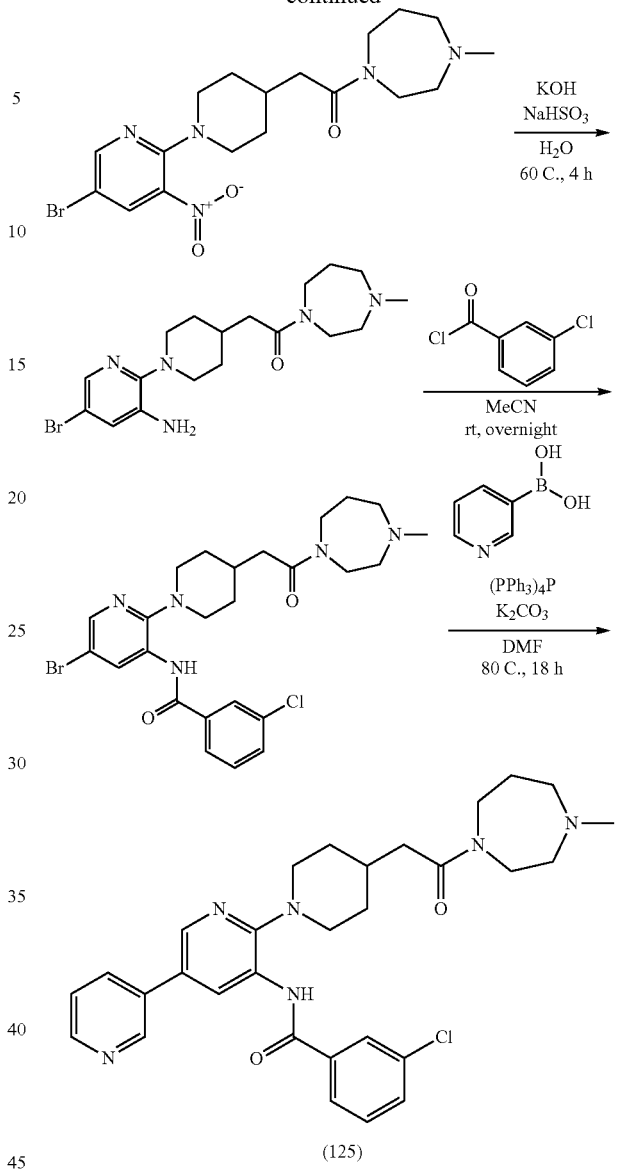

(125)

To a suspension of 1.00 g (2.69 mmol) of (5'-bromo-3'-nitro-3,4,5,6-tetrahydro-2H-[1,2']bipyridinyl-4-yl)-acetic acid ethyl ester in a 1:1 mixture of water:methanol (50 mL) is added 2.0 mL (5.0 mmol) of sodium hydroxide as a 10% aqueous solution. The mixture is heated at 60° C. for 1 hour then cooled to room temperature and the pH of the mixture is adjusted to approximately pH 5 by the addition of a 2 N solution of hydrochloric acid. The mixture is extracted with ethyl acetate and the combined organic phase is dried over anhydrous sodium sulfate and concentrated under reduced pressure to provide 0.700 g (75.7%) of (5'-bromo-3'-nitro-3,4,5,6-tetrahydro-2H-[1,2']bipyridinyl-4-yl)-acetic acid as an orange oil. No further purification is performed.

To a solution of 0.350 g (1.02 mmol) of (5'-bromo-3'-nitro-3,4,5,6-tetrahydro-2H-[1,2']bipyridinyl-4-yl)-acetic acid in dimethylformamide (5 mL) is added 0.450 g (1.19 mmol) of O-(benzotriazol-1-yl)-N,N,N',N'-tetramethyluronium tetrafluoroborate followed by 0.380 mL (2.13 mmol) of pyridine. The mixture is stirred at room temperature for 1 hour then 0.225 mg (1.97 mmol) of N-methylhomopiperizine is added and the mixture is stirred at room temperature for 1 h. The mixture is diluted with water and extracted with ethyl acetate. The combined organic phase is washed with water followed by brine then dried over anhydrous sodium sulfate and concentrated under reduced pressure. The residue is purified by flash silica gel chromatography to provide 0.310 g (69.2%) of 2-(5'-bromo-3'-nitro-3,4,5,6-tetrahydro-2H-[1,2']bipyridinyl-4-yl)-1-(4-methyl-[1,4]diazepan-1-yl)-ethanone as an orange oil.

To a mixture of 0.500 g (1.13 mmol) of 2-(5'-bromo-3'-nitro-3,4,5,6-tetrahydro-2H-[1,2']bipyridinyl-4-yl)-1-(4-methyl-[1,4]diazepan-1-yl)-ethanone in water (25 mL) is added 1.0 g (17 mmol) of potassium hydroxide followed by 1.2 g (11 mmol) of sodium hydrosulfite. The mixture is heated at 60° C. for 4 hours then cooled to room temperature and the pH of the solution adjusted to neutral by the addition of a 2 N solution of hydrochloric acid. The mixture is extracted with a 3:1 mixture of methylene chloride:isopropanol and the combined organic phase is dried over anhydrous sodium sulfate and concentrated under reduced pressure to provide 0.261 g (56.0%) of 2-(3'-amino-5'-bromo-3,4,5,6-tetrahydro-2H-[1,2']bipyridinyl-4-yl)-1-(4-methyl-[1,4]diazepan-1-yl)-ethanone.

To a solution of 0.350 g (0.853 mmol) of 2-(3'-amino-5'-bromo-3,4,5,6-tetrahydro-2H-[1,2']bipyridinyl-4-yl)-1-(4-methyl-[1,4]diazepan-1-yl)-ethanone in acetonitrile (50 mL) is added 0.15 g (0.853 mmol) of 3-chlorobenzoyl chloride. The mixture is stirred overnight at room temperature during which time a solid precipitates from solution. The formed solid is collected by filtration, washed with cold diethyl ether and dried on the filter pad to provide 0.308 g (66.0%) of N-{5'-bromo-4-[2-(4-methyl-[1,4]diazepan-1-yl)-2-oxo-ethyl]-3,4,5,6-tetrahydro-2H-[1,2']bipyridinyl-3'-yl}-3-chloro-benzamide in N,N-dimethylformamide as a white solid.

To a solution of 0.050 g (0.091 mmol) of N-{5'-bromo-4-[2-(4-methyl-[1,4]diazepan-1-yl)-2-oxo-ethyl]-3,4,5,6-tetrahydro-2H-[1,2']bipyridinyl-3'-yl}-3-chloro-benzamide in N,N-dimethylformamide (3 mL) is added 0.011 g (0.091 mmol) of 3-pyridyl boronic acid followed by 0.100 g (0.725 mmol) of potassium carbonate and 0.010 g (0.009 mmol) of tetrakis(triphenylphosphine)palladium(0). The mixture is flushed with argon for 2 minutes and heated at 80° C. for 18 hours. The mixture is filtered and purified by preparative reverse phase HPLC to provide 0.007 g (14%) of the title compound (125) as a white solid. [M+H]+=547.8.

The following compound can be prepared analogously:
3-Chloro-N-{4-[2-(4-methyl-[1,4]diazepan-1-yl)-2-oxo-ethyl]-3,4,5,6-tetrahydro-2H-[1,2';5',4"]terpyridin-3'-yl}-benzamide, C$_{30}$H$_{35}$ClN$_6$O$_2$, [M+H]$^+$=547.8.

Example 19

Synthesis of 3-Chloro-N-[5'-chloro-4-(2-oxo-2-piperidin-1-yl-ethyl)-3,4,5,6-tetrahydro-2H-[1,2']bipyridinyl-3'-yl]-benzamide (127)

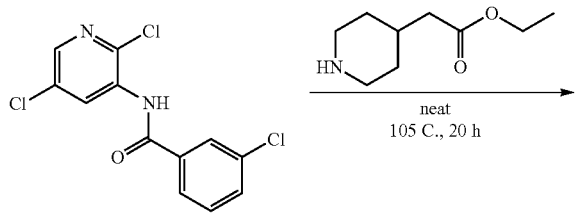

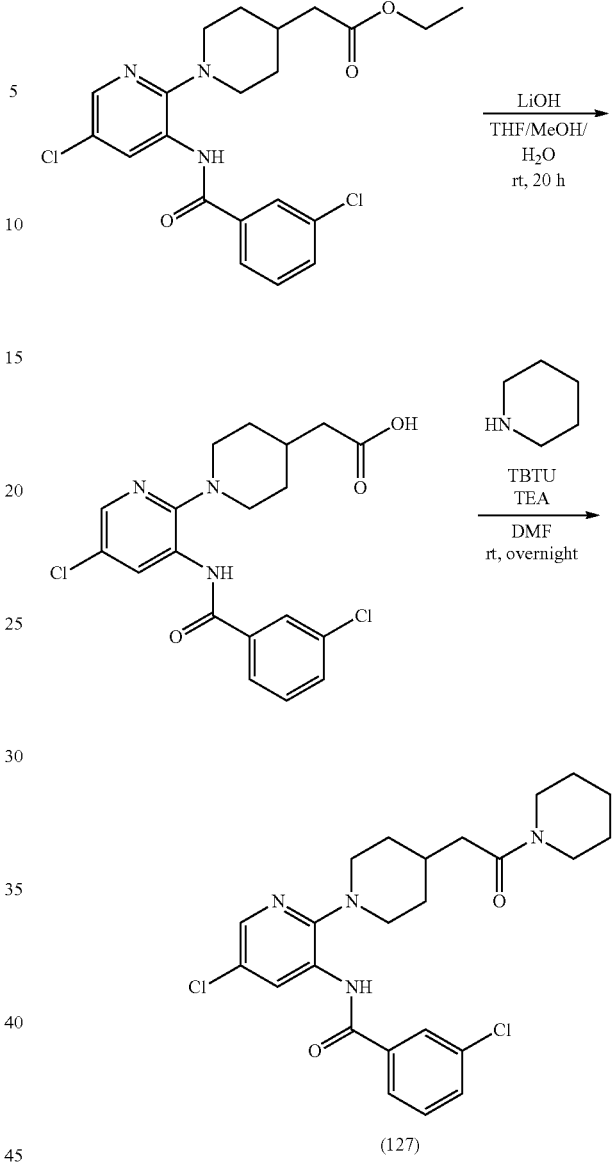

A mixture of 5.00 g (16.6 mmol) of 3-chloro-N-(2,5-dichloro-pyridin-3-yl)-benzamide and 4.26 g (24.9 mmol) of piperazin-1-yl-acetic acid ethyl ester in a solvent free condition is heated to 105° C. and stirred for 20 hours. The residue is purified by flash silica gel chromatography to give 5.98 g (82.6%) of {4-[5-chloro-3-(3-chloro-benzoylamino)-pyridin-2-yl]-piperazin-1-yl}-acetic acid ethyl ester as a light yellow solid.

To a solution of 5.98 g (13.7 mmol) of the above ester in a mixture of THF (20 mL) and MeOH (10 mL) is added water (5 mL) and 1.64 g (68.5 mmol) of lithium hydroxide. The reaction is stirred at room temperature for 20 hours. The solvent is removed under reduced pressure and water (30 mL) is added to the resulting solid. The pH of the resulting aqueous solution is adjusted to approximately pH 4 by adding concentrated hydrochloric acid causing a solid to precipitate from solution. The precipitate is collected by filtration, washed with water, and dried under vacuum to give 4.2 g (75% yield) of 4-[5-chloro-3-(3-chloro-benzoylamino)-pyridin-2-yl]-piperazin-1-yl}-acetic acid as a white solid.

The mixture of 0.030 g (0.073 mmol) of the above acid, 0.019 g (0.22 mmol) of piperdine, 0.035 g (0.11 mmol) of O-(benzotriazol-1-yl)-N,N,N',N'-tetramethyluronium tetrafluoroborate, and 0.036 mL (0.22 mmol) of triethylamine in N,N-dimethylformamide (3 mL) is allowed to stir at room temperature overnight. The mixture is concentrated under reduced pressure and the residue is purified using preparative reverse phase HPLC to give 0.020 g (57%) of title compound (127) as a colorless solid. [M+H]$^+$=475.4.

The following compounds can be prepared analogously:

3-Chloro-N-{5'-chloro-4-[2-(4-hydroxy-piperidin-1-yl)-2-oxo-ethyl]-3,4,5,6-tetrahydro-2H-[1,2']bipyridinyl-3'-yl}-benzamide, C$_{24}$H$_{28}$Cl$_2$N$_4$O$_3$, [M+H]$^+$=491.3;

3-Chloro-N-{5'-chloro-4-[2-(4-methyl-[1,4]diazepan-1-yl)-2-oxo-ethyl]-3,4,5,6-tetrahydro-2H-[1,2']bipyridinyl-3'-yl}-benzamide, C$_{25}$H$_{31}$Cl$_2$N$_5$O$_2$, [M+H]$^+$=504.3;

3-Chloro-N-{5'-chloro-4-[2-(4-methoxy-piperidin-1-yl)-2-oxo-ethyl]-3,4,5,6-tetrahydro-2H-[1,2']bipyridinyl-3'-yl}-benzamide, C$_{25}$H$_{30}$Cl$_2$N$_4$O$_3$, [M+H]$^+$=505.2;

3-Chloro-N-{5'-chloro-4-[2-(2-methyl-piperidin-1-yl)-2-oxo-ethyl]-3,4,5,6-tetrahydro-2H-[1,2']bipyridinyl-3'-yl}-benzamide, C$_{25}$H$_{30}$Cl$_2$N$_4$O$_2$, [M+H]$^+$=489.2;

3-Chloro-N-{5'-chloro-4-[2-((S)-2-methyl-piperidin-1-yl)-2-oxo-ethyl]-3,4,5,6-tetrahydro-2H-[1,2']bipyridinyl-3'-yl}-benzamide, C$_{25}$H$_{30}$Cl$_2$N$_4$O$_2$, [M+H]$^+$=487.1;

3-Chloro-N-{5'-chloro-4-[2-((R)-2-methyl-piperidin-1-yl)-2-oxo-ethyl]-3,4,5,6-tetrahydro-2H-[1,2']bipyridinyl-3'-yl}-benzamide, C$_{25}$H$_{30}$Cl$_2$N$_4$O$_2$, [M+H]$^+$=489.2;

3-Chloro-N-{5'-chloro-4-[2-(4-hydroxy-piperidin-1-yl)-2-oxo-ethyl]-1'-oxy-3,4,5,6-tetrahydro-2H-[1,2']bipyridinyl-3'-yl}-benzamide, C$_{24}$H$_{28}$Cl$_2$N$_4$O$_4$, [M+H]$^+$=507.1;

N-{5'-Chloro-4-[2-(4-methyl-[1,4]diazepan-1-yl)-2-oxo-ethyl]-3,4,5,6-tetrahydro-2H-[1,2']bipyridinyl-3'-yl}-4-methanesulfonyl-benzamide, C$_{26}$H$_{34}$ClN$_5$O$_4$S, [M+H]$^+$=548.3;

N-{5'-Chloro-4-[2-(4-methyl-[1,4]diazepan-1-yl)-2-oxo-ethyl]-3,4,5,6-tetrahydro-2H-[1,2']bipyridinyl-3'-yl}-4-methoxy-benzamide, C$_{26}$H$_{34}$ClN$_5$O$_3$, [M+H]$^+$=444.3;

N-[4-(tert-Butylcarbamoyl-methyl)-5'-chloro-3,4,5,6-tetrahydro-2H-[1,2']bipyridinyl-3'-yl]-3-chloro-benzamide, C$_{23}$H$_{28}$Cl$_2$N$_4$O$_2$, [M+H]$^+$=463.7;

3-Chloro-N-{5'-chloro-4-[(1-methyl-1-phenyl-ethylcarbamoyl)-methyl]-3,4,5,6-tetrahydro-2H-[1,2']bipyridinyl-3'-yl}-benzamide, C$_{28}$H$_{30}$Cl$_2$N$_4$O$_2$, [M+H]$^+$=525.7;

3-Chloro-N-[5'-chloro-4-(pyridin-4-ylcarbamoylmethyl)-3,4,5,6-tetrahydro-2H-[1,2']bipyridinyl-3'-yl]-benzamide, C$_{24}$H$_{23}$Cl$_2$N$_5$O$_2$, [M+H]$^+$=484.7;

3-Chloro-N-(5'-chloro-4-phenylcarbamoylmethyl-3,4,5,6-tetrahydro-2H-[1,2']bipyridinyl-3'-yl)-benzamide, C$_{25}$H$_{24}$Cl$_2$N$_4$O$_2$, [M+H]$^+$=483.6;

3-Chloro-N-[5'-chloro-4-(pyridin-3-ylcarbamoylmethyl)-3,4,5,6-tetrahydro-2H-[1,2']bipyridinyl-3'-yl]-benzamide, C$_{24}$H$_{23}$Cl$_2$N$_5$O$_2$, [M+H]$^+$=486.5;

3-Chloro-N-[5'-chloro-4-(thiazol-2-ylcarbamoylmethyl)-3,4,5,6-tetrahydro-2H-[1,2']bipyridinyl-3'-yl]-benzamide, C$_{22}$H$_{21}$Cl$_2$N$_5$O$_2$S, [M+H]$^+$=490.6;

3-Chloro-N-{5'-chloro-4-[(1-methyl-piperidin-3-ylcarbamoyl)-methyl]-3,4,5,6-tetrahydro-2H-[1,2']bipyridinyl-3'-yl}-benzamide, C$_{25}$H$_{31}$Cl$_2$N$_5$O$_2$, [M+H]$^+$=504.8; and 3-Chloro-N-{5'-chloro-4-[((R)-1-methyl-piperidin-3-ylcarbamoyl)-methyl]-3,4,5,6-tetrahydro-2H-[1,2']bipyridinyl-3'-yl}-benzamide, C$_{25}$H$_{31}$Cl$_2$N$_5$O$_2$, [M+H]$^+$=504.7.

Example 20

Synthesis of 3-chloro-N-{5'-cyano-4-[2-(4-hydroxy-piperidin-1-yl)-2-oxo-ethyl]-3,4,5,6-tetrahydro-2H-[1,2']bipyridinyl-3'-yl}-benzamide (145)

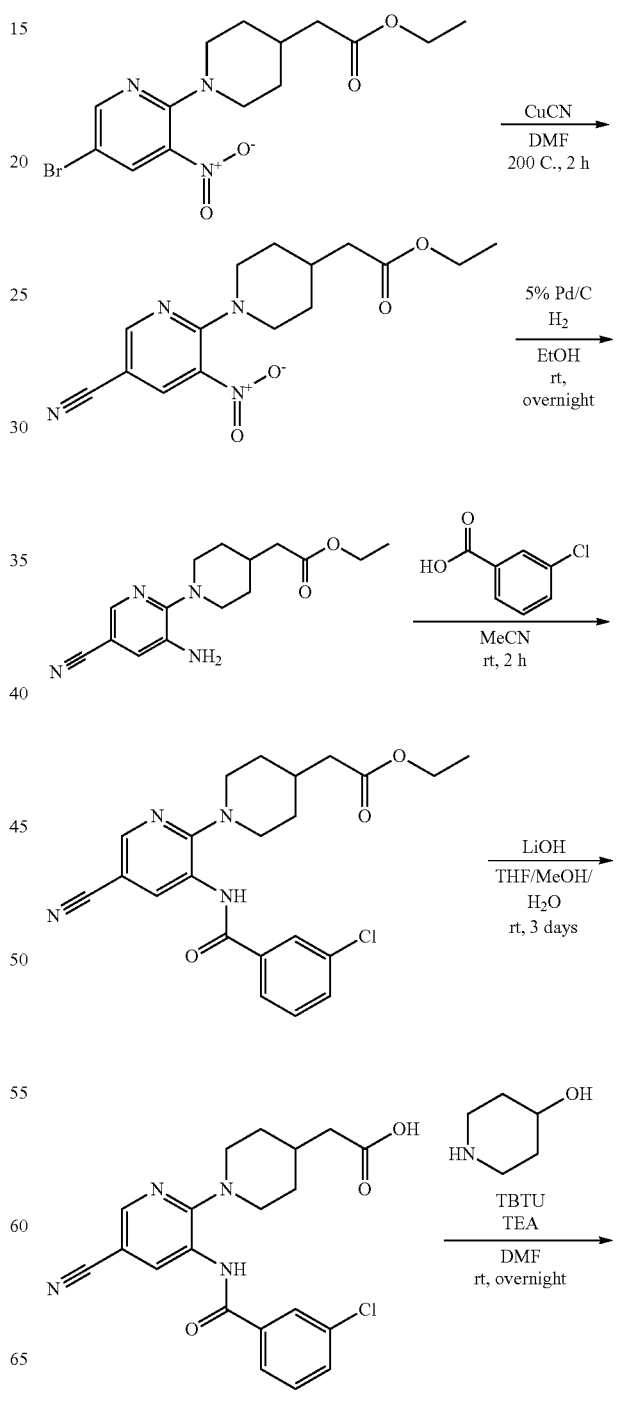

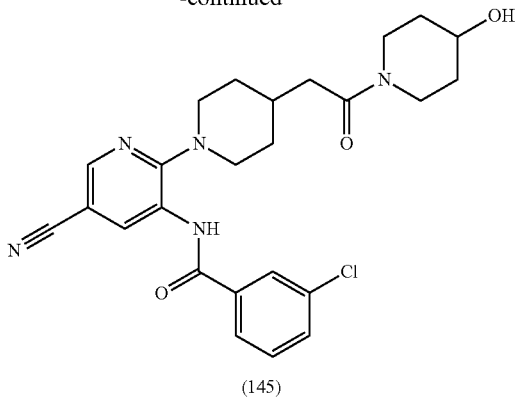

(145)

A mixture of 0.100 g (0.269 mmol) of 5'-bromo-3'-nitro-3,4,5,6-tetrahydro-2H-[1,2']bipyridinyl-4-yl)-acetic acid ethyl ester and 0.029 g (0.32 mmol) of copper (I) cyanide in N,N-dimethylformamide (2 mL) is heated in a microwave at 200° C. for 2 hours. The mixture is cooled to room temperature and poured into water which results in the formation of a precipitate. The precipitate is collected by filtration and washed with methylene chloride. The filtrate is concentrated and the residue is purified by flash silica gel chromatography to give 0.045 g (53%) of (5'-cyano-3'-nitro-3,4,5,6-tetrahydro-2H-[1,2']bipyridinyl-4-yl)-acetic acid ethyl ester as an orange oil.

To a solution of 0.045 g (0.14 mmol) of (5'-cyano-3'-nitro-3,4,5,6-tetrahydro-2H-[1,2']bipyridinyl-4-yl)-acetic acid ethyl ester in ethanol is added 0.015 g (0.0070 mmol) of 5% palladium on carbon. The mixture is placed under an atmosphere of hydrogen and stirred at room temperature overnight. The mixture is filtered through diatomaceous earth and concentrated under reduced pressure to give 0.043 g (95%) of (3'-amino-5'-cyano-3,4,5,6-tetrahydro-2H-[1,2']bipyridinyl-4-yl)-acetic acid ethyl ester as a red oil.

To a solution of 0.043 g (0.15 mol) of (3'-amino-5'-cyano-3,4,5,6-tetrahydro-2H-[1,2']bipyridinyl-4-yl)-acetic acid ethyl ester in acetonitrile (3 mL) is added 0.021 mL (0.16 mmol) of 3-chlorobenzoyl chloride. The mixture is stirred at room temperature for 2 hours then concentrated under reduced pressure. The residue is taken up in a saturated aqueous solution of ammonium chloride and extracted with ethyl acetate. The combined organic phase is dried over anhydrous sodium sulfate and concentrated under reduced pressure. The residue is purified by flash silica gel chromatography to give 0.047 g (73%) of [3'-(3-chloro-benzoylamino)-5'-cyano-3,4,5,6-tetrahydro-2H-[1,2']bipyridinyl-4-yl]-acetic acid ethyl ester as a light yellow solid.

To a solution of 0.047 g (0.11 mmol) of [3'-(3-chloro-benzoylamino)-5'-cyano-3,4,5,6-tetrahydro-2H-[1,2']bipyridinyl-4-yl]-acetic acid ethyl ester in a mixture of THF (5 mL) and MeOH (2 mL) is added water (1 mL) and 0.013 g (0.55 mmol) of lithium hydroxide. The reaction mixture is stirred at room temperature for three days. The solvent is removed under reduced pressure and the residue is taken back up into water. The pH of the resulting aqueous solution is adjusted to approximately pH2 by adding concentrated hydrochloric acid which results in a solid precipitating from solution. The formed precipitate is collected by filtration, washed with water, and dried under vacuum to give 0.035 g (80%) of [3'-(3-chloro-benzoylamino)-5'-cyano-3,4,5,6-tetrahydro-2H-[1,2']bipyridinyl-4-yl]-acetic acid as yellow solid.

A mixture of 0.015 g (0.038 mmol) of [3'-(3-chloro-benzoylamino)-5'-cyano-3,4,5,6-tetrahydro-2H-[1,2']bipyridinyl-4-yl]-acetic acid, 0.019 g (0.19 mmol) of 4-hydroxypiperdine, 0.016 g (0.049 mmol) of O-(benzotriazol-1-yl)-N,N,N',N'-tetramethyluronium tetrafluoroborate, and 0.016 mL (0.11 mmol) of triethylamine in N,N-dimethylformamide (2 mL) is allowed to stir at room temperature overnight. The mixture is concentrated under reduced pressure and the residue is diluted with water which results in a solid precipitating. The light red solid is collected by filtration and washed with water. The collected material is purified using preparative reverse phase HPLC to give 0.011 g (61%) of the title compound (145) as a colorless solid. [M+H]$^+$=482.2

The following compounds can be prepared analogously:

3-Chloro-N-{5'-cyano-4-[2-(4-methyl-[1,4]diazepan-1-yl)-2-oxo-ethyl]-3,4,5,6-tetrahydro-2H-[1,2']bipyridinyl-3'-yl}-benzamide, $C_{26}H_{31}ClN_6O_2$, [M+H]$^+$=495.3;

N-[4-(tert-Butylcarbamoyl-methyl)-5'-cyano-3,4,5,6-tetrahydro-2H-[1,2']bipyridinyl-3'-yl]-3-chloro-benzamide, $C_{24}H_{28}ClN_5O_2$, [M+H]$^+$=454.8;

3-Chloro-N-[5'-cyano-4-(pyridin-3-ylcarbamoylmethyl)-3,4,5,6-tetrahydro-2H-[1,2']bipyridinyl-3'-yl]-benzamide, $C_{25}H_{23}ClN_6O_2$, [M+H]$^+$=475.8;

3-Chloro-N-{5'-cyano-4-[(1-methyl-piperidin-3-ylcarbamoyl)-methyl]-3,4,5,6-tetrahydro-2H-[1,2']bipyridinyl-3'-yl}-benzamide, $C_{26}H_{31}ClN_6O_2$, [M+H]$^+$=495.9; and N-{5'-Cyano-4-[((R)-1-methyl-piperidin-3-ylcarbamoyl)-methyl]-3,4,5,6-tetrahydro-2H-[1,2']bipyridinyl-3'-yl}-3-trifluoromethyl-benzamide, $C_{27}H_{31}F_3N_6O_2$, [M+H]$^+$=529.9.

Example 21

Synthesis of N-[4-(tert-butylcarbamoyl-methyl)-5'-methanesulfonyl-3,4,5,6-tetrahydro-2H-[1,2']bipyridinyl-3'-yl]-3-chloro-benzamide (151)

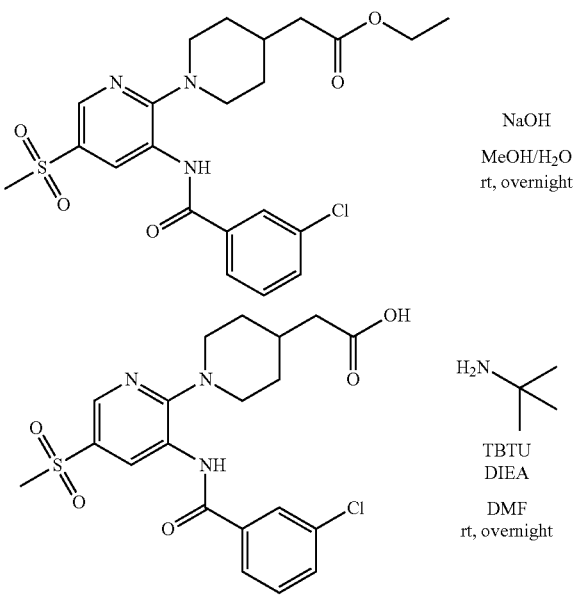

-continued

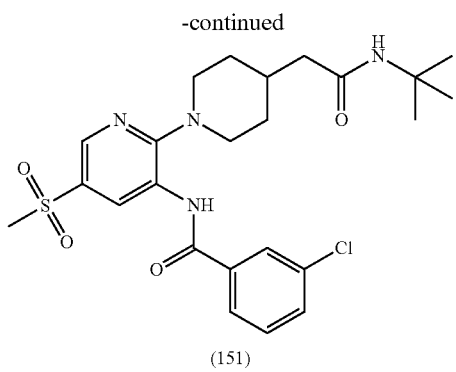

(151)

To a suspension of 1.41 g (2.94 mmol) of [3'-(3-Chlorobenzoylamino)-5'-methanesulfonyl-3,4,5,6-tetrahydro-2H-[1,2']bipyridinyl-4-yl]-acetic acid ethyl ester in a 1:1 mixture of water:methanol (30 mL) is added 4.0 mL (10 mmol) of sodium hydroxide as a 10% aqueous solution. After stirring at room temperature overnight the methanol is removed under reduced pressure and the pH of the resulting solution is adjusted to approximately pH 5 by the addition of a 2 N solution of hydrochloric acid. The mixture is extracted with ethyl acetate and the combined organic phase is dried over anhydrous sodium sulfate and concentrated under reduced pressure to provide 1.10 g (82.9%) of [3'-(3-chloro-benzoylamino)-5'-methanesulfonyl-3,4,5,6-tetrahydro-2H-[1,2']bipyridinyl-4-yl]-acetic acid as an orange oil.

To a solution of 0.050 g (0.11 mmol) of [3'-(3-chlorobenzoylamino)-5'-methanesulfonyl-3,4,5,6-tetrahydro-2H-[1,2']bipyridinyl-4-yl]-acetic acid in N,N-dimethylformamide (2 mL) is added 0.050 g (0.53 mmol) of O-(benzotriazol-1-yl)-N,N,N',N'-tetramethyluronium tetrafluoroborate followed by 0.060 mL (0.39 mmol) of N,N-diisopropylethylamine. The mixture is shaken at room temperature for 1 h then 0.017 mL (0.16 mmol) of tert-butylamine is added and the mixture is shaken at room temperature overnight. The mixture is diluted with a 1:1 mixture of water:acetonitrile with 0.1% trifluoroacetic acid. The residue is purified by reversed phase preparative HPLC using an eluent of acetonitrile:water with 0.1% trifluoroacetic acid additive to provide, after removal of the eluent, 0.012 g (21%) of N-[2-{4-[2-(tert-butylamino)-2-oxoethyl]piperidin-1-yl}-5-(methylsulfonyl)pyridin-3-yl]-3-chlorobenzamide (151) as a white solid. $[M+H]^+=507.7$.

The following compounds can be prepared analogously:
3-Chloro-N-{4-[(cycloheptylmethyl-carbamoyl)-methyl]-5'-methanesulfonyl-3,4,5,6-tetrahydro-2H-[1,2']bipyridinyl-3'-yl}-benzamide, $C_{28}H_{37}ClN_4O_4S$ $[M+H]^+=561.3$;
3-Chloro-N-{5'-methanesulfonyl-4-[(1-pyridin-3-yl-ethylcarbamoyl)-methyl]-3,4,5,6-tetrahydro-2H-[1,2']bipyridinyl-3'-yl}-benzamide, $C_{27}H_{30}ClN_5O_4S$ $[M+H]^+=556.3$;
3-Chloro-N-(4-{[(1,5-dimethyl-1H-pyrazol-3-ylmethyl)-carbamoyl]-methyl}-5'-methanesulfonyl-3,4,5,6-tetrahydro-2H-[1,2']bipyridinyl-3'-yl)-benzamide, $C_{26}H_{31}ClN_6O_4S$ $[M+H]^+=559.2$;
3-Chloro-N-{4-[(3,3-dimethyl-butylcarbamoyl)-methyl]-5'-methanesulfonyl-3,4,5,6-tetrahydro-2H-[1,2']bipyridinyl-3'-yl}-benzamide, $C_{26}H_{35}ClN_4O_4S$, $[M+H]^+=535.4$;
3-Chloro-N-{5'-methanesulfonyl-4-[(1-pyridin-2-yl-ethylcarbamoyl)-methyl]-3,4,5,6-tetrahydro-2H-[1,2']bipyridinyl-3'-yl}-benzamide, $C_{27}H_{30}ClN_5O_4S$ $[M+H]^+=556.3$;
3-Chloro-N-{5'-methanesulfonyl-4-[(1-pyridin-4-yl-ethylcarbamoyl)-methyl]-3,4,5,6-tetrahydro-2H-[1,2']bipyridinyl-3'-yl}-benzamide, $C_{27}H_{30}ClN_5O_4S$ $[M+H]^+=556.3$;
3-Chloro-N-{5'-methanesulfonyl-4-[(1-methyl-piperidin-4-ylcarbamoyl)-methyl]-3,4,5,6-tetrahydro-2H-[1,2']bipyridinyl-3'-yl}-benzamide, $C_{26}H_{34}ClN_5O_4S$, $[M+H]^+=548.3$;
3-Chloro-N-(5'-methanesulfonyl-4-{[(1-methyl-piperidin-4-ylmethyl)-carbamoyl]-methyl}-3,4,5,6-tetrahydro-2H-[1,2']bipyridinyl-3'-yl)-benzamide, $C_{27}H_{36}ClN_5O_4S$, $[M+H]^+=562.4$;
3-Chloro-N-(4-cyclohexylcarbamoylmethyl-5'-methanesulfonyl-3,4,5,6-tetrahydro-2H-[1,2']bipyridinyl-3'-yl)-benzamide, $C_{26}H_{33}ClN_4O_4S$, $[M+H]^+=533.3$;
3-Chloro-N-(4-{[1-(4-fluoro-phenyl)-cyclopropylcarbamoyl]-methyl}-5'-methanesulfonyl-3,4,5,6-tetrahydro-2H-[1,2']bipyridinyl-3'-yl)-benzamide, $C_{29}H_{30}ClFN_4O_4S$, $[M+H]^+=585.3$;
3-Chloro-N-(5'-methanesulfonyl-4-{[1-(3-methoxy-phenyl)-cyclopropylcarbamoyl]-methyl}-3,4,5,6-tetrahydro-2H-[1,2']bipyridinyl-3'-yl)-benzamide, $C_{30}H_{33}ClN_4O_5S$, $[M+H]^+=597.3$;
3-Chloro-N-{4-[(cyclohexylmethyl-carbamoyl)-methyl]-5'-methanesulfonyl-3,4,5,6-tetrahydro-2H-[1,2']bipyridinyl-3'-yl}-benzamide, $C_2H_{35}ClN_4O_4S$, $[M+H]^+=547.4$;
3-Chloro-N-{4-[(cyclopropylmethyl-carbamoyl)-methyl]-5'-methanesulfonyl-3,4,5,6-tetrahydro-2H-[1,2']bipyridinyl-3'-yl}-benzamide, $C_{24}H_{29}ClN_4O_4S$, $[M+H]^+=505.3$;
3-Chloro-N-{4-[((S)-1-cyclohexyl-ethylcarbamoyl)-methyl]-5'-methanesulfonyl-3,4,5,6-tetrahydro-2H-[1,2']bipyridinyl-3'-yl}-benzamide, $C_{28}H_{37}ClN_4O_4S$, $[M+H]^+=561.4$;
3-Chloro-N-(4-cyclopentylcarbamoylmethyl-5'-methanesulfonyl-3,4,5,6-tetrahydro-2H-[1,2']bipyridinyl-3'-yl)-benzamide, $C_{25}H_3ClN_4O_4S$, $[M+H]^+=519.3$;
3-Chloro-N-[4-((R)-indan-1-ylcarbamoylmethyl)-5'-methanesulfonyl-3,4,5,6-tetrahydro-2H-[1,2']bipyridinyl-3'-yl]-benzamide, $C_{29}H_{31}ClN_4O_4S$, $[M+H]^+=567.3$;
3-Chloro-N-[4-((S)-indan-1-ylcarbamoylmethyl)-5'-methanesulfonyl-3,4,5,6-tetrahydro-2H-[1,2']bipyridinyl-3'-yl]-benzamide, $C_{29}H_{31}ClN_4O_4S$ $[M+H]^+=567.3$;
3-Chloro-N-{5'-methanesulfonyl-4-[((R)-1-phenyl-ethylcarbamoyl)-methyl]-3,4,5,6-tetrahydro-2H-[1,2']bipyridinyl-3'-yl}-benzamide, $C_{28}H_{31}ClN_4O_4S$ $[M+H]^+=555.3$;
3-Chloro-N-(4-{[2-(4-fluoro-phenyl)-ethylcarbamoyl]-methyl}-5'-methanesulfonyl-3,4,5,6-tetrahydro-2H-[1,2']bipyridinyl-3'-yl)-benzamide, $C_{28}H_{30}ClFN_4O_4S$, $[M+H]^+=573.3$;
3-Chloro-N-{5'-methanesulfonyl-4-[((S)-1-phenyl-ethylcarbamoyl)-methyl]-3,4,5,6-tetrahydro-2H-[1,2']bipyridinyl-3'-yl}-benzamide, $C_{28}H_{31}ClN_4O_4S$ $[M+H]^+=555.3$;
3-Chloro-N-[5'-methanesulfonyl-4-({[(S)-1-(tetrahydro-furan-2-yl)methyl]-carbamoyl}-methyl)-3,4,5,6-tetrahydro-2H-[1,2']bipyridinyl-3'-yl]-benzamide, $C25H31ClN4O5S$, $[M+H]^+=535.3$;
3-Chloro-N-[5'-methanesulfonyl-4-({[(R)-1-(tetrahydro-furan-2-yl)methyl]-carbamoyl}-methyl)-3,4,5,6-tetrahydro-2H-[1,2']bipyridinyl-3'-yl]-benzamide, $C_{25}H_{31}ClN_4O_5S$, $[M+H]^+=535.3$;
3-Chloro-N-{5'-methanesulfonyl-4-[(1-oxazol-4-yl-cyclopropylcarbamoyl)-methyl]-3,4,5,6-tetrahydro-2H-[1,2']bipyridinyl-3'-yl}-benzamide, $C_{26}H_{28}ClN_5O_5S$, $[M+H]^+=558.3$;
3-Chloro-N-(4-{[1-(3-cyclopropyl-[1,2,4]oxadiazol-5-yl)-cyclopropylcarbamoyl]-methyl}-5'-methanesulfonyl-3,4,5,6-tetrahydro-2H-[1,2']bipyridinyl-3'-yl)-benzamide, $C_{28}H_{31}ClN_6O_5S$, $[M+H]^+=599.3$;

3-Chloro-N-(4-{[1-(5-cyclopropyl-[1,2,4]oxadiazol-3-yl)-cyclopropylcarbamoyl]-methyl}-5'-methanesulfonyl-3,4,5,6-tetrahydro-2H-[1,2']bipyridinyl-3'-yl)-benzamide, $C_{28}H_{31}ClN_6O_5S$, $[M+H]^+$=599.3;

3-Chloro-N-{5'-methanesulfonyl-4-[(1-thiophen-2-yl-ethylcarbamoyl)-methyl]-3,4,5,6-tetrahydro-2H-[1,2']bipyridinyl-3'-yl}-benzamide, $C_{26}H_{29}ClN_4O_4S_2$, $[M+H]^+$=561.3;

3-Chloro-N-{5'-methanesulfonyl-4-[2-((R)-2-methoxymethyl-pyrrolidin-1-yl)-2-oxo-ethyl]-3,4,5,6-tetrahydro-2H-[1,2']bipyridinyl-3'-yl}-benzamide, $C_{26}H_{33}ClN_4O_5S$, $[M+H]^+$=549.3;

3-Chloro-N-(5'-methanesulfonyl-4-{[(R)-(tetrahydro-furan-3-yl)carbamoyl]-methyl}-3,4,5,6-tetrahydro-2H-[1,2']bipyridinyl-3'-yl)-benzamide, $C_{24}H_{29}ClN_4O_5S$, $[M+H]^+$=521.3;

3-Chloro-N-{5'-methanesulfonyl-4-[(2-oxo-2,3-dihydro-1H-indol-3-ylcarbamoyl)-methyl]-3,4,5,6-tetrahydro-2H-[1,2']bipyridinyl-3'-yl}-benzamide, $C_{28}H_{28}ClN_5O_5S$, $[M+H]^+$=582.3;

3-Chloro-N-(5'-methanesulfonyl-4-{[(R)-1-(3-methoxy-phenyl)-ethylcarbamoyl]-methyl}-3,4,5,6-tetrahydro-2H-[1,2']bipyridinyl-3'-yl)-benzamide, $C_{29}H_{33}ClN_4O_5S$, $[M+H]^+$=585.3;

3-Chloro-N-{4-[(1-furan-2-yl-ethylcarbamoyl)-methyl]-5'-methanesulfonyl-3,4,5,6-tetrahydro-2H-[1,2']bipyridinyl-3'-yl}-benzamide, $C_{26}H_{29}ClN_4O_5S$, $[M+H]^+$=545.3;

3-Chloro-N-(4-{[1-(4-ethyl-4H-[1,2,4]triazol-3-yl)-ethylcarbamoyl]-methyl}-5'-methanesulfonyl-3,4,5,6-tetrahydro-2H-[1,2']bipyridinyl-3'-yl)-benzamide, $C_{26}H_{32}ClN_7O_4S$, $[M+H]^+$=574.3;

N-{4-[(1-Acetyl-piperidin-4-ylcarbamoyl)-methyl]-5'-methanesulfonyl-3,4,5,6-tetrahydro-2H-[1,2']bipyridinyl-3'-yl}-3-chloro-benzamide, $C_{27}H_{34}ClN_5O_5S$, $[M+H]^+$=576.3;

3-Chloro-N-{5'-methanesulfonyl-4-[(2-oxo-azepan-3-ylcarbamoyl)-methyl]-3,4,5,6-tetrahydro-2H-[1,2']bipyridinyl-3'-yl}-benzamide, $C_{26}H_{32}ClN_5O_5S$, $[M+H]^+$=562.3;

3-Chloro-N-{5'-methanesulfonyl-4-[(1-methyl-piperidin-3-ylcarbamoyl)-methyl]-3,4,5,6-tetrahydro-2H-[1,2']bipyridinyl-3'-yl}-benzamide, $C_{26}H_{34}ClN_5O_4S$, $[M+H]^+$=548.3;

3-Chloro-N-(4-{[1-(2,4-dichloro-phenyl)-ethylcarbamoyl]-methyl}-5'-methanesulfonyl-3,4,5,6-tetrahydro-2H-[1,2']bipyridinyl-3'-yl)-benzamide, $C_{28}H_{29}Cl_3N_4O_4S$, $[M+H]^+$=625.2;

3-Chloro-N-{5'-methanesulfonyl-4-[((S)-1-phenyl-propylcarbamoyl)-methyl]-3,4,5,6-tetrahydro-2H-[1,2']bipyridinyl-3'-yl}-benzamide, $C_{29}H_{33}ClN_4O_4S$, $[M+H]^+$=569.3;

3-Chloro-N-{5'-methanesulfonyl-4-[((R)-1-phenyl-propylcarbamoyl)-methyl]-3,4,5,6-tetrahydro-2H-[1,2']bipyridinyl-3'-yl}-benzamide, $C_{29}H_{33}ClN_4O_4S$, $[M+H]^+$=569.3;

3-Chloro-N-(5'-methanesulfonyl-4-{[1-(6-methanesulfonyl-pyridin-3-yl)-propylcarbamoyl]-methyl}-3,4,5,6-tetrahydro-2H-[1,2']bipyridinyl-3'-yl)-benzamide, $C_{29}H_{34}ClN_5O_6S_2$, $[M+H]^+$=648.3;

3-Chloro-N-{4-[(1-cyano-cyclopropylcarbamoyl)-methyl]-5'-methanesulfonyl-3,4,5,6-tetrahydro-2H-[1,2']bipyridinyl-3'-yl}-benzamide, $C_{24}H_{26}ClN_5O_4S$, $[M+H]^+$=516.3;

3-Chloro-N-{4-[(3,4-dichloro-benzylcarbamoyl)-methyl]-5'-methanesulfonyl-3,4,5,6-tetrahydro-2H-[1,2']bipyridinyl-3'-yl}-benzamide, $C_{27}H_{27}Cl_3N_4O_4S$ $[M+H]^+$=611.2;

N-(4-{[1-(5-Bromo-pyridin-3-yl)-propylcarbamoyl]-methyl}-5'-methanesulfonyl-3,4,5,6-tetrahydro-2H-[1,2']bipyridinyl-3'-yl)-3-chloro-benzamide, $C_{28}H_{31}BrClN_5O_4S$, $[M+H]^+$=650.2;

N-(4-{[1-(6-Bromo-pyridin-3-yl)-propylcarbamoyl]-methyl}-5'-methanesulfonyl-3,4,5,6-tetrahydro-2H-[1,2']bipyridinyl-3'-yl)-3-chloro-benzamide, $C_{28}H_{31}BrClN_5O_4S$, $[M+H]^+$=650.2;

3-Chloro-N-{5'-methanesulfonyl-4-[2-(4-methyl-[1,4]diazepan-1-yl)-2-oxo-ethyl]-3,4,5,6-tetrahydro-2H-[1,2']bipyridinyl-3'-yl}-benzamide, $C_{26}H_{34}ClN_5O_4S$, $[M+H]^+$=548.2;

3-Chloro-N-{4-[2-(4-hydroxy-piperidin-1-yl)-2-oxo-ethyl]-5'-methanesulfonyl-3,4,5,6-tetrahydro-2H-[1,2']bipyridinyl-3'-yl}-benzamide, $C_{25}H_{31}ClN_4O_5S$ $[M+H]^+$=535.2;

3-Chloro-N-{5'-methanesulfonyl-4-[2-(4-methoxy-piperidin-1-yl)-2-oxo-ethyl]-3,4,5,6-tetrahydro-2H-[1,2']bipyridinyl-3'-yl}-benzamide, $C_{26}H_{33}ClN_4O_5S$ $[M+H]^+$=549.2;

3-Chloro-N-[5'-methanesulfonyl-4-(2-[1,4]oxazepan-4-yl-2-oxo-ethyl)-3,4,5,6-tetrahydro-2H-[1,2']bipyridinyl-3'-yl]-benzamide, $C_{25}H_{31}ClN_4O_5S$ $[M+H]^+$=535.2;

N-{5'-Methanesulfonyl-4-[2-(4-methyl-[1,4]diazepan-1-yl)-2-oxo-ethyl]-3,4,5,6-tetrahydro-2H-[1,2']bipyridinyl-3'-yl}-4-methoxy-benzamide, $C_{27}H_{37}N_5O_5S$, $[M+H]^+$=509.3;

3-Chloro-N-(2-{4-[2-(4-hydroxy-4-methyl-piperidin-1-yl)-2-oxo-ethyl]-piperidin-1-yl}-5-methanesulfonyl-phenyl)-benzamide, $C_{27}H_{34}ClN_3O_5S$, $[M+H]^+$=516.3;

3-Chloro-N-[4-(2-[1,4]diazepan-1-yl-2-oxo-ethyl)-5'-methanesulfonyl-3,4,5,6-tetrahydro-2H-[1,2']bipyridinyl-3'-yl]-benzamide, $C_{25}H_{32}ClN_5O_4S$, $[M+H]^+$=534.2;

N-{4-[2-(4-Acetyl-[1,4]diazepan-1-yl)-2-oxo-ethyl]-5'-methanesulfonyl-3,4,5,6-tetrahydro-2H-[1,2']bipyridinyl-3'-yl}-3-chloro-benzamide, $C_{27}H_{34}ClN_5O_5S$, $[M+H]^+$=576.7;

3-Chloro-N-{5'-methanesulfonyl-4-[2-oxo-2-(3-oxo-piperazin-1-yl)-ethyl]-3,4,5,6-tetrahydro-2H-[1,2']bipyridinyl-3'-yl}-benzamide, $C_{24}H_{28}ClN_5O_5S$, $[M+H]^+$=534.6;

3-Chloro-N-{4-[2-(4,4-difluoro-piperidin-1-yl)-2-oxo-ethyl]-5'-methanesulfonyl-3,4,5,6-tetrahydro-2H-[1,2']bipyridinyl-3'-yl}-benzamide, $C_{25}H_{29}ClF_2N_4O_4S$, $[M+H]^+$=555.7;

N-{4-[2-(4-Acetyl-piperazin-1-yl)-2-oxo-ethyl]-5'-methanesulfonyl-3,4,5,6-tetrahydro-2H-[1,2']bipyridinyl-3'-yl}-3-chloro-benzamide, $C_{26}H_{32}ClN_5O_5S$, $[M+H]^+$=562.7;

3-Chloro-N-[5'-methanesulfonyl-4-((1S,4S)-2-2-oxa-5-azabicyclo[2.2.1]hept-5-yl-2-oxo-ethyl)-3,4,5,6-tetrahydro-2H-[1,2']bipyridinyl-3'-yl]-benzamide, $C_{25}H_{29}ClN_4O_5S$, $[M+H]^+$=533.6;

3-Chloro-N-{4-[2-((2R,6S)-2,6-dimethyl-morpholin-4-yl)-2-oxo-ethyl]-5'-methanesulfonyl-3,4,5,6-tetrahydro-2H-[1,2']bipyridinyl-3'-yl}-benzamide, $C_{26}H_{33}ClN_4O_5S$, $[M+H]^+$=549.7;

3-Chloro-N-[5'-methanesulfonyl-4-(2-morpholin-4-yl-2-oxo-ethyl)-3,4,5,6-tetrahydro-2H-[1,2']bipyridinyl-3'-yl]-benzamide, $C_{24}H_{29}ClN_4O_5S$, $[M+H]^+$=521.7;

3-Chloro-N-[5'-methanesulfonyl-4-(2-oxo-2-piperidin-1-yl-ethyl)-3,4,5,6-tetrahydro-2H-[1,2']bipyridinyl-3'-yl]-benzamide, $C_{25}H_{31}ClN_4O_4S$, $[M+H]^+$=519.7;

3-Chloro-N-{5'-methanesulfonyl-4-[2-(4-methanesulfonyl-piperazin-1-yl)-2-oxo-ethyl]-3,4,5,6-tetrahydro-2H-[1,2']bipyridinyl-3'-yl}-benzamide, $C_{25}H_{32}ClN_5O_6S_2$, $[M+H]^+$=598.7;

3-Chloro-N-{4-[2-(3,3-difluoro-piperidin-1-yl)-2-oxo-ethyl]-5'-methanesulfonyl-3,4,5,6-tetrahydro-2H-[1,2']bipyridinyl-3'-yl}-benzamide, $C_{25}H_{29}ClF_2N_4O_4S$, $[M+H]^+$=555.6;

N-[4-((1R,4S)-2-2-Aza-bicyclo[2.2.1]hept-2-yl-2-oxo-ethyl]-5'-methanesulfonyl-3,4,5,6-tetrahydro-2H-[1,2']bipyridinyl-3'-yl]-3-chloro-benzamide, $C_{26}H_{31}ClN_4O_4S$, $[M+H]^+$=531.7;

3-Chloro-N-{4-[2-(1,1-dioxo-1lambda*6*-thiomorpholin-4-yl)-2-oxo-ethyl]-5'-methanesulfonyl-3,4,5,6-tetrahydro-2H-[1,2']bipyridinyl-3'-yl}-benzamide, $C_{24}H_{29}ClN_4O_6S_2$, $[M+H]^+$=569.6;

3-Chloro-N-{5'-methanesulfonyl-4-[2-oxo-2-(4-trifluoromethyl-piperidin-1-yl)-ethyl]-3,4,5,6-tetrahydro-2H-[1,2']bipyridinyl-3'-yl}-benzamide, $C_{26}H_{30}ClF_3N_4O_4S$, $[M+H]^+$=587.7;

3-Chloro-N-{4-[2-(hexahydro-pyrrolo[1,2-a]pyrazin-2-yl)-2-oxo-ethyl]-5'-methanesulfonyl-3,4,5,6-tetrahydro-2H-[1,2']bipyridinyl-3'-yl}-benzamide, $C_{27}H_{34}ClN_5O_4S$, $[M+H]^+$=560.7;

3-Chloro-N-{5'-methanesulfonyl-4-[2-((S)-2-methyl-piperidin-1-yl)-2-oxo-ethyl]-3,4,5,6-tetrahydro-2H-[1,2']bipyridinyl-3'-yl}-benzamide, $C_{26}H_{33}ClN_4O_4S$, $[M+H]^+$=533.7;

3-Chloro-N-{5'-methanesulfonyl-4-[(5-methyl-4,5,6,7-tetrahydro-thiazolo[5,4-c]pyridin-2-ylcarbamoyl)-methyl]-3,4,5,6-tetrahydro-2H-[1,2']bipyridinyl-3'-yl}-benzamide, $C_{27}H_{31}ClN_6O_4S_2$, $[M+H]^+$=603.7;

3-Chloro-N-{4-[(4-fluoro-benzylcarbamoyl)-methyl]-5'-methanesulfonyl-3,4,5,6-tetrahydro-2H-[1,2']bipyridinyl-3'-yl}-benzamide, $C_{27}H_{28}ClFN_4O_4S$, $[M+H]^+$=559.7;

N-[4-(Benzylcarbamoyl-methyl)-5'-methanesulfonyl-3,4,5,6-tetrahydro-2H-[1,2']bipyridinyl-3'-yl]-3-chloro-benzamide, $C_2H_{29}ClN_4O_4S$, $[M+H]^+$=541.7;

3-Chloro-N-(5'-methanesulfonyl-4-{[(pyridin-3-ylmethyl)-carbamoyl]-methyl}-3,4,5,6-tetrahydro-2H-[1,2']bipyridinyl-3'-yl)-benzamide, $C_{26}H_{28}ClN_5O_4S$, $[M+H]^+$=542.7;

3-Chloro-N-[4-(isopropylcarbamoyl-methyl)-5'-methanesulfonyl-3,4,5,6-tetrahydro-2H-[1,2']bipyridinyl-3'-yl]-benzamide, $C_{23}H_{29}ClN_4O_4S$, $[M+H]^+$=493.7;

3-Chloro-N-{4-[2-((2S,6R)-2,6-dimethyl-piperidin-1-yl)-2-oxo-ethyl]-5'-methanesulfonyl-3,4,5,6-tetrahydro-2H-[1,2']bipyridinyl-3'-yl}-benzamide, $C_{27}H_{35}ClN_4O_4S$, $[M+H]^+$=547.8;

3-Chloro-N-{4-[(4-cyano-phenylcarbamoyl)-methyl]-5'-methanesulfonyl-3,4,5,6-tetrahydro-2H-[1,2']bipyridinyl-3'-yl}-benzamide, $C_{27}H_{26}ClN_5O_4S$, $[M+H]^+$=552.1;

3-Chloro-N-(5'-methanesulfonyl-4-{[(pyridin-2-ylmethyl)-carbamoyl]-methyl}-3,4,5,6-tetrahydro-2H-[1,2']bipyridinyl-3'-yl)-benzamide, $C_{26}H_{28}ClN_5O_4S$, $[M+H]^+$=542.8;

3-Chloro-N-{5'-methanesulfonyl-4-[(2,2,2-trifluoro-ethylcarbamoyl)-methyl]-3,4,5,6-tetrahydro-2H-[1,2']bipyridinyl-3'-yl}-benzamide, $C_{22}H_{24}ClF_3N_4O_4S$, $[M+H]^+$=533.8;

3-Chloro-N-{4-[(4-chloro-benzylcarbamoyl)-methyl]-5'-methanesulfonyl-3,4,5,6-tetrahydro-2H-[1,2']bipyridinyl-3'-yl}-benzamide, $C_{27}H_{28}Cl_2N_4O_4S$, $[M+H]^+$=575.8;

3-Chloro-N-(4-cyclopropylcarbamoylmethyl-5'-methanesulfonyl-3,4,5,6-tetrahydro-2H-[1,2']bipyridinyl-3'-yl)-benzamide, $C_{23}H_{27}ClN_4O_4S$, $[M+H]^+$=491.8;

3-Chloro-N-{5'-methanesulfonyl-4-[(4-methoxy-benzylcarbamoyl)-methyl]-3,4,5,6-tetrahydro-2H-[1,2']bipyridinyl-3'-yl}-benzamide, $C_{28}H_{31}ClN_4O_5S$, $[M+H]^+$=571.8;

3-Chloro-N-{4-[(2,6-dimethyl-phenylcarbamoyl)-methyl]-5'-methanesulfonyl-3,4,5,6-tetrahydro-2H-[1,2']bipyridinyl-3'-yl}-benzamide, $C_{28}H_{31}ClN_4O_4S$ $[M+H]^+$=555.8;

3-Chloro-N-{4-[(2,2-difluoro-ethylcarbamoyl)-methyl]-5'-methanesulfonyl-3,4,5,6-tetrahydro-2H-[1,2']bipyridinyl-3'-yl}-benzamide, $C_{22}H_{25}ClF_2N_4O_4S$, $[M+H]^+$=515.7;

3-Chloro-N-{5'-methanesulfonyl-4-[(1-methyl-1-phenyl-ethylcarbamoyl)-methyl]-3,4,5,6-tetrahydro-2H-[1,2']bipyridinyl-3'-yl}-benzamide, $C_{29}H_{33}ClN_4O_4S$ $[M+H]^+$=569.8;

N-[4-(tert-Butylcarbamoyl-methyl)-5'-methanesulfonyl-3,4,5,6-tetrahydro-2H-[1,2']bipyridinyl-3'-yl]-3-trifluoromethyl-benzamide, $C_{25}H_{31}F_3N_4O_4S$ $[M+H]^+$=541.8;

N-[4-(tert-Butylcarbamoyl-methyl)-5'-methanesulfonyl-3,4,5,6-tetrahydro-2H-[1,2']bipyridinyl-3'-yl]-4-methoxy-benzamide, $C_{25}H_{34}N_4O_5S$, $[M+H]^+$=503.8;

N-[4-(tert-Butylcarbamoyl-methyl)-5'-methanesulfonyl-3,4,5,6-tetrahydro-2H-[1,2']bipyridinyl-3'-yl]-3-chloro-4-trifluoromethoxy-benzamide, $C_{25}H_{30}ClF_3N_4O_5S$, $[M+H]^+$=591.8;

N-[4-(tert-Butylcarbamoyl-methyl)-5'-methanesulfonyl-3,4,5,6-tetrahydro-2H-[1,2']bipyridinyl-3'-yl]-4-methanesulfonyl-benzamide, $C_{25}H_{34}N_4O_6S_2$, $[M+H]^+$=551.8;

N-{4-[(Benzyl-ethyl-carbamoyl)-methyl]-5'-methanesulfonyl-3,4,5,6-tetrahydro-2H-[1,2']bipyridinyl-3'-yl}-3-chloro-benzamide, $C_{29}H_{33}ClN_4O_4S$, $[M+H]^+$=569.8;

3-Chloro-N-[5'-methanesulfonyl-4-(pyridin-4-ylcarbamoyl-methyl)-3,4,5,6-tetrahydro-2H-[1,2']bipyridinyl-3'-yl]-benzamide, $C_{25}H_{26}ClN_5O_4S$, $[M+H]^+$=528.1;

3-Chloro-N-{5'-methanesulfonyl-4-[(2-methoxy-benzylcarbamoyl)-methyl]-3,4,5,6-tetrahydro-2H-[1,2']bipyridinyl-3'-yl}-benzamide, $C_{28}H_{31}ClN_4O_5S$, $[M+H]^+$=571.8;

3-Chloro-N-[4-(isobutylcarbamoyl-methyl)-5'-methanesulfonyl-3,4,5,6-tetrahydro-2H-[1,2']bipyridinyl-3'-yl]-benzamide, $C_{24}H_3ClN_4O_4S$, $[M+H]^+$=507.8;

3-Chloro-N-(4-ethylcarbamoylmethyl-5'-methanesulfonyl-3,4,5,6-tetrahydro-2H-[1,2']bipyridinyl-3'-yl)-benzamide, $C_{22}H_{27}ClN_4O_4S$, $[M+H]^+$=479.8;

3-Chloro-N-{4-[(isopropyl-methyl-carbamoyl)-methyl]-5'-methanesulfonyl-3,4,5,6-tetrahydro-2H-[1,2']bipyridinyl-3'-yl}-benzamide, $C_{24}H_{31}ClN_4O_4S$, $[M+H]^+$=507.8;

3-Chloro-N-{5'-methanesulfonyl-4-[(2-methyl-benzylcarbamoyl)-methyl]-3,4,5,6-tetrahydro-2H-[1,2']bipyridinyl-3'-yl}-benzamide, $C_{28}H_{31}ClN_4O_4S$, $[M+H]^+$=555.8;

3-Chloro-N-{4-[(3-fluoro-benzylcarbamoyl)-methyl]-5'-methanesulfonyl-3,4,5,6-tetrahydro-2H-[1,2']bipyridinyl-3'-yl}-benzamide, $C_{27}H_{28}ClFN_4O_4S$, $[M+H]^+$=560.8;

3-Chloro-N-{5'-methanesulfonyl-4-[(3-methoxy-benzylcarbamoyl)-methyl]-3,4,5,6-tetrahydro-2H-[1,2']bipyridinyl-3'-yl}-benzamide, $C_{28}H_{31}ClN_4O_5S$, $[M+H]^+$=571.8;

3-Chloro-N-{4-[(2-fluoro-benzylcarbamoyl)-methyl]-5'-methanesulfonyl-3,4,5,6-tetrahydro-2H-[1,2']bipyridinyl-3'-yl}-benzamide, $C_{27}H_{28}ClFN_4O_4S$, $[M+H]^+$=559.8;

3-Chloro-N-{4-[(2-chloro-benzylcarbamoyl)-methyl]-5'-methanesulfonyl-3,4,5,6-tetrahydro-2H-[1,2']bipyridinyl-3'-yl}-benzamide, $C_{27}H_{28}Cl_2N_4O_4S$, $[M+H]^+$=575.8;

3-Chloro-N-{4-[(2,3-dichloro-benzylcarbamoyl)-methyl]-5'-methanesulfonyl-3,4,5,6-tetrahydro-2H-[1,2']bipyridinyl-3'-yl}-benzamide, $C_{27}H_{27}Cl_3N_4O_4S$ $[M+H]^+$=611.7;

Biphenyl-4-carboxylic acid [4-(tert-butylcarbamoyl-methyl)-5'-methanesulfonyl-3,4,5,6-tetrahydro-2H-[1,2']bipyridinyl-3'-yl]-amide, $C_{30}H_{36}N_4O_4S$, $[M+H]^+$=549.9;

Naphthalene-2-carboxylic acid [4-(tert-butylcarbamoyl-methyl)-5'-methanesulfonyl-3,4,5,6-tetrahydro-2H-[1,2']bipyridinyl-3'-yl]-amide, $C_{28}H_{34}N4O_4S$, $[M+H]^+$=523.9;

N-[4-(tert-Butylcarbamoyl-methyl)-5'-methanesulfonyl-3,4,5,6-tetrahydro-2H-[1,2']bipyridinyl-3'-yl]-3,5-dichloro-benzamide, $C_{24}H_{30}C_{12}N_4O_4S$, $[M+H]^+$=541.7;

N-[4-(tert-Butylcarbamoyl-methyl)-5'-methanesulfonyl-3,4,5,6-tetrahydro-2H-[1,2']bipyridinyl-3'-yl]-5-chloro-6-methoxy-nicotinamide, $C_{24}H_{32}ClN_5O_5S$, $[M+H]^+$=538.8;

3-Chloro-N-{5'-methanesulfonyl-4-[(4-methyl-cyclohexyl-carbamoyl)-methyl]-3,4,5,6-tetrahydro-2H-[1,2']bipyridinyl-3'-yl}-benzamide, $C_{27}H_{35}ClN_4O_4S$, $[M+H]^+$=547.8;

N-{4-[(1-Aza-bicyclo[2.2.2]oct-3-ylcarbamoyl)-methyl]-5'-methanesulfonyl-3,4,5,6-tetrahydro-2H-[1,2']bipyridinyl-3'-yl}-3-chloro-benzamide, $C_{27}H_{34}ClN_5O_4S$, $[M+H]^+$=560.9;

N-{5'-Methanesulfonyl-4-[(1-methyl-piperidin-3-ylcarbamoyl)-methyl]-3,4,5,6-tetrahydro-2H-[1,2']bipyridinyl-3'-yl}-3-trifluoromethyl-benzamide, $C_{27}H_{34}F_3N_5O_4S$, $[M+H]^+$=582.9;

N-{5'-Methanesulfonyl-4-[2-(4-methyl-[1,4]diazepan-1-yl)-2-oxo-ethyl]-3,4,5,6-tetrahydro-2H-[1,2']bipyridinyl-3'-yl}-3-trifluoromethyl-benzamide, $C_{27}H_{34}F_3N_5O_4S$, $[M+H]^+$=582.8;

N-[5'-Methanesulfonyl-4-((S)-piperidin-3-ylcarbamoylmethyl)-3,4,5,6-tetrahydro-2H-[1,2']bipyridinyl-3'-yl]-3-trifluoromethyl-benzamide, $C_{26}H_{32}F_3N_5O_4S$, $[M+H]^+$=568.8;

N-[5'-Methanesulfonyl-4-((R)-piperidin-3-ylcarbamoylmethyl)-3,4,5,6-tetrahydro-2H-[1,2']bipyridinyl-3'-yl]-3-trifluoromethyl-benzamide, $C_{26}H_{32}F_3N_5O_4S$, $[M+H]^+$=568.8;

4-Trifluoromethyl-pyridine-2-carboxylic acid [4-(tert-butylcarbamoyl-methyl)-5'-methanesulfonyl-3,4,5,6-tetrahydro-2H-[1,2']bipyridinyl-3'-yl]-amide, $C_{24}H_{30}F_3N_5O_4S$, $[M+H]^+$=542.8;

4-Chloro-pyridine-2-carboxylic acid [4-(tert-butylcarbamoyl-methyl)-5'-methanesulfonyl-3,4,5,6-tetrahydro-2H-[1,2']bipyridinyl-3'-yl]-amide, $C_{23}H_{30}ClN_5O_4S$, $[M+H]^+$=508.8;

N-[4-(tert-Butylcarbamoyl-methyl)-5'-methanesulfonyl-3,4,5,6-tetrahydro-2H-[1,2']bipyridinyl-3'-yl]-2-chloro-isonicotinamide, $C_{23}H_{30}ClN_5O_4S$, $[M+H]^+$=508.6;

N-{5'-Methanesulfonyl-4-[((R)-1-methyl-piperidin-3-ylcarbamoyl)-methyl]-3,4,5,6-tetrahydro-2H-[1,2']bipyridinyl-3'-yl}-3-trifluoromethyl-benzamide, $C_{27}H_{34}F_3N_5O_4S$, $[M+H]^+$=582.8;

N-{5'-Methanesulfonyl-4-[((S)-1-methyl-piperidin-3-ylcarbamoyl)-methyl]-3,4,5,6-tetrahydro-2H-[1,2']bipyridinyl-3'-yl}-3-trifluoromethyl-benzamide, $C_{27}H_{34}F_3N_5O_4S$, $[M+H]^+$=582.9;

N-{5'-Methanesulfonyl-4-[((R)-1-methyl-pyrrolidin-3-ylcarbamoyl)-methyl]-3,4,5,6-tetrahydro-2H-[1,2']bipyridinyl-3'-yl}-3-trifluoromethyl-benzamide, $C_{26}H_{32}F_3N_5O_4S$, $[M+H]^+$=568.8;

N-{5'-Methanesulfonyl-4-[((S)-1-methyl-pyrrolidin-3-ylcarbamoyl)-methyl]-3,4,5,6-tetrahydro-2H-[1,2']bipyridinyl-3'-yl}-3-trifluoromethyl-benzamide, $C_{26}H_{32}F_3N_5O_4S$, $[M+H]^+$=568.8;

N-{4-[((R)-1-Acetyl-piperidin-3-ylcarbamoyl)-methyl]-5'-methanesulfonyl-3,4,5,6-tetrahydro-2H-[1,2']bipyridinyl-3'-yl}-3-trifluoromethyl-benzamide, $C_{28}H_{34}F_3N_5O_5S$, $[M+H]^+$=610.8;

N-{4-[((S)-1-Acetyl-piperidin-3-ylcarbamoyl)-methyl]-5'-methanesulfonyl-3,4,5,6-tetrahydro-2H-[1,2']bipyridinyl-3'-yl}-3-trifluoromethyl-benzamide, $C_{28}H_{34}F_3N_5O_5S$, $[M+H]^+$=610.9;

N-{4-[((R)-1-Acetyl-pyrrolidin-3-ylcarbamoyl)-methyl]-5'-methanesulfonyl-3,4,5,6-tetrahydro-2H-[1,2']bipyridinyl-3'-yl}-3-trifluoromethyl-benzamide, $C_{27}H_{32}F_3N_5O_5S$, $[M+H]^+$=596.8;

N-{4-[((S)-1-Acetyl-pyrrolidin-3-ylcarbamoyl)-methyl]-5'-methanesulfonyl-3,4,5,6-tetrahydro-2H-[1,2']bipyridinyl-3'-yl}-3-trifluoromethyl-benzamide, $C_{27}H_{32}F_3N_5O_5S$, $[M+H]^+$=596.8;

3-Chloro-N-{4-[(4,4-difluoro-cyclohexylcarbamoyl)-methyl]-5'-methanesulfonyl-3,4,5,6-tetrahydro-2H-[1,2']bipyridinyl-3'-yl}-benzamide, $C_{26}H_{31}ClF_2N_4O_4S$ $[M+H]^+$=569.8;

Benzothiazole-2-carboxylic acid [4-(tert-butylcarbamoyl-methyl)-5'-methanesulfonyl-3,4,5,6-tetrahydro-2H-[1,2']bipyridinyl-3'-yl]-amide, $C_{25}H_{31}N_5O_4S_2$, $[M+H]^+$=530.7;

3-Chloro-N-(5-methanesulfonyl-2-{4-[2-(4-methoxy-4-methyl-piperidin-1-yl)-2-oxo-ethyl]-piperidin-1-yl}-phenyl)-benzamide, $C_{28}H_{36}ClN_3O_5S$ $[M+H]^+$=547.3; and 3-Chloro-N-(5-methanesulfonyl-2-{4-[2-(4-methyl-[1,4]diazepan-1-yl)-2-oxo-ethyl]-piperidin-1-yl}-phenyl)-benzamide, $C_{27}H_{35}ClN_4O_4S$, $[M+H]^+$=548.3.

Example 22

3-Chloro-N-[5'-chloro-4-((2S,6R)-2,6-dimethyl-piperidine-1-carbonyl)-3,4,5,6-tetrahydro-2H-[1,2']bipyridinyl-3'-yl]-benzamide (273)

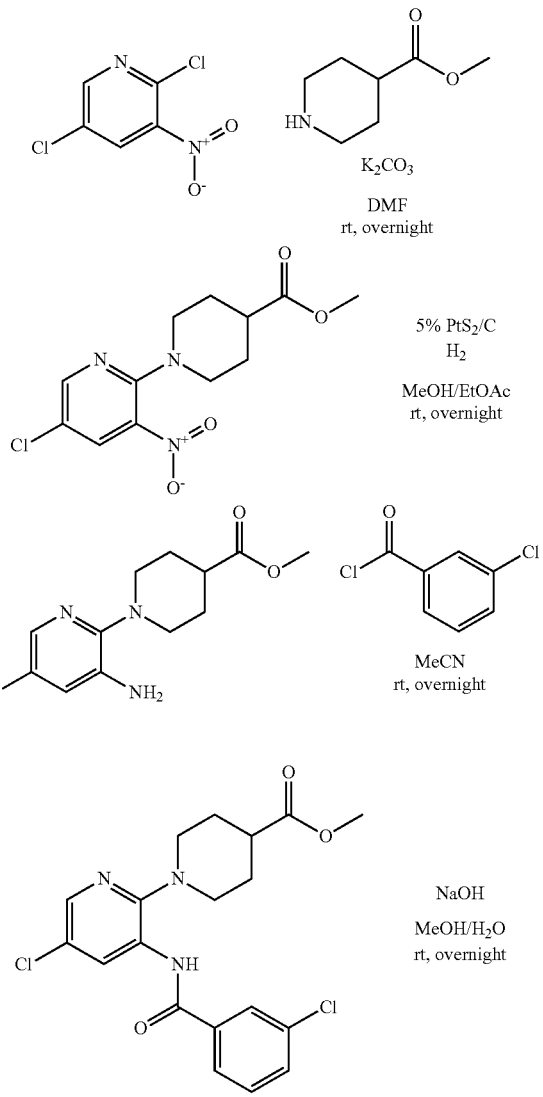

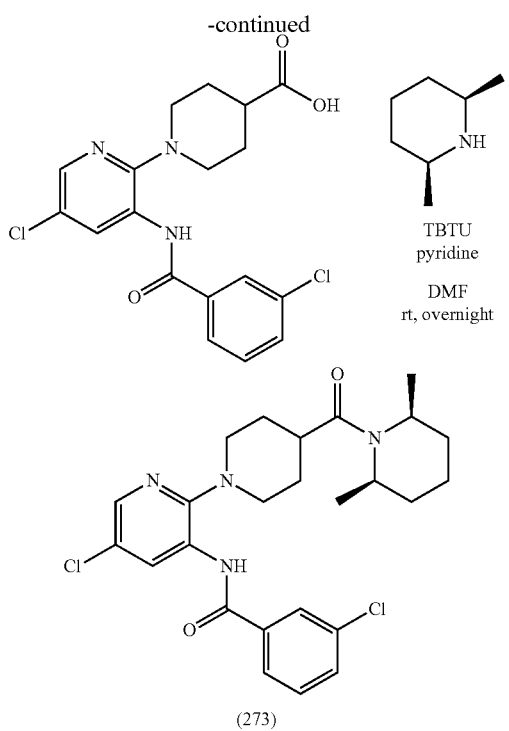

To a solution of 1.0 g (5.2 mmol) of 3-nitro-2,5-dichloropyridine in N,N-dimethylformamide (20 mL) is added 0.75 g (5.8 mmol) of methyl isonipocoate followed by 7 g (50 mmol) of potassium carbonate. The mixture is stirred at room temperature overnight then diluted with water and extracted with ethyl acetate. The combined organic phase is washed with water followed by brine then dried over anhydrous sodium sulfate and concentrated under reduced pressure. The residue is purified by flash silica gel chromatography to provide 1.1 g (71%) of 5'-chloro-3'-nitro-3,4,5,6-tetrahydro-2H-[1,2']bipyridinyl-4-carboxylic acid methyl ester as a red oil.

In a round bottom flask is placed 0.20 g (0.039 mmol) of 5% platinum sulfide on carbon. The vessel is evacuated and refilled with argon three times. To the flask is added a solution of 0.50 g (1.7 mmol) of 5'-chloro-3'-nitro-3,4,5,6-tetrahydro-2H-[1,2']bipyridinyl-4-carboxylic acid methyl ester in a 1:1 mixture of ethyl acetate:methanol (30 mL). The mixture is placed under an atmosphere of hydrogen and stirred at room temperature overnight. The mixture is filtered through a pad of diatomaceous earth and concentrated under reduced pressure to provide 0.45 g (quant.) of 3'-amino-5'-chloro-3,4,5,6-tetrahydro-2H-[1,2']bipyridinyl-4-carboxylic acid methyl ester as a dark oil.

To a solution of 0.45 g (1.7 mmol) of 3'-amino-5'-chloro-3,4,5,6-tetrahydro-2H-[1,2']bipyridinyl-4-carboxylic acid methyl ester in acetonitrile (20 mL) is added 0.23 mL (1.0 mmol) of 3-chlorobenzoyl chloride. The mixture is stirred at room temperature overnight then concentrated under reduced pressure and the residue is taken up in water and extracted with ethyl acetate. The combined organic phase is washed with a 10% aqueous solution of sodium hydroxide followed by brine then dried over anhydrous sodium sulfate and concentrated under reduced pressure. The residue is purified by flash silica gel chromatography to provide, after concentration of the eluent, a yellow oil. The oil is dissolved in methanol and upon standing a solid precipitates from solution. The material is collected by filtration and dried on the filter pad to provide 0.38 g (56%) of 5'-chloro-3'-(3-chloro-benzoylamino)-3,4,5,6-tetrahydro-2H-[1,2']bipyridinyl-4-carboxylic acid methyl ester as a white solid.

To a suspension of 0.480 g (1.18 mmol) of 5'-chloro-3'-(3-chloro-benzoylamino)-3,4,5,6-tetrahydro-2H-[1,2']bipyridinyl-4-carboxylic acid methyl ester in a 1:1 mixture of water:methanol (10 mL) is added 1.0 mL (2.5 mmol) of sodium hydroxide as a 10% aqueous solution. The mixture is stirred at room temperature overnight then concentrated under reduced pressure to remove volatile organics. The pH is adjusted to approximately pH 5 by the addition of a 2N solution of hydrochloric acid causing a solid to precipitate from solution. The material is collected by filtration, washed with water, and dried on the filter pad to provide 0.35 g (75%) of 5'-chloro-3'-(3-chloro-benzoylamino)-3,4,5,6-tetrahydro-2H-[1,2']bipyridinyl-4-carboxylic acid as a light yellow solid.

To a solution of 0.040 g (0.11 mmol) of 5'-chloro-3'-(3-chloro-benzoylamino)-3,4,5,6-tetrahydro-2H-[1,2']bipyridinyl-4-carboxylic acid in N,N-dimethylformamide (2 mL) is added 0.048 g (0.15 mmol) of O-(benzotriazol-1-yl)-N,N,N',N'-tetramethyluronium tetrafluoroborate followed by 0.042 mL (0.304 mmol) of triethylamine. The mixture is stirred at room temperature for 1 h then 0.034 g (0.304 mmol) of cis-2,6-dimethylpiperidine is added and the mixture is stirred at room temperature overnight. The mixture is concentrated under reduced pressure and the residue is purified by preparative reverse phase HPLC to provide 0.002 g (4%) of the title compound (273) as a white solid. [M+H]$^+$=489.2.

The following compounds can be prepared analogously:

N-[4-(Azepane-1-carbonyl)-5'-chloro-3,4,5,6-tetrahydro-2H-[1,2']bipyridinyl-3'-yl]-3-chloro-benzamide, $C_{24}H_{28}Cl_2N_4O_2$, [M+H]$^+$=475.3;

3-Chloro-N-[5'-chloro-4-(pyrrolidine-1-carbonyl)-3,4,5,6-tetrahydro-2H-[1,2']bipyridinyl-3'-yl]-benzamide, $C_{22}H_{24}Cl_2N_4O_2$, [M+H]$^+$=447.2;

3-Chloro-N-[5'-chloro-4-(4-methyl-[1,4]diazepane-1-carbonyl)-3,4,5,6-tetrahydro-2H-[1,2']bipyridinyl-3'-yl]-benzamide, $C_{24}H_{29}Cl_2N_5O_2$, [M+H]$^+$=490.3;

3-Chloro-N-[5'-chloro-4-(4-hydroxy-piperidine-1-carbonyl)-3,4,5,6-tetrahydro-2H-[1,2']bipyridinyl-3'-yl]-benzamide, $C_{23}H_{26}Cl_2N_4O_3$, [M+H]$^+$=477.2;

Example 23

Synthesis of 3-chloro-N-(5-chloro-2-{4-[2-(4-hydroxy-piperidin-1-yl)-2-oxo-ethyl]-piperidin-1-yl}-phenyl)-benzamide (278)

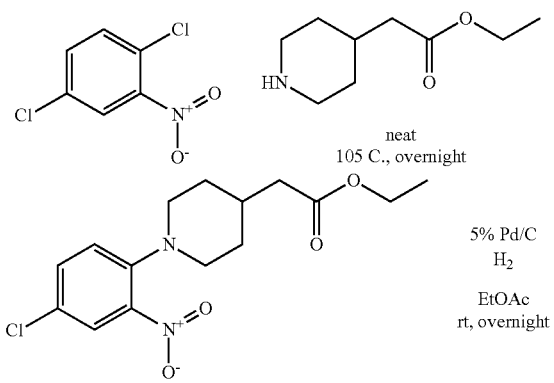

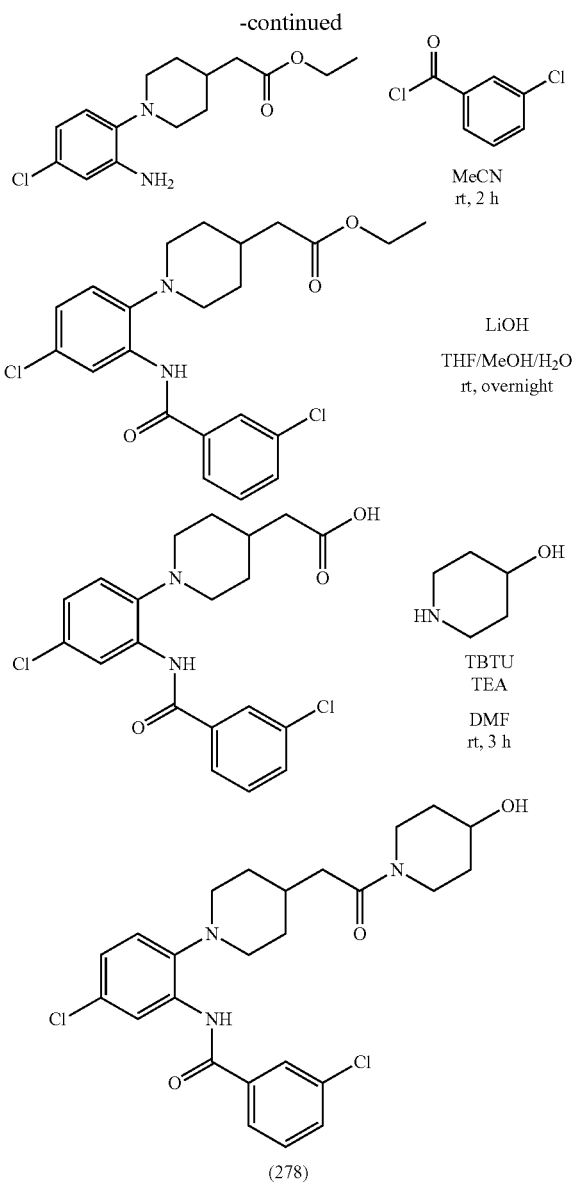

(278)

A mixture of 0.500 g (2.60 mmol) of 2,5-dichloronitrobenzene and 1.0 mL (mmol) of 2-(piperdin-4-yl)-acetic acid ethyl ester is heated overnight at 105° C. The mixture is cooled to room temperature, diluted with water, and extracted with ethyl acetate. The combined organic phase is washed with brine, dried over anhydrous sodium sulfate, and concentrated under reduced pressure. The residue is purified by flash silica gel chromatography to provide 0.803 g (94.4%) of [1-(4-chloro-2-nitro-phenyl)-piperidin-4-yl]-acetic acid ethyl ester as a red oil.

To a solution of 0.800 g (2.49 mmol) of [1-(4-chloro-2-nitro-phenyl)-piperidin-4-yl]-acetic acid ethyl ester in ethanol (30 mL) is added 0.10 g (0.05 mmol) of 5% palladium on carbon. The mixture is placed under an atmosphere of hydrogen and stirred at room temperature overnight. The mixture is filtered through a pad of diatomaceous earth and concentrated under reduced pressure to provide 0.710 g (97.7%) of [1-(2-amino-4-chloro-phenyl)-piperidin-4-yl]-acetic acid ethyl ester as a dark foam.

To a solution of 0.710 g (2.39 mmol) of [1-(2-amino-4-chloro-phenyl)-piperidin-4-yl]-acetic acid ethyl ester in acetonitrile (25 mL) is added 0.37 mL (2.9 mmol) of 3-chlorobenzoyl chloride. The mixture is stirred at room temperature for 2 hours then concentrated under reduced pressure. The residue is treated with a saturated aqueous solution of ammonium chloride and extracted with ethyl acetate. The combined organic phase is dried over anhydrous sodium sulfate and concentrated under reduced pressure. The residue is purified by flash silica gel chromatography to provide 0.590 g (56.7%) of {1-[4-chloro-2-(3-chloro-benzoylamino)-phenyl]-piperidin-4-yl}-acetic acid ethyl ester as a white solid.

To a solution of 0.590 g (1.35 mmol) of {1-[4-chloro-2-(3-chloro-benzoylamino)-phenyl]-piperidin-4-yl}-acetic acid ethyl ester in a mixture of tetrahydrofuran (10 mL) and methanol (4 mL) is added water (2 mL) followed by 0.16 g (6.8 mmol) of lithium hydroxide. The mixture is stirred overnight at room temperature. The mixture is concentrated under reduced pressure to remove volatile organics and the pH of the resulting solution is adjusted to approximately pH 4 by the addition of concentrated hydrochloric acid. A green oil forms at the bottom of the mixture. The aqueous layer is removed by decanting and the green oil is concentrated under reduced pressure to provide 0.46 g (83%) of {1-[4-chloro-2-(3-chloro-benzoylamino)-phenyl]-piperidin-4-yl}-acetic acid as a green solid.

A mixture of 0.100 g (0.246 mmol) of {1-[4-chloro-2-(3-chloro-benzoylamino)-phenyl]-piperidin-4-yl}-acetic acid, 0.124 g (1.23 mmol) of 4-hydroxypiperdine, 0.10 g (0.32 mmol) of O-(benzotriazol-1-yl)-N,N,N',N'-tetramethyluronium tetrafluoroborate, and 0.10 mL (0.74 mmol) of triethylamine in N,N-dimethylformamide (3 mL) are stirred at room temperature for 3 hours. The mixture is concentrated under reduced pressure and the residue is purified by preparative reverse phase HPLC to provide 0.040 g (33%) of the title compound (278) as a colorless solid. [M+H]$^+$=490.2.

The following compound can be prepared analogously:
3-Chloro-N-(5-chloro-2-{4-[2-(4-methyl-[1,4]diazepan-1-yl)-2-oxo-ethyl]-piperidin-1-yl}-phenyl)-benzamide, $C_{26}H_{32}Cl_2N_4O_2$, [M+H]$^+$=503.3.

Example 24

Synthesis of N-{2-[4-(tert-butylcarbamoyl-methyl)-piperidin-1-yl]-phenyl}-3-chloro-benzamide (280)

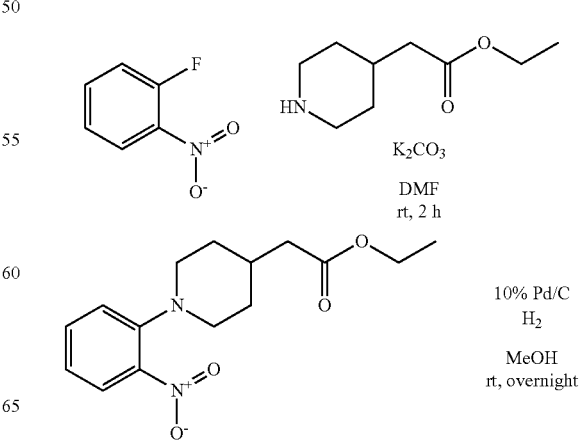

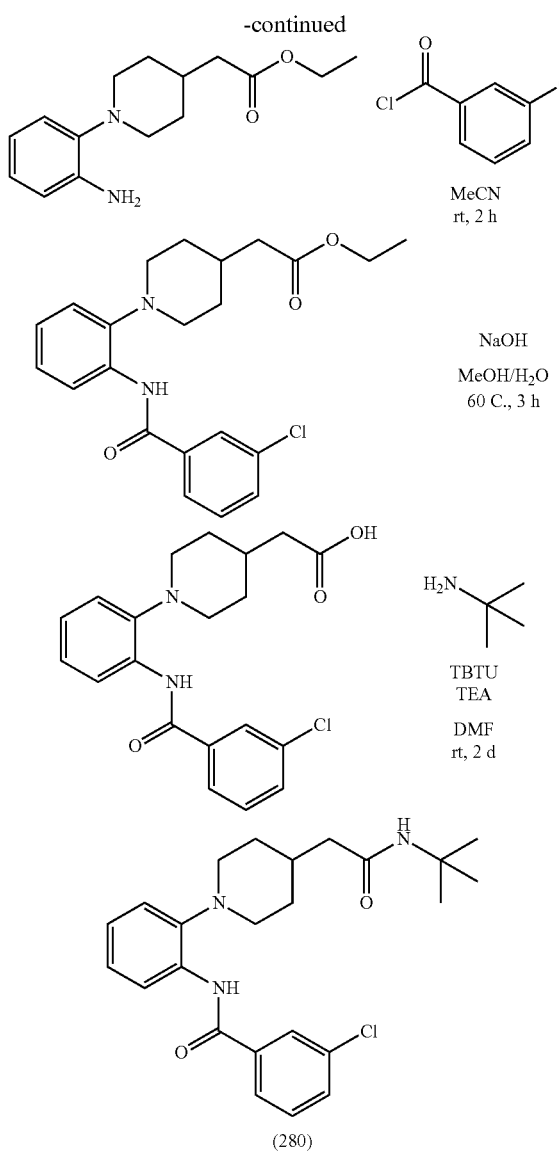

(280)

To a solution of 1.00 g (7.09 mmol) of 2-nitrofluorobenzene in N,N-dimethylformamide (50 mL) is added 1.3 g (7.6 mmol) of 2-(piperdin-4-yl)-acetic acid ethyl ester followed by 1.0 g (7.2 mmol) of potassium carbonate. The mixture is stirred at room temperature for 2 hours. The mixture is diluted with water and washed with ethyl acetate. The combined organic phase is washed with water followed by brine then dried over anhydrous sodium sulfate and concentrated under reduced pressure. The residue is purified by flash silica gel chromatography to provide 1.85 g (89%) of [1-(2-nitro-phenyl)-piperidin-4-yl]-acetic acid ethyl ester as an orange oil.

To a solution of 1.85 g (6.33 mmol) of [1-(2-nitro-phenyl)-piperidin-4-yl]-acetic acid ethyl ester in methanol (100 mL) is added 0.65 g (0.61 mmol) of 10% palladium on carbon. The mixture is placed under an atmosphere of hydrogen and shaken at room temperature overnight. The mixture is filtered through a pad of diatomaceous earth and concentrated under reduced pressure to provide 1.60 g (96.4%) of [1-(2-amino-phenyl)-piperidin-4-yl]-acetic acid ethyl ester as an orange oil.

To a solution of 0.500 g (1.91 mmol) of [1-(2-amino-phenyl)-piperidin-4-yl]-acetic acid ethyl ester in acetonitrile (100 mL) is added 0.25 mL (1.9 mmol) of 3-chlorobenzoyl chloride. The mixture is stirred at room temperature overnight. The mixture is concentrated under reduced pressure and the residue is purified by flash silica gel chromatography to provide 0.34 g (44%) of {1-[2-(3-chloro-benzoylamino)-phenyl]-piperidin-4-yl}-acetic acid ethyl ester as a clear oil.

To a suspension of 0.34 g (0.85 mmol) of {1-[2-(3-chloro-benzoylamino)-phenyl]-piperidin-4-yl}-acetic acid ethyl ester in a 1:1 mixture of water:methanol (10 mL) is added 0.64 mL (1.6 mmol) of sodium hydroxide as a 10% aqueous solution. The mixture is heated to 60° C. for 3 hours then cooled to room temperature, diluted with water, and the pH of the mixture is adjusted to approximately pH 5 by the addition of a 2 N solution of hydrochloric acid. The mixture is extracted with ethyl acetate and the combined organic phase is dried over anhydrous sodium sulfate and concentrated under reduced pressure to provide 0.29 g (92%) of {1-[2-(3-chloro-benzoylamino)-phenyl]-piperidin-4-yl}-acetic acid as a yellow oil.

To a solution of 0.050 g (0.13 mmol) of {1-[2-(3-chloro-benzoylamino)-phenyl]-piperidin-4-yl}-acetic acid in dimethylformamide (2 mL) is added 0.060 g (0.16 mmol) of O-(benzotriazol-1-yl)-N,N,N',N'-tetramethyluronium tetrafluoroborate followed by 0.035 mL (0.43 mmol) of pyridine. The mixture is stirred at room temperature for 1 h then 0.020 mL (0.19 mmol) of tert-butylamine is added and the mixture is stirred at room temperature overnight. To the mixture is added an additional 0.10 mL (0.96 mmol) of tert-butyl amine and the mixture is stirred for an additional 24 hours. The mixture is purified by reverse phase preparative HPLC using water:acetonitrile with 0.1% trifluoroacetic acid additive as the eluent to provide 0.054 g (74%) of the title compound (280) as a white powder. [M+H]$^+$=428.9.

The following compound can be prepared analogously:
3-Chloro-N-{2-[4-(pyridin-3-ylcarbamoylmethyl)-piperidin-1-yl]-phenyl}-benzamide, $C_{25}H_{25}ClN_4O_2$, [M+H]$^+$=449.8.

Example 25

Synthesis of 3-chloro-N-{5-chloro-2-[4-(2-oxo-2-piperidin-1-yl-ethyl)-piperazin-1-yl]-pyridin-3-yl}-benzamide (282)

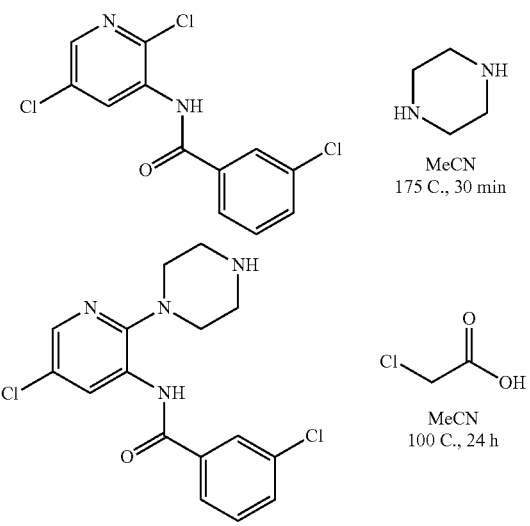

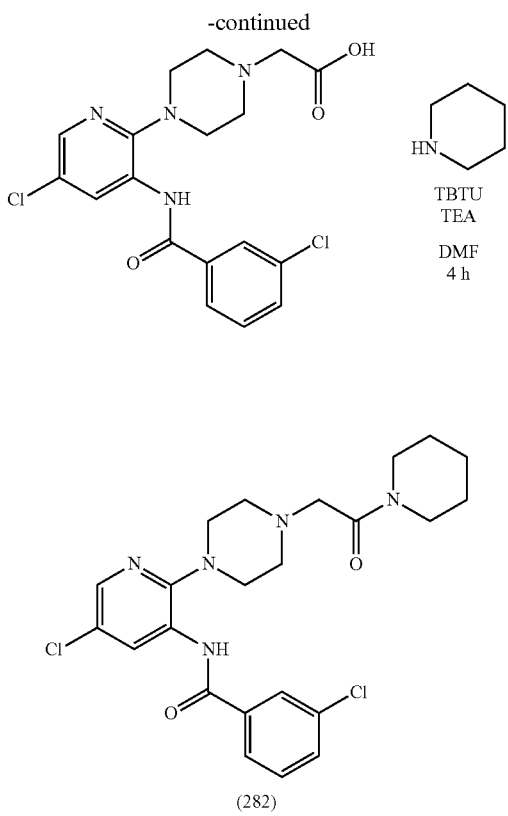

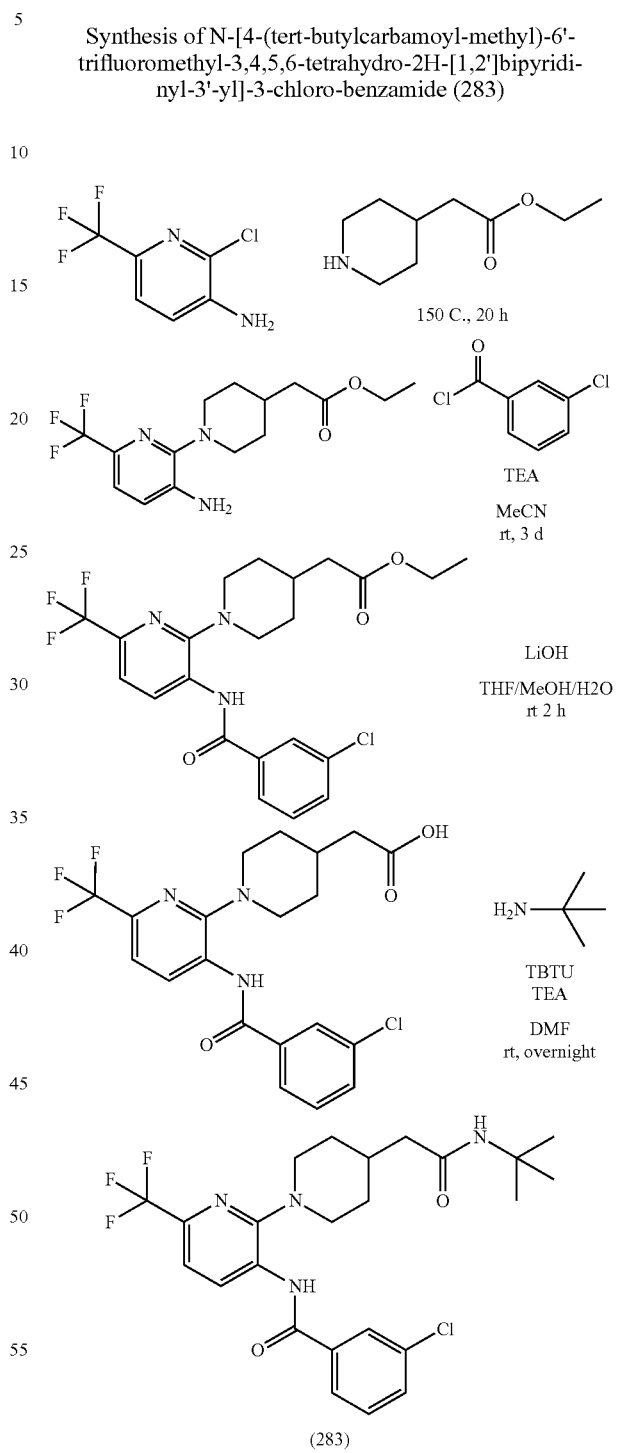

provide 0.0060 g (47%) of the title compound (282) as a colorless solid. [M+H]⁺=476.2.

Example 26

Synthesis of N-[4-(tert-butylcarbamoyl-methyl)-6'-trifluoromethyl-3,4,5,6-tetrahydro-2H-[1,2']bipyridinyl-3'-yl]-3-chloro-benzamide (283)

A solution of 0.500 g (1.66 mmol) of 3-chloro-N-(2,5-dichloro-pyridin-3-yl)-benzamide and 0.71 g (8.3 mmol) of piperazine in acetonitrile (5 mL) are heated to 175° C. for 30 minutes in a microwave reactor. The mixture is concentrated under reduced pressure and the residue is purified by flash silica gel chromatography to provide 0.320 g (54.9%) of 3-chloro-N-(5-chloro-2-piperazin-1-yl-pyridin-3-yl)-benzamide as a colorless solid.

A mixture of 0.100 g (0.285 mmol) of 3-chloro-N-(5-chloro-2-piperazin-1-yl-pyridin-3-yl)-benzamide and 0.040 g (0.43 mmol) of chloroacetic acid in N,N-dimethylformamide is stirred overnight at room temperature then heated to 100° C. for 24 hours. The mixture is cooled to room temperature, diluted with water, and extracted with ethyl acetate. The aqueous phase is concentrated under reduced pressure and the residue is purified by preparative reverse phase HPLC to provide 0.009 g (11%) of {4-[5-chloro-3-(3-chloro-benzoylamino)-pyridin-2-yl]-piperazin-1-yl}-acetic acid as a white solid.

A mixture of 0.011 g (0.027 mmol) of {4-[5-chloro-3-(3-chloro-benzoylamino)-pyridin-2-yl]-piperazin-1-yl}-acetic acid in N,N-dimethylformamide (1 mL), 0.011 g (0.13 mmol) of piperdine, 0.011 g (0.10 mmol) of O-(benzotriazol-1-yl)-N,N,N',N'-tetramethyluronium tetrafluoroborate, and 0.011 mL (0.081 mmol) of triethylamine is stirred at room temperature for 4 hours. The mixture is concentrated under reduced pressure and the residue is diluted with water causing a solid to precipitate from solution. The material is collected by filtration, washed with water and dried on the filter pad to A neat mixture of 0.500 g (2.54 mmol) of 3-amino-2-chloro-6-trifluoromethylpyridine and 0.870 g (5.09 mmol) of piperazin-1-yl-acetic acid ethyl ester is heated to 150° C. and stirred for 20 h. The mixture is cooled to room temperature, diluted with water, and extracted with ethyl acetate. The combined organic layer is washed with water followed by brine and then dried over anhydrous sodium sulfate and concentrated under reduced pressure. The crude material is purified by flash silica gel chromatography to provide 0.650 g (77.1%) of (3'-amino-6'-trifluoromethyl-3,4,5,6-tetrahydro-2H-[1,2']bipyridinyl-4-yl)-acetic acid ethyl ester as a brown oil.

To a mixture of 0.150 g (0.453 mmol) of (3'-amino-6'-trifluoromethyl-3,4,5,6-tetrahydro-2H-[1,2']bipyridinyl-4-yl)-acetic acid ethyl ester in acetonitrile (3 mL) is added 0.19 mL (1.4 mmol) of triethylamine followed by 0.069 mL (0.54 mmol) of 3-chlorobenzoyl chloride. The mixture is stirred overnight at room temperature then an additional 0.21 mL (1.6 mmol) of 3-chlorobenzoyl chloride is added and the mixture is stirred for an additional two days. The mixture is concentrated under reduced pressure and purified by flash silica gel chromatography to provide 0.23 g (quant.) of [3'-(3-chloro-benzoylamino)-6'-trifluoromethyl-3,4,5,6-tetrahydro-2H-[1,2']bipyridinyl-4-yl]-acetic acid ethyl ester.

To a mixture of 0.230 g (0.489 mmol) of [3'-(3-chloro-benzoylamino)-6'-trifluoromethyl-3,4,5,6-tetrahydro-2H-[1,2']bipyridinyl-4-yl]-acetic acid ethyl ester in a 2:1 mixture of tetrahydrofuran:methanol (12 mL) is added 0.058 g (2.4 mmol) of lithium hydroxide as a solution in water (2 mL). The mixture is stirred at room temperature for 2 hours then concentrated under reduced pressure. The residue is diluted with water and the pH of the mixture is adjusted to pH 2 by the addition of concentrated hydrochloric acid causing a solid to precipitate from solution. The formed precipitate is collected by filtration and dried to provide 0.21 g (quant) of [3'-(3-chloro-benzoylamino)-6'-trifluoromethyl-3,4,5,6-tetrahydro-2H-[1,2']bipyridinyl-4-yl]-acetic acid as a white solid.

A mixture of 0.100 g (0.226 mmol) of [3'-(3-chloro-benzoylamino)-6'-trifluoromethyl-3,4,5,6-tetrahydro-2H-[1,2']bipyridinyl-4-yl]-acetic acid, 0.050 g (0.68 mmol) tert-butyl amine, 0.094 g (0.296 mmol) of O-(benzotriazol-1-yl)-N,N,N',N'-tetramethyluronium tetrafluoroborate, and 0.094 mL (0.68 mmol) of triethylamine in N,N-dimethylformamide (2 mL) is stirred at room temperature for 2 hours. The mixture is diluted with water and purified using preparative reverse phase HPLC to give 0.020 g (18%) of the title compound (283) as colorless foam. [M+H]$^+$=497.2.

The following compounds can be prepared analogously:
3-Chloro-N-{6'-cyano-4-[2-(4-methyl-[1,4]diazepan-1-yl)-2-oxo-ethyl]-3,4,5,6-tetrahydro-2H-[1,2']bipyridinyl-3'-yl}-benzamide, $C_{26}H_{31}ClN_6O_2$, [M+H]$^+$=495.2.
N-[4-(tert-Butylcarbamoyl-methyl)-6'-cyano-3,4,5,6-tetrahydro-2H-[1,2']bipyridinyl-3'-yl]-3-chloro-benzamide, $C_{24}H_{28}ClN_5O_2$, [M+H]$^+$=454.2.

Example 27

Synthesis of N-[4-(tert-butylcarbamoyl-methyl)-6'-methanesulfonyl-3,4,5,6-tetrahydro-2H-[1,2']bipyridinyl-3'-yl]-3-chloro-benzamide (286)

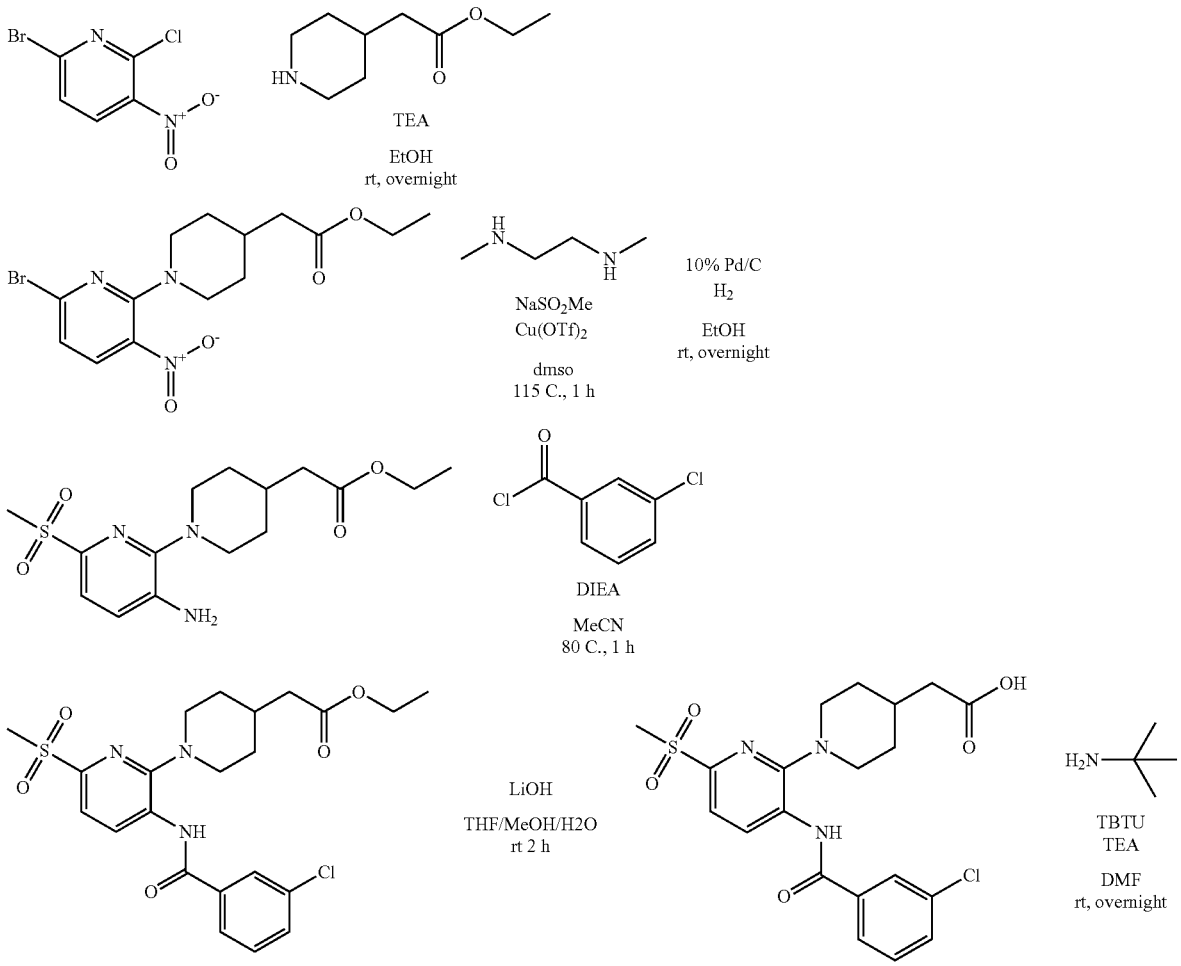

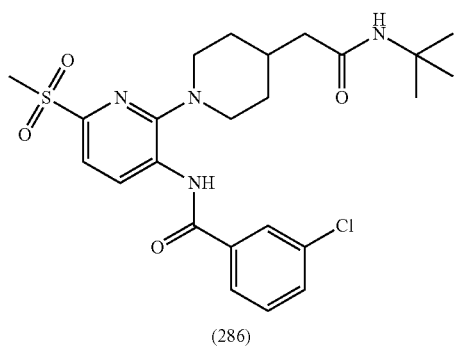

(286)

A mixture of 0.200 g (0.709 mmol) of 2,6-dibromo-3-nitropyridine, 0.121 g (0.709 mmol) of piperazin-1-yl-acetic acid ethyl ester, and 0.020 mL (1.4 mmol) of triethylamine in ethanol (3 mL) is stirred overnight at room temperature. The mixture is concentrated under reduced pressure and purified by flash silica gel chromatography to provide 0.200 g (75.7%) of (6'-bromo-3'-nitro-3,4,5,6-tetrahydro-2H-[1,2']bipyridinyl-4-yl)-acetic acid ethyl ester as a yellow oil.

A mixture of 0.200 g (0.537 mmol) of (6'-bromo-3'-nitro-3,4,5,6-tetrahydro-2H-[1,2']bipyridinyl-4-yl)-acetic acid ethyl ester, 0.095 g (1.1 mmol) of dimethylethylenediamine, 0.11 g (1.1 mmol) of sodium methanesulfinate, and 0.21 g (0.59 mmol) of copper (II) triflate in dimethylsulfoxide (3 mL) is heated in a microwave reactor at 115° C. for 1 hour. The mixture is cooled to room temperature, diluted with water and extracted with ethyl acetate. The combined organic phase is dried over anhydrous sodium sulfate, concentrated under reduced pressure and purified by flash silica gel chromatography to provide, 0.095 g (48%) of (6'-methanesulfonyl-3'-nitro-3,4,5,6-tetrahydro-2H-[1,2']bipyridinyl-4-yl)-acetic acid ethyl ester as a red oil.

A mixture of 0.090 g (0.24 mmol) of (6'-methanesulfonyl-3'-nitro-3,4,5,6-tetrahydro-2H-[1,2']bipyridinyl-4-yl)-acetic acid ethyl ester and 0.015 g (0.014 mmol) of 10% palladium on carbon in ethanol (8 mL) is stirred overnight under an atmosphere of hydrogen. The mixture is passed through a pad of diatomaceous earth and concentrated under reduced pressure to provide 0.076 g (94%) of (3'-amino-6'-methanesulfonyl-3,4,5,6-tetrahydro-2H-[1,2']bipyridinyl-4-yl)-acetic acid ethyl ester as a black oil.

To a mixture of 0.080 g (0.23 mmol) of (3'-amino-6'-methanesulfonyl-3,4,5,6-tetrahydro-2H-[1,2']bipyridinyl-4-yl)-acetic acid ethyl ester in acetonitrile (5 mL) is added 0.12 mL (0.70 mmol) of N,N-diisopropylethylamine followed by 0.032 mL (0.28 mmol) of 3-chlorobenzoyl chloride. The mixture is heated at 80° C. for 1 h then an additional 0.096 mL (0.84 mmol) of 3-chlorobenzoyl chloride is added. The mixture is stirred at 80° C. for an additional 10 minutes then cooled to room temperature and concentrated under reduced pressure. The residue is purified by flash silica gel chromatography to provide 0.055 g (49%) of [3'-(3-chloro-benzoylamino)-6'-methanesulfonyl-3,4,5,6-tetrahydro-2H-[1,2']bipyridinyl-4-yl]-acetic acid ethyl ester as a colorless foam.

To a mixture of 0.055 g (0.11 mmol) of [3'-(3-chloro-benzoylamino)-6'-methanesulfonyl-3,4,5,6-tetrahydro-2H-[1,2']bipyridinyl-4-yl]-acetic acid ethyl ester in a 2:1 mixture of tetrahydrofuran:methanol (6 mL) is added 0.014 g (0.57 mmol) of lithium hydroxide as a solution in water (1 mL). The mixture is stirred overnight at room temperature then concentrated under reduced pressure. The residue is diluted with water and the pH of the mixture is adjusted to pH 2 by the addition of concentrated hydrochloric acid causing a solid to precipitate from solution. The formed precipitate is collected by filtration and dried to provide 0.023 g (44%) of [3'-(3-chloro-benzoylamino)-6'-methanesulfonyl-3,4,5,6-tetrahydro-2H-[1,2']bipyridinyl-4-yl]-acetic acid as a yellow solid.

A mixture of 0.023 g (0.226 mmol) of [3'-(3-chloro-benzoylamino)-6'-methanesulfonyl-3,4,5,6-tetrahydro-2H-[1,2']bipyridinyl-4-yl]-acetic acid, 0.011 g (0.15 mmol) of tert-butyl amine, 0.021 g (0.066 mmol) of O-(benzotriazol-1-yl)-N,N,N',N'-tetramethyluronium tetrafluoroborate, and 0.021 mL (0.15 mmol) of triethylamine in N,N-dimethylformamide (2 mL) is stirred at room temperature for 2 hours. The mixture is diluted with water and purified using preparative reverse phase HPLC to give 0.016 g (62%) of the title compound (286) as colorless foam. $[M+H]^+$=507.2.

Assessment of Biological Properties

Compounds are assessed for the ability to block the interaction of CXCR3 and IP-10 in a functional cellular assay measuring calcium flux in CXCR3 transfected cells.

Cyno-CHO cells, stably expressing recombinant CXCR3 and G-alpha-16 are grown in F12 medium (Mediatech #45000-360) supplemented with 10% (V/V) FBS (Mediatech #35-01500), 1% Geneticin (Invitrogen #10131-027) and 0.2% Zeocin (Invitrogen #R250-05). The cells are spun down and re-suspended in growth media to a concentration of 4.8 E5 cells/mL. 25 microL of cell suspension is added to each well of a BD-384-well TC treated plate, providing 12,000 cells/well. The plate is incubated at 37° C./5% $CO_2$ overnight. On the day of the assay, the plates are removed, the media is flicked out and 25 microL of Ca-4 dye in assay buffer (HBSS, 10 mM HEPES ph 7.4), containing 2 mM probenacid is added to each well. The cell assay plates are then incubated at 37° C./5% $CO_2$ for one hour.

Test compounds are dissolved in DMSO and diluted to 1.045 mM in DMSO. Just prior to assay, 2.75 microL of appropriately diluted test compound are added to each well of a 384 well plate containing 45 microL of HBSS buffer. After mixing, 5 microL of diluted compound are added to each well of the cell assay plate for a final assay concentration of 10 microM. The plate is incubated at room temperature for 15 min. 10 microL of IP-10 stock solution in HBSS (4× EC80 concentration) are added to each well of the cell assay plate except those cells reserved as blank wells containing buffer only. Intracellular calcium flux is recorded on the HAMAMTSU FDSS6000, using excitation at 480 nm and emission at 540 nm. Data are analyzed using Activity Base software.

In general, the preferred potency range ($IC_{50}$) of compounds in the above assay is between 1 nM to 3 μM, and the most preferred potency range is 1 nM to 20 nM. The following table shows IC$_{50}$s for representative compounds of the invention in the above assay.

TABLE 2

| Compound # Table 1 | IC$_{50}$ (nM) |
|---|---|
| 6 | 2 |
| 17 | 18 |
| 18 | 15 |
| 19 | 11 |
| 25 | 4 |
| 36 | 9 |
| 39 | 3 |
| 40 | 5 |
| 41 | 3 |
| 42 | 2 |
| 43 | 20 |
| 78 | 12 |
| 79 | 11 |
| 82 | 11 |
| 86 | 5 |
| 90 | 19 |
| 92 | 12 |
| 97 | 20 |
| 103 | 13 |
| 112 | 2 |
| 115 | 20 |
| 118 | 8 |
| 119 | 7 |
| 120 | 3 |
| 124 | 9 |
| 127 | 6 |
| 128 | 20 |
| 129 | 12 |
| 130 | 3 |
| 131 | 4 |
| 132 | 4 |
| 133 | 7 |
| 135 | 6 |
| 136 | 20 |
| 137 | 16 |
| 138 | 17 |
| 141 | 20 |
| 143 | 6 |
| 144 | 5 |
| 146 | 6 |
| 149 | 6 |
| 150 | 10 |
| 151 | 15 |
| 152 | 7 |
| 153 | 12 |
| 160 | 8 |
| 161 | 10 |
| 162 | 12 |
| 163 | 6 |
| 166 | 10 |
| 167 | 6 |
| 168 | 11 |
| 169 | 10 |
| 174 | 15 |
| 177 | 10 |
| 181 | 8 |
| 182 | 11 |
| 186 | 11 |
| 189 | 9 |
| 193 | 11 |
| 197 | 15 |
| 199 | 20 |
| 200 | 12 |
| 214 | 9 |
| 215 | 16 |
| 216 | 16 |
| 219 | 9 |
| 231 | 7 |
| 236 | 19 |
| 239 | 13 |
| 242 | 16 |
| 243 | 11 |

TABLE 2-continued

| Compound # Table 1 | IC$_{50}$ (nM) |
|---|---|
| 244 | 15 |
| 245 | 11 |
| 246 | 9 |
| 247 | 13 |
| 252 | 9 |
| 254 | 15 |
| 261 | 8 |
| 262 | 11 |
| 266 | 16 |
| 269 | 8 |
| 271 | 6 |
| 272 | 7 |
| 278 | 10 |

Methods of Use

The compounds of the invention are effective antagonists of the interaction of CXCR3 and its ligands and thus inhibit CXCR3 activation. Therefore, in one embodiment of the invention, there is provided methods of treating CXCR3-mediated disorders using compounds of the invention. In another embodiment, there is provided methods of treating inflammatory, autoimmune and cardiovascular diseases using compounds of the invention.

Without wishing to be bound by theory, by inhibiting the activity of CXCR3 the compounds of the invention block the migration of T-cells and other leukocytes that express CXCR3. Thus, the inhibition of CXCR3 activity is an attractive means for preventing and treating a variety of autoimmune and immunological diseases exacerbated by the influx of these leukocytes. These include multiple sclerosis, rheumatoid arthritis, psoriasis, inflammatory bowel disease, COPD and kidney disease. Furthermore, a genetic deletion study and a study in LDL receptor KO mice with a CXCR3 antagonist have both shown that inhibition of CXCR3 activity attenuates atherosclerotic lesion formation. Thus inhibition of CXCR3 activity is also an attractive means for treating and preventing atherosclerosis and secondary atherothrombotic events such as myocardial infarction and stroke.

For treatment of the above-described diseases and conditions, a therapeutically effective dose will generally be in the range of approximately 0.01 mg to about 100 mg/kg of body weight per dosage of a compound of the invention; preferably, from about 0.1 mg to about 20 mg/kg of body weight per dosage. For example, for administration to a 70 kg person, the dosage range would be approximately 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:
1. A compound of formula (I):

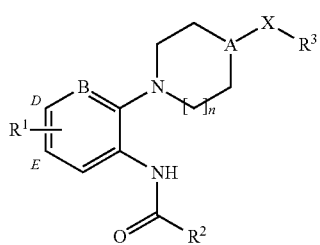

wherein:
A is —CH—;
B is N;
X is —CH$_2$—, —CH$_2$C(O)—, or —CH$_2$CH$_2$—;
R$^1$ is in the D- or E-position and is selected from H, —CN, halogen, —CF$_3$, —OCF$_3$, C$_{1-3}$alkyl, C$_{1-3}$alkoxy, —CH$_2$OH, —S(O)$_2$CH$_3$, —S(O)$_2$NH$_2$, amino, mono- or dimethylamino, —NHC(O)C$_{1-3}$alkyl, —NO$_2$, —C(O)NH$_2$, —C(O)C$_{1-3}$alkyl, phenyl and pyridyl; and if R$^1$ may also be selected from —C(O)NHC$_{1-3}$alkyl, —C(O)NHC$_{3-6}$cycloalkyl and —C(O)N(C$_{1-3}$alkyl)$_2$;

R$^2$ is phenyl, naphthyl, 2-pyridyl, 4-pyridyl or benzothiazolyl each optionally substituted with one to two R$^6$, wherein R$^6$ is not ortho to the —C(O)NH— group;
R$^3$ is heterocyclyl selected from azabicyclo[2.2.1]hept-2-yl, azepan-1-yl, 1,4-diazepan-1-yl, hexahydropyrrolo[1,2-a]pyrazin-2-yl, morpholin-4-yl, 2-oxa-5-azabicyclo[2.2.1]hept-5-yl, oxazepan-4-yl, piperazin-1-yl and piperidin-1-yl or —N(R$^4$)(R$^5$), or
R$^3$ is heteroaryl selected from benzimidazol-1-yl, imidazol-1-yl, pyrazol-1-yl imidazo[4,5-b]pyridine-3-yl and 1H-pyrrolo[2,3-b]pyridine-1-yl, with the proviso that X is —CH$_2$CH$_2$—,
wherein each heteroaryl or heterocyclyl group is optionally and independently substituted with one to two R$^7$;
R$^4$ is H or C$_{1-3}$alkyl;
R$^5$ is selected from
(A) C$_{2-6}$alkyl,
(B) —(CH$_2$)$_{0-1}$C$_{3-7}$cycloalkyl,
(C) —CH(CH$_3$)C$_{3-7}$cycloalkyl,
(D) —C(R$^8$)(R$^9$)phenyl,
(E) —[C(R$^8$)(R$^9$)]$_{0-1}$heteroaryl,
(F) —[C(R$^8$)(R$^9$)]$_{0-1}$heterocyclyl,
(G) —C(O)NHR$^{10}$, wherein R$^{10}$ is selected from ethyl, benzyl and phenyl,
(H) —S(O)$_2$CH$_2$phenyl,
(I) cyclopropyl, optionally substituted with a CN,
(J) —CH$_2$CF$_3$,
(K) —CH$_2$CF$_2$H,
(L) —NHC(O)CH(CH$_3$)phenyl
(M) —C(O)(1-methylpiperidin-3-yl),
(N) —CH$_2$C(O)NHC$_{1-3}$ alkyl, and
(O) indan-1-yl,
(P) —CH$_2$C(O)N(C$_{1-3}$alkyl)$_2$,
wherein each C$_{2-5}$alkyl, heteroaryl, heterocyclyl or phenyl is optionally and independently substituted with one to four R$^7$;
R$^6$ is independently selected from halogen, —CF$_3$, —OCF$_3$, CN, —NO$_2$, —SO$_2$CH$_3$, C$_{1-3}$alkoxy, C$_{1-4}$alkyl, phenoxy, benzoyl and phenyl;
R$^7$ is independently selected from C$_{1-4}$alkyl, C$_{3-6}$cycloalkyl, C$_{1-3}$alkoxy, —CH$_2$OC$_{1-3}$alkyl, —OH, oxo, —CHO, —C(O)C$_{1-3}$alkyl, halogen, —CF$_3$, —CN, and —S(O)$_2$C$_{1-3}$alkyl;
R$^8$ and R$^9$ are independently selected from H and C$_{1-2}$alkyl; or R$^8$ and R$^9$, together with the carbon they are bonded to, may form a cyclopropyl ring;
n is 1;
or a pharmaceutically acceptable salt thereof.
2. The compound of claim 1, wherein:
R$^1$ is in the E-position and is selected from H, —CN, halogen, —CF$_3$, —OCF$_3$, C$_{1-3}$alkyl, C$_{1-3}$alkoxy, —CH$_2$OH, —S(O)$_2$CH$_3$, —S(O)$_2$NH$_2$, amino, mono- or dimethylamino, —NHC(O)C$_{1-3}$alkyl, —NO$_2$, —C(O)NH$_2$, —C(O)C$_{1-3}$alkyl, phenyl and pyridyl; R$^1$ may also be selected from —C(O)NHC$_{1-3}$alkyl, —C(O)NHC$_{3-6}$cycloalkyl and —C(O)N(C$_{1-3}$alkyl)$_2$;
R$^5$ is selected from
(A) C$_{2-6}$alkyl,
(B) —(CH$_2$)$_{0-1}$C$_{3-7}$cycloalkyl,
(C) —CH(CH$_3$)C$_{3-7}$cycloalkyl,
(D) —C(R$^8$)(R$^9$)phenyl
(E) —[C(R$^8$)(R$^9$)]$_{0-1}$heteroaryl, wherein the heteroaryl is selected from furan-2-yl, 1,2,4-oxadiazol-3-yl, 1,3-oxazol-4-yl, pyrazol-3-yl, 2-, 3- or 4-pyridinyl, thiophen-2-yl, thiazol-2-yl and 1,2,4-triazol-2-yl, thiophen-2-yl, thiazol-2-yl and 1,2,4-triazol-2-yl, (F) —[C($R^8$)($R^9$)]$_{0-1}$heterocyclyl, wherein the heterocyclyl is selected from azabicyclo[2.2.2]oct-3-yl, azepan-3-yl, 2,3-dihydro-1H-indol-3-yl, piperidin-3-yl, piperidin-4-yl, pyrrolidin-3-yl, tetrahydrofuran2-yl, tetrahydrofuran-3-yl and 4,5,6,7-tetrahydro[1,3]thiazolo[5,4-c]pyridine-2-yl,
(G) —C(O)NH$R^{10}$, wherein $R^{10}$ is selected from ethyl, benzyl and phenyl,
(H) —S(O)$_2$CH$_2$phenyl,
(I) cyclopropyl, optionally substituted with a CN,
(J) —CH$_2$CF$_3$,
(K) —CH$_2$CF$_2$H,
(L) —NHC(O)CH(CH$_3$)phenyl
(M) —NHC(O)(1-methylpiperidin-3-yl),
(N) —CH$_2$C(O)NHC$_{1-3}$ alkyl, and
(O) indan-1-yl,
wherein each C$_{2-5}$alkyl, heteroaryl, heterocyclyl or phenyl is optionally and independently substituted with one to four $R^7$;
or a pharmaceutically acceptable salts thereof.

3. The compound of claim 2, wherein:
$R^1$ is in the E-position and is selected from H, —CN, —F, —Cl, —CH$_3$, —S(O)$_2$CH$_3$, —S(O)$_2$NH$_2$, phenyl and pyridyl; and if $R^1$ may also be selected from —C(O)NHC$_{1-3}$alkyl, —C(O)NHcyclopropyl and —C(O)N(C$_{1-3}$alkyl)$_2$;
$R^2$ is phenyl, 2-pyridyl or 4-pyridyl each optionally substituted with one to two $R^6$ wherein $R^6$ is not ortho to the —C(O)NH— group;
$R^4$ is H; and
$R^5$ is selected from
(A) C$_{2-6}$alkyl,
(B) —(CH$_2$)$_{0-1}$C$_{3-7}$cycloalkyl,
(C) —CH(CH$_3$)C$_{3-7}$cycloalkyl,
(D) —C($R^8$)($R^8$)phenyl,
(E) —[C($R^8$)($R^9$)]$_{0-1}$heteroaryl, wherein the heteroaryl is selected from furan-2-yl, 1,2,4-oxadiazol-3-yl, 1,3-oxazol-4-yl, pyrazol-3-yl, 2-, 3- or 4-pyridinyl, thiophen-2-yl, thiazol-2-yl and 1,2,4-triazol-2-yl,
(F) —[C($R^8$)($R^9$)]$_{0-1}$heterocyclyl, wherein the heterocyclyl is selected from azabicyclo[2.2.2]oct-3-yl, azepan-3-yl, 2,3-dihydro-1H-indol-3-yl, piperidin-3-yl, piperidin-4-yl, pyrrolidin-3-yl, tetrahydrofuran2-yl, tetrahydrofuran-3-yl and 4,5,6,7-tetrahydro[1,3]thiazolo[5,4-c]pyridine-2-yl,
(G) —C(O)NH$R^{10}$, wherein $R^{10}$ is selected from ethyl, benzyl and phenyl,
(H) —S(O)$_2$CH$_2$phenyl,
(I) cyclopropyl, optionally substituted with a CN,
(J) —CH$_2$CF$_3$,
(K) —CH$_2$CF$_2$H,
(L) —NHC(O)CH(CH$_3$)phenyl
(M) —NHC(O)(1-methylpiperidin-3-yl),
(N) —CH$_2$C(O)NHC$_{1-3}$ alkyl, and
(O) indan-1-yl,
wherein each C$_{2-5}$alkyl, heteroaryl, heterocyclyl or phenyl is optionally and independently substituted with one to four $R^7$;
or a pharmaceutically acceptable salt thereof.

4. The compound of claim 1, wherein:
$R^1$ is in the E-position and is selected from H, —CN, —Cl, —S(O)$_2$CH$_3$ and —S(O)$_2$NH$_2$; and if $R^1$ may also be —C(O)NHcyclopropyl or —C(O)N(Et)$_2$;
$R^2$ is phenyl optionally substituted with one to two $R^6$ wherein $R^6$ is not ortho to the —C(O)NH— group;
$R^3$ is heterocyclyl selected from azabicyclo[2.2.1]hept-2-yl, azepan-1-yl, 1,4-diazepan-1-yl, hexahydropyrrolo[1,2-a]pyrazin-2-yl, morpholin-4-yl, 2-oxa-5-azabicyclo[2.2.1]hept-5-yl, oxazepan-4-yl, piperazin-1-yl and piperidin-1-yl, or —N($R^4$)($R^5$)
wherein each heterocyclyl is optionally substituted with one to two $R^7$;
$R^4$ is H;
$R^5$ is selected from
(A) C$_{2-6}$alkyl,
(B) —(CH$_2$)$_{0-1}$C$_{3-7}$cycloalkyl,
(C) —CH(CH$_3$)C$_{3-7}$cycloalkyl,
(D) —C($R^8$)($R^8$)phenyl,
(E) —[C($R^8$)($R^9$)]$_{0-1}$heteroaryl, wherein the heteroaryl is selected from furan-2-yl, 1,2,4-oxadiazol-3-yl, 1,3-oxazol-4-yl, pyrazol-3-yl, 2-, 3- or 4-pyridinyl, thiophen-2-yl, thiazol-2-yl and 1,2,4-triazol-2-yl,
(F) —[C($R^8$)($R^9$)]$_{0-1}$heterocyclyl, wherein the heterocyclyl is selected from azabicyclo[2.2.2]oct-3-yl, azepan-3-yl, 2,3-dihydro-1H-indol-3-yl, piperidin-3-yl, piperidin-4-yl, pyrrolidin-3-yl, tetrahydrofuran2-yl, tetrahydrofuran-3-yl and 4,5,6,7-tetrahydro[1,3]thiazolo[5,4-c]pyridine-2-yl,
(G) —C(O)NH$R^{10}$, wherein $R^{10}$ is selected from ethyl, benzyl and phenyl,
(H) —S(O)$_2$CH$_2$phenyl,
(I) cyclopropyl, optionally substituted with a CN,
(J) —CH$_2$CF$_3$,
(K) —CH$_2$CF$_2$H,
(L) —NHC(O)CH(CH$_3$)phenyl
(M) —NHC(O)(1-methylpiperidin-3-yl),
(N) —CH$_2$C(O)NHC$_{1-3}$ alkyl, and
(O) indan-1-yl,
wherein each C$_{2-5}$alkyl, heteroaryl, heterocyclyl or phenyl is optionally and independently substituted with one to four $R^7$; and
$R^6$ is independently selected from —Cl, —CF$_3$, —OCF$_3$, CN, —SO$_2$CH$_3$ and —OCH$_3$;
or a pharmaceutically acceptable salts thereof.

5. The compound of claim 4, wherein:
$R^2$ is phenyl substituted with $R^6$ wherein $R^6$ is not ortho to the —C(O)NH— group;
$R^5$ is selected from
(A) C$_{2-6}$alkyl,
(B) —(CH$_2$)$_{0-1}$C$_{3-7}$cycloalkyl,
(C) —CH(CH$_3$)C$_{3-7}$cycloalkyl,
(D) —C($R^8$)($R^9$)phenyl
(E) —[C($R^8$)($R^9$)]$_{0-1}$heteroaryl, wherein the heteroaryl is selected from furan-2-yl, 1,2,4-oxadiazol-3-yl, 1,3-oxazol-4-yl, pyrazol-3-yl, 2-, 3- or 4-pyridinyl, thiophen-2-yl, thiazol-2-yl and 1,2,4-triazol-2-yl,
(F) —[C($R^8$)($R^9$)]$_{0-1}$heterocyclyl, wherein the heterocyclyl is selected from azabicyclo[2.2.2]oct-3-yl, azepan-3-yl, 2,3-dihydro-1H-indol-3-yl, piperidin-3-yl, piperidin-4-yl, pyrrolidin-3-yl, tetrahydrofuran2-yl and tetrahydrofuran-3-yl, and
(G) —C(O)NH$R^{10}$, wherein $R^{10}$ is selected from ethyl, benzyl and phenyl,
wherein each C$_{2-5}$alkyl, heteroaryl, heterocyclyl or phenyl is optionally and independently substituted with one to two $R^7$;
$R^6$ is selected from 3-Cl, 3-CF$_3$, 4-OCH$_3$ and 4-SO$_2$CH$_3$; and
$R^7$ is independently selected from —CH$_3$, —CH$_2$CH$_3$, cyclopropyl, OCH$_3$, —OH, —C(O)CH$_3$, Br, Cl, F, —CF$_3$, —CN, and —S(O)$_2$CH$_3$;
or a pharmaceutically acceptable salt thereof.

6. The compound of claim 5, wherein X is —CH$_2$C(O)—, or a pharmaceutically acceptable salt thereof.

7. The compound according to claim 1 selected from the group consisting of
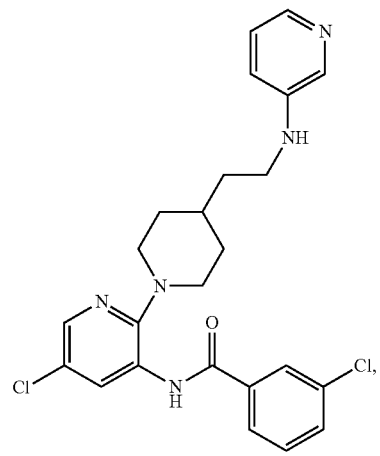
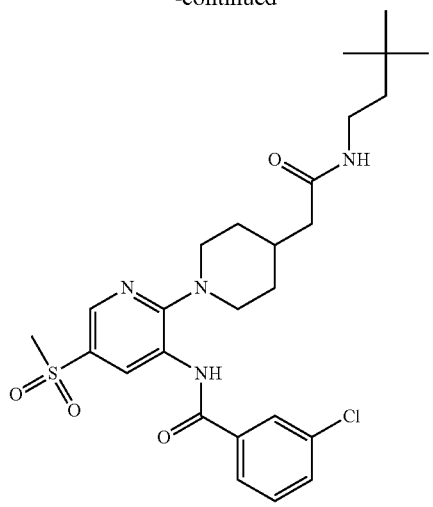
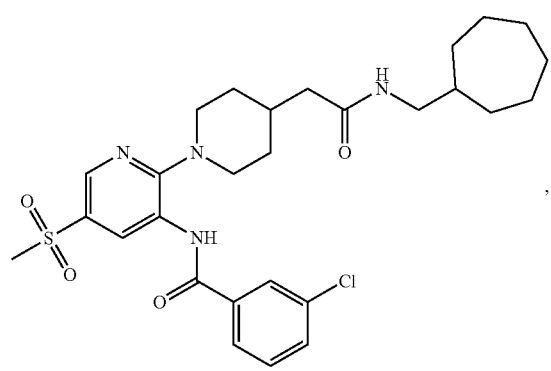
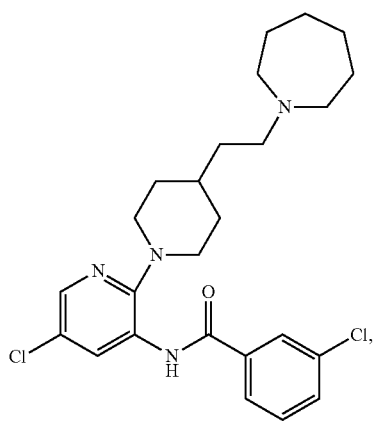
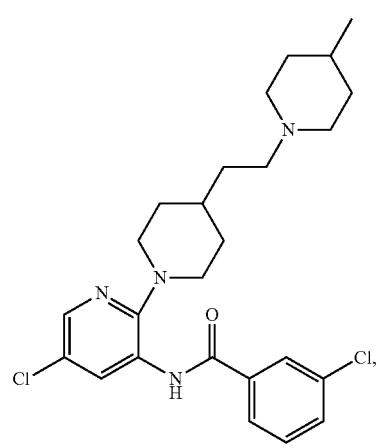
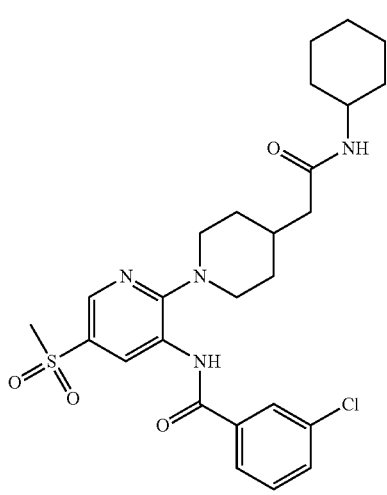

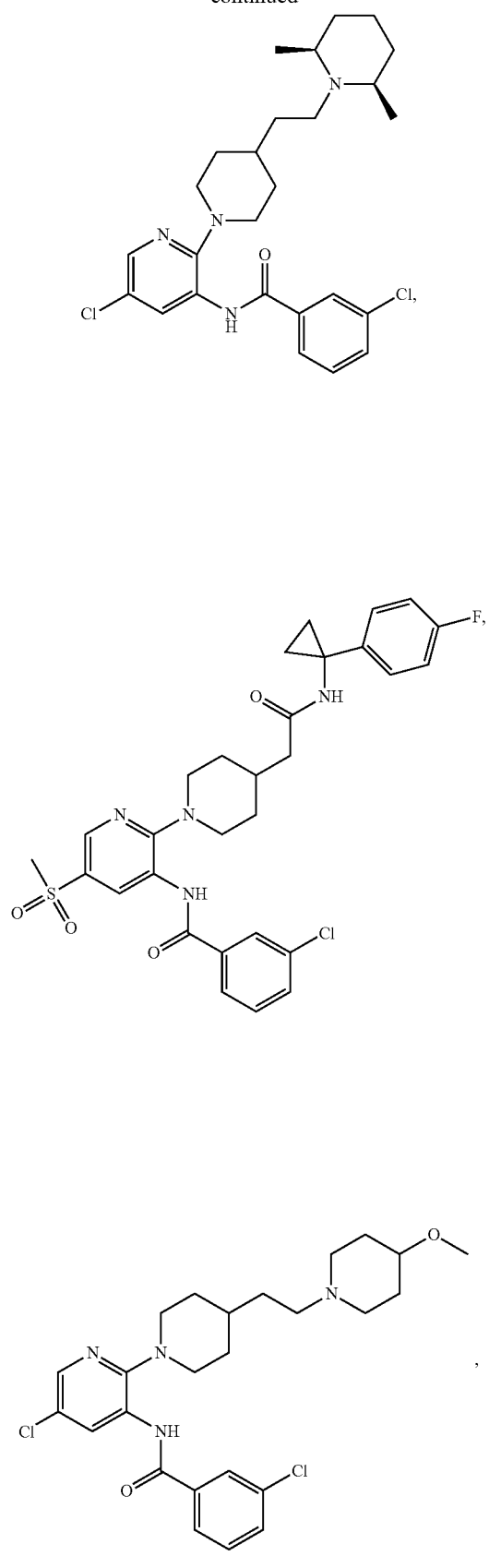
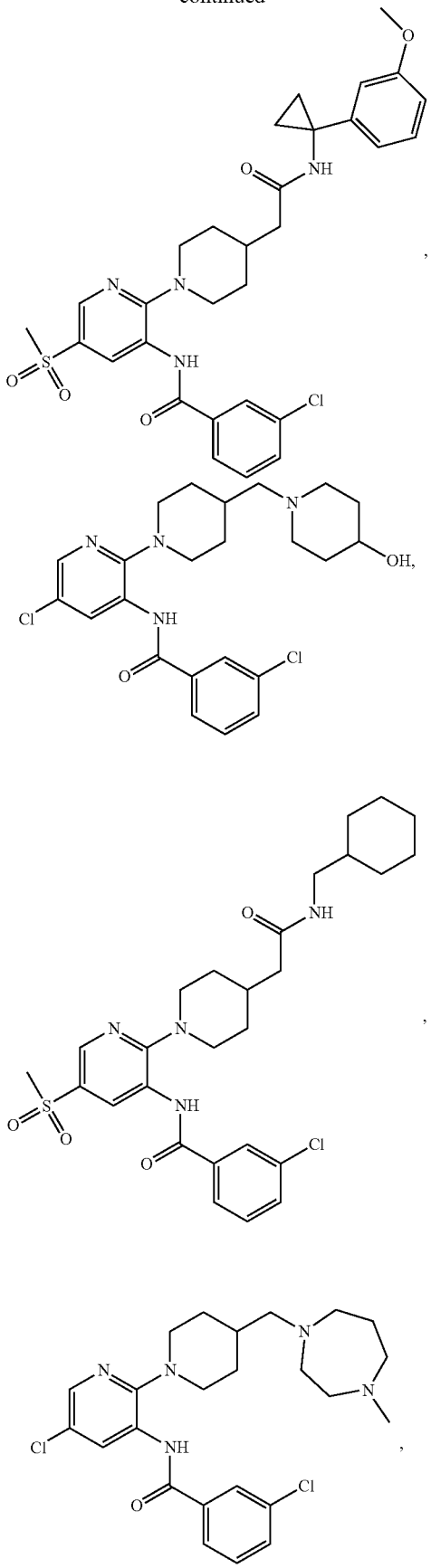

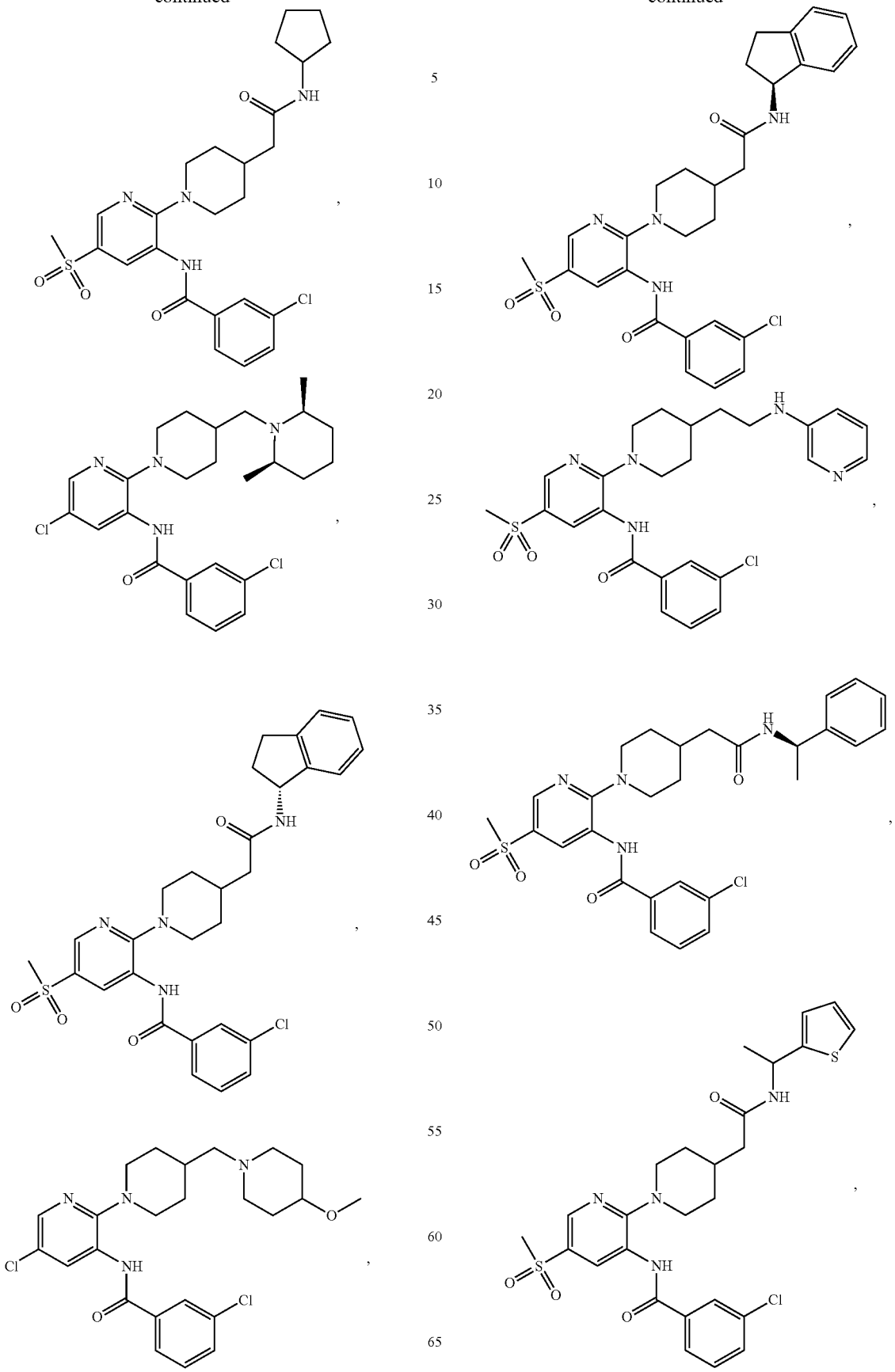

241
-continued
242
-continued
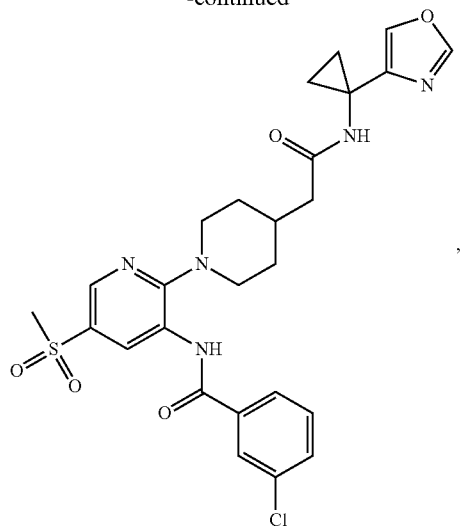
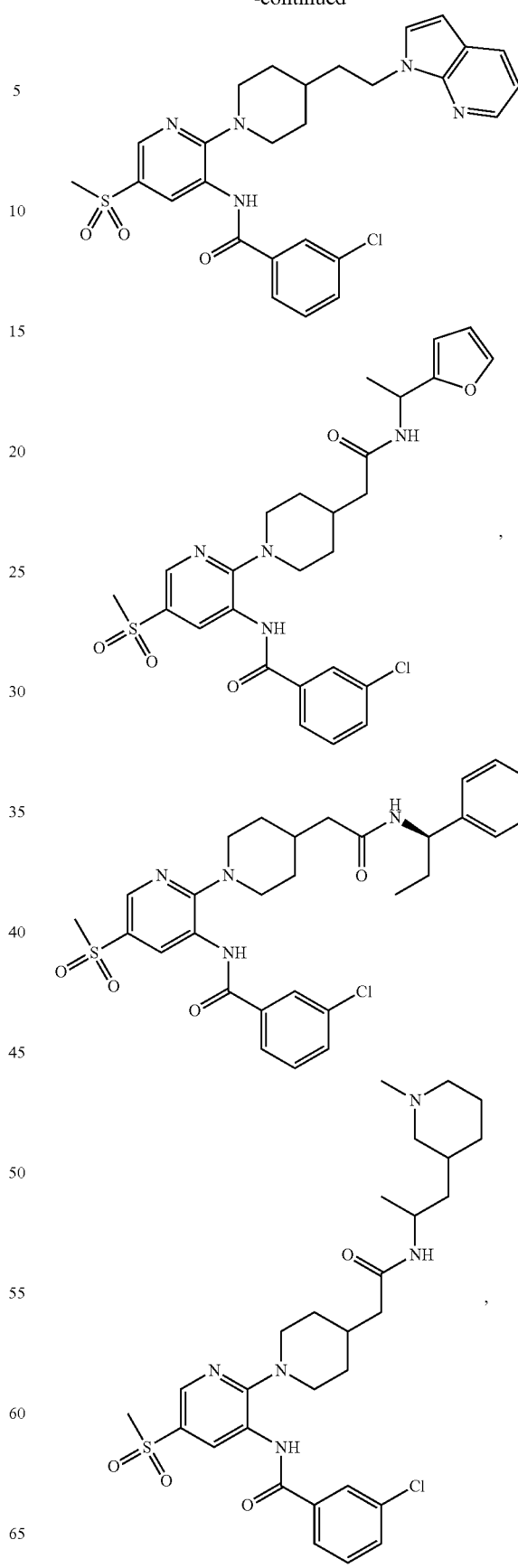

243
-continued
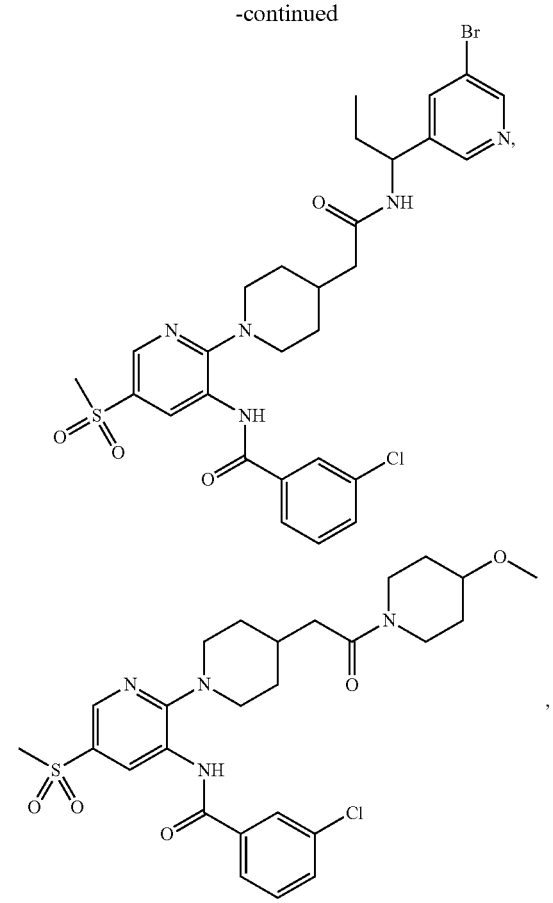
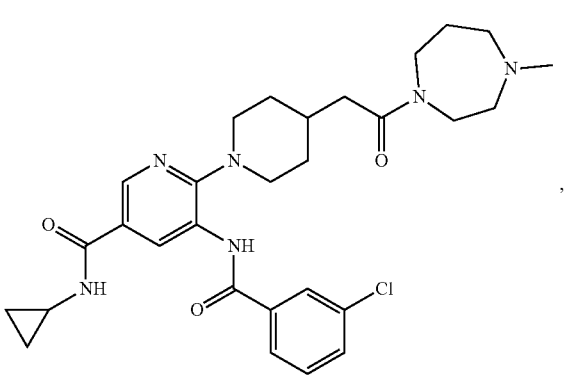
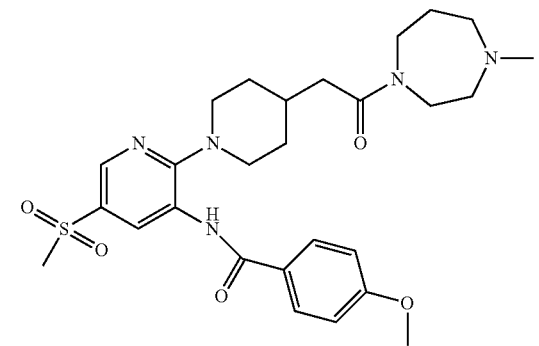
244
-continued
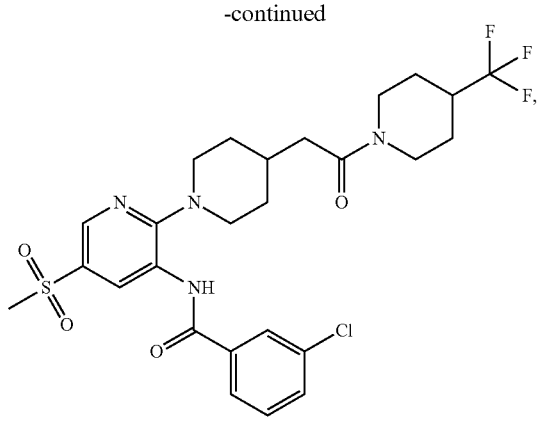
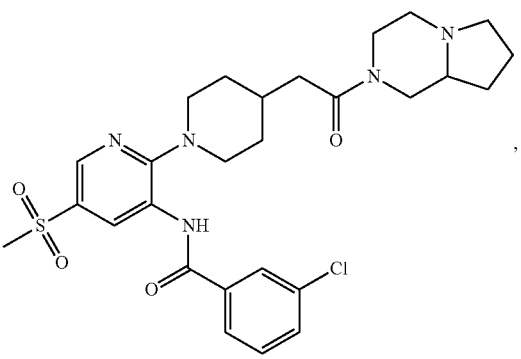
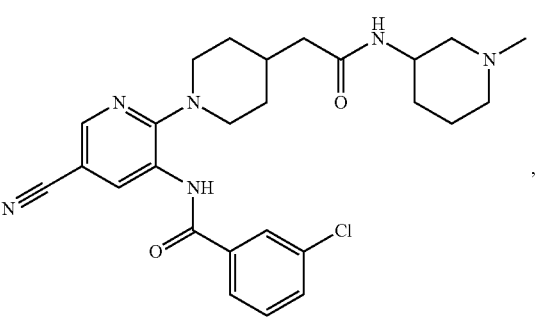
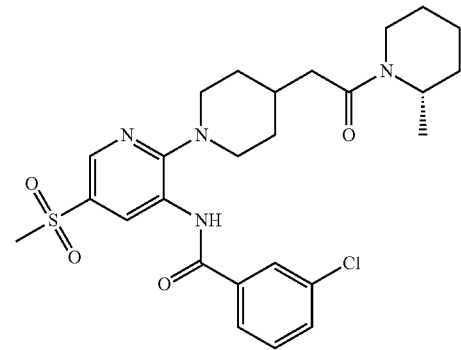

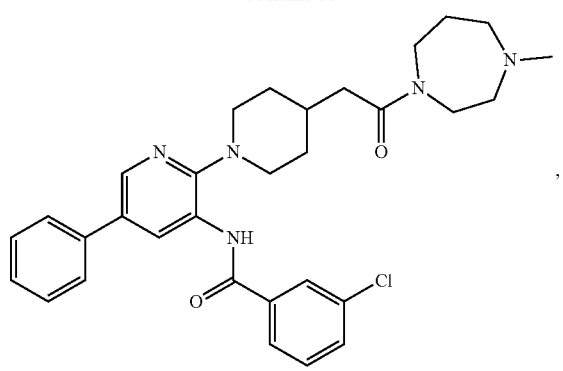
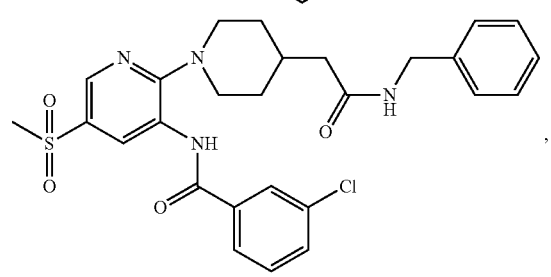
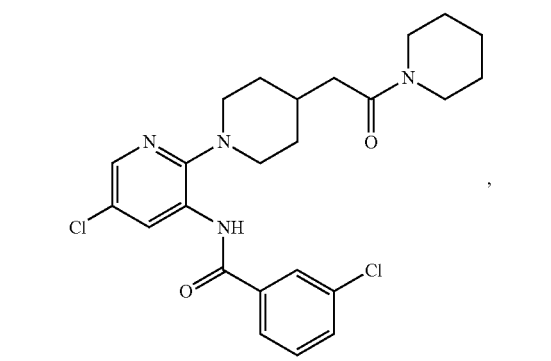
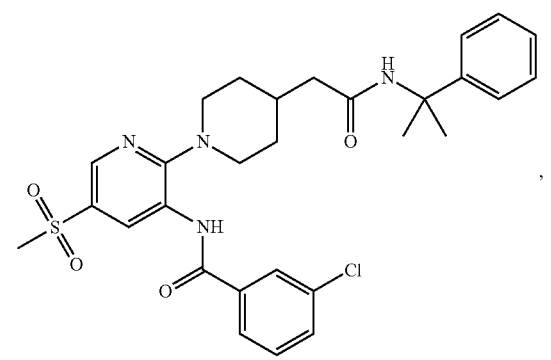
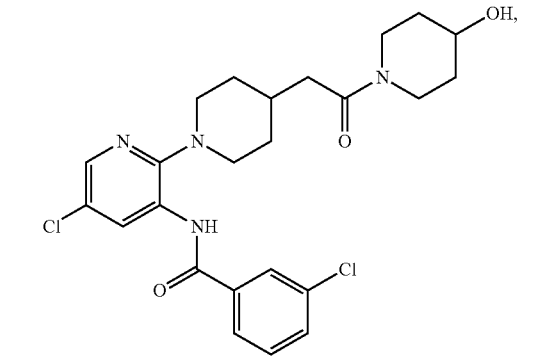
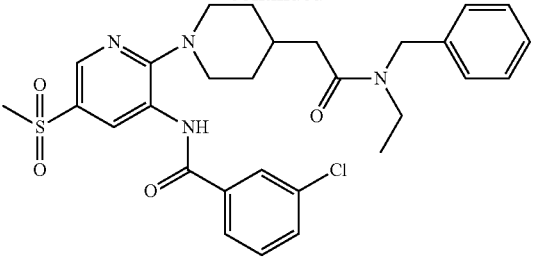
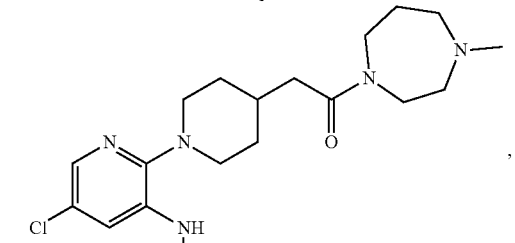
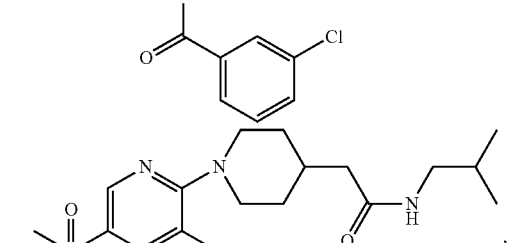
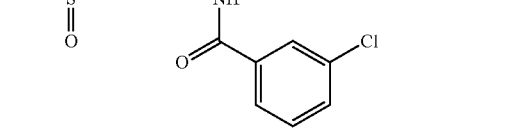
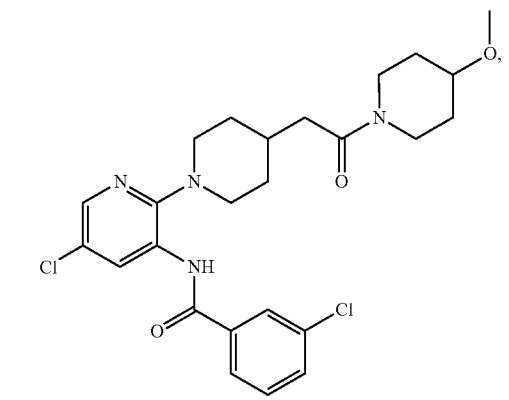
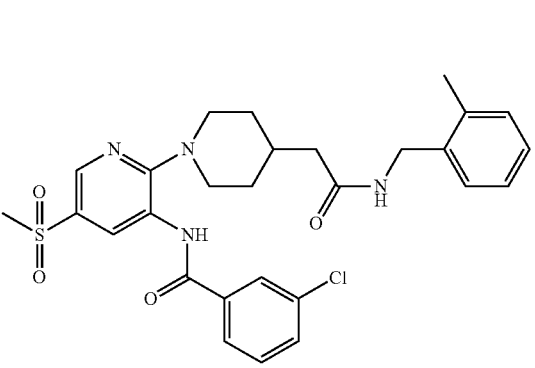

247
-continued
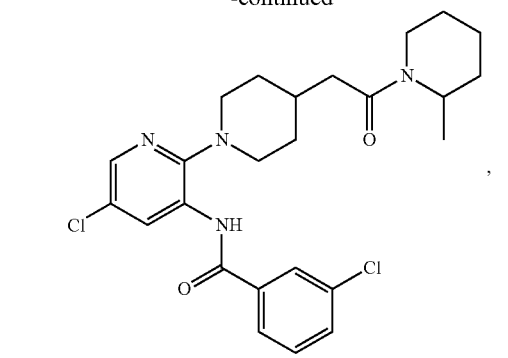
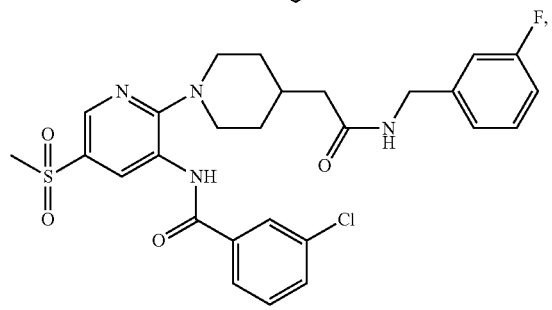
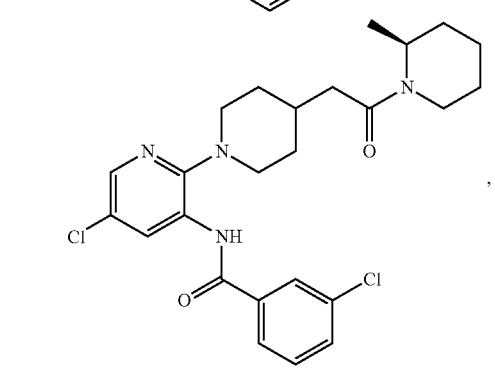
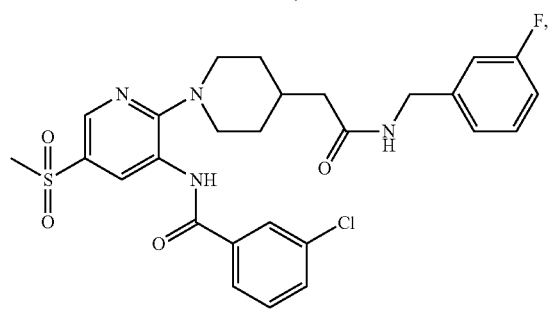
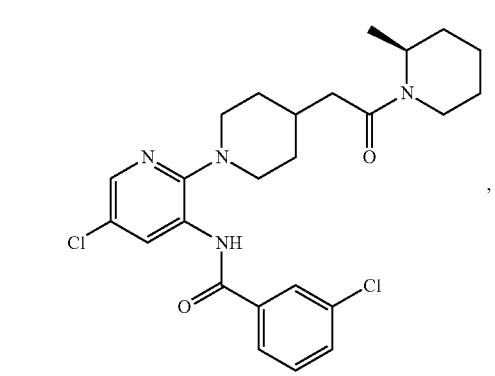
248
-continued
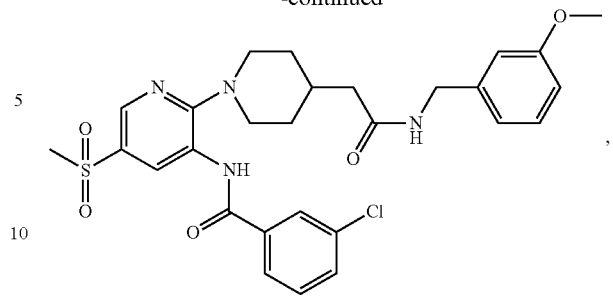
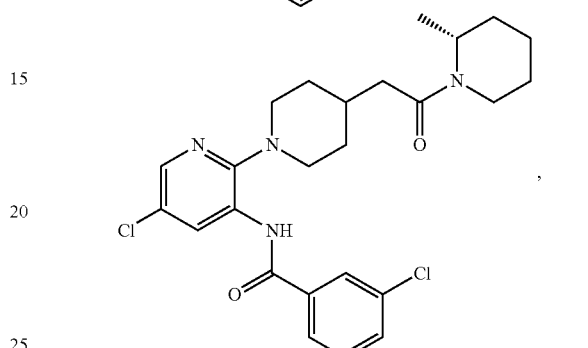
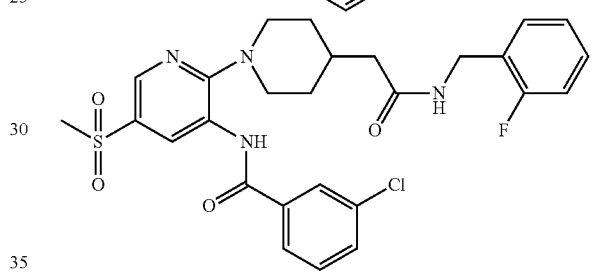
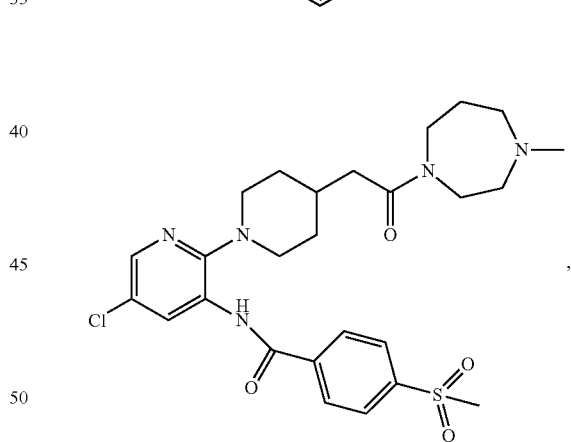
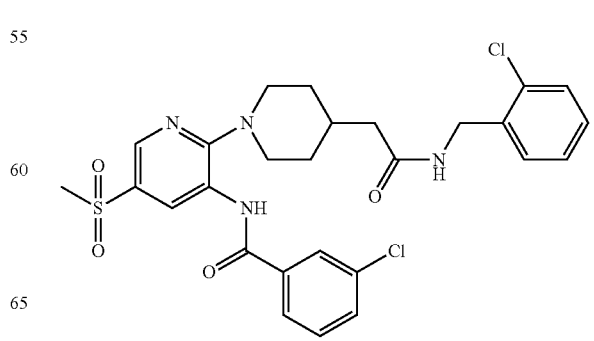

249
-continued
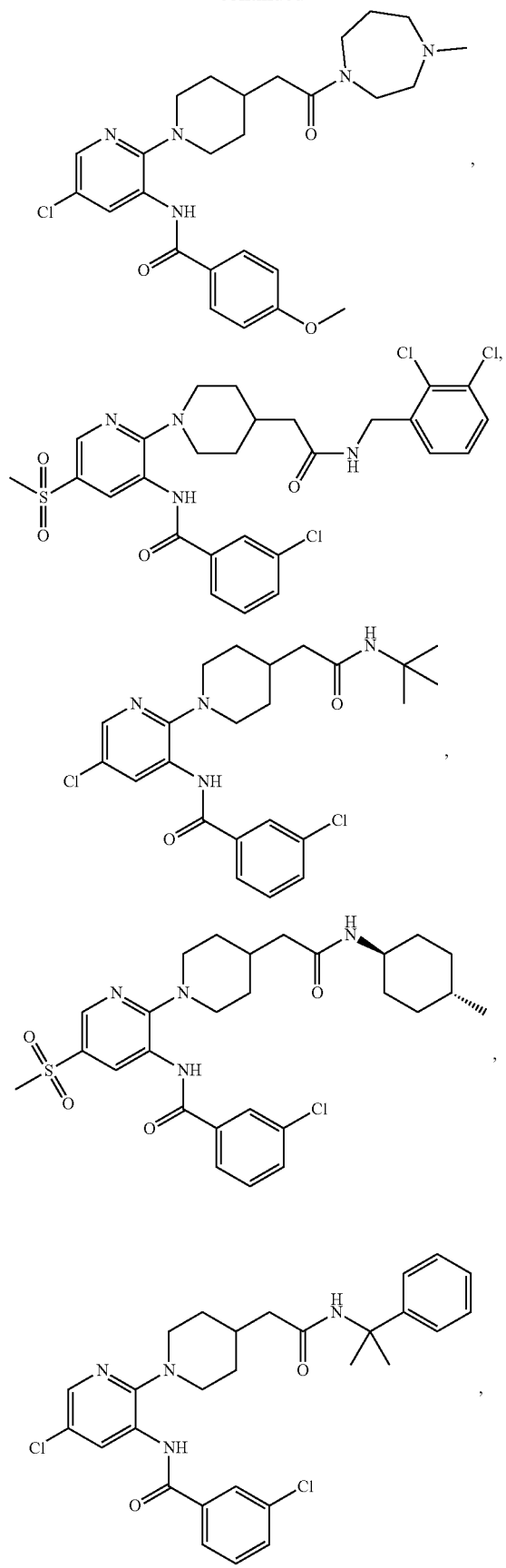
250
-continued
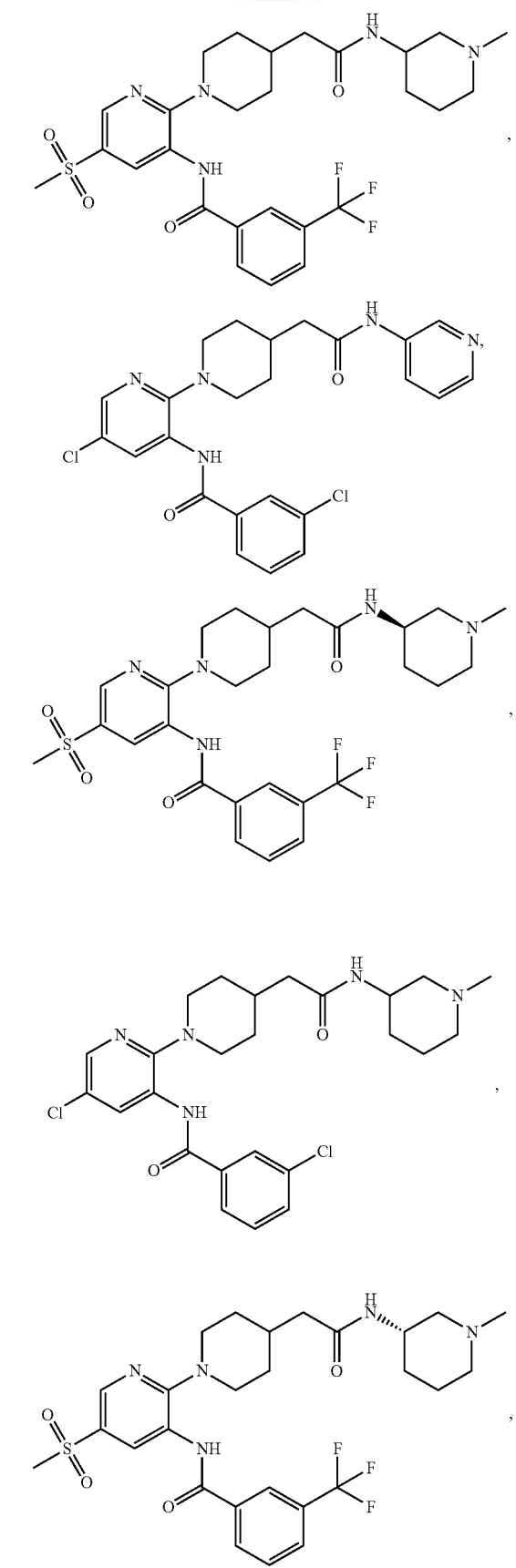

251
-continued
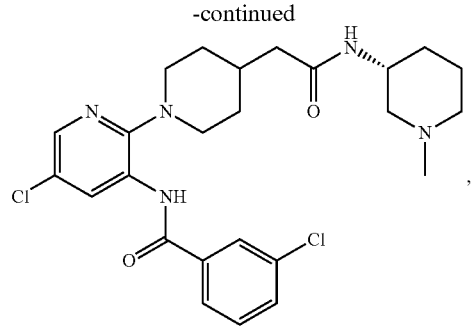
,
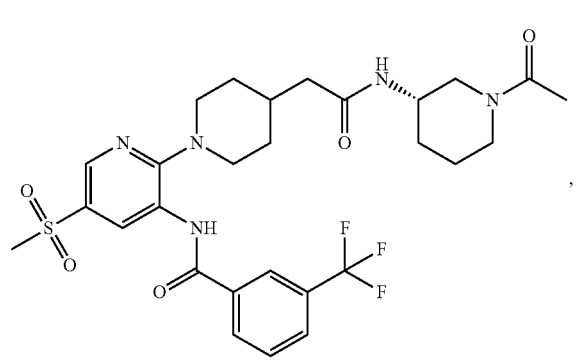
,
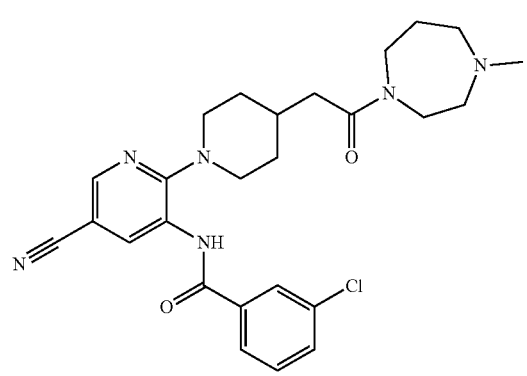
,
252
-continued
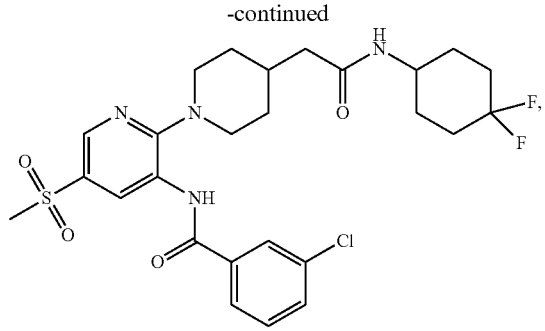
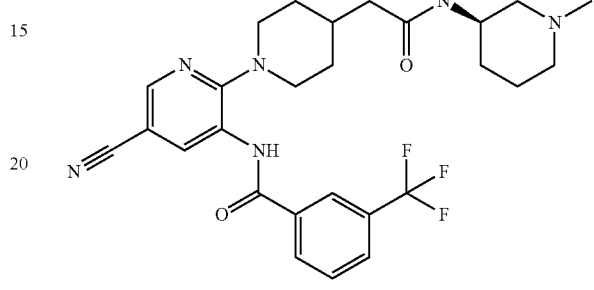
and
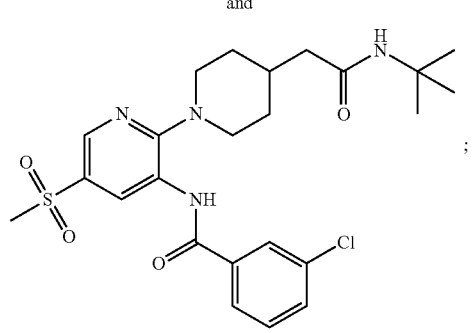
;
and the pharmaceutically acceptable salts thereof.
8. A pharmaceutical composition comprising the compound of claim 1, or a pharmaceutically acceptable salt thereof, and a pharmaceutically acceptable excipient.
\* \* \* \* \*